US012239647B2

(12) United States Patent
Fowler

(10) Patent No.: US 12,239,647 B2
(45) Date of Patent: Mar. 4, 2025

(54) ALS TREATMENT USING INDUCED REGULATORY T (iTREG) CELLS

(71) Applicant: RAPA THERAPEUTICS, LLC, Rockville, MD (US)

(72) Inventor: Daniel Harding Fowler, Bethesda, MD (US)

(73) Assignee: Rapa Therapeutics, LLC, Rockville, MD (US)

( * ) Notice: Subject to any disclaimer, the term of this patent is extended or adjusted under 35 U.S.C. 154(b) by 839 days.

(21) Appl. No.: 17/320,891

(22) Filed: May 14, 2021

(65) Prior Publication Data

US 2021/0275591 A1 Sep. 9, 2021

Related U.S. Application Data

(63) Continuation of application No. PCT/US2019/061818, filed on Nov. 15, 2019.

(60) Provisional application No. 62/927,075, filed on Oct. 28, 2019, provisional application No. 62/768,176, filed on Nov. 16, 2018.

(51) Int. Cl.

| | |
|---|---|
| ***A61P 25/28*** | (2006.01) |
| ***A61K 9/00*** | (2006.01) |
| ***A61K 31/513*** | (2006.01) |
| ***A61K 31/675*** | (2006.01) |
| ***A61K 31/7056*** | (2006.01) |
| ***A61K 38/17*** | (2006.01) |
| ***A61K 39/00*** | (2006.01) |
| ***C12N 5/0783*** | (2010.01) |
| ***G01N 33/50*** | (2006.01) |

(52) U.S. Cl.

CPC .......... *A61K 31/513* (2013.01); *A61K 9/0019* (2013.01); *A61K 31/675* (2013.01); *A61K 31/7056* (2013.01); *A61K 38/1793* (2013.01); *A61K 39/4611* (2023.05); *A61K 39/4621* (2023.05); *A61K 39/46432* (2023.05); *A61P 25/28* (2018.01); *C12N 5/0637* (2013.01); *G01N 33/5088* (2013.01); *A61K 2239/31* (2023.05); *A61K 2239/38* (2023.05); *A61K 2239/47* (2023.05); *C12N 2501/06* (2013.01); *C12N 2501/15* (2013.01); *C12N 2501/2302* (2013.01); *C12N 2501/2304* (2013.01); *G01N 2333/46* (2013.01); *G01N 2800/52* (2013.01)

(58) Field of Classification Search

CPC .... A61K 35/17; A61K 9/0019; A61K 31/513; A61K 31/675; A61K 38/1793; A61K 39/0008; A61K 39/4611; A61K 39/4621; A61K 2039/577; A61K 31/7056; A61K 2300/00; A61K 39/46432; A61P 25/28; C12N 5/0637; C12N 2501/2302; G01N 2800/52

See application file for complete search history.

(56) References Cited

U.S. PATENT DOCUMENTS

| | | | |
|---|---|---|---|
| 8,075,921 | B2 | 12/2011 | Fowler et al. |
| 9,644,179 | B2 | 5/2017 | Riley et al. |
| 2004/0175827 | A1 | 9/2004 | Fowler et al. |
| 2004/0241153 | A1 | 12/2004 | Fowler et al. |
| 2007/0134793 | A1 | 6/2007 | Hoshi et al. |
| 2008/0214590 | A1 | 9/2008 | Toma |
| 2008/0233610 | A1 | 9/2008 | Thomson et al. |
| 2012/0114623 | A1 | 5/2012 | Zhang |
| 2012/0263764 | A1 | 10/2012 | Watson |
| 2013/0280208 | A1 | 10/2013 | Stepkowski et al. |
| 2013/0344081 | A1 | 12/2013 | Kaji |
| 2014/0154228 | A1 | 6/2014 | Volk et al. |
| 2017/0306416 | A1 | 10/2017 | Bedoya et al. |
| 2018/0250376 | A1 | 9/2018 | Liu et al. |
| 2019/0203195 | A1 | 7/2019 | Chen et al. |

FOREIGN PATENT DOCUMENTS

| | | | |
|---|---|---|---|
| CN | 101808629 | A | 8/2010 |
| EP | 2853590 | B1 | 7/2018 |
| EP | 2978450 | B1 | 9/2018 |
| JP | 2014-508715 | A | 4/2014 |
| WO | 2012110200 | A1 | 8/2012 |
| WO | 2012143516 | A1 | 10/2012 |
| WO | 2013176197 | A1 | 11/2013 |
| WO | 2016025847 | A1 | 2/2016 |
| WO | 2016138091 | A2 | 9/2016 |
| WO | 2016196471 | A1 | 12/2016 |
| WO | 2017/059122 | A1 | 4/2017 |

(Continued)

OTHER PUBLICATIONS

Chapoval, S et. al. "Regulation of the T helper cell type 2 (Th2)/T regulatory cell (Treg) balance by IL-4 and STAT6", 2010, Journal of Leukocyte Biology, 87, 1011-1018. (Year: 2010).*

Anraku, M et. al. "Synergistic Antitumor Effects of Regulatory T Cell Blockade Combined with Pemetrexed in Murine Malignant Mesothelioma", 2010, J Immunol, 185(2), 956-966. (Year: 2010).*

Cai, S et. al. "Dedifferentiation: A New Approach in Stem Cell Research", 2007, BioScience, 57(8), 655-662. (Year: 2007).*

Cobaleda, C and Busslinger, M, "Developmental plasticity of lymphocytes", 2008, Current Opinion in Immunology, 20, 139-148. (Year: 2008).*

(Continued)

*Primary Examiner* — Nelson B Moseley, II
*Assistant Examiner* — Alyssa Rae Stonebraker
(74) *Attorney, Agent, or Firm* — Barnes & Thornburg LLP

(57) ABSTRACT

T cells harvested from an ALS patient are subjected to a de-differentiation and re-differentiation process to yield $T_{REG}$/Th2 hybrid T cells and are then administered to the ALS patient as a cell therapy. The harvested T cells are first cultured in medium containing vitamin D, temsirolimus, and an IL-2 signaling inhibitor to de-differentiate the cells and then the de-differentiated cells are then transferred to a culture medium with IL-2, IL-4, and TGF-β.

17 Claims, 100 Drawing Sheets

(56) References Cited

FOREIGN PATENT DOCUMENTS

| | | | |
|---|---|---|---|
| WO | 2017100403 | A1 | 6/2017 |
| WO | 2017114497 | A1 | 7/2017 |
| WO | 2018024894 | A1 | 2/2018 |
| WO | 2018/106958 | A1 | 6/2018 |
| WO | 2018165198 | A1 | 9/2018 |

OTHER PUBLICATIONS

Cobaleda, C et. al. "Conversion of mature B cells into T cells by dedifferentiation to uncommitted progenitors", 2007, Nature, 449, 473-479. (Year: 2007).*

Appel, S.H., et al., "Expansion and Infusion of T-Regulatory Cells in Amyotrophic Lateral Sclerosis" Aug. 4, 2017; retrieved from the internet <https://clinicaltrials.gov/ct2/show/NCT03241784>; pp. 1-5; p. 2/5, paragraphs 1-4.

Duggleby, R. et al. "Clinical Grade Regulatory CD4+ T Cells (Tregs): Moving Toward Cellular-Based Immunomodulatory Therapies" Frontiers in Immunology, Feb. 13, 2018; vol. 9, No. 252; pp. 1-13; p. 2, col. 2, paragraph 3; p. 7, col. 1, paragraph 1-col. 2, paragraph 1; DOI: 10.3389/fimmu.2018.00252.

Heylmann, D. et al. "Human CD4+CD25+ Regulatory T Cells Are Sensitive to Low Dose Cyclophosphamide: Implications for the Immune Response", PLoS One. Dec. 23, 2013; vol. 8, No. 12; pp. 1-10; abstract; p. 9, col. 1, paragraph 3; DOI.

Mandrioli, J., et al., "Rapamycin Treatment for Amyotrophic Lateral Sclerosis: Protocol for a phase II randomized, double-blind, placebo controlled, multicenter, clinical trial (RAP-ALS trial)" Medicine (Baltimore), Jun. 2018; vol. 97, No. 24; pp. 1-10; abstract; p. 8, col. 1, paragraph 3; p. 9, col. 2, paragraph 2; DOI: 10.1097/MD.0000000000011119.

Neuroscience Trials Australia, "Phase 2a Open Label Study, Safety and Tolerability of Combination Antiretroviral Therapy (Triumeq) in Participants with Amyotrophic Lateral Sclerosis (ALS)—The Lighthouse Project" Mar. 28, 2018; retrieved from the internet.

RAPA Therapeutics LLC, Phase I Trial of Autologous Hybrid TREGfTh2 Cell Therapy (RAPA-501) for Amyotrophic Lateral Sclerosis. Jan. 3, 2020; retrieved from the internet <https://clinicaltrials.gov/ct2/show/NCT04220190>; pp. 1-4; whole document.

International Search Report dated Apr. 24, 2020, prepared in International Application No. PCT/US2019/061818.

International Preliminary Report on Patentability dated May 15, 2021, prepared in International Application No. PCT/US2019/061818.

Written Opinion dated Apr. 24, 2020, prepared in International Application No. PCT/US2019/061818.

International Search Report dated Apr. 17, 2020, prepared in International Application No. PCT/US2019/061789.

International Preliminary Report on Patentability dated May 18, 2021, prepared in International Application No. PCT/US2019/061789.

International Search Report dated Feb. 11, 2020, prepared in International Application No. PCT/US2019/061811.

International Preliminary Report on Patentability dated May 18, 2021, prepared in International Application No. PCT/US2019/061811.

Yu et al. "Dynamic expression of transcription factors T-bet and GATA-32 by regulatory T cells maintains immunotolerance," Nat Immunol, Dec. 15, 2014 (Dec. 14, 2014), vol. 16, No. 2 pp. 197-206. entire document.

Copsel et al. "Very Low Nos. of CD4+FoxP3+Tregs Expanded in Donors via TL1A-Ig and Low-Dose IL-2 Exhibit a Distinct Activation/Functional Prfile and Suppress GVHD in a Preclinical Model," Biol Blood Marrow Transplant, May 8, 2018 (May 8, 2018), vol. 24, No. 9, pp. 1788-1794. entire document.

Hirata et al. "CD150high Bone Marrow Tregs Maintain Hemotopoietic Stem Cell Quiescence and Immune Privilege via Adenosine," Cell Stem Cell, Feb. 15, 2018 (Feb. 15, 2018), vol. 22, No. 3, pp. 445-453. entire document.

Chapman et al. "mTOR coordinates transciptional programs and mitochondrial metabolism of activated Treg subsets to protect tissue homeostatis," Nat Commun, May 29, 2018 (May 29, 2018), vol. 9, No. 1, pp. 1-15. entire document.

Zeng et al. "mTORC1 couples immune signals and metabolic programming to establish T(reg)-cell function," Nature, Jun. 30, 2013 (May 30, 2013), vol. 449, No. 7459, pp. 485-490.

NCT03359538, Rapamycin Treatment for ALS (RAP-ALS), available at https://clinicaltrials.gov/ct2/show/NCT03359538 (2021).

NCT02437110, HERV-K Suppression Using Antiretroviral Therapy in Volunteers With Amyotrophic Lateral Sclerosis (ALS), available at https://clinicaltrials.gov/ct2/show/NCT02437110 (2022).

NCT02363452, Reverse Transcriptase Inhibitors in AGS (RTIs in AGS), available at https://clinicaltrials.gov/ct2/show/NCT02363452 (2019).

Yoshii, Saori R. and Mizushima, Noboru, "Monitoring and Measuring Autophagy," Int. J. Mol. Sci. 18:1865 (2017).

Maestro, et al., "Vitamin D receptor 2016: novel ligands and structural insights," Expert Opinion on Therapeutic Patents 26(11):1291-1306 (2016).

"Comparison of anti-CD3 and anti-CD28-coated beads with soluble anti-CD3 for expanding human T cells: Differingimpact on CD8 T cell phenotype and responsiveness to restimulation, Li and Kurlander, Journal of TranslationalMedicine 2010, 8:104 (http://www.translational-medicine.com/content/8/1/104)."

"How do Regulatory T Cells Work?, A. Corthay, Centre for Immune Regulation, Institute of Immunology, University of Oslo and Oslo University Hospital, Feb. 25, 2009, Scandinavian Journal of Immunology 70, 326-336."

Office Action mailed Dec. 28, 2023 for Chinese Application No. 201980089240.4.

Search Report mailed Dec. 27, 2023 for Chinese Application No. 201980089240.4.

Mossoba, Miriam E., et al., Pentostatin Plus Cyclophosphamide Safely and Effectively Prevents Immunotoxin Immunogenicity in Murine Hosts, Clinical Cancer Research, pp. 3697-3705 (Dec. 31, 2011).

Zhou, Jing, et al. ""Tumor immunotherapy using chimeric antigen receptormodified T cells," Journal of Chifeng University (Natural Science Edition), Issue 2, pp. 128-132 (Jan. 25, 2017)".

Extended European Search Report issued on May 21, 2024 in European Patent Application 21803933.7.0.

Lan, Q., "Induced Foxp3e+ regulatory T cells: a potential new weapon to treat autoimmune and inflammatory diseases?" Journal of Molecular Cell Biology, vol. 4, No. 1, pp. 22-28, XP093158269, Nov. 22, 2011.

Thanh-Long, M. Nguyen, In vitro Induced Regulatory T Cells ae Unique from Endogenous Regulatory T Cells and Effective at Suppressing Late Stages of Ongoing Autoimmunity, Plos One, vol. 9, No. 8, p. e104698, XP0931158641, Aug. 13, 2014.

Hideyuki, Yoshida, "CDK inhibitors suppress Th17 and promote iTreg differentiation, and amerliorate experimental autoimmune encephalomyelitis in mice," Biochemical and Biophysical Research Communications, vol. 435, No. 3, pp. 378-384, XP093158642, Jun. 1, 2013.

Fowler, et al., "Rapamycin-resistant effector T-cell therapy," Immunological Reviews, pp. 210-255.

Office Action issued on Oct. 24, 2023 for Japanese Patent Application No. 2021-526727.

Ueki, Tomoyuki, et al. "Pre-treatment with cyclophosphamide or OX40 (CD134) costimulation targeting regulatory T cell function enhances the anti-tumor immune effect of adoptively transferred CD8+ T cells from wild-type mice," Molecular Medicine Reports, 2009, 2, pp. 615-620.

Journal of Clinical and Experimental Medicine, 2015, 252(1), pp. 105-110.

Martinez, Ann, et al. "Drugs in clinical development for the treatment of amyotrophic lateral sclerosis," Expert Opinion on Investigational Drugs, 2017, 26(4), pp. 403-414, DOI: 10.1080/13543784.2017.1302426.

Extended European Search Report issued on Dec. 22, 2022 in European Patent Application 19884703.0.

Alsuliman A et al., Cytotherapy 18(10), 1312-1324, Oct. 2016.

(56) References Cited

OTHER PUBLICATIONS

Thonhoff J R et al., Neurology: Neuroimmuniology & Neuroinflammation 5(4):e465, Jun. 30, 2018.
Xu L et al., Immunity 47(3), 538-551.e5, Sep. 19, 2017.
Sun I-H et al., The Journal of Immunology 201(2), 481-492, Jul. 15, 2018.
NCT03241784, T-Regulatory Cells in Amyotrophic Lateral Sclerosis, available at https://clinicaltrials.gov/ct2/show/study/NCT03241784?term=nCT03241784&draw=2&rank=1, Aug. 14, 2018.
NCT02868580, Safety and Tolerability of Antiretroviral (Triumeq) in Patients With Amyotrophic Lateral Sclerosis (ALS), (Lighthouse) available at https://clinicaltrials.gov/ct2/show/NCT02868580?term=NCT02868580&draw=2&rank=1,Aug. 16, 2016.
Office Action mailed Jul. 31, 2024 for Chinese Patent Application No. 201980089240.4.
Supplementary Search Report mailed Jul. 31, 2024 for Chinese Patent Application No. 201980089240.4.
Wohlfert, et al., "GATA3 controls Foxp3+ regulatory T cell fate during inflammation in mice," vol. 121, Issue 11, pp. 4503-4515 (Nov. 30, 2011).
Li, Ji, et al. "Crossover Subsets of Cd+ T Lymphocytes in the Intestinal Lamina Propria of Patients with Crohn's Disease and Ulcerative Colitis," Digestive Diseases and Sciences, vol. 62, pp. 2357-2368 (Jun. 1, 2017).

* cited by examiner

| | | | | | | | | | |
|---|---|---|---|---|---|---|---|---|---|
| Temsirolimus | No | Y | Y | Y | Y | Y | Y, Lo | No | Y |
| Vitamin D | No | Y | Y | Y | Y, Lo | Y, Hi | Y | Y | Y |
| Anti-IL-2 Receptor | No | No | Y | Y | Y | Y | Y | Y | Y |
| 3/28 Beads | 1:3 | 1:3 | 1:3 | 1:3 | 1:3 | 1:3 | 1:3 | 1:3 | 1:1 |
| Serum | Y | Y | Y | N | Y | Y | Y | Y | Y |

| | | | | | | |
|---|---|---|---|---|---|---|
| Temsirolimus | No | Y | Y | Y | Y, Lo | No |
| Vitamin D | No | Y | Y | Y, Lo | Y | Y |
| Anti-IL-2 Receptor | No | No | Y | Y | Y | Y |
| 3/28 Beads | 1:3 | 1:3 | 1:3 | 1:3 | 1:3 | 1:3 |
| Serum | Y | Y | Y | Y | Y | Y |

Fig. 23B

| TCR Gene I.D.: Up-Regulated Post-Enbrel | Expression Pre-Enbrel | Expression Post-Enbrel |
|---|---|---|
| CASSSTGDSYGYTF:TRBV12-3:TRBD1:TRBJ1-2:12:16:25:26 | 0.01 | 486.910395 |
| CASSRGGGPFDEQFF:TRBV12-3:TRBD1:TRBJ2-1:10:14:19:20 | 0.01 | 382.293833 |
| CASSYTYEQYF:TRBV12-4:.:TRBJ2-7:12:-1:-1:16 | 0.01 | 336.733749 |
| CASSVDELLAGGQSPSTDTQYF:TRBV12-4:TRBD2:TRBJ2-3:11:24:34:45 | 0.01 | 247.225867 |

| TCR Gene I.D.: Down-Regulated Post-Enbrel | Expression Pre-Enbrel | Expression Post-Enbrel |
|---|---|---|
| CASSSTGDSYGYTF:TRBV12-4:TRBD1:TRBJ1-2:12:16:25:26 | 398.697014 | 0.01 |
| CASSYTYEQYF:TRBV12-3:.:TRBJ2-7:12:-1:-1:16 | 327.829549 | 0.01 |
| CASSPGQLNTEAFF:TRBV12-4:TRBD1:TRBJ1-1:10:11:20:22 | 272.227753 | 0.01 |
| CASSRGGGPFDEQFF:TRBV12-4:TRBD1:TRBJ2-1:10:14:19:20 | 259.758441 | 0.01 |

RAPA-501 Cells are Enriched for a T Stem Memory Phenotype
($CD4^+CD45RA^+CD62L^+CCR7^+CD95^+CD27^+$)

Fig. 36B

| TCR Gene I.D.: Up-Regulated Post-Enbrel | Expression Pre-Enbrel | Expression Post-Enbrel |
|---|---|---|
| CASSSTGDSYGYTF:TRBV12-3:TRBD1:TRBJ1-2:12:16:25:26 | 0.01 | 486.910395 |
| CASSRGGGPFDEQFF:TRBV12-3:TRBD1:TRBJ2-1:10:14:19:20 | 0.01 | 382.293833 |
| CASSYTYEQYF:TRBV12-4::TRBJ2-7:12:-1:-1:16 | 0.01 | 336.733749 |
| CASSVDELLAGSQSPSTDTQYF:TRBV12-4:TRBD2:TRBJ2-3:11:24:34:45 | 0.01 | 247.225867 |

| TCR Gene I.D.: Down-Regulated Post-Enbrel | Expression Pre-Enbrel | Expression Post-Enbrel |
|---|---|---|
| CASSSTGDSYGYTF:TRBV12-4:TRBD1:TRBJ1-2:12:16:25:26 | 598.697014 | 0.01 |
| CASSYTYEQYF:TRBV12-3::TRBJ2-7:12:-1:-1:16 | 327.829549 | 0.01 |
| CASSPGQLNTEAFF:TRBV12-4:TRBD1:TRBJ1-1:10:11:20:22 | 272.227753 | 0.01 |
| CASSRGGGPFDEQFF:TRBV12-4:TRBD1:TRBJ2-1:10:14:19:20 | 259.758441 | 0.01 |

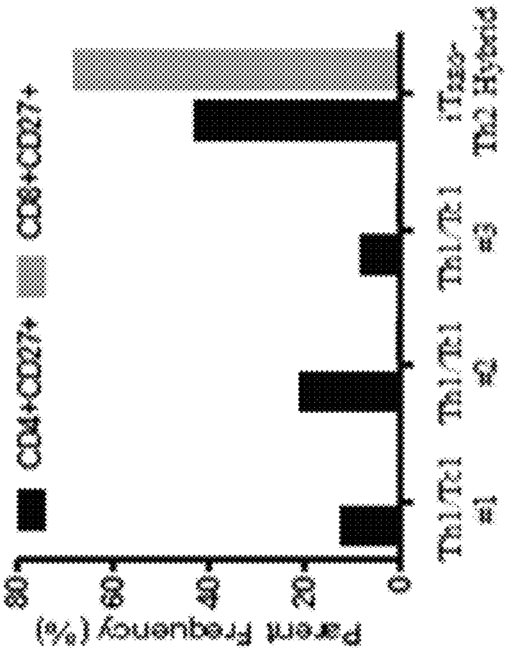
Fig. 37
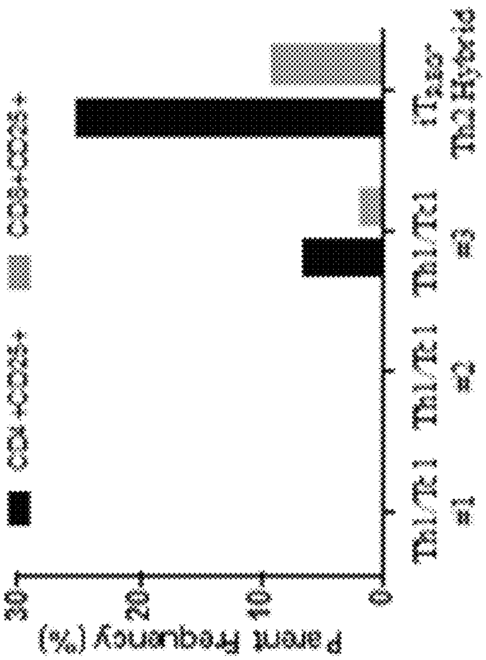

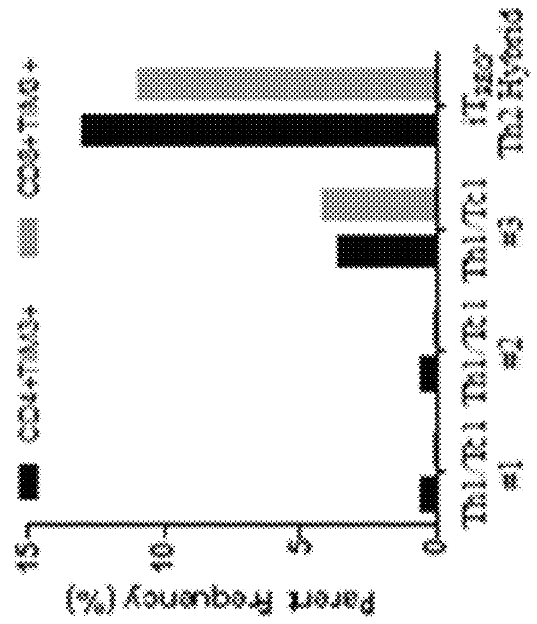
Fig. 38
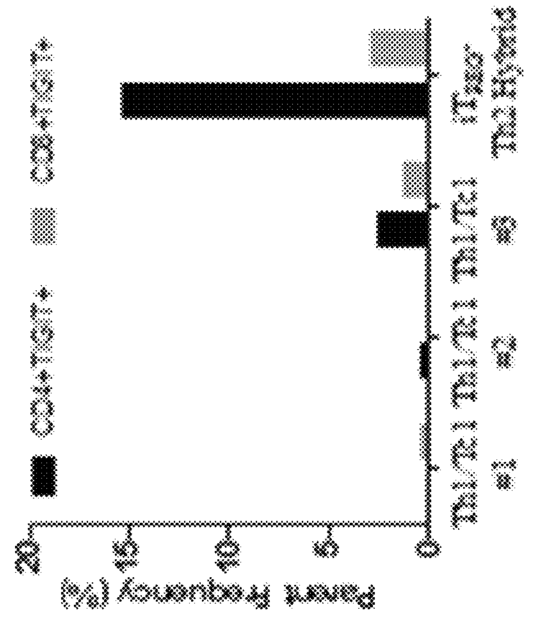

Culture Input T cells

Culture Day 2

Elimination of Fate
Quiescent Metabolism

RAPA-501 Product
(Culture Day 6)

Hybrid $T_{REG}$/Th2 Fate
Stem-like Memory

ALS TREATMENT USING INDUCED REGULATORY T (iTREG) CELLS

CROSS-REFERENCE TO RELATED APPLICATIONS

The present application is a continuation of International Application No. PCT/US2019/061818, filed Nov. 15, 2019, the entire contents of which is incorporated herein by reference its entirety. International Application No. PCT/US2019/061818 claims priority to U.S. Provisional Application No. 62/768,176, filed Nov. 16, 2018 and to U.S. Provisional Application No. 62/927,075, filed Oct. 28, 2019, the entirety of each of which is incorporated herein by reference.

BACKGROUND

Adoptive T cell therapy is an emerging intervention for the effective treatment of cancer and infectious disease, auto-immunity, and neuro-degenerative disease. It is increasingly clear that the transfer of T cells with a more primitive differentiation state, which translates into a higher proliferative potential and other key attributes, is associated with improved in vivo effects after adoptive transfer. However, most forms of adoptive T cell therapy require an ex vivo manufacturing step, which typically results in further cellular differentiation; this is particularly problematic, as T cells from the adult human are already primarily in an advanced state of differentiation (termed effector memory cells) and often exist in a senescent state that is under the control of checkpoint inhibitory molecules. Approaches can be taken to alleviate this limitation, including the isolation (purification) of more naïve T cell subsets at the time of culture initiation; however, this approach is restricted in part by the small number of naïve T cells present in the adult human peripheral blood. Accordingly, a great need exists for isolated T cells in primitive differentiation states.

It is well known that even highly differentiated cells possess an inherent capacity for de-differentiation towards a more primitive state. Indeed, in the most extreme examples, differentiated cells can be manipulated to attain an induced pluripotent stem cell (iPSC) state, whereby such iPS cells share key characteristics with embryonic stem cells and can then be further modulated towards re-differentiation to divergent tissue fates; cellular therapy using such iPSC methodologies has numerous potential clinical applications. Generation of iPS cells from differentiated somatic cells was initially demonstrated by the transfer of key transcription factors via viral or non-viral mediated approaches, including Sox2, Oct3/4, KLF4, and c-myc or Sox2, Oct3/4, Nanog, and Lin28.

However, the ability to convert somatic cells to iPS cells is inefficient and dependent in-part upon the degree of somatic cell differentiation. As one example, the ability to convert mature murine immune T cells into iPS cells is 300-fold less efficient relative to conversion of murine hematopoietic stem cells into iPS cells. Nonetheless, using gene transfer methods, it was demonstrated that mature human peripheral blood T cells maintain a capacity for conversion to an iPS cell state. Over the past decade, investigators have also characterized transcription factors associated with the earliest stages of T cell differentiation. However, the re-differentiation of T cells from various types of stem cell precursors is a relatively inefficient process that typically takes one-to-two months.

Although the biology of de-differentiation is becoming increasingly characterized, a great deal remains unknown in terms of the specific transcription factors and transcription factor kinetics associated with de-differentiation. It is also important to recognize that gene transfer methods of achieving de-differentiation are laborious and associated with complications such as teratoma generation that must be addressed through additional genetic interventions such as cell fate suicide gene programming. As a potential alternative, various pharmacologic interventions can be utilized to achieve some degree of de-differentiation. As one example, calcineurin-inhibition during cell culture by use of the immune suppressive agent cyclosporine resulted in molecular alterations that replaced the need for gene delivery of Sox2 transcription factor for the promotion of murine iPS cells. In addition, rapamycin, which is an immune suppression drug that inhibits the mammalian target of rapamycin (mTOR), can result in a de-differentiation effect on end-stage effector T cells through starvation-induced up-regulation of the transcription factor KLF2, which in turn increases the T central-memory molecules CD62L and CCR7. In addition, rapamycin and resultant inhibition of mTOR signaling is critical for the maintenance of cellular quiescence in naïve T cells having a reduced state of differentiation. It is important to note that the mTOR pathway is comprised of both an mTORC1 complex (which contains the Raptor sub-unit) and the mTORC2 complex (which contains the Rictor sub-unit). Inhibition of both mTORC1 and mTORC2 has been associated with an increase in memory T cell promotion and maintenance. Of note, rapamycin can only directly inhibit mTORC1; however, with prolonged rapamycin-mediated inhibition of mTORC1, down-stream inhibition of mTORC2 can occur. Reduction in T cell growth factor signaling via mTOR inhibition or other pathway inhibition is also known to up-regulate another key molecule associated with T cells of more primitive differentiation status, namely, IL-7 receptor alpha (CD127). In further studies, inhibition of the T cell mTOR pathway through the pharmacologic agent rapamycin or the Wnt-β-catenin signaling activator TWS11 promoted the de-differentiation of human naïve T cells towards a less-differentiated, T stem cell memory population that was previously identified and characterized in murine and human T cells. In further experimental model research, pharmacologic inhibition of the AKT signaling pathway or combined inhibition of the PI3 kinase and vasoactive intestinal peptide signaling pathways resulted in the generation of T cells with a reduced differentiation status and increased T cell function upon adoptive transfer.

It has been demonstrated that blockade of mTOR through ex vivo culture of human T cells in rapamycin reduces T cell expression of molecules associated with effector differentiation, such as cytokine secretion molecules and cytolytic effector molecules.

In addition, the 1, 25-hydroxylated form of Vitamin D ("Vitamin D" as used herein) can inhibit human T cell effector function. The inhibitory effect of Vitamin D on human T cell proliferation can be synergistic with immune suppressive drug exposure using agents such as cyclosporine A or rapamycin. However, previous research indicated that the inhibitory effect of Vitamin D on T cell effectors was relatively specific for Th1-type molecules rather than Th2-type molecules. Furthermore, Vitamin D was shown to promote the immune suppressive regulatory T ($T_{REG}$) cell population.

In a somewhat contradictory finding, it was determined that human CD8+ T cells express high levels of the Vitamin D receptor, and individuals with the highest values tended to have high levels of T cell effector function and immune senescence.

In more recent research, using a murine model of *Mycobacterium tuberculosis* infection, it was demonstrated that Vitamin D was critical for macrophage elimination of intracellular pathogens through a mechanism that involved IFN-γ production and autophagy. In addition, in human non-small cell cancer cell lines, Vitamin D signaling can promote a cytotoxic form of autophagy that contributes to an anti-tumor effect when combined with radiation. Finally, Vitamin D receptor signaling promotes autophagy in normal human mammary tissue; loss of such Vitamin D receptor signaling was associated with an increased risk of developing breast cancer. In spite of this evidence linking Vitamin D to autophagy in innate immunity (macrophage context), there exists a paucity of data relating to Vitamin D effects on autophagy in T cells during adaptive immunity, and in this context, whether the potential effects of Vitamin D and rapamycin on T cell autophagy are redundant.

These somewhat conflicting results pertaining to the potential role of Vitamin D in T cell biology likely relates to the recently discovered, wide-spread effects of Vitamin D on the entire genome, both at the mRNA level and at the microRNA level. As such, the effects of Vitamin D on immunity need to be evaluated in a context-dependent framework.

Regulatory T ($T_{REG}$) cells are essential for the maintenance of immune tolerance. A reduction in the quantity or quality of $T_{REG}$ cells is a fundamental cause of a multitude of primary auto-immune diseases, including type I diabetes mellitus (T1DM), multiple sclerosis, rheumatoid arthritis, and systemic lupus erythematosus, to name just a few. In addition, $T_{REG}$-deficiency has been associated with acceleration in the natural history of primary neurodegenerative diseases. Finally, $T_{REG}$-deficiency is associated with severe complications in the solid organ and hematopoietic cell transplantation setting, most notably, an increased rate of graft rejection and graft-versus-host disease (GVHD). Given this critical role of $T_{REG}$ cells in the maintenance of immune homeostasis, many experimental approaches have been developed to promote $T_{REG}$ cells for the treatment of disease. One such promising approach is the adoptive transfer of $T_{REG}$ cells, which exist in two main sub-types: (1) natural (n) $T_{REG}$ cells, which are derived from the thymus ("n$T_{REG}$" or "natural $T_{REG}$"), which involutes with age, thereby reducing the number of n$T_{REG}$ cells available for adoptive transfer; and (2) inducible (i) $T_{REG}$ cells, which are converted in the periphery from the more plentiful pool of effector T cells. Because n$T_{REG}$ cells are limiting in number, attempts to use n$T_{REG}$ cells for adoptive T cell therapy have relied upon ex vivo manufacturing methods for isolation and subsequent expansion of n$T_{REG}$ cells. Clinical trials of n$T_{REG}$ cells for adoptive cell therapy are in the early stages of implementation, primarily in phase I/phase II clinical trials for the prevention of GVHD and for the treatment of T1DM. In contrast, other challenges exist for the possibility of using i$T_{REG}$ cells (ex vivo produced $T_{REG}$ cells including $T_{REG}$ and $T_{REG}$/Th2 cells of the present disclosure) in adoptive cell therapy, namely: (1) although peripheral effector T cells are relatively plentiful, they primarily exist in a state of effector memory maturation with limited replicative and therapeutic potential; and (2) such peripheral effector T cells have a high degree of pre-existing effector differentiation towards T cell subsets that contribute to disease pathogenesis, namely, the Th1- and Th17-type subsets. As such, if i$T_{REG}$ cell therapy is to become highly feasible, it will be necessary to develop an ex vivo manufacturing method that both: (1) causes a de-differentiation of effector T cells towards a less-differentiated memory phenotype that has an increased proliferative potential and demonstrable improvement in $T_{REG}$ cell therapeutic potential; and (2) extinguishes pathogenic Th1- and Th17-type pathways while promoting T cell differentiation towards the $T_{REG}$ phenotype.

The manufacture of i$T_{REG}$ cells is initiated by collection of lymphocyte-containing peripheral blood mononuclear cells from the subject to be treated (in the case of autologous therapy) or from a normal donor (in the case of allogeneic therapy). Typically, this collection is performed in the steady-state, that is, without any growth factor administration; however, in the allogeneic context, collection is sometimes performed in the context of administration of molecules such as granulocyte colony stimulating factor (G-CSF) or plerixifor, as described in DiPersio J F, Stadtmauer E A, Nademanee A, et al. Plerixafor and G-CSF versus placebo and G-CSF to mobilize hematopoietic stem cells for autologous stem cell transplantation in patients with multiple myeloma. Blood. 2009; 113(23): 5720-5726. In this disclosure, we describe that anti-TNF-α therapeutic agents can be administered prior to collection of lymphocytes for i$T_{REG}$ manufacturing for the purpose of enriching culture input T cells for the $T_{REG}$ phenotype. That is, we demonstrate that the anti-TNF-α agent etanercept, which is a recombinant receptor that preferentially inhibits serum, cell-free TNF-α with relative preservation of the cell surface, membrane-bound form of TNF-α, induces a global change in the T cell receptor (TCR) repertoire when measured by RNA sequencing. Because membrane-bound TNF-α provides a positive signal to $T_{REG}$ cells through the TNFR2 receptor, our method offers a robust intervention to enrich for $T_{REG}$ cells prior to i$T_{REG}$ cell manufacturing. Other therapeutics that preferentially inhibit serum, cell-free TNF-α can also be used for this intervention, including but not limited to the anti-TNF-α monoclonal antibody, adalimumab.

Amyotrophic lateral sclerosis (ALS) is a primary neurodegenerative disease involving the cerebral cortex, brainstem, and spinal cord that results in progressive disability and typically death due to respiratory failure. ALS is a familial disease in 10% of patients due to various genetic events; the remainder of patients have sporadic ALS, where the etiology is not known but may involve environmental factors. The most recent registry data (2013) indicates that the prevalence of ALS in the United States was approximately 16,000 cases; these data also indicate that ALS disproportionately affects whites, males, and individuals in the 60 to 69 age group. Military veterans and potentially, professional American football players, appear to be at increased risk for developing ALS, thereby suggesting that chemical exposure or traumatic brain injury may increase the risk of developing the disease. ALS is a heterogeneous disease with various clinical presentations and rates of progression. Although the average survival of ALS patient is between two to four years from diagnosis, survival can be as short as months or over a decade. It is difficult to estimate prognosis in ALS patients because disease scoring systems such as the patient-reported ALSFRS-R score (ALS Functional Rating Score, Revised) do not account for the linear and non-linear aspects of disease progression. This difficulty in estimating the rate of disease progression represents a limitation for clinical trials in ALS and indicates that potential disease biomarkers, including the immunologic monitoring that we have developed, should be emphasized as a component of protocol therapy. The clinical onset of ALS is insidious, with most patients presenting with upper or lower limb weakness or speaking or swallowing difficulty (bulbar-onset). ALS remains a diagnosis of exclusion, as there are no definitive blood, spinal fluid, or radiologic exams; as a result, ALS is typically a diagnosis of exclusion after other diseases have been ruled-out. This process of ruling out other diseases can typically take up to one year and thereby delays therapeutic attempts and clinical trial accrual; this delay in referral likely has consequences because, at the time of eventual ALS diagnosis, up to 50% of motor neurons may no longer be functional. Given this situation, it is typically recommended to accrue ALS patients to investigational trials at a relatively early point after diagnosis.

ALS is a primary neurodegenerative disease, with neuro-inflammation acting as a secondary, propagating factor. Evidence for this conclusion is derived in part from the observation that a functional abnormality in the TAR DNA-binding protein 43 (TDP-43) occurs in the vast majority of familial and sporadic ALS patients. TDP-43, which in the healthy state is restricted to the nucleus, is an RNA and DNA binding protein that is susceptible to aggregation, thereby accounting for the cytoplasmic inclusion bodies seen in the neurons of ALS patients. The precise mechanisms that result in alteration of the TDP-43 pathway remain to be fully elucidated, but appear to involve various cellular stress events or amplification of genomic elements (retrotransposable elements, RTE) that replicate themselves via RNA intermediates. Ultimately, such events lead to a multi-faceted programmed cell death in neurons, including programmed necrosis. Of note, the necrotic cell death pattern that occurs in ALS patients has been shown to be particularly immunogenic relative to the more orderly apoptotic cell death; indeed, TNF-α, which is a known molecular mediator of motor neuron death in ALS, can produce the necrotic form of cell death. Necrotic cell death can lead to the release of self-antigens that can then be presented to the adaptive immune system for the induction of autoimmunity; in addition, because protein aggregates themselves may be immunogenic, it is possible that protein aggregates that occur in ALS patients (including but not limited to TDP-43; SOD-1; p62) might be targets of an autoimmune response that emanates after neurodegeneration. Indeed, it has recently been shown that monocytes from ALS patients develop an inflammatory phenotype when pulsed with exosomes containing TDP-43.

In response to primary neurodegeneration, there is broad evidence that the innate inflammasome and the adaptive peripheral immune system combine to illicit further ALS disease progression. In the superoxide dismutase-1 (SOD1) transgenic mouse model of ALS, $CD3^+$ T cell infiltration of the spinal cord and microglial cell activation were recognized as pro-inflammatory factors that contributed to disease progression. Furthermore, transfer of wild-type microglial cells with reduced inflammatory propensity relative to host microglial cells in the PU.1 knockout mouse model of ALS reduced neurodegeneration and improved survival. In addition, a protective role for $CD4^+$ T cells was described for the first time in the SOD1 murine model of ALS, thereby indicated the double-edged sword nature of the peripheral immune T cell pool in ALS (acting as either propagating or protective factor). In ALS patients, direct evidence for the deleterious role of the peripheral adaptive immune system T cells can be ascertained by the demonstration that T cells infiltrating the spinal cord express an oligoclonal T cell receptor (TCR) repertoire. Furthermore, professional antigen-presenting-cells (dendritic cells) emanating from the peripheral immune system can be isolated in ALS patient spinal cord tissue in close association with inflammatory periphery-derived monocytes and resident CNS microglial cells. Additionally, in ALS patients, purified monocytes express a pro-inflammatory RNA expression profile, including an increase in the innate inflammatory molecule IL-1-β, which can then drive the IL-23 pathway that promotes $CD4^+$T-helper-1 (Th1), $CD8^+$T-cytotoxic-1 (Tc1), and $CD4^+$ Th17-mediated neurodegenerative immunity. In subsequent studies, the phenotype of the protective $CD4^+$ T cell subset in the SOD1 murine model of ALS was characterized as a regulatory T ($T_{REG}$) cell population that reduced inflammation through a mechanism mediated in part through the counter-regulatory Th2-type cytokines IL-4 and IL-10.

This biology is consistent with an abundance of data in neuro-inflammation research indicating that: microglial cells are a key cellular constituent in the brain that drives neurodegeneration; and microglial cells and CNS-infiltrating peripheral $CD4^+$ T cells interact and influence disease pathogenesis. Consistent with the murine modeling results, patients with a peripheral immune system enriched for $FoxP3^+$ $T_{REG}$ cells and Th2-type T cells had a reduced progression rate of ALS relative to patients with primarily a pro-inflammatory Th1-type immune profile. Furthermore, it was recently found that ALS patient $T_{REG}$ cells are dysfunctional, with such dysfunction correlating with disease progression rate and severity. A current clinical trial is evaluating the use of multiple infusions of $nT_{REG}$ cells plus low-dose IL-2 administration for therapy of ALS (ClinicalTrials.gov; NCT03241784); IL-2 is a cytokine that stimulates the STAT5 signaling pathway and thereby can promote the in vivo expansion of $nT_{REG}$ cells.

Induced (i) $T_{REG}$ cells are not derived from the thymus as in the $nT_{REG}$ cell population; rather, the $iT_{REGS}$ are a population that is converted from otherwise pathogenic post-thymic T cell subsets such as Th1 cells. Although both $nT_{REGS}$ and $iT_{REGS}$ play important and non-redundant roles in the dampening of inflammatory responses, development of an $iT_{REG}$ therapy is relatively advantageous in terms of regulatory T cell potency and ease of manufacturing. Furthermore, adoptive $iT_{REG}$ therapy of ALS will be particularly effective if used in combination with the immune monitoring techniques and host treatment regimen (pentostatin, cyclophosphamide, lamivudine) that we describe here.

Riluzole (Rilutek®), which was the first drug approved for ALS therapy in 1995, is only mildly efficacious in reducing the morbidity and mortality of ALS. Despite significant clinical research whereby more than 60 molecules have been investigated for ALS therapy, there have been only two additional molecules that have shown modest clinical success, namely the anti-oxidant edaravone and the tyrosine kinase inhibitor masitinib. Edaravone (Radicava®), which was recently FDA-approved for therapy of ALS, provides minimal clinical benefit, is expensive, and requires a 2-weeks on, 2 weeks-off daily continuous i.v. infusion therapy; masitinib is not FDA-approved. A phase II trial of rapamycin for therapy of ALS is currently just now being initiated (ClinicalTrials.gov Identifier: NCT03359538). Rapamycin may also represent a favorable pharmaceutical agent to use in ALS due to the tendency of this agent to promote $T_{REG}$ cell reconstitution. However, prolonged therapy with rapamycin has substantial toxicity, requires pharmacologic monitoring, can have a paradoxical effect in terms of actually worsening ALS in some models, and can limit the expansion of adoptively transferred T cell populations.

As such, given the current state of very limited therapeutic options, there is a great need to evaluate novel strategies for the therapy of ALS. In this application, we describe a novel treatment approach of ALS that centers around inducible (i) regulatory T ($T_{REG}$) cell therapy.

SUMMARY

The present disclosure is directed to methods for de-differentiation of T cells and differentiation of such cells to $T_{REG}$ or $T_{REG}$/Th2 cells.

In some embodiments, the initial de-differentiation method can include initiating the culture with an input cell populations harvested in the steady-state (without drug administration).

In some embodiments, the method comprises initiating the de-differentiation culture with an input cell populations harvested from a subject (in the autologous context) or a normal donor (in the allogeneic context) who has been or is being treated with an anti-TNF-α therapeutic agent that is preferentially selective for inhibition of the serum, cell-free form of TNF-α with relative preservation of membrane-bound TNF-α. Such therapeutic agents include but are not limited to the recombinant receptor etanercept, which can be administered at the conventional dose of 25 or 50 mg per week by subcutaneous injection, or the monoclonal antibody adalimumab, which can be administered at the conventional dose of 40 mg per week or 40 mg every other week by intravenous injection. In all of these cases, the dosing of the anti-TNF-α therapeutic can be adjusted according to the desired biomarker change, which can include but is not limited to alteration of the TCR repertoire by RNA sequencing analysis and a shift towards type 2 TNF receptors (TNFR2) and a shift away from type 1 TNF receptors (TNFR1), as measured by flow cytometry.

In some embodiments, the method comprises inoculating a culture input population of cells comprising T cells from a subject at a cell density in a culture medium comprising vitamin D, temsirolimus and an IL-2 signaling inhibitor; adding anti-CD3/anti-CD28 coated magnetic beads to said T cells and culture medium at a bead:T cell ratio of 1:1 or less to stimulate said T cells, or, in the most extreme example, no addition of anti-CD3/anti-CD28 co-stimulation; incubating said culture input population of cells and culture medium for a period of time to yield de-differentiated T cells. It is also possible to perform this de-differentiation procedure in the absence of any bead co-stimulation.

In any of the foregoing embodiments, the method may further comprise harvesting said de-differentiated T cells.

In any of the foregoing embodiments, the method may further comprise, after harvesting said de-differentiated T cells: packaging at least a portion of said de-differentiated T cells in a package; and freezing said package containing said portion of said de-differentiated T cells.

In any of the foregoing embodiments, the method may further comprise before inoculating said culture input population of cells into said culture medium: harvesting said culture input population of cells from said subject.

In any of the foregoing embodiments, the method may further comprise measuring an expression level of RAPTOR or RICTOR in said culture input population of cells wherein said period of time lasts until the expression level of RAPTOR or RICTOR, respectively, in said culture input population of cells is reduced by at least 50% and more preferably 90% relative to a control population of T cells, and wherein said control population of T cells are manufactured under the same conditions as the culture input population of cells without temsirolimus, IL-2 signaling inhibitor and Vitamin D.

In any of the foregoing embodiments, the method may further comprise measuring an expression level of RAPTOR or RICTOR and a housekeeping protein in said culture input population of cells, wherein said period of time lasts until the expression level of RAPTOR or RICTOR, normalized by the housekeeping protein, in the manufactured T cells is at least 50% and more preferably 90% lower than the expression level of RAPTOR or RICTOR, respectively, normalized by the housekeeping protein, in the control population of T cells manufactured under the same conditions as the culture input population of cells without temsirolimus, IL-2 signaling inhibitor and Vitamin D.

The present disclosure is also directed to a de-differentiated T cell produced by the methods of any of the foregoing embodiments.

The present disclosure is also directed to a composition comprising a population of de-differentiated cells, wherein at least a portion of said population of said de-differentiated cells express at least 50% and more preferably 90% less of RAPTOR or RICTOR as compared to a control population of T cells manufactured under the same conditions as the culture input population of cells without temsirolimus, IL-2 signaling inhibitor and Vitamin D.

In any of the foregoing embodiments, the method may further comprise measuring at least a portion of said population of said de-differentiated cells whereby they express at least a 10% and more preferably a 50% change in RNA expression of the following molecules relative to a control population of T cells, namely: reduction in T cell effector molecules including but not limited to granzyme B, IL-10, and IFN-γ; increase in transcription factors associated with cells of reduced differentiation status, including but not limited to Nanog, KLF4, and KLF10; increase in expression of molecules preferentially expressed on naïve T cell subsets, including but not limited to CD127, the IL-7 receptor alpha chain; reduction in transcription factors associated with Th1-type differentiation, including but not limited to T-BET and STAT1; and relative preservation of transcription factors that promote cell survival, including but not limited to HIF-1 alpha.

In any of the foregoing embodiments, the method may further comprise measuring at least a portion of said population of said de-differentiated cells whereby they express at least a 10% and more preferably a 50% change in expression of molecules indicative of cells that have undergone autophagy. As one, example, the said de-differentiated cells have increased expression of p62 by western blot analysis relative to control T cells. Other standard methods that measure autophagy may also be used, such as those described in Yoshii S R, Mizushima N. Monitoring and Measuring Autophagy. International Journal of Molecular Sciences. 2017; 18(9): 1865.

The present disclosure is also directed to a de-differentiated T cell produced by the methods of any of the foregoing embodiments.

The present disclosure is also directed to a composition comprising a population of de-differentiated cells, wherein at least a portion of said population of said de-differentiated cells express at least a 10% and more preferably a 50% change in RNA expression of the following molecules relative to a control population of T cells, namely: reduction in T cell effector molecules including but not limited to granzyme B, IL-10, and IFN-γ; increase in transcription factors associated with cells of reduced differentiation status, including but not limited to Nanog, KLF4, and KLF10; increase in expression of molecules preferentially expressed on naïve T cell subsets, including but not limited to CD127, the IL-7 receptor alpha chain; reduction in transcription factors associated with Th1-type differentiation, including but not limited to T-BET and STAT1; and relative preservation of transcription factors that promote cell survival, including but not limited to HIF-1 alpha.

The present disclosure is also directed to a composition comprising a population of de-differentiated cells, as defined by said de-differentiated cells expressing at least a 10% and more preferably a 50% change in expression of molecules indicative of cells that have undergone autophagy. As one, example, the said de-differentiated cells have increased expression of p62 by western blot analysis relative to control T cells. Other methods that measure autophagy can also be applied, such as those described in Yoshii S R, Mizushima N. Monitoring and Measuring Autophagy. International Journal of Molecular Sciences. 2017; 18(9): 1865.

The present disclosure is also directed to a composition comprising a population of de-differentiated cells, wherein at least a portion of said population of said de-differentiated cells express less than 50% of both RAPTOR and RICTOR as compared to a control population of T cells.

The present disclosure is directed to methods for differentiating de-differentiated T cells to $T_{REG}$ or $T_{REG}$/Th2 cells.

In some embodiments, the method comprises culturing de-differentiated T cells of the present disclosure, or that are otherwise de-differentiated, in a culture medium comprising IL-2, IL-4 and TGF-β; adding anti-CD3/anti-CD28 coated magnetic beads at a ratio of 3:1 (bead:T cell ratio); and incubating said de-differentiated T cells for a period of time to yield $T_{REG}$/Th2 cells.

In some embodiments, the method comprises culturing de-differentiated T cells having reduced expression of at least 50% less of RAPTOR or RICTOR relative to a control population of T cells manufactured under the same conditions as the culture input population of cells without temsirolimus, IL-2 signaling inhibitor and Vitamin D, in a culture medium comprising IL-2, IL-4 and TGF-β; adding anti-CD3/anti-CD28 coated magnetic beads at a ratio of 3:1 (bead:T cell ratio); and incubating said de-differentiated T cells for a period of time to yield $T_{REG}$/Th2 cells.

In some embodiments, the method comprises culturing de-differentiated T cells having reduced expression of at least 90% less of RAPTOR or RICTOR relative to a control population of T cells manufactured under the same conditions as the culture input population of cells without temsirolimus, IL-2 signaling inhibitor and Vitamin D, in a culture medium comprising IL-2 and TGF-β; adding anti-CD3/anti-CD28 coated magnetic beads at a ratio of 3:1 (bead:T cell ratio); and incubating said de-differentiated T cells for a period of time to yield $T_{REG}$ cells.

In any of the foregoing embodiments, the culture medium can further comprise pemetrexed.

The present disclosure is also directed to a $T_{REG}$ or $T_{REG}$/Th2 cell produced by any of the foregoing methods.

The present disclosure is also directed to methods for treating amyotrophic lateral sclerosis in a subject in need thereof.

In some embodiments, the method comprises subjecting said subject to one or more primary treatment cycles, each of said one or more primary treatment cycles comprising: administering to said subject pentostatin; and/or administering to said subject cyclophosphamide; and subjecting said subject to one or more immune therapy treatment cycles comprising: administering to said subject a composition comprising a therapeutically effective amount of manufactured $T_{REG}$ cells.

In some embodiments, a method comprises a first treatment cycle, a second treatment cycle, optionally, one or more additional treatment cycles, and one or more immune therapy treatment cycles, said first treatment cycle comprising: administering pentostatin to said subject, and/or administering cyclophosphamide to said subject; said second treatment cycle comprising: administering pentostatin to said subject, and/or administering cyclophosphamide to said subject; each of said one or more additional treatment cycles comprising: administering pentostatin to said subject, and/or administering cyclophosphamide to said subject each of said one or more immune therapy treatment cycles comprising: administering pentostatin to said subject, and/or administering cyclophosphamide to said subject, and administering manufactured $T_{REG}$ cells to said subject.

In some embodiments, a method comprises one or more treatment cycles comprising: administering to said subject a therapeutically effective amount of manufactured $T_{REG}$ cells.

In some embodiments, a method can comprise administering to said subject a therapeutically effective amount of manufactured $T_{REG}$ cells.

BRIEF DESCRIPTION OF THE DRAWINGS

FIGS. 1A-1D illustrate that the combination of Vitamin D and temsirolimus reduces effector molecule expression in human CD4+ and CD8+ T cells.

FIGS. 2A-2D illustrate that the combination of Vitamin D and temsirolimus increases expression of stem cell-associated transcription factors and the primitive T cell molecule IL-7 receptor-alpha in human CD4+ and CD8+ T cells.

FIGS. 3A-3C illustrate that the combination of Vitamin D and temsirolimus reduces expression of transcription factors associated with effector Th1/Tc1 cells without reducing expression of a transcription factor associated with T cell survival, HIF-1-α.

FIGS. 9A-9C illustrate the effect of culture components during the de-differentiation interval on CD4+ T cell expression of memory markers (at day 13 of culture).

FIGS. 10A-10B illustrate the effect of culture components during the de-differentiation interval on CD8+ T cell expression of memory markers.

FIG. 11A depicts the IFN-γ secretion for cells treated under various conditions.

FIG. 11B depicts the GM-CSF secretion for cells treated under various conditions.

FIG. 11C depicts the TNF-α secretion for cells treated under various conditions.

FIG. 11D depicts the IL-17 secretion for cells treated under various conditions.

FIG. 12A depicts the IL-2 secretion for cells treated under various conditions.

FIG. 12B depicts the IL-4 secretion for cells treated under various conditions.

FIG. 12C depicts the IL-5 secretion for cells treated under various conditions.

FIG. 12D depicts the IL-13 secretion for cells treated under various conditions.

FIGS. 14-A14C illustrate that the culture of de-differentiated T cells in hybrid Th2/TReg polarization condition results in the generation of naïve and triple-positive T central memory CD4+ T cells.

FIG. 15A depicts the percentage of CD8+CD62L+CCR7+ CD127+ cells out of total CD8 cells for cells treated under various conditions.

FIGS. 15A-15B illustrates that culture of de-differentiated T cells in hybrid Th2/TReg polarization condition results in the generation of triple-positive T central memory CD8+ T cells.

FIGS. 16A-16C illustrate that the culture of de-differentiated T cells in hybrid Th2/TReg polarization condition results in the generation of T cells with a primitive Th2 cell cytokine phenotype: IL-2, IL-4, and IL-5 secretion.

FIGS. 17A-17C illustrate that the culture of de-differentiated T cells in hybrid Th2/TReg polarization condition results in the generation of T cells with a primitive Th2 cell cytokine phenotype: IL-10, IL-13, and IL-17 secretion.

FIGS. 18A-18C illustrates that the culture of de-differentiated T cells in hybrid Th2/$T_{REG}$ polarization condition results in the generation of T cells with a primitive Th2 cell cytokine phenotype: IFN-gamma, TNF-alpha, and GM-CSF secretion.

FIGS. 19A-19D illustrate that extended culture of de-differentiated T cells in the hybrid Th2/$T_{REG}$ polarization condition containing pemetrexed results in the generation of CD4+ T cells expressing FOXP3 and GATA3 transcription factors.

FIGS. 20A-20D illustrate that extended culture of de-differentiated T cells in the hybrid Th2/$T_{REG}$ polarization condition containing pemetrexed results in the generation of CD8+ T cells expressing FOXP3 and GATA3 transcription factors.

FIGS. 21A-21C illustrate that extended culture of de-differentiated T cells in the hybrid Th2/$T_{REG}$ polarization condition results in the generation of T cells expressing with a predominant Th2 cytokine phenotype: IL-4, IL-5, and IL-13 secretion.

FIGS. 22A-22C illustrate that extended culture of de-differentiated T cells in the hybrid Th2/$T_{REG}$ polarization condition results in the generation of T cells expressing with a predominant Th2 cytokine phenotype: IL-2, IFN-gamma, and GM-CSF secretion.

FIGS. 23A and 23B illustrate that the anti-TNF-α therapy etanercept therapy results in marked alteration of the TCR repertoire when measured by RNA sequencing, thereby representing a new approach for subject treatment prior to lymphocyte collection by apheresis.

FIGS. 36A-36B illustrate that the anti-TNF-α therapy etanercept therapy results in marked alteration of the TCR repertoire when measured by RNA sequencing, thereby representing a new approach for subject treatment prior to lymphocyte collection by apheresis.

DETAILED DESCRIPTION

Figure 1A:
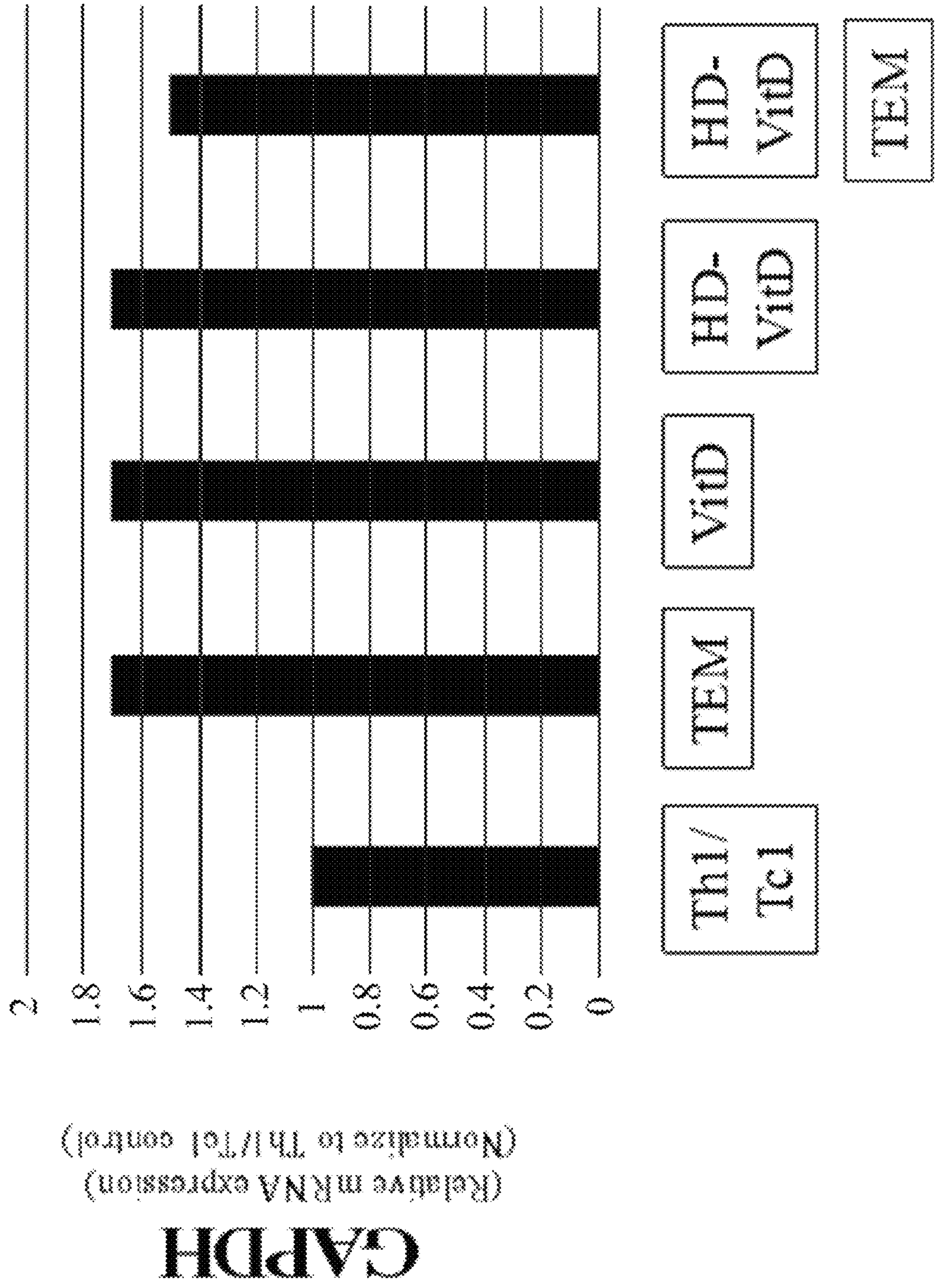
FIG. 1A depicts normalized GAPDH mRNA expression for the control cells and cells treated under various conditions.
Figure 1B:
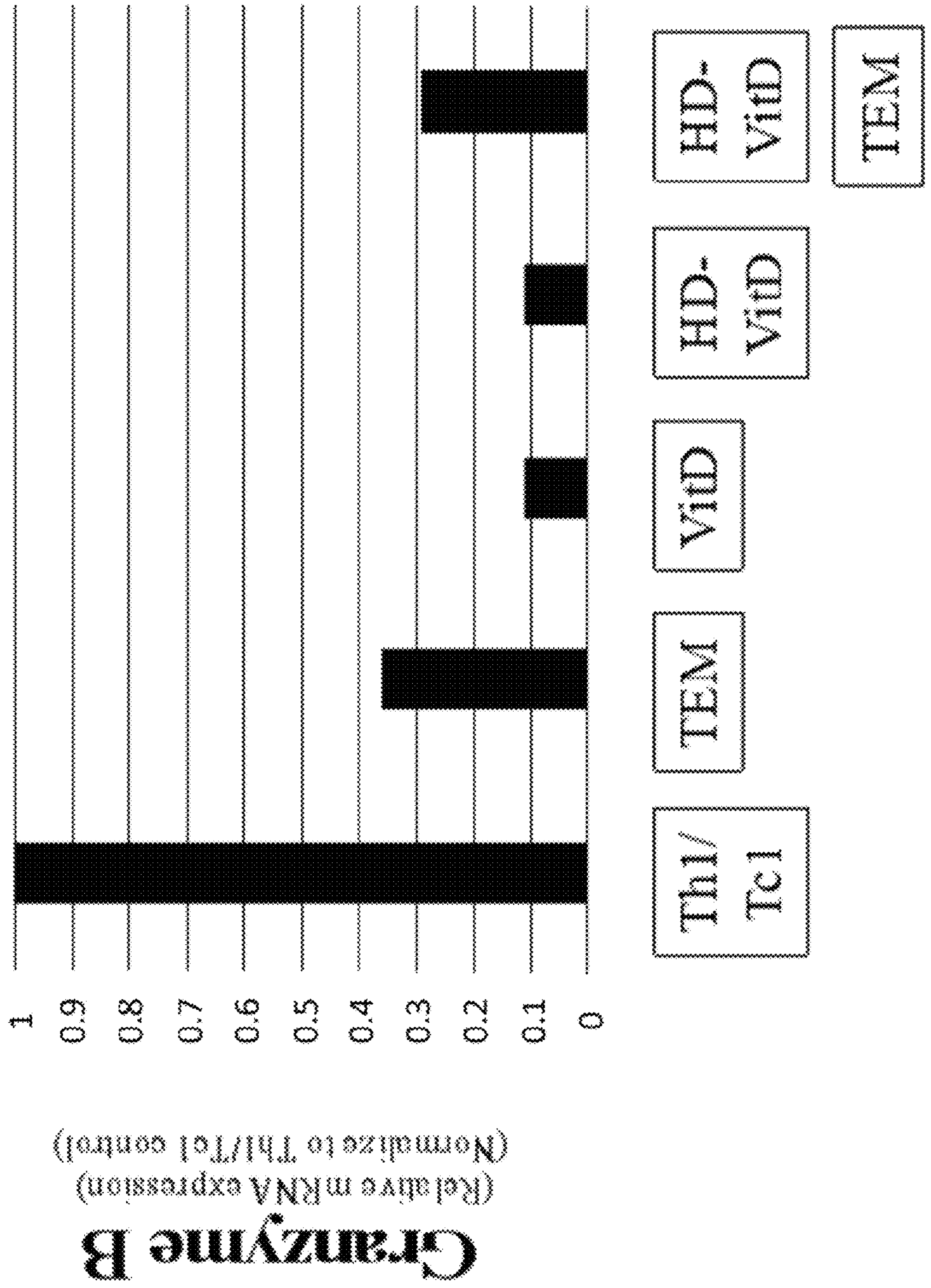
FIG. 1B depicts normalized granzyme B mRNA expression for the control cells and cells treated under various conditions.

The present disclosure provides a method for T cell de-differentiation and resulting cells, a method for manufacturing of human hybrid regulatory T/Th2 cells (hybrid $T_{REG}$/Th2 cells) from de-differentiated T cells, and a method for ALS Treatment Using Induced Regulatory T ($iT_{REG}$) Cells.

Definitions

As used herein, the singular forms "a", "an" and "the" include plural referents unless the context clearly dictates otherwise.

The use of the term "or" in the claims and the present disclosure is used to mean "and/or" unless explicitly indicated to refer to alternatives only or the alternatives are mutually exclusive.

Use of the term "about", when used with a numerical value, is intended to include +/−10%. For example, if a number of amino acids is identified as about 200, this would include 180 to 220 (plus or minus 10%).

The terms "patient," "individual," and "subject" are used interchange-ably herein, and refer to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

"Sample" is used herein in its broadest sense. A sample comprising cells, polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" can refer to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

"Treatment cycle" as used herein can generally refer to any of the primary treatment cycles, a first treatment cycle, a second treatment cycle or one or more additional treatment cycles.

"Immune cells" as used herein, is meant to include any cells of the immune system that may be assayed, including, but not limited to, B lymphocytes, also called B cells, T lymphocytes, also called T cells, natural killer (NK) cells, natural killer T (NKT) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, activation of other immune cells, such as B-cells) or for the cytokines they produce.

As used herein, the term "de-differentiated T cell" refers to a T cell that has been de-differentiated by any of the methods of the present disclosure. In certain aspects, the de-differentiated T cell has reduced expression of RAPTOR or RICTOR relative to a control population of T cells manufactured under the same conditions without temsirolimus, IL-2 signaling inhibitor and Vitamin D. The "de-differentiated T cell" does not include T cells as collected from a patient, i.e. naturally occurring T cells.

As used herein, the term "anti-CD3/anti-CD28" should be understood to refer to anti-CD3/anti-CD28 antibodies. For example, "anti-CD3/anti-CD28 magnetic beads" should be understood to refer to magnetic beads having anti-CD3/anti-CD28 antibody moieties associated therewith. In instances where it is disclosed that no anti-CD3/anti-CD28 co-stimulation is provided, even by a specific form such as anti-CD3/anti-CD28 magnetic beads, it should be understood that this can also exclude co-stimulation with other forms of anti-CD3/anti-CD28.

It should also be understood that, in the present disclosure, where co-stimulation by anti-CD3/anti-CD28 antibodies is performed, this co-stimulation can be provided in any form of anti-CD3/anti-CD28 antibodies. By way of example, but not limitation, where co-stimulation is indicated as being performed by using anti-CD3/anti-CD28 beads, anti-CD3/anti-CD28 nanoparticles or microparticles can be used. In instances where it is disclosed that no anti-CD3/anti-CD28 co-stimulation is provided, even by a specific form such as anti-CD3/anti-CD28 magnetic beads, it should be understood that this can also exclude co-stimulation with other forms of anti-CD3/antiCD28.

As used herein, the term "human hybrid TREG/Th2 cells," "iTREG" and "TREG/Th2 cells," unless otherwise noted, refer to cells that have been differentiated by methods of the present disclosure. The "human hybrid TREG/Th2 cells," "iTREG" and "TREG/Th2 cells" of the present disclosure do not include T cells as collected from a patient, i.e. naturally occurring T cells.

As used herein, the term "manufactured TREG cells" refers to cells produced by the de-differentiation and re-differentiation methods of the present disclosure and can be understood to include TREG cells and human hybrid TREG/Th2 cells unless otherwise noted.

As used herein "control Th1/Tc1 cells," unless otherwise noted, refers to cells that have not been treated with vitamin D, temsirolimus or the IL-2 signaling inhibitor and, rather, have been co-stimulated with anti-CD3/anti-CD28 magnetic coated beads at a ratio of 3:1 (beads:T cell) in media supplemented with 20 IU/mL IL-2 and 20,000 IU/mL of IFN-α and otherwise cultured the same as the cells to which they are being compared. It should also be understood that where a control population of cells (or control T cell) is referred to as having been treated without culture additives, including temsirolimus, vitamin D and the IL-2 signaling inhibitor, or in the context of de-differentiated cells, this population (or T cell) has been further co-stimulated with anti-CD3/anti-CD28 magnetic coated beads at a ratio of 3:1 (beads:T cell) in media supplemented with 20 IU/mL IL-2 and 20,000 IU/ml of IFN-α and otherwise cultured the same as the cells to which they are being compared, i.e. they are "control Th1/Tc1 cells."

The present disclosure provides new methodology for the ex vivo generation of T cells of a reduced differentiation state that is based upon the conversion of differentiated effector memory T cells into less differentiated central-memory type T cells using a novel pharmacologic combination and defined T cell co-stimulatory conditions.

Figure 41:
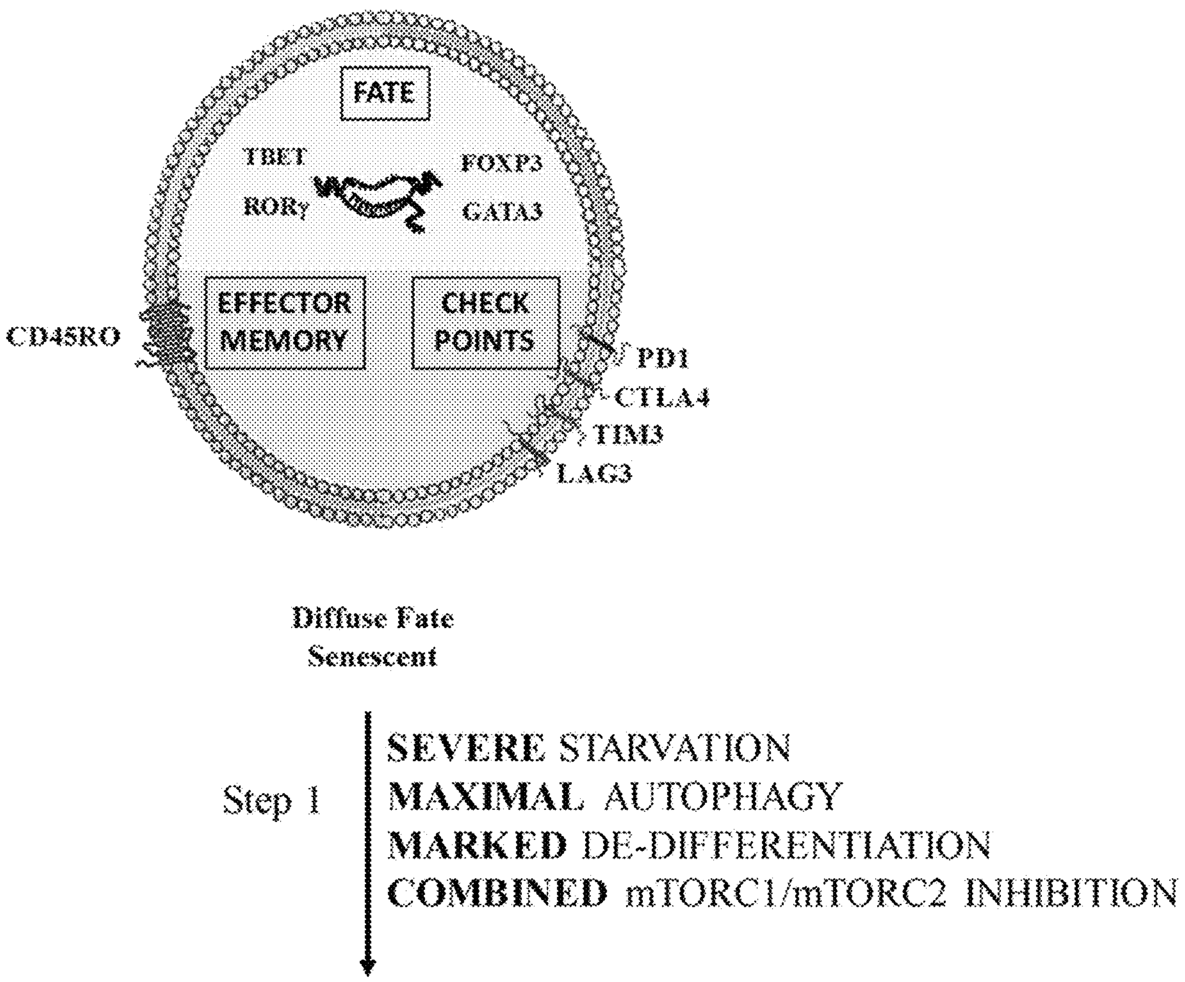
FIG. 41 depicts an exemplary workflow of a de-differentiation method of the present disclosure.
Figure 41:
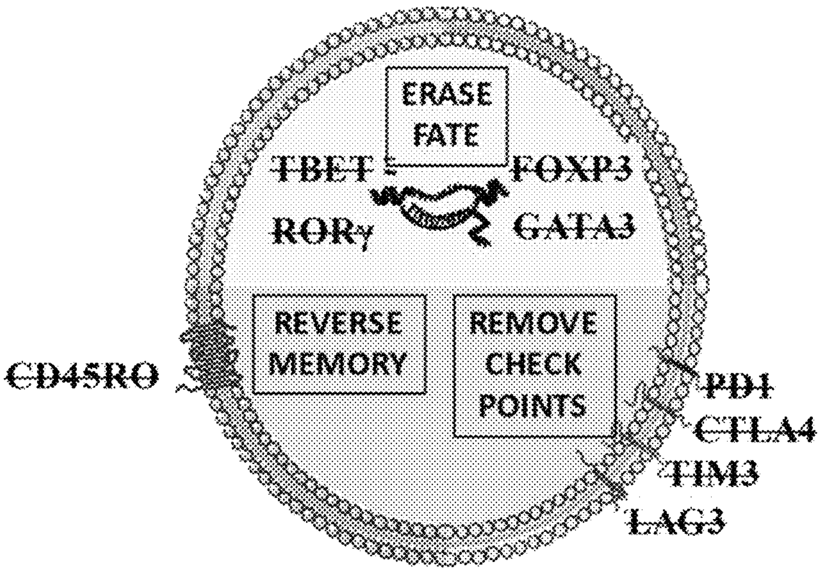
Figure 41:
Figure 41:
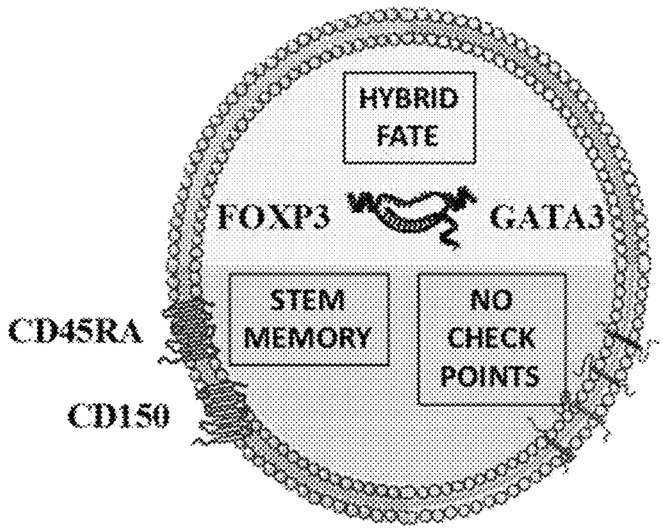

As shown in FIG. 41, a de-differentiated T cell of the present disclosure can have a quiescent phenotype with low or no expression of checkpoint inhibitor receptors (such as PD1, CTLA4, TIM3, and LAG3), memory markers (such as CD45RO) and fate molecules (such as TBET, RORY, FOXP3 and GATA3). The re-differentiated T cell can have a hybrid fate characterized GATA3 and FOXP3 expression, as well as stem cell memory characterized by CD45RA and CD150 expression and no checkpoint protein expression.

Figure 42:
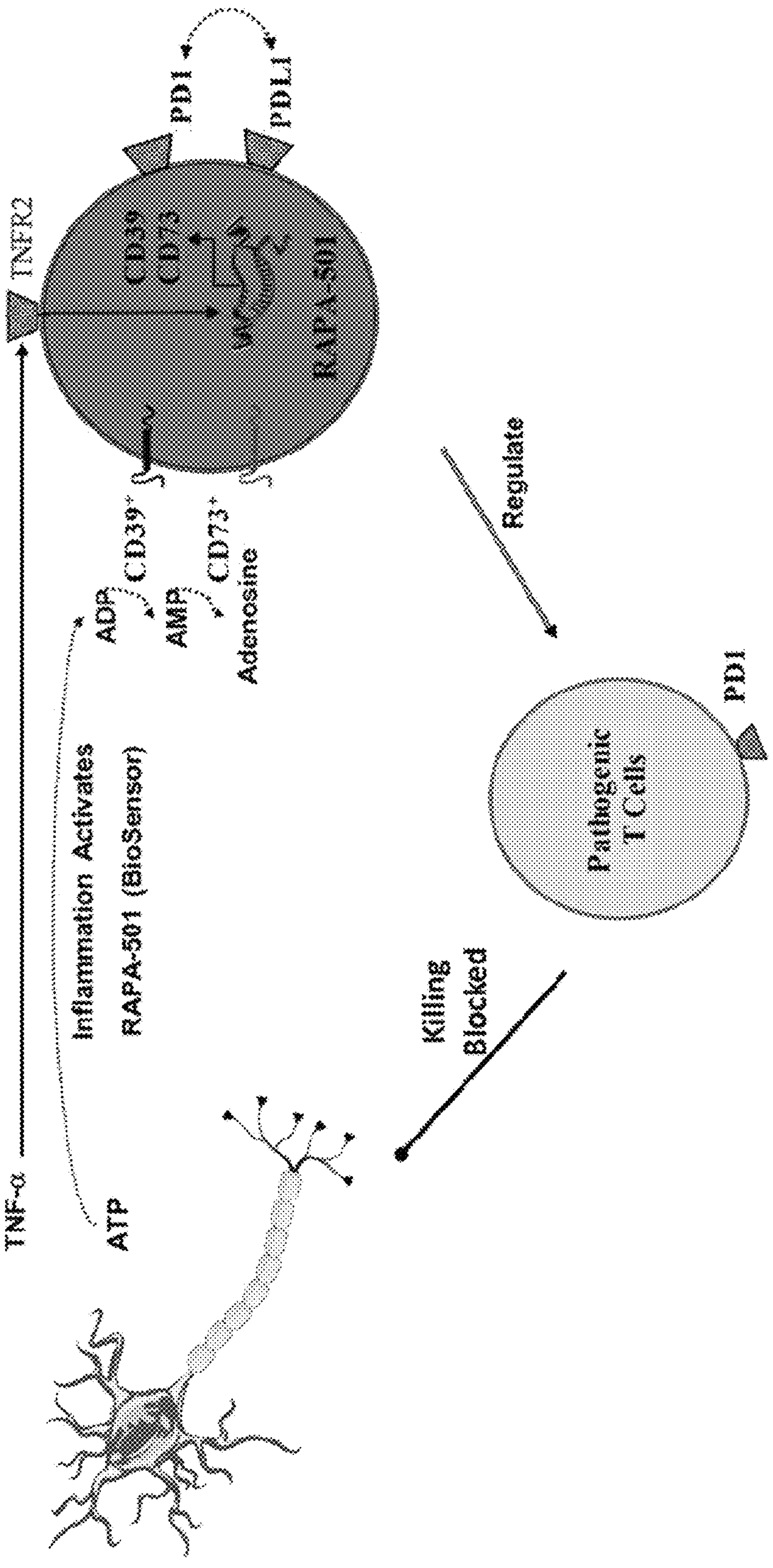
FIG. 42 depicts a putative mechanism of action for the hybrid $T_{REG}$/Th2 cells of the present disclosure.

As shown in FIG. 42, a putative mechanism of action of the hybrid $T_{REG}$/Th2 cells of the present disclosure whereby the hybrid $T_{REG}$/Th2 cell can be activated by inflammation via the CD39 or CD73 receptors and by TNF-α, which can enable the cell to regulate pathogenic T cells to prevent killing.

Method for T Cell De-Differentiation and Resulting Cells

We present a new methodology for the ex vivo generation of T cells of a reduced differentiation state that is based upon the conversion of differentiated effector memory T cells into less differentiated central-memory type T cells using a novel pharmacologic combination and defined T cell co-stimulatory conditions.

In an embodiment, the method comprises inoculating a culture input population of cells comprising T cells from a subject at a cell density in a culture medium comprising vitamin D, temsirolimus and an IL-2 signaling inhibitor; adding anti-CD3/anti-CD28 coated magnetic beads to said T cells and culture medium at a bead:T cell ratio of 1:1 or less to stimulate said T cells or without adding any co-stimulation beads; incubating said culture input population of cells and culture medium for a period of time to yield de-differentiated T cells. In some embodiments, the subject has been treated with an anti-TNF-α therapy prior to collection of the culture input population of cells. In some embodiments, the anti-TNF-α therapy is etanercept or adalimumab. In some embodiments, no co-stimulation with anti-CD3/anti-CD28 is performed.

In any of the foregoing embodiments, said culture medium can not contain IL-2 and no IL-2 can be added to said culture medium.

In any of the foregoing embodiments, said cell density can be about 1.5×106 T cells per mL to 18×106 T cells per mL. By way of example but not limitation, 6×106 T cells per mL to 18×106 T cells per mL, 12×106 T cells per mL to 18×106 T cells per mL, 1.5×106 T cells per mL to 12×106 T cells per mL, 1.5×106 T cells per mL to 6×106 T cells per mL, 6×106 T cells per mL to 12×106 T cells per mL, or 1.5×106 T cells per mL, 3×106 T cells per mL, 6×106 T cells per mL, 9×106 T cells per mL, 12×106 T cells per mL, 15×106 T cells per mL, or 18×106 T cells per mL. In some embodiments, by way of example but not limitation, it is anticipated that it may be preferable to initiate cell culture at higher densities such at 9×106 T cells per mL or 18×106 T cells per mL.

In any of the foregoing embodiments, said temsirolimus can be present at a concentration of about 0.3 μM to about 10 μM. By way of example but not limitation, said temsirolimus can be present in said culture medium at a concentration of about 0.3 μM to about 1 μM, 0.3 μM to about 0.75μ, 0.3μ M to about 0.5μ, 0.5μ M to about 1μ, 0.75μ M to about 1μ, 0.5μ M to about 0.75 μM, 0.3 μM to about 10 μM, 0.3 μM to about 5 μM, 0.3 μM to about 3.3 μM, 1 μM to about 3.3 μM, 5 μM to about 10 μM, 3.3 μM to about 10 μM, 3.3 μM to about 5 μM, or, by way of example but not limitation, at a concentration of about 0.3 μM, 0.4 μM, 0.5 μM, 0.6 UM, 0.7 μM, 0.8 μM, 0.9 μM, or 1 μM, 2 μM, 3 μM, 3.3 μM, 4 μM, 5 μM, 6 μM, 7 μM, 8 μM, 9 μM, or 10 μM.

In any of the foregoing embodiments, said IL-2 signaling inhibitor can be an anti-IL-2 receptor antibody or fragment thereof. By way of example but not limitation, said IL-2 signaling inhibitor can be basiliximab or daclizumab. By way of example but not limitation, said IL-2 signaling inhibitor is present in said culture medium at a concentration of 5 to 50 μg/mL, 5 to 40 μg/mL, 5 to 30 μg/mL, 5 to 20 μg/mL, 5 to 10 μg/mL, 10 to 50 μg/mL, 20 to 50 μg/mL, 30 to 50 μg/mL, 40 to 50 μg/mL, 30 to 40 μg/mL, 20 to 40 μg/mL, 10 to 40 μg/mL, 5 to 40 μg/mL, 5 to 30 μg/mL, 5 to 20 μg/mL, 5 to 10 μg/mL, 10 to 20 μg/mL, 10 to 30 μg/mL, 20 to 30 μg/mL, or, by way of example but not limitation, at a concentration of about 5 μg/mL, 10 μg/mL, 15 μg/mL, 20 μg/mL, 25 μg/mL, 30 μg/mL, 35 μg/mL, 40 μg/mL, 45 μg/mL, or 50 μg/mL.

In any of the foregoing embodiments, by way of example but not limitation, said period of time can be about 1.5 days to about 5 days, 1.5 days to about 3.5 days, 1.5 days to about 2.5 days, 2.5 days to about 3.5 days, 2.5 days to about 5 days, 3.5 days to about 5 days, or, about 1.5 days, 2 days, 2.5 days, 3 days, 3.5 days, 4 days, 4.5 days, or 5 days. In some embodiments, the level of mTORC1 and mTORC2 reduction may be used as a guide to determine optimal culture interval. In some embodiments other molecular signatures of the de-differentiated cells can be used to determine optimal culture interval, including but not limited to: RNA expression of T cell effector molecules (i.e., decreased IFN-γ); RNA expression of transcription factors (i.e., increased KLF4); evidence of an autophagy signature (i.e., increased p62); and up-regulation of markers present on naïve T cell subsets (i.e., increased CD127).

In any of the foregoing embodiments, by way of example but not limitation, said bead:T cell ratio can be 1:3 or no co-stimulation can be performed. By way of example but not limitation, said bead:T cell ratio can be between 1:1 and 1:12, 1:1 and 1:3, 1:3 to 1:12. By way of further example but not limitation, said bead:T cell ratio can be 1:1, 1:2, 1:3, 1:4, 1:5, 1:6, 1:7, 1:8, 1:9, 1:10, 1:11 or 1:12. Finally, in the most extreme example, no anti-CD3/anti-CD28 co-stimulation can be utilized, i.e. in some embodiments, no anti-CD3/anti-CD28 co-stimulation is performed during the initial de-differentiation process.

In any of the foregoing embodiments, co-stimulation of the culture input population of cells can be achieved using anti-CD3/anti-CD28 containing nanoparticles which can be used at a reduced concentration than recommended. By way of example, but not limitation, such nanoparticles can be used at about 0.01× to about 0.1×, about 0.025× to about 0.1×, about 0.05× to about 0.1×, about 0.075× to about 0.1×, about 0.01× to about 0.075×, about 0.01× to about 0.05×, about 0.01× to about 0.025×, about 0.025× to about 0.075×, about 0.025× to about 0.05×, about 0.05× to about 0.075×, or about 0.01×, about 0.025×, about 0.05×, about 0.075×, or about 0.01× the recommended dose. By way of example but not limitation, a reagent such as Miltenyi® T Cell TransAct™ could be used at a reduced dose compared to the recommended dose of 10 μL per 1×106 T cells such as, by way of example but not limitation, 1.1 μL (a nine-fold decrease) or about 0.11×. Finally, in the most extreme example, no anti-CD3/anti-CD28 co-stimulation can be utilized, i.e. in some embodiments, no anti-CD3/anti-CD28 co-stimulation is performed during the initial de-differentiation process.

Alternatively, if anti-CD3/anti-CD28 co-stimulation is to be used for producing manufactured T cells, the source of co-stimulation can be provided by dissolvable anti-CD3/anti-CD28 microparticles. By way of example, but not limitation, the dissolvable anti-CD3/anti-CD28 microparticles can be used at 20% of the strength recommended by the manufacturer (e.g. Cloudz®; Bio-Techne). By way of further example, the dissolvable anti-CD3-anti-CD28 microparticles can be used at 5%, 10%, 15%, 20%, 25% or 30% of the manufacturer's recommended strength.

In any of the foregoing embodiments, the anti-CD3/anti-CD28 stimulation, if performed, can be performed using anti-CD3/anti-CD28 in an amount sufficient to achieve the desired de-differentiated cell properties.

In any of the foregoing embodiments, said culture medium can further comprise 5% human serum. By way of example but not limitation said culture medium can comprise at least 1%, 2% 3%, 4%, 5%, 6%, 7%, 8%, 9%, 10%, 11%, 12%, 13%, 14%, 15%, 16%, 17%, 18%, 19% or 20% human serum and any range comprising values therebetween.

In any of the foregoing embodiments, said culture medium can comprise X-Vivo 20 medium. Any appropriate culture medium for culturing T cells can be used.

In any of the foregoing embodiments, by way of example but not limitation, said vitamin D can be present in said culture medium at about 0.03 nM to about 1 nM, 0.03 nM to about 0.5 nM, 0.03 nM to about 0.1 nM, 0.03 nM to about 0.05 nM, 0.05 nM to about 0.1 nM, 0.05 nM to about 0.5 nM, 0.05 nM to about 1 nM, 0.1 nM to about 1 nM, 0.1 nM to about 0.5 nM, or 0.5 nM to about 1 nM, or by way of example but not limitation, said vitamin D is present at a concentration of about 0.03 nM, 0.05 nM, 0.1 nM, 0.5 nM, or 1 nM.

In any of the foregoing embodiments, the method can further comprise measuring an expression level of RAPTOR or RICTOR and a housekeeping protein in said culture input population of cells, wherein said period of time lasts until the expression level of RAPTOR or RICTOR, respectively, in the manufactured T cells is at least 50% reduced relative to a control population of T cells, wherein said control population of T cells are manufactured under the same conditions as the culture input population of cells without temsirolimus, IL-2 signaling inhibitor and Vitamin D. In some embodiments, the period of time lasts until the expression level of RAPTOR or RICTOR, respectively, in the manufactured T cells is reduced by 50% or more relative to the control population of T cells manufactured under the same conditions as the culture input population of cells without temsirolimus, IL-2 signaling inhibitor and Vitamin D. By way of example, but not limitation, the period of time can last until the expression level of RAPTOR or RICTOR, respectively, is reduced by at least 50%, 60%, 70%, 80%, 90%, 95%, 99% or more relative to the control population of T cells manufactured under the same conditions as the culture input population of cells without temsirolimus, IL-2 signaling inhibitor and Vitamin D.

In any of the foregoing embodiments, said housekeeping protein can be actin. In some embodiments, the housekeeping protein can be GAPDH. In any of the foregoing embodiments, the step of measuring the expression level can be performed by Western blot analysis.

In any of the foregoing embodiments, the period of time can last until the expression level of RAPTOR or RICTOR in said culture input population of cells is reduced by at least 50% relative to a control population of T cells manufactured under the same conditions as the culture input population of cells without temsirolimus, IL-2 signaling inhibitor and Vitamin D. In some embodiments, the reduction in the expression level of RAPTOR or RICTOR can be at least 50%, 60%, 70%, 80%, 90%, 95%, 99% or more relative to the control population of T cells.

In any of the foregoing embodiments, the period of time of the initial de-differentiation culture can last until the RNA expression pattern is at least 10% and more optimally 50% different relative to control T cells cultured under the same conditions without temsirolimus, vitamin D and the IL-2 signaling inhibitor, namely: reduction in T cell effector molecules including but not limited to granzyme B, IL-10, and IFN-γ; increase in transcription factors associated with cells of reduced differentiation status, including but not limited to Nanog, KLF4, and KLF10; increase in expression of molecules preferentially expressed on naïve T cell subsets, including but not limited to CD127, the IL-7 receptor alpha chain; reduction in transcription factors associated with Th1-type differentiation, including but not limited to T-BET and STAT1; and relative preservation of transcription factors that promote cell survival, including but not limited to HIF-1 alpha.

In any of the foregoing embodiments, the period of time of the initial de-differentiation culture can last until the RNA expression pattern is at least 10% and more optimally 50% different relative to control T cells cultured under the same conditions without temsirolimus, vitamin D and the IL-2 signaling inhibitor, namely: whereby there is least a 10% and more preferably a 50% change in expression of molecules indicative of cells that have undergone autophagy. As one, example, the said de-differentiated cells have increased expression of p62 by western blot analysis relative to control T cells; other methods of measuring autophagy can also be utilized, by way of example but not limitation, those described in Yoshii S R, Mizushima N. Monitoring and Measuring Autophagy. International Journal of Molecular Sciences. 2017; 18(9): 1865.

In any of the foregoing embodiments, the culture medium may not contain human serum, temsirolimus, Vitamin D, the IL-2 signaling inhibitor or any combination thereof can be absent from the culture medium at the time of culture initiation. In such embodiments, human serum, temsirolimus, Vitamin D or the IL-2 signaling inhibitor can be added to the culture medium at about the same time as inoculation of the culture input population of cells or at a subsequent time.

By way of example and not limitation, an intravenous formulation of 1,25-vitamin D ("Calcitriol") can be used. This formulation is preferable because it is fully soluble in culture media and has the 1, 25 hydroxylation that is naturally produced in the kidneys and therefore must be present when adding vitamin D to culture. Trade name for calcitriol includes Rocaltrol, Calcijex, and Decostriol). It is also envisioned that other vitamin D receptor (VDR) ligands may be substituted for calcitriol, including but not limited to lithocholic acid, as described in Maestro et al; Vitamin D receptor 2016: novel ligands and structural insights; Expert Opinion on Therapeutic Patents; Volume 26, 2016, issue 11.

In some embodiments, a de-differentiated T cell that can be obtained by any of the methods of the present disclosure is provided. In some embodiments, a composition comprising a population of de-differentiated T cells is provided. In some embodiments, at least a portion of the de-differentiated T cells express less than 50% of RAPTOR or RICTOR relative to a control population of T cells manufactured under the same conditions as the culture input population of cells without temsirolimus, IL-2 signaling inhibitor and Vitamin D. In some embodiments, a de-differentiated T cell expresses less than 50% RAPTOR or RICTOR relative to a control population of T cells manufactured under the same conditions as the culture input population of cells without temsirolimus, IL-2 signaling inhibitor and Vitamin D. By way of example, but not limitation, said de-differentiated T cell or population of de-differentiated T cells can express 50%, 45%, 40%, 35%, 30%, 25%, 20%, 15%, 10%, 5%, 1% or less RAPTOR or RICTOR relative to a control T cell or population of T cells, respectively, manufactured under the same conditions as the culture input population of cells without temsirolimus, IL-2 signaling inhibitor and Vitamin D.

In some embodiments a de-differentiated T cell population or de-differentiated T cell can be characterized by a reduction in RNA expression for cytolytic molecules relative to a control T cell population incubated under the same conditions without temsirolimus, vitamin D and the IL-2 signaling inhibitor, including, but not limited granzyme B and/or for cytokine molecules including, but not limited to IFN-γ. Such a reduction can be, by way of example but not limitation, at least 10%, at least 20%, at least 30%, at least 40%, at least 50% or more.

In some embodiments a de-differentiated T cell population or de-differentiated T cell can be characterized by an increase in RNA expression for transcription factors associated with iPSCs relative to a control T cell population incubated under the same conditions without temsirolimus, vitamin D and the IL-2 signaling inhibitor, including, but not limited to Nanog, KLF4, and KLF10 and/or for molecules associated with naïve T cells including, but not limited to the IL-7 receptor, CD127. Such an increase can be, by way of example but not limitation, at least 10%, at least 20%, at least 30%, at least 40%, at least 50% or more.

In some embodiments a de-differentiated T cell population or de-differentiated T cell can be characterized by a reduction in RNA expression for transcription factors associated with Th1 effector T cells relative to a control T cell population incubated under the same conditions without temsirolimus, vitamin D and the IL-2 signaling inhibitor, including, but not limited T-Bet and STAT1 with a concomitant maintenance about equivalent HIF-1-α expression. Such a reduction can be, by way of example but not limitation, at least 10%, at least 20%, at least 30%, at least 40%, at least 50% or more. By way of example, but not limitation, the HIF-1-α expression can be within about 20%, 15%, 10% or 5% or the control T cell population.

In some embodiments a de-differentiated T cell population or de-differentiated T cell can be characterized by an increase in protein expression of p62 relative to a control population of T cells incubated under the same conditions without temsirolimus, vitamin D and the IL-2 signaling inhibitor. Such an increase can be, by way of example but not limitation, at least 10%, at least 20%, at least 30%, at least 40%, at least 50% or more.

Method for Manufacturing of Human Hybrid Regulatory T/Th2 Cells (Hybrid $T_{REG}$/Th2 Cells) and $T_{REG}$ from De-Differentiated T Cells In the present disclosure, we provide an ex vivo manufacturing process that results in the generation of iTREG cells enhanced for an early state of differentiation combined with depletion of Th1- and Th17-type polarization. This method requires a two-step process, the first step consisting of T cell de-differentiation, the second step iTREG cell manufacturing. Manufacture of human iTREG cells from this de-differentiated T cell substrate can be performed using a novel combination of cytokines (standard iTREG use of IL-2 and TGF-β cytokines plus additional use of the cytokine classically-associated with Th2 differentiation, IL-4) and, optionally, a novel pharmaceutical agent, pemetrexed as described herein. In some embodiments, the iTREG cells can be generated without pemetrexed. Because such cells have expression of both TREG and Th2 molecules, cells generated by this method are termed 'human hybrid TREG/Th2 cells'.

In some embodiments, the method comprises culturing de-differentiated T cells of the present disclosure in a culture medium comprising IL-2, IL-4 and TGF-β; adding anti-CD3/anti-CD28 coated magnetic beads, such as at a ratio of 3:1 (bead:T cell ratio); and incubating said de-differentiated T cells for a period of time to yield TREG/Th2 cells. In some embodiments, the method comprises culturing a population of de-differentiated T cells of the present disclosure. The ratio of anti-CD3/anti-CD28 beads can be varied so long as the co-stimulation is sufficient to differentiate the cells.

In some embodiments, the method comprises culturing de-differentiated T cells having reduced expression of RAPTOR or RICTOR relative to a control population of T cells manufactured under the same conditions without temsirolimus, IL-2 signaling inhibitor and Vitamin D, in a culture medium comprising IL-2, IL-4 and TGF-β; adding anti-CD3/anti-CD28 coated magnetic beads, such as at a ratio of 3:1 (bead:T cell ratio); and incubating said de-differentiated T cells for a period of time to yield TREG/Th2 cells. In some embodiments, the method comprises culturing a population of de-differentiated T cells of the present disclosure. The ratio of anti-CD3/anti-CD28 beads can be varied so long as the co-stimulation is sufficient to differentiate the cells. In some embodiments, the expression of RAPTOR or RICTOR is normalized by a housekeeping protein, such as, by way of example, but not limitation, actin or GAPDH.

In any of the foregoing embodiments, IL-2 can be present in said culture medium at a concentration of about 100 IU/ml to 10,000 IU/ml, 100 IU/ml to 1,000 IU/ml, 1,000 IU/ml to 10,000 IU/ml, or, about 100 IU/ml, 1,000 IU/ml, or 10,000 IU/ml.

In any of the foregoing embodiments the culture medium can further comprise IL-4. In any of the foregoing embodiments, IL-4 can be present in said culture medium at a concentration of about 100 IU/mL to 1000 IU/MI, 100 IU/mL to 1000 IU/mL, 100 IU/mL to 250 IU/mL, 100 IU/mL to 500 IU/mL, 250 IU/mL to 1000 IU/mL, 500 IU/mL to 1000 IU/mL, 250 IU/mL to 500 IU/mL, or, 100 IU/mL, 200 IU/mL, 300 IU/mL, 400 IU/mL, 500 IU/mL, 600 IU/mL, 700 IU/mL, 800 IU/mL, 900 IU/mL, or 1000 IU/mL. In some embodiments, by way of example but not limitation, lower concentrations such as 100 IU/mL can be used if there is a desire to achieve reduced Th2 polarization.

In any of the foregoing embodiments, TGF-β can be present in said culture medium at a concentration of about 10 ng/mL. By way of example, but not limitation, the concentration of TGF-β can be about 5 ng/ml, 6 ng/mL, 7 ng/mL, 8 ng/ml, 9 ng/ml or 10 ng/mL.

In any of the foregoing embodiments for differentiation, said bead:T cell ratio can be 3:1. In some embodiments, an equivalent amount, having the same effect, of alternative forms of anti-CD3/anti-CD28 can be used. In some embodiments, the amount of co-stimulation is sufficient to saturate the cells. In any of the foregoing embodiments, the amount of co-stimulation can be sufficient to increase the expression of GATA3 and FOXP3 in the human hybrid TREG/Th2 cells.

In any of the foregoing embodiments the culture medium can further comprise pemetrexed. By way of example but not limitation, pemetrexed can be present in said culture medium at a concentration from about 1 nM to 100 nM, 5 nM to 100 nM, 10 nM to 100 nM, 25 nM to 100 nM, 50 nM to 100 nM, 75 nM to 100 nM, 50 nM to 75 nM, 25 nM to 75 nM, 10 nM to 50 nM, 10 nM to 25 nM, or at such values as 5 nM, 10 nM, 25 nM, 50 nM, 75 nM, or 100 nM. In some embodiments, the culture medium does not comprise pemetrexed and pemetrexed is not added to the culture medium.

In any of the foregoing embodiments said period of time for incubating said de-differentiated T cells can be, by way of example but not limitation, between 3 days to 40 days, 2 days to 20 days, 3 days to 10 days, 3 days to 6 days, 6 days to 10 days, 10 days to 40 days, 10 days to 20 days, 10 days to 15 days, 15 days to 40 days, 20 days to 40 days, 30 days to 40 days, 20 days to 30 days, or 15 days to 30 days, or 15 days to 20 days. In some embodiments, by way of example but not limitation, shorter intervals of culture such as 3 days to 10 days can be considered if hybrid Th2/$T_{REG}$ cells of very limited differentiation status.

The present disclosure is also directed to methods and a $T_{REG}$ cell produced by any of the foregoing methods without the use of IL-4.

In some embodiments, a TREG or TREG/Th2 cell produced by the methods of the present disclosure can have increased expression by flow cytometry of at least one of CD25, CD27, 2B4, BTLA, CTLA4, TIGIT, TIM3, ICOS, LAIR1, and OX40 relative to control Th1/Tc1 cells. In some embodiments, this increase can be, by way of example but not limitation, at least 10%, at least 20%, at least 30%, at least 40%, at least 50%, at least 60%, at least 70%, at least 80%, at least 90% or more.

In some embodiments, a TREG or TREG/Th2 cell produced by the methods of the present disclosure can have decreased secretion of inflammatory cytokines relative to control Th1/Tc1 cells. By way of example, but not limitation, such cyotkines can include IFN-γ and TNF-α. In some embodiments, this decrease can be, by way of example but not limitation, at least 10%, at least 20%, at least 30%, at least 40%, at least 50%, at least 60%, at least 70%, at least 80%, at least 90% or more.

In some embodiments, a TREG or TREG/Th2 cell produced by the methods of the present disclosure can have reduced TBET and increase FOXP3 expression relative to control Th1/Tc1 cells and/or increased IL-4 secretion and increased expression of GATA3 relative to control Th1/Tc1 cells. In some embodiments, this decrease or increase can be, by way of example but not limitation, at least 10%, at least 20%, at least 30%, at least 40%, at least 50%, at least 60%, at least 70%, at least 80%, at least 90% or more.

In some embodiments, a population of TREG or TREG/Th2 cells can have at least 5% of CD4+ or CD8+ cells that express GATA3. By way of example, but not limitation, a population of TREG or TREG/Th2 cells can have at least 10%, at least 15%, at least 20%, at least 25%, at least 30%, at least 40%, at least 45%, at least 50%, or at least 60% of CD4+ or CD8+ T cells that express GATA3. In some embodiments, whether the cells express GATA3 is determined by flow cytometry. In some embodiments, population of $T_{REG}$ Or $T_{REG}$/Th2 cells can exhibit an increased frequency of $CD4^+$ or $CD8^+$ T cells expressing GATA3 relative to a control T cell population characteristic of the T cells from which the population of $T_{REG}$ Or $T_{REG}$/Th2 cells was produced. In some embodiments, the increased frequency can be an increase of 50% or more. By way of example, but not limitation, the increase can be by 50%, 100%, 200%, 300%, 500%, 1000%, 2000%, 3000% or more.

In some embodiments, a population of TREG or TREG/Th2 cells can have at least 5% of CD4+ or CD8+ cells that express FoxP3. By way of example, but not limitation, a population of TREG or TREG/Th2 cells can have at least 10%, at least 15%, at least 20%, at least 25%, at least 30%, at least 40%, or at least 45% of CD4+ or CD8+ T cells that express FoxP3. In some embodiments, whether the cells express FoxP3 is determined by flow cytometry. In some embodiments, population of $T_{REG}$ Or $T_{REG}$/Th2 cells can exhibit an increased frequency of $CD4^+$ or $CD8^+$ T cells expressing FOXP3 relative to a control T cell population characteristic of the T cells from which the population of $T_{REG}$ Or $T_{REG}$/Th2 cells was produced. In some embodiments, the increased frequency can be an increase of 50% or more. By way of example, but not limitation, the increase can be by 50%, 100%, 200%, 300%, 500%, 1000%, 2000%, 3000% or more.

In some embodiments, a population of TREG or TREG/Th2 cells can have at least 10% of CD4+ or CD8+ cells that express CD73. By way of example, but not limitation, a population of TREG or TREG/Th2 cells can have at least 10%, at least 15%, at least 20%, or at least 25% of CD4+ T cells that express CD73. By way of further example, but not limitation, a population of TREG or TREG/Th2 cells can have at least 10%, at least 15%, at least 20%, at least 25%, at least 30%, at least 40%, at least 50%, at least 60%, at least 70%, at least 75%, or at least 80% of CD8+ T cells that express CD73. In some embodiments, whether the cells express CD73 is determined by flow cytometry. In some embodiments, population of $T_{REG}$ Or $T_{REG}$/Th2 cells can exhibit an increased frequency of $CD4^+$ or $CD8^+$ T cells expressing CD73 relative to a control T cell population characteristic of the T cells from which the population of $T_{REG}$ Or $T_{REG}$/Th2 cells was produced. In some embodiments, the increased frequency can be an increase of 50% or more. By way of example, but not limitation, the increase can be by 50%, 100%, 200%, 300%, 500%, 1000%, 2000%, 3000% or more.

In some embodiments, a population of $T_{REG}$ or $T_{REG}$/Th2 cells can have at least 10% of CD4+ or CD8+ cells that express CD103. By way of example, but not limitation, a population of $T_{REG}$ or $T_{REG}$/Th2 cells can have at least 10%, at least 15%, at least 20%, at least 25%, at least 30%, at least 40%, at least 50%, at least 60%, at least 70%, at least 75%, at least 80%, at least 85%, at least 90%, or at least 95% of CD4+ or CD8+ T cells that express CD103. In some embodiments, whether the cells express CD103 is determined by flow cytometry. In some embodiments, population of $T_{REG}$ Or $T_{REG}$/Th2 cells can exhibit an increased frequency of CD4+ or $CD8^+$ T cells expressing CD103 relative to a control T cell population characteristic of the T cells from which the population of $T_{REG}$ Or $T_{REG}$/Th2 cells was produced. In some embodiments, the increased frequency can be an increase of 50% or more. By way of example, but not limitation, the increase can be by 50%, 100%, 200%, 300%, 500%, 1000%, 2000%, 3000% or more.

In some embodiments, a population of $T_{REG}$ Or $T_{REG}$/Th2 cells can have at least 5% of $CD4^+$ or $CD8^+$ cells that express both FOXP3 and GATA3 as measured by flow cytometry. By way of example, but not limitation, the population of $T_{REG}$ Or $T_{REG}$/Th2 cells can have at least 5%, 10%, 20%, 30%, 40%, or 50% of CD4+ or CD8+ cells that express both FOXP3 and GATA3.

In some embodiments, a population of $T_{REG}$ or $T_{REG}$/Th2 cells can have at least 20% of CD4+ or CD8+ T cells that express CD150. By way of example, but not limitation, a population of $T_{REG}$ or $T_{REG}$/Th2 cells can have at least 20%, at least 25%, at least 30%, at least 35%, at least 40%, at least 45% or at least 50% of CD4+ or CD8+ T cells that express CD150. In some embodiments, a population of $T_{REG}$ or $T_{REG}$/Th2 cells can an increased frequency of cells that express CD150 relative to a control population of T cells incubated without exposure to mTOR inhibitors. In some embodiments, whether the cells express CD150 is determined by flow cytometry. In some embodiments, population of $T_{REG}$ or $T_{REG}$/Th2 cells can exhibit an increased frequency of $CD4^+$ or $CD8^+$ T cells expressing CD150 relative to a control T cell population characteristic of the T cells from which the population of $T_{REG}$ Or $T_{REG}$/Th2 cells was produced. In some embodiments, the increased frequency can be an increase of 50% or more. By way of example, but not limitation, the increase can be by 50%, 100%, 200%, 300%, 500%, 1000%, 2000%, 3000% or more.

In some embodiments, a population of $T_{REG}$ or $T_{REG}$/Th2 cells can express at least 5 pg/mL/1×106 cells/day of IL-4 after co-stimulation with anti-CD3/anti-CD28 beads at a bead:T cell ratio of 3:1. By way of example, but not limitation, a population of $T_{REG}$ or $T_{REG}$/Th2 cells can express at least 5, at least 10, at least 20, at least 30, at least 40, at least 50, at least 60, at least 70, at least 80, at least 90, or at least 100 pg/mL/1×106 cells/day IL-4.

In some embodiments, a population of TREG or TREG/Th2 cells can express at least 100 μg/mL/1×106 cells/day of IL-2 after co-stimulation with anti-CD3/anti-CD28 beads at a bead:T cell ratio of 3:1.

In some embodiments, a population of TREG or TREG/Th2 cells can express less than 100 pg/mL/1×106 cells/day of IFN-γ or GM-CSF after co-stimulation with anti-CD3/anti-CD28 beads at a bead:T cell ratio of 3:1.

In some embodiments, a population of TREG or TREG/Th2 cells can express less than 10 pg/mL/1×106 cells/day of TNF-α or IL-17 after co-stimulation with anti-CD3/anti-CD28 beads at a bead:T cell ratio of 3:1.

In some embodiments, a TREG or TREG/Th2 cell can express both GATA3 and FOXP3. In some embodiment, a TREG or TREG/Th2 cell can express GATA3, FOXP3, CD103 and CD73. In some embodiments, a population of TREG or TREG/Th2 cells can be characterized by at least 5% of the T cells expressing GATA3, at least 5% of the T cells expressing FOXP3, at least 5% of the T cells expressing CD103 and at least 5% of the T cells expressing CD73, as measured by flow cytometry.

In any of the foregoing embodiments, the TREG or TREG/Th2 cell or population thereof can have at least one or any combination of the foregoing recited properties to the extent the properties are not incompatible.

Method for ALS Treatment Using Induced Regulatory T ($iT_{REG}$) Cells

In this protocol, we will use the pentostatin plus cyclophosphamide regimen as an immune depletion and immune suppression method that will enhance the $iT_{REG}$ cell therapy of ALS. This PC regimen may have a direct beneficial effect due to its ability to deplete and suppress the Th1-type immune cells that are associated with ALS pathogenesis; in addition, the PC regimen will serve as the host conditioning that will increase the immunologic T cell space for more effective $iT_{REG}$ cell therapy. Specifically, for this protocol, we have reduced the dosage of the PC regimen to help mitigate any potential adverse effects of the regimen in the new ALS patient population. For this protocol, we have: reduced the starting dose of pentostatin from 4 mg/$m^2$ to 1 mg/$m^2$; reduced the number of pentostatin infusions from a previous value of four infusions per cycle versus the current protocol value of one infusion per cycle; and reduced the initial cyclophosphamide dose from 200 mg per day to 100 mg per day. And second, we have reduced the intensity of the PC regimen in terms of the stated goal regarding the depth of immune depletion to be rendered by the PC regimen. Because a more cautious approach is mandated in the ALS patient population, the current protocol PC regimen seeks to more modestly reduce the ALC count, namely, to a value just under 750 cells per microliter. This level of immune depletion, in general, is not associated with profound, long-term immune incompetence in terms of high rates of opportunistic infection.

It is expected, without being bound to theory, that the PC regimen will deplete and suppress the Th1/Tc1-type adaptive immune subsets that are implicated in the progression of ALS pathogenesis. However, this therapy does not address the underlying primary events in ALS, namely: the misfolded RNA species, the insufficient autophagy for clearance of deleterious the deleterious RNA/DNA products, and subsequent RNA/DNA activation of innate inflammation at the level of the P2X7 receptor-driven NLRP3 inflammasome. Such inflammasome activation, which has been shown to be operational in ALS models, drives subsequent IL-1-β activation that is one of the earliest and most potent pro-inflammatory signal that then drives adaptive T cell inflammation mediated largely by the Th1/Tc1 subsets. Indeed, it has recently been proposed that NLRP3 inhibition represents a novel approach to the therapy of a wide variety of neurodegenerative diseases. Nucleoside reverse transcriptase inhibitors (NRTI) are anti-viral agents approved for therapy of HIV disease that may also play a role in the therapy of ALS. Patients with ALS can have increased levels of human endogenous retrovirus-K (HERV-K) that drive disease pathogenesis in model systems, in part by regulation by TDP-43 deposits that are a key mechanistic component in ALS; towards clinical translation of this biology, a clinical trial has been initiated (NCT02437110) that is evaluating the HIV anti-viral cocktail of Darunavir, Ritonavir, Raltegravir, and Zidovudine. The NRTI molecule lamivudine (3TC) has also been described to inhibit the P2X7 receptor that drives NLRP3 activation that occurs in ALS. Based in part on these observations, a phase II clinical trial (NCT02363452) has been initiated to evaluate the ability of a three-drug regimen of lamivudine, zidovudine, and abacavir to reduce inflammation in patients with Aicardi-Goutières Syndrome (AGS), which is a disease that mimics the innate inflammatory events in ALS, namely: accumulation of intracellular RNA species, activation of inflammasome pathways, and resultant generation of systemic Th1-driven inflammation. Because lamivudine has been characterized as a potent inhibitor of the NLRP3 inflammasome and because of the desire to generate a treatment regimen that is well tolerated in the ALS patient population, we have elected to pursue single-agent NRTI therapy with lamivudine in this protocol.

Therefore, it is expected, without being bound to theory, that a sequential strategy whereby one first depletes and suppresses the Th1/Tc1 response (via the PC regimen) and then secondarily controls the driving-force inflammasome activation will represent a new approach to provide sustainable regulation to the complex neuro-inflammatory networks involved in ALS. Use of lamivudine in the ALS treatment platform may also be beneficial in terms of our next step, which is to further incorporate $iT_{REG}$ cell therapy into the platform. That is, each of the three therapeutic modalities (pentostatin/cyclophosphamide; lamivudine; and $iT_{REG}$ cells) operates at least in part by shunting the trafficking of ATP away from the P2X7-driven, NLRP3-mediated inflammasome and towards the immunosuppressive molecule, adenosine. First, pentostatin increases adenosine by inhibiting adenosine deaminase, thereby preventing the conversion of adenosine to inosine; second, lamivudine is a known inhibitor of P2X7, thereby directly inhibiting the inflammasome; and third, $iT_{REG}$ cells provide CD39- and CD73-mediated ecto-nucleotidase activity that processes ATP towards adenosine. With respect to this last process, it is important to note that microglial cells inherently utilize CD39 and CD73 to dampen neuroinflammation.

In sum, these data provide evidence that the primary neurodegenerative process in ALS gives rise to a secondary inflammatory response that on the one hand can drive disease progression yet on the other hand can point to therapeutic interventions at multiple steps, including: control of inflammasome activation, depletion and suppression of Th1/Tc1-type subsets, and promotion of $T_{REG}$-type subsets. Given this information, there exists great interest in evaluating immune modulation therapies in ALS patients. It is our hypothesis that optimal control of neuro-inflammation in ALS patients will require a three-pronged therapy that addresses each of the above-mentioned components, namely: (1) control of innate inflammasome activation (through lamivudine administration, as described below); (2) reduction in pre-existing Th1-type inflammatory cells (through the pentostatin/cyclophosphamide regimen, as further detailed below); and (3) promotion of $iT_{REG}$ cells through adoptive T cell transfer. There are several reasons to explain why such a combination approach may be necessary. First, if the underlying inflammasome activation is not addressed through maintenance therapy, then any immunologic and therapeutic gains accomplished during host conditioning therapy and $T_{REG}$ cell therapy will likely be eroded by the primary underlying neurodegenerative process. Second, stand-alone infusion of even an optimized $T_{REG}$ cell population into a host with uncontrolled Th1-driven inflammation represents a daunting immunologic challenge for many reasons: the pre-existent Th1-type cells can manifest differentiation plasticity upon the adoptively transferred $T_{REG}$ cells, thereby converting a protective $T_{REG}$ population into a pathogenic subset that can contribute to disease pathogenesis. And third, the efficacy of adoptively transferred T cell populations is intricately linked to the degree of immunologic T cell space, which can be defined in large part by the presence of T cell growth factors such as IL-7 and IL-15; the creation of such immunologic space is created by host preparative regimens, including the pentostatin plus cyclophosphamide (PC) regimen, which have been utilized for decades in allogeneic hematopoietic stem cell transplantation, and now in the field of using adoptive T cell transfer for cancer therapy. Of note, prior clinical trials involving $T_{REG}$ cell therapy of neurodegenerative or autoimmune diseases have not incorporated host preparative regimens such as the PC regimen.

In some embodiments, the method comprises subjecting said subject to one or more primary treatment cycles, each of said one or more primary treatment cycles comprising: administering to said subject pentostatin; and/or administering to said subject cyclophosphamide; and subjecting said subject to one or more immune therapy treatment cycles comprising: administering to said subject a composition comprising a therapeutically effective amount of manufactured $T_{REG}$ cells. One of skill in the art can determine the therapeutically effective amount by methods known in the art and as disclosed herein.

In the foregoing embodiments, each of said one or more immune therapy treatment cycles can further comprise administering to said subject a nucleoside reverse transcriptase inhibitor. Said nucleoside reverse transcriptase inhibitor can be an inhibitor of the NLRP3 inflammasome; or said nucleoside reverse transcriptase inhibitor can be lamivudine. Each of said one or more immune therapy treatment cycles can further comprise: administering to said subject pentostatin; and/or administering to said subject cyclophosphamide. Said step of administering to said subject pentostatin during each of said one or more immune therapy treatment cycles can be performed on days 1 and 4 of each of said one or more immune therapy treatment cycles. Said step of administering to said subject pentostatin during each of said one or more immune therapy treatment cycles can be performed on days 1, 2, 3, 4 and 5 of each of said one or more immune therapy treatment cycles. Said method can comprise two or more immune therapy treatment cycles and each of said two or more immune therapy treatment cycles are separated, by way of example and not limitation, by 0 to 4 weeks, 0 to 3 weeks, 0 to 2 weeks, 0 to 1 weeks, and any value between such as, by way of example but not limitation, 0 weeks, 1 week, 2 weeks, 3 weeks, or 4 weeks. Each of said one or more immune therapy treatment cycles can be 18 weeks long. Each of said one or more immune therapy treatment cycles can further comprise administering to said subject an adenosine receptor modulating agent. Other nucleoside reverse transcriptase inhibitors can be used including, by way of example but not limitation, those disclosed in U.S. Pat. No. 9,326,983, which is incorporated herein by reference, lamivudine, zidovudine, stavudine, cordycepin, azidothymidine, abacavir, compounds of the structure (Formula I)

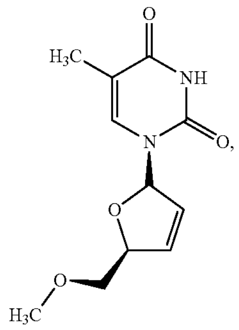

compounds of the structure (Formula II)

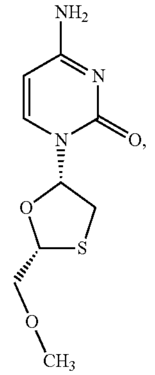

chemical derivatives thereof, pharmaceutically acceptable salts thereof, and combinations thereof.

In the foregoing embodiments, by way of example but not limitation, said one or more primary treatment cycles can be between 2 weeks and 5 weeks, 2 weeks and 4 weeks, 2 weeks and 3 weeks, 3 weeks and 4 weeks, or 4 weeks and 5 weeks, and any value between such as, by way of example but not limitation, 2 weeks, 3 weeks, 4 weeks, or 5 weeks. Said method can comprise two or more primary treatment cycles, wherein each of said two or more primary treatment cycles is separated by 0 to 2 weeks. By way of example but not limitation, each of said two or more primary treatment cycles is separated by 0 to 1 weeks or 1 to 2 weeks, and any value between such as, by way of example but not limitation, 1 day, 1 week, or 2 weeks.

In the foregoing embodiments, the method may further comprise, prior to said one or more primary treatment cycles: harvesting peripheral lymphocytes from said subject. The method may further comprise, after harvesting peripheral lymphocytes from said subject: culturing said peripheral lymphocytes to yield said manufactured $T_{REG}$ cells. The method may further comprise, after said one or more primary treatment cycles: harvesting peripheral lymphocytes from said subject. The method may further comprise, after harvesting peripheral lymphocytes from said subject after said one or more primary treatment cycles: culturing said peripheral lymphocytes to yield said manufactured $T_{REG}$ cells. The method may further comprise, after each of said one or more primary treatment cycles: measuring absolute lymphocyte count (ALC) in said subject and, if ALC<750 per μl proceeding to said one or more immune therapy treatment cycles. In some embodiments that target ALC value can vary and, by way of example but not limitation, be 0, 250, 500, 750, 1000, 1250 or 1500 cells per microliter.

In the foregoing embodiments, a first of said one or more immune therapy treatment cycles and a last of said one or more primary treatment cycles are separated by 0 to 2 weeks. By way of example but not limitation, each of said two or more immune therapy treatment cycles is separated by 0 to 1 weeks or 1 to 2 weeks, and any value between such as, by way of example but not limitation, 0 weeks, 1 week, or 2 weeks.

In the foregoing embodiments, by way of example but not limitation, the dose of pentostatin can be a dose of 0.5 $mg/m^2$ to 4 $mg/m^2$, 1 $mg/m^2$ to 4 $mg/m^2$, 2 $mg/m^2$ to 4 $mg/m^2$ and any value between such as, by way of example but not limitation 0.5 $mg/m^2$, 1 $mg/m^2$, 1.5 $mg/m^2$, 2 $mg/m^2$, 2.5 $mg/m^2$, 3 $mg/m^2$, 3.5 $mg/m^2$ and 4 $mg/m^2$. Said pentostatin can be administered on any days of each of said one or more primary treatment cycles. By way of example, but not limitation, pentostatin can be administered to a subject on day 1 or days 1 and 4 of each of said one or more primary treatment cycles.

In the foregoing embodiments, cyclophosphamide can be administered to the subject at a dose of 50 mg to 400 mg. By way of example but not limitation, the dose of cyclophosphamide can be a dose of between any combination of 50, 100, 150, 200, 250, 300, 350, or 400 mg and 400, 350, 300, 250, 200, 150, 100, or 50 mg and any value between such as, by way of example but not limitation 50 mg, 100 mg, 150 mg, 200 mg, 250 mg, 300 mg, 350 mg, or 400 mg. By way of example but not limitation, cyclophosphamide can be administered on days 1, 2 and 3 or days 1, 2, 3, 4, and 5 of each of said one or more primary treatment cycles.

In the foregoing embodiments, said pentostatin and cyclophosphamide can be administered to said subject in a single composition. Said single composition can be administered to said subject intravenously. Said steps of administering to said subject pentostatin and cyclophosphamide can comprise: administering to said subject a first composition comprising pentostatin; and administering to said subject a second composition comprising cyclophosphamide.

In the foregoing embodiments, said lamivudine can be administered to said subject at a dose between 150 mg daily and 150 mg twice daily.

In the foregoing embodiments, said manufactured $T_{REG}$ cells can be administered to said subject during each of said one or more immune therapy treatment cycles at a dose between, by way of example and not limitation, $1\times10^6$ cells per kg of the subject's body weight and 5×106 cells per kg of the subject's body weight, $2\times10^6$ cells per kg of the subject's body weight and $5\times10^6$ cells per kg of the subject's body weight, $3\times10^6$ cells per kg of the subject's body weight and $5\times10^6$ cells per kg of the subject's body weight, $4\times10^6$ cells per kg of the subject's body weight and $5\times10^6$ cells per kg of the subject's body weight, $1\times10^6$ cells per kg of the subject's body weight and $4\times10^6$ cells per kg of the subject's body weight, $1\times10^6$ cells per kg of the subject's body weight and $3\times10^6$ cells per kg of the subject's body weight, $1\times10^6$ cells per kg of the subject's body weight and $2\times10^6$ cells per kg of the subject's body weight, and any values between such as, by way of example but not limitation, $1\times10^6$ cells per kg of the subject's body weight, $2\times10^6$ cells per kg of the subject's body weight, $3\times10^6$ cells per kg of the subject's body weight, $4\times10^6$ cells per kg of the subject's body weight, or $5\times10^6$ cells per kg of the subject's body weight. By way of example, but not limitation, from about $1\times10^6$ to about $200\times10^6$ cells/infusion of manufactured $T_{REG}$ cells can be administered. By way of further example, but not limitation, from about $1\times10^6$ to about $200\times10^6$, $10\times10^6$ to about $200\times10^6$, $50\times10^6$ to about $200\times10^6$, $100\times10^6$ to about $200\times10^6$, at least $1\times10^6$, $10\times10^6$, $50\times10^6$, $100\times10^6$, or $200\times10^6$ cells/infusion of manufactured $T_{REG}$ cells can be administered. In some embodiments, about $40\times10^6$ cells/infusion can be administered. In some embodiments, about $120\times10^6$ cells/infusion can be administered. Said manufactured $T_{REG}$ cells can comprise a ratio of central memory to effector memory cells selected from 1:1, 3:1, 10:1, 1:3 and 1:10. Said composition comprising manufactured $T_{REG}$ cells can further comprise normal $T_{REG}$ cells. Said manufactured $T_{REG}$ cells can be administered to said subject on day 8 of each of said one or more immune therapy treatment cycles. In some embodiments, $iT_{REGS}$ and $nT_{REGS}$ can be administered to a subject in combination.

In some embodiments, a method can comprise a first treatment cycle, a second treatment cycle, optionally, one or more additional treatment cycles, and one or more immune therapy treatment cycles, said first treatment cycle comprising: administering pentostatin to said subject, and/or administering cyclophosphamide to said subject; said second treatment cycle comprising: administering pentostatin to said subject, and/or administering cyclophosphamide to said subject; each of said one or more additional treatment cycles comprising: administering pentostatin to said subject, and/or administering cyclophosphamide to said subject each of said one or more immune therapy treatment cycles comprising: administering pentostatin to said subject, and/or administering cyclophosphamide to said subject, and administering manufactured $T_{REG}$ cells to said subject.

In the foregoing embodiments, said first treatment cycle can be 14 days long. Said step of administering pentostatin to said subject can be performed on day 1 of said first treatment cycle. Pentostatin can be administered to said subject at a dose of 1 $mg/m^2$ during said first treatment cycle. Cyclophosphamide can be administered to said subject at a dose of 100 mg during said first treatment cycle. Said step of administering cyclophosphamide to said subject can be repeated during said first treatment cycle, by way of example but not limitation, said step of administering cyclophosphamide to said subject can be performed on days 1, 2, and 3 of said first treatment cycle.

In the foregoing embodiments, said second treatment cycle can be 14 days long. Said step of administering pentostatin to said subject during said second treatment cycle can be performed on day 1 of said second treatment cycle. Pentostatin can be administered to said subject at a dose of 2 $mg/m^2$ during said second treatment cycle. Said step of administering cyclophosphamide to said subject during said second treatment cycle can be repeated during said second treatment cycle. By way of example but not limitation, said step of administering cyclophosphamide to said subject during said second treatment cycle can be performed on days 1, 2, and/or 3 of said second treatment cycle. Cyclophosphamide can be administered to said subject at a dose of 100 mg during said second treatment cycle.

In the foregoing embodiments, said subject can be subjected to said one or more additional treatment cycles. Each of said one or more additional treatment cycles can be each 14 days long. Said one or more additional treatment cycles can be separated by 0 to 2 weeks. By way of example but not limitation, each of said two or more additional treatment cycles can be separated by 0 to 1 weeks or 1 to 2 weeks, and any value between such as, by way of example but not limitation, 0 weeks, 1 week, or 2 weeks. Said step of administering pentostatin to said subject during each of said one or more additional treatment cycles can be performed on days 1 and/or 4 of said one or more additional treatment cycles. Pentostatin can be administered to said subject at a dose of 2 $mg/m^2$ during each of said one or more additional treatment cycles. Said step of administering cyclophosphamide to said subject can be repeated during each of said one or more additional treatment cycles. Said step of administering cyclophosphamide to said subject during each of said one or more additional treatment cycles can be performed on days 1, 2, 3, 4 and/or 5 of each of said one or more additional treatment cycles. Cyclophosphamide can be administered to said subject at a dose of 100 mg to 200 mg during each of said one or more additional treatment cycles. Said additional cycle can further comprise prior to administering pentostatin to said subject during each of said one or more additional treatment cycles: measuring the creatinine clearance (CrCl) of said subject and adjusting a dose of pentostatin to be administered to said subject based on the CrCl, wherein pentostatin is administered at 2 $mg/m^2$ when CrCl>60 mL/min/1.73 $m^2$, wherein pentostatin is administered at 1 $mg/m^2$ when 60 mL/min/1.73 $m^2$>CrCl>30 mL/min/1.73 $m^2$, and wherein pentostatin is not administered when CrCl<30 mL/min/1.73 $m^2$. Said additional cycle can further comprise prior to administering cyclophosphamide to said subject during each of said one or more additional treatment cycles: measuring absolute neutrophil count (ANC) and adjusting a dose of cyclophosphamide to be administered to said subject based on ANC, wherein cyclophosphamide is administered at a dose of 100 mg when ANC>1000 per microliter, wherein cyclophosphamide is administered at a dose of 50 mg when ANC is 500-999 per microliter, and wherein cyclophosphamide is not administered when ALC<50 per microliter or ANC<500 per microliter. Said one or more additional treatment cycles can comprise at least two additional treatment cycles, a final of said at least two additional treatment cycles comprising prior to administering cyclophosphamide to said subject during said final of said at least two treatment cycles: measuring absolute lymphocyte count (ALC) and absolute neutrophil count (ANC) and adjusting a dose of cyclophosphamide to be administered to said subject based on the ALC and ANC, wherein cyclophosphamide can be administered at a dose of 200 mg when ALC>1250 per microliter, wherein cyclophosphamide can be administered at a dose of 100 mg when ANC>1000 per microliter and 750<ALC<1250 per microliter, wherein cyclophosphamide can be administered at a dose of 50 mg when ANC is 500-999 per microliter, and wherein cyclophosphamide may not be administered when ANC<500 per microliter and/or ALC<750 per microliter.

In the foregoing embodiments, said treatment cycle, said second treatment cycle and each of said one or more additional treatment cycles can be separated by 0 to 2 weeks. By way of example but not limitation, said treatment cycle, said second treatment cycle and each of said one or more additional treatment cycles can be separated by 0 to 1 weeks or 1 to 2 weeks, and any value between such as, by way of example but not limitation, 0 weeks, 1 week, or 2 weeks.

In the foregoing embodiments, the method can further comprise prior to administering pentostatin to said subject in said first treatment cycle: measuring the creatinine clearance (CrCl) of said subject and adjusting a dose of pentostatin to be administered to said subject based on the CrCl, wherein pentostatin is administered at 1 $mg/m^2$ when CrCl>60 mL/min/1.73 $m^2$, wherein pentostatin is administered at 0.5 $mg/m^2$ when 60 mL/min/1.73 $m^2$>CrCl>30 mL/min/1.73 $m^2$, and wherein pentostatin is not administered when CrCl<30 mL/min/1.73 $m^2$.

In the foregoing embodiments, the method can further comprise prior to administering cyclophosphamide to said subject in said first treatment cycle: measuring absolute neutrophil count (ANC) and adjusting a dose of cyclophosphamide to be administered to said subject based on the ALC and ANC, wherein cyclophosphamide is administered at a dose of 100 mg when ANC>1000 per microliter, wherein cyclophosphamide is administered at a dose of 50 mg when ANC is 500-999 per microliter, and wherein cyclophosphamide is not administered when ANC<500 per microliter.

In the foregoing embodiments, the method can further comprise prior to administering pentostatin to said subject during said second treatment cycle: measuring the creatinine clearance (CrCl) of said subject and adjusting a dose of pentostatin to be administered to said subject based on the CrCl, wherein pentostatin is administered at 2 $mg/m^2$ when CrCl>60 mL/min/1.73 $m^2$, wherein pentostatin is administered at 1 $mg/m^2$ when 60 mL/min/1.73 $m^2$>CrCl>30 mL/min/1.73 $m^2$, and wherein pentostatin is not administered when CrCl<30 mL/min/1.73 $m^2$.

In the foregoing embodiments, the method can further comprise prior to administering cyclophosphamide to said subject during said second treatment cycle: measuring absolute neutrophil count (ANC) and adjusting a dose of cyclophosphamide to be administered to said subject based on the ANC, wherein cyclophosphamide can be administered at a dose of 100 mg when ANC>1000 per microliter, wherein cyclophosphamide can be administered at a dose of 50 mg when ANC is 500-999 per microliter, and wherein cyclophosphamide may not be administered when ANC<500 per microliter.

In the foregoing embodiments, the method can further comprise, prior to each of said one or more additional treatment cycles: measuring absolute lymphocyte count (ALC) in said subject and adjusting the treatment of said subject based on the ALC, wherein if ALC<750 per microliter, administering to said subject a maintenance treatment cycle comprising subjecting said patient to said one or more immune therapy treatment cycles, and wherein if ALC>750 per microliter subjecting patient to said one or more additional treatment cycles.

In the foregoing embodiments, the method can further comprise, prior to each of said one or more additional treatment cycles: measuring absolute lymphocyte count (ALC) in said subject and adjusting the treatment of said subject based on the ALC, wherein if ALC<750 per microliter, administering to said subject a maintenance treatment cycle comprising administering to said subject a nucleoside reverse transcriptase inhibitor and no further of said one or more additional treatment cycles prior to said maintenance treatment cycle, and wherein if ALC>750 per microliter continuing to subject patient to said one or more additional treatment cycles.

In the foregoing embodiments, each of said one or more immune therapy treatment cycles can be, by way of example but not limitation, 18 weeks long. In some embodiments, immune therapy treatment cycles can be separated by 0 to 4 weeks. Immune therapy treatment cycles can be repeated, including indefinitely. Repeating of the immune therapy cycles can be according to a regimen or in the event of relapse. By way of example but not limitation, the immune therapy cycles can occur 1-4 times per year. Pentostatin can be administered to said subject on days 1 and 4 of each of said one or more immune therapy treatment cycles at a dose of 2 mg/m$^2$. Cyclophosphamide can be administered to said subject on days 1, 2, 3, 4, and/or 5 of each of said one or more immune therapy treatment cycles at a dose of 100 mg. Each of said one or more immune therapy treatment cycles can further comprise: administering to said subject a nucleoside reverse transcriptase inhibitor. Said nucleoside reverse transcriptase inhibitor can be lamivudine. Said lamivudine can be administered to said subject during each of said one or more immune therapy treatment cycles at a dose of 150 mg daily to 150 mg twice daily. Each of said one or more immune therapy treatment cycles can further comprise: during each of said one or more immune therapy treatment cycles: measuring the creatinine clearance (CrCl) of said subject and adjusting a dose of lamivudine to be administered to said subject based on the CrCl, wherein lamivudine is administered at 150 mg twice daily when CrCl>50 mL/min/1.73 m$^2$, wherein lamivudine is administered at 150 mg daily when 50 mL/min>CrCl>30 mL/min/1.73 m$^2$, and wherein lamivudine is not administered when CrCl<30 mL/min/1.73 m$^2$.

In the foregoing embodiments, a method can comprise administering to said subject a therapeutically effective amount of manufactured $T_{REG}$ cells.

In the foregoing embodiments, said manufactured $T_{REG}$ cells can be administered to said subject on day 8 of each of said one or more immune therapy treatment cycles. By way of example but not limitation, manufactured $T_{REG}$ cells can be administered to the subject on any day of said immune therapy cycles such as days 1, 2, 3, 4, 5, 6, 7, 8, 9, 10, 11, 12, 13, 14 or 15.

In the foregoing embodiments, said manufactured $T_{REG}$ cells can be administered at a dose between $1\times10^6$ cells per kg of the subject's body weight and $5\times10^6$ cells per kg of the subject's body weight, by way of example and not limitation, $1\times10^6$ cells per kg of the subject's body weight and $5\times10^6$ cells per kg of the subject's body weight, $2\times10^6$ cells per kg of the subject's body weight and $5\times10^6$ cells per kg of the subject's body weight, $3\times10^6$ cells per kg of the subject's body weight and $5\times10^6$ cells per kg of the subject's body weight, $4\times10^6$ cells per kg of the subject's body weight and $5\times10^6$ cells per kg of the subject's body weight, $1\times10^6$ cells per kg of the subject's body weight and $4\times10^6$ cells per kg of the subject's body weight, $1\times10^6$ cells per kg of the subject's body weight and $3\times10^6$ cells per kg of the subject's body weight, $1\times10^6$ cells per kg of the subject's body weight and $2\times10^6$ cells per kg of the subject's body weight, and any values between such as, by way of example but not limitation, $1\times10^6$ cells per kg of the subject's body weight, $2\times10^6$ cells per kg of the subject's body weight, $3\times10^6$ cells per kg of the subject's body weight, $4\times10^6$ cells per kg of the subject's body weight, or $5\times10^6$ cells per kg of the subject's body weight.

Each of said one or more treatment cycles can further comprise: administering to said subject pentostatin; and/or administering to said subject cyclophosphamide. Pentostatin can be administered to said subject at a dose of between 1 mg/m$^2$ and 2 mg/m$^2$, and any value between such as, by way of example but not limitation 1 mg/m$^2$, 1.5 mg/m$^2$, or 2 mg/m$^2$. A dose of said cyclophosphamide can be between 100 mg and 200 mg, and any value between such as, by way of example but not limitation 100 mg, 150 mg, or 200 mg. Said pentostatin can be administered to said subject on days 1 and 4 of each of said one or more treatment cycles. Said cyclophosphamide can be administered to said subject on days 1, 2, 3, 4 and/or 5 of each of said one or more treatment cycles. Said subject can have been previously treated with pentostatin and cyclophosphamide. Each of said one or more treatment cycles can further comprise administering to said subject a nucleoside reverse transcriptase inhibitor. Said nucleoside reverse transcriptase inhibitor can be an inhibitor of the NLRP3 inflammasome. Said nucleoside reverse transcriptase inhibitor can be lamivudine. Each of said one or more treatment cycles can be 4 weeks apart.

In the foregoing embodiments, the method can further comprise administering to said subject normal $T_{REG}$ cells simultaneously with said manufactured $T_{REG}$ cells. In the foregoing embodiments, the method can further comprise prior to said one or more treatment cycles: harvesting peripheral lymphocytes from said subject. In the foregoing embodiments, the method can further comprise, after harvesting peripheral lymphocytes from said subject: culturing said peripheral lymphocytes to yield said manufactured $T_{REG}$ cells.

EXAMPLES

The following examples are provided to better illustrate the methods of the present disclosure and the resultant de-differentiated and i$T_{REG}$ or re-differentiated T cells. These examples are not intended to be limiting or to otherwise alter the scope of the methods, cells and compositions disclosed in the present disclosure.

Example 1: Combination Vitamin D and Temsirolimus Reduces T Cell Effector Molecules We directly evaluated the individual effect of Vitamin D, mTOR inhibition (using the parenteral form of rapamycin, temsirolimus), and the combination of Vitamin D plus temsirolimus on human T cell effector molecule expression (see FIG. 1).

FIGS. 1A-1D illustrate that the combination of Vitamin D and temsirolimus reduces effector molecule expression in human CD4$^+$ and CD8$^+$ T cells. For columns #2 through #5, T cells were subjected to a 3-day de-differentiation interval that included a low-level of anti-CD3/anti-CD28 co-stimulation (bead-to-T cell ratio; 1:3); a high-dose of temsirolimus (1 μM); vitamin D (0.1 or 1.0 nM); and culture in X-Vivo 20 media. The first column represents a control culture (no temsirolimus, no Vitamin D, use of a bead-to-T cell ratio of 3:1; and inclusion of the type I polarizing cytokine IFN-α (20,000 IU/mL, unless otherwise stated, this amount is used in the following examples 1-11 for the control culture)). The second column represents the culture that had the low bead-to-T cell ratio and temsirolimus but did not contain Vitamin D; in contrast, the third column represents the culture that had Vitamin D (0.1 nM) but no temsirolimus. The fourth column represents the culture with high-dose ("HD") vitamin D (1.0 nM) but no temsirolimus. The fifth column represents the culture that had both a high-dose of vitamin D (1.0 nM) combined with temsirolimus. At the end of the de-differentiation interval, cells were harvested, RNA was isolated, and RNA expression analysis was performed by Luminex Quantigene method. All results shown represent relative RNA expression, with results normalized to a value of 1.0 for the Th1/Tc1 control culture.

A 3-day culture interval was used that included a low level of T cell co-stimulation (anti-CD3/anti-CD28 bead-to-T cell ratio of 1:3; typical ratio used in literature is the inverse, 3:1), temsirolimus (1 μM), Vitamin D at doses of either 0.1 or 1.0 nM, or the combination of temsirolimus and the higher-dose of Vitamin D. After culture, RNA was harvested and the level of effector molecule expression was compared to the control culture.

Figure 1C:
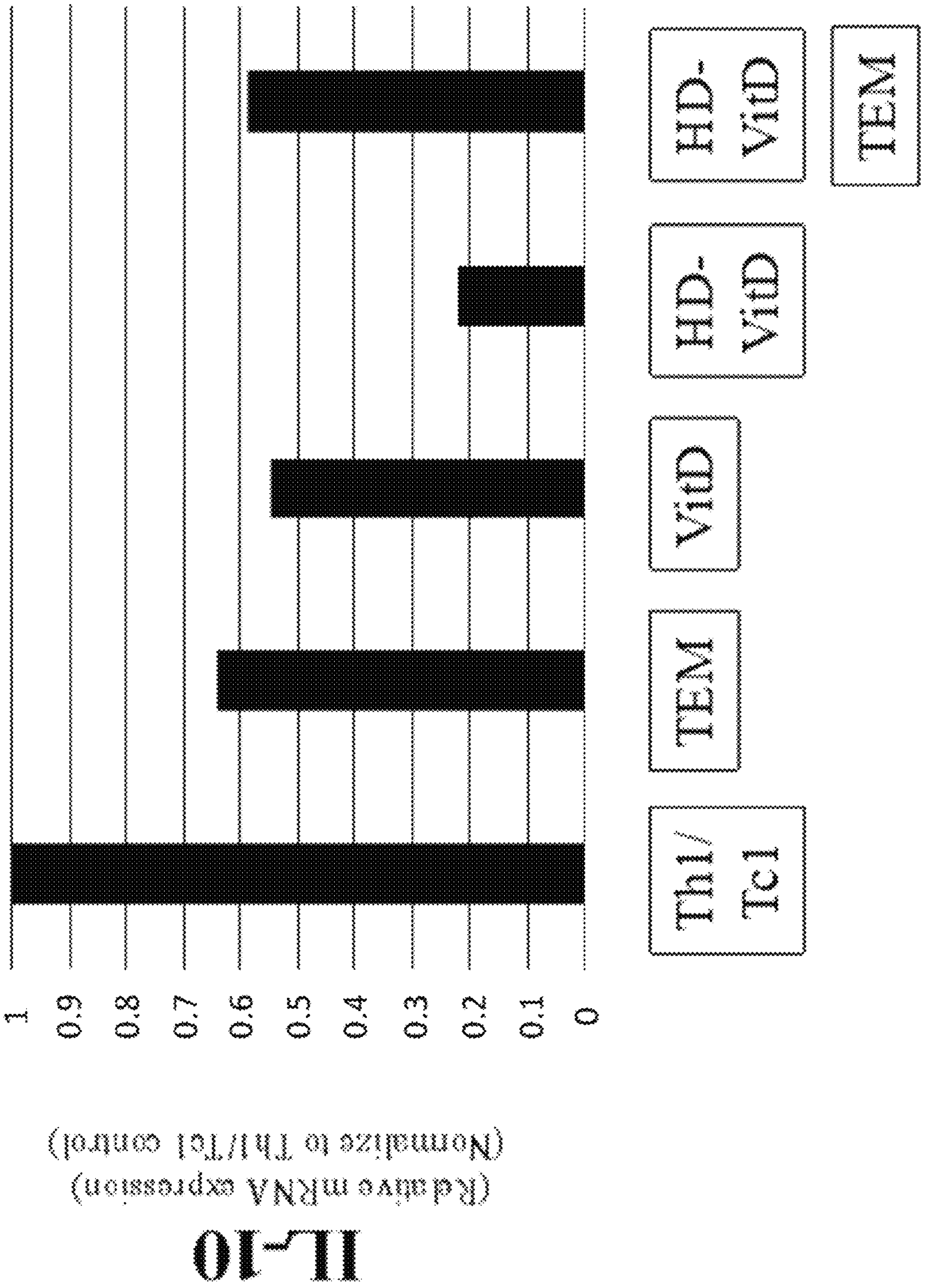
FIG. 1C depicts normalized IL-10 mRNA expression for the control cells and cells treated under various conditions.
Figure 1D:
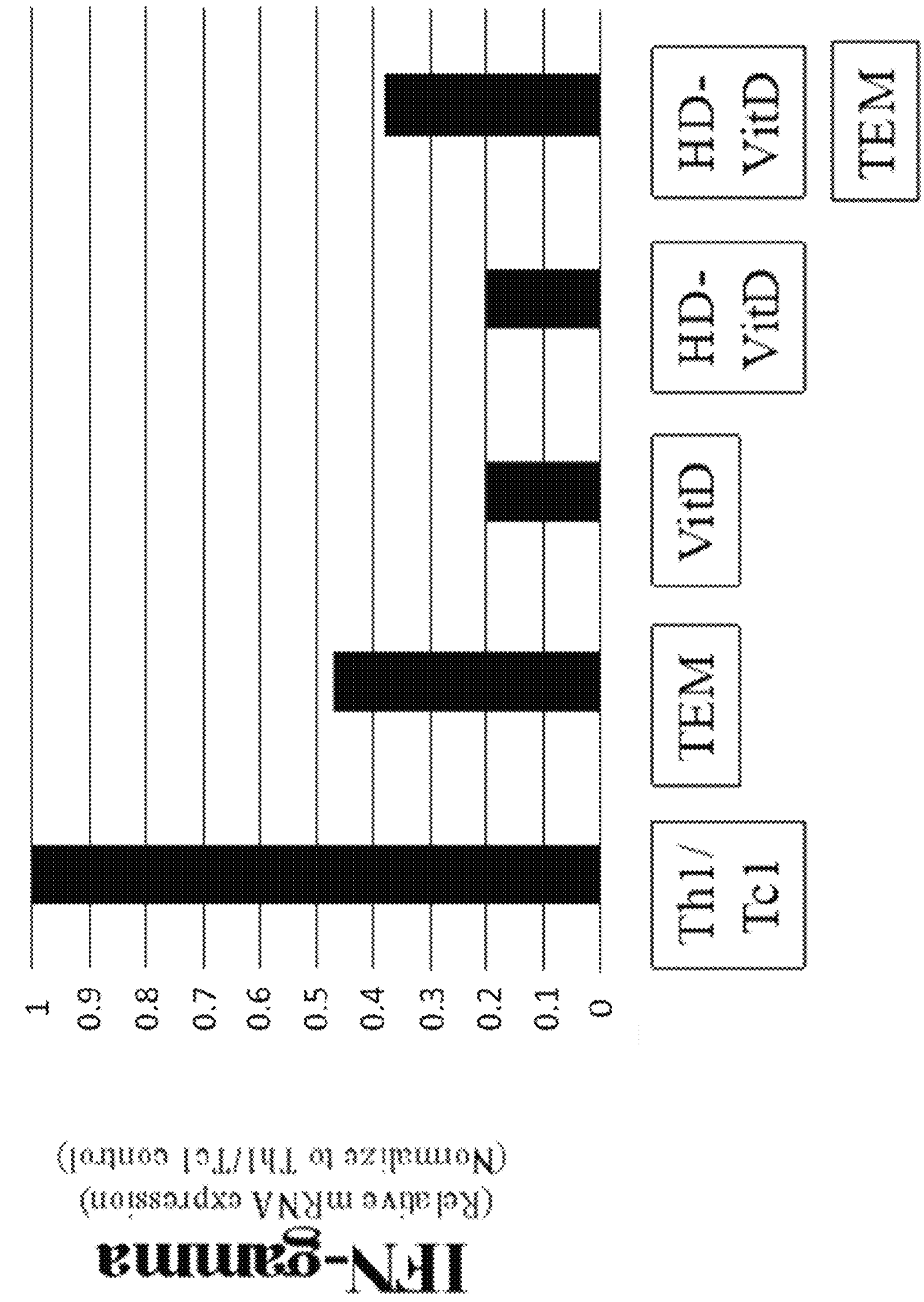
FIG. 1D depicts normalized IFN-γ mRNA expression for the control cells and cells treated under various conditions.

As FIG. 1A shows, the various cultures had similar RNA expression of housekeeping control genes, including GAPDH. In marked contrast, relative to the control Th1/Tc1 cell culture that did not receive Vitamin D or temsirolimus, the culture addition of temsirolimus, Vitamin D, or the combination of temsirolimus plus Vitamin D resulted in the reduction in the RNA expression of T cell effector molecules, including the cytotoxic molecule Granzyme B (FIG. 1B) and the cytokine molecules IL-10 (a Th2 cytokine; FIG. 1C) and IFN-gamma (a Th1 cytokine; FIG. 1D). Thus, Granzyme B and IFN-γ as markers of de-differentiation indicate that Vitamin D is effective at concentrations from 0.1 to 1.0 nM. Temsirolimus at a dose of 1 μM acts alone beneficially as an agent of de-differentiation (column 2, reduction in granzyme B and IFN-gamma) and does not abrogate the effect of Vitamin D when used in combination (column 5).

As such, using low-level co-stimulation (1:3 ratio of anti-CD3/anti-CD28 beads to T cells) and a short 3-day culture interval, the addition of temsirolimus, Vitamin D, or the combination of temsirolimus plus Vitamin D can be utilized to reduce both Th1 and Th2 cytokine effectors and cytotoxic effector mechanisms.

Example 2: Combination Vitamin D and Temsirolimus Alters Key Transcription Factors Associated with De-Differentiation We also evaluated the effect of Vitamin D, temsirolimus, or the combination on the expression of key transcription factors after a low-level of co-stimulation.

FIGS. 2A-2D illustrate that the combination of Vitamin D and temsirolimus increases expression of stem cell-associated transcription factors and the primitive T cell molecule IL-7 receptor-alpha in human $CD4^+$ and $CD8^+$ T cells. The combination of Vitamin D and temsirolimus reduces effector molecule expression in human $CD4^+$ and $CD8^+$ T cells. For columns #2 through #5, T cells were subjected to a 3-day de-differentiation interval that included a low-level of anti-CD3/anti-CD28 co-stimulation (bead-to-T cell ratio; 1:3); a high-dose of temsirolimus (1 μM); vitamin D (0.1 or 1.0 nM); and culture in X-Vivo 20 media. The first column represents a control culture (no temsirolimus, no Vitamin D, use of a bead-to-T cell ratio of 3:1; and inclusion of the type I polarizing cytokine IFN-α). The second column represents the culture that had the low bead-to-T cell ratio and temsirolimus but did not contain Vitamin D; in contrast, the third column represents the culture that had Vitamin D (0.1 nM) but no temsirolimus. The fourth column represents the culture with high-dose ("HD") vitamin D (1.0 nM) but no temsirolimus. The fifth column represents the culture that had both a high-dose of vitamin D (1.0 nM) combined with temsirolimus. At the end of the de-differentiation interval, cells were harvested, RNA was isolated, and RNA expression analysis was performed by Luminex Quantigene method. All results shown represent relative RNA expression, with results normalized to a value of 1.0 for the Th1/Tc1 control culture.

Figure 2A:
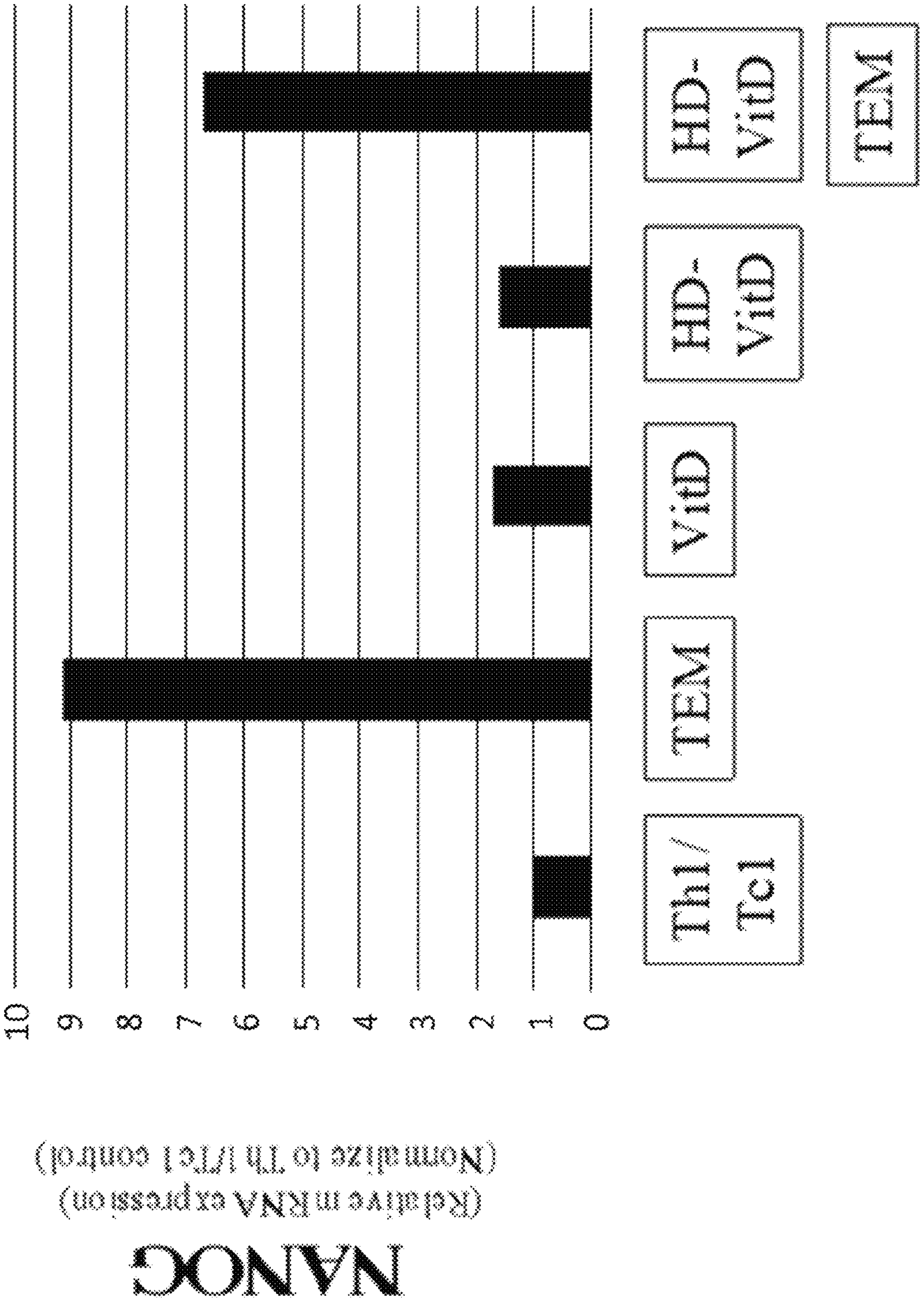
FIG. 2A depicts normalized NANOG mRNA expression for the control cells and cells treated under various conditions.

As FIG. 2A shows, temsirolimus or the combination of temsirolimus plus Vitamin D resulted in up-regulation of the Nanog transcription factor, which is recognized as one of the few key factors required for somatic cell de-differentiation towards an iPSC state. Previously, in human fibroblasts, mTOR inhibition using rapamycin was found to increase Nanog expression; in contrast, Vitamin D receptor signaling was found to reduce the expression of transcription factors associated with the iPSC state.

As such, using a low-level of co-stimulation, temsirolimus increases the iPSC transcription factor Nanog; this promoting effect of temsirolimus is not abrogated by Vitamin D at concentrations ranging from 0.1 to 1.0 nM.

Figure 2B:
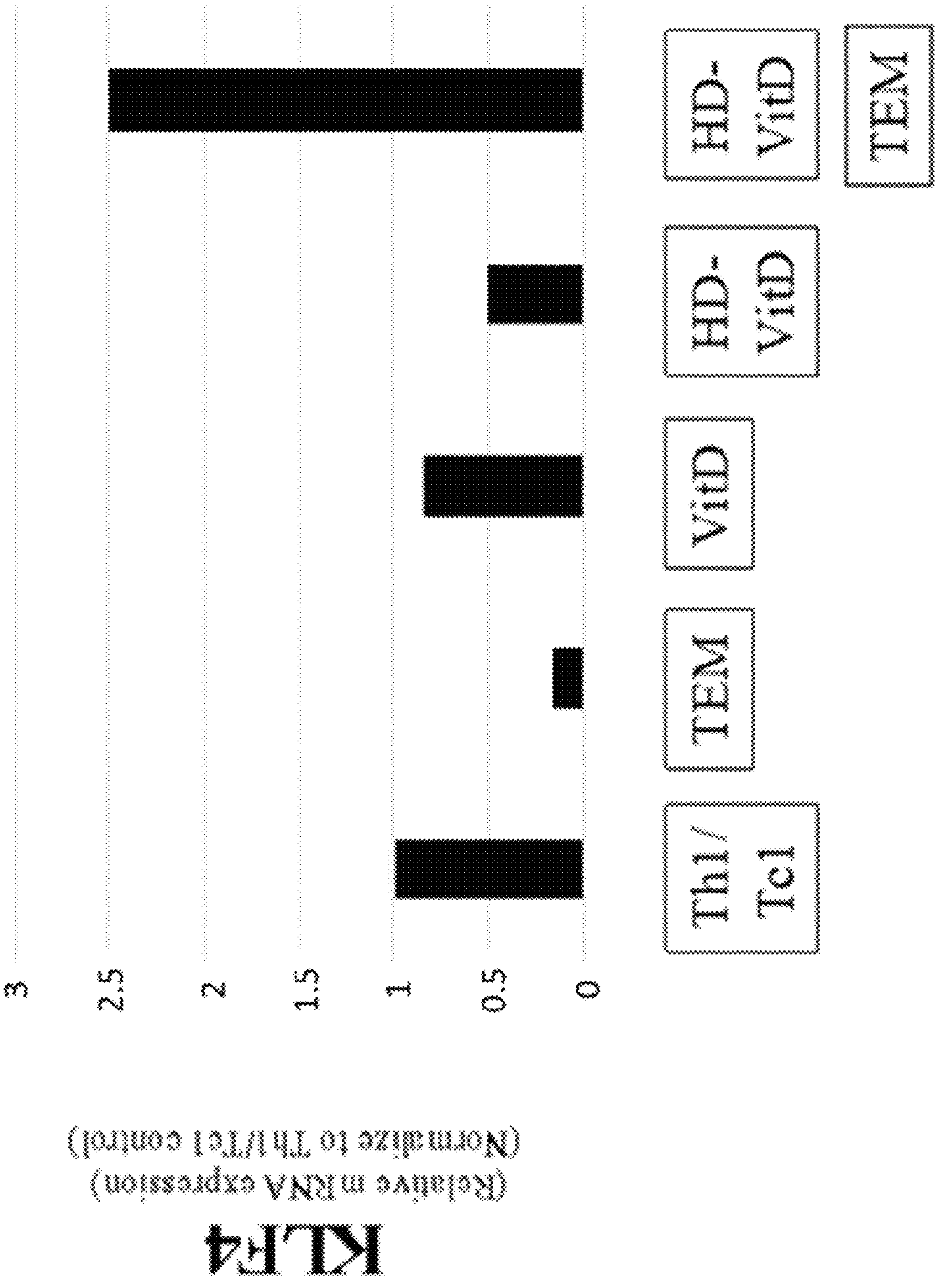
FIG. 2B depicts normalized KLF4 mRNA expression for the control cells and cells treated under various conditions.

By comparison, neither temsirolimus nor Vitamin D alone increased the RNA expression of the KLF4 molecule, which is also one of the classical transcription factors associated with the iPSC state. However, the combination of temsirolimus plus Vitamin D (1.0 nM) increased KLF4 RNA expression. As such, it is preferable to include both temsirolimus and Vitamin D in T cell de-differentiation attempts. As FIG. 2B shows, although neither temsirolimus or Vitamin D acts alone to beneficially up-regulate the de-differentiation molecule KLF4, the combination of temsirolimus (1 μM) and Vitamin D (1.0 nM) synergistically up-regulate KLF4.

Figure 2C:
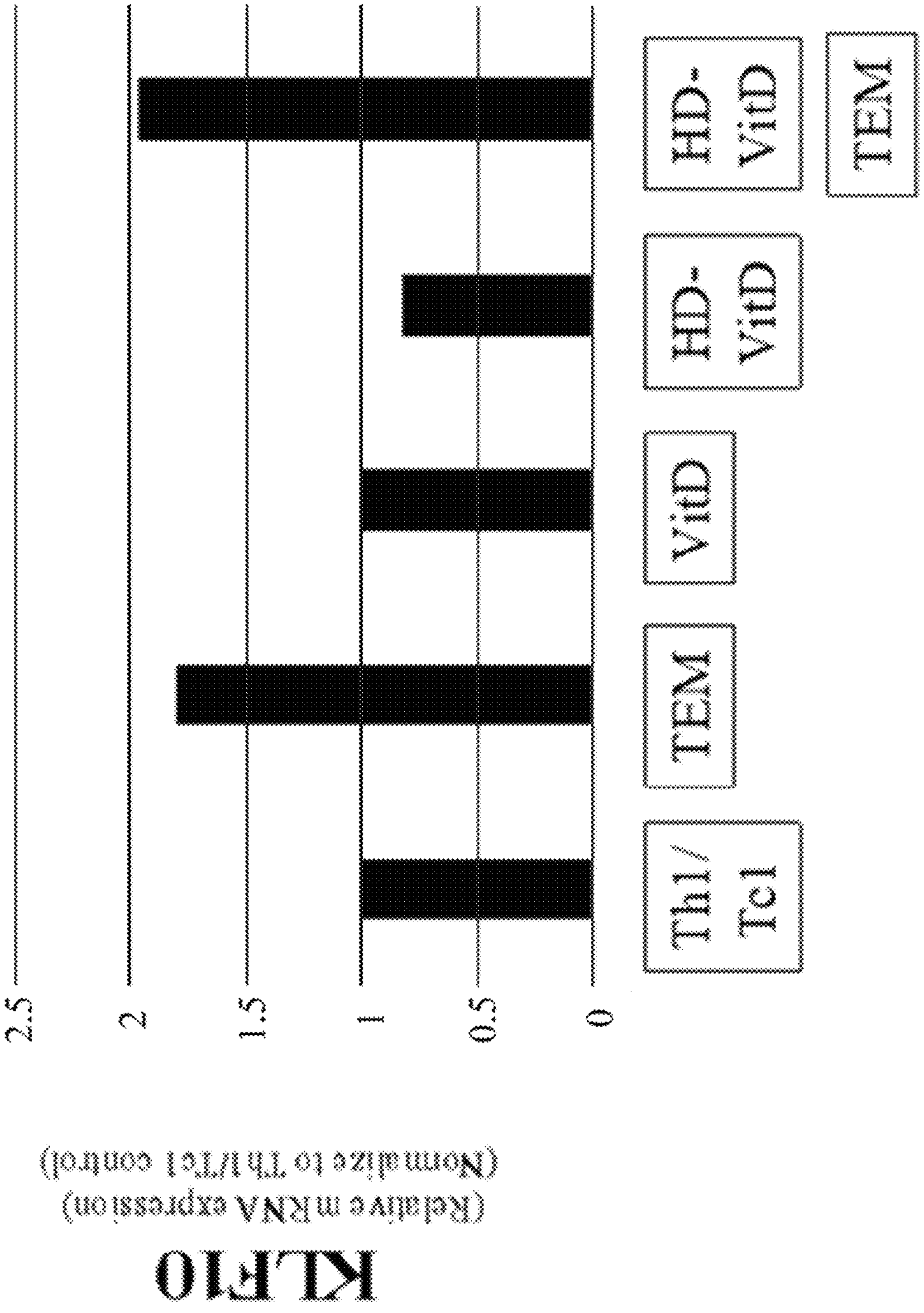
FIG. 2C depicts normalized KLF10 mRNA expression for the control cells and cells treated under various conditions.

A related transcription factor, KLF10, was also up-regulated when the combination of temsirolimus plus Vitamin D (1.0 nM) was utilized. As FIG. 2C shows, temsirolimus at a dose of 1 μM acts alone to beneficially up-regulate the de-differentiation molecules KLF10, Nanog, and IL-7 receptor alpha; although Vitamin D does not act alone to up-regulate these molecules, it does not abrogate the effect of temsirolimus when used in combination (column 5).

Figure 2D:
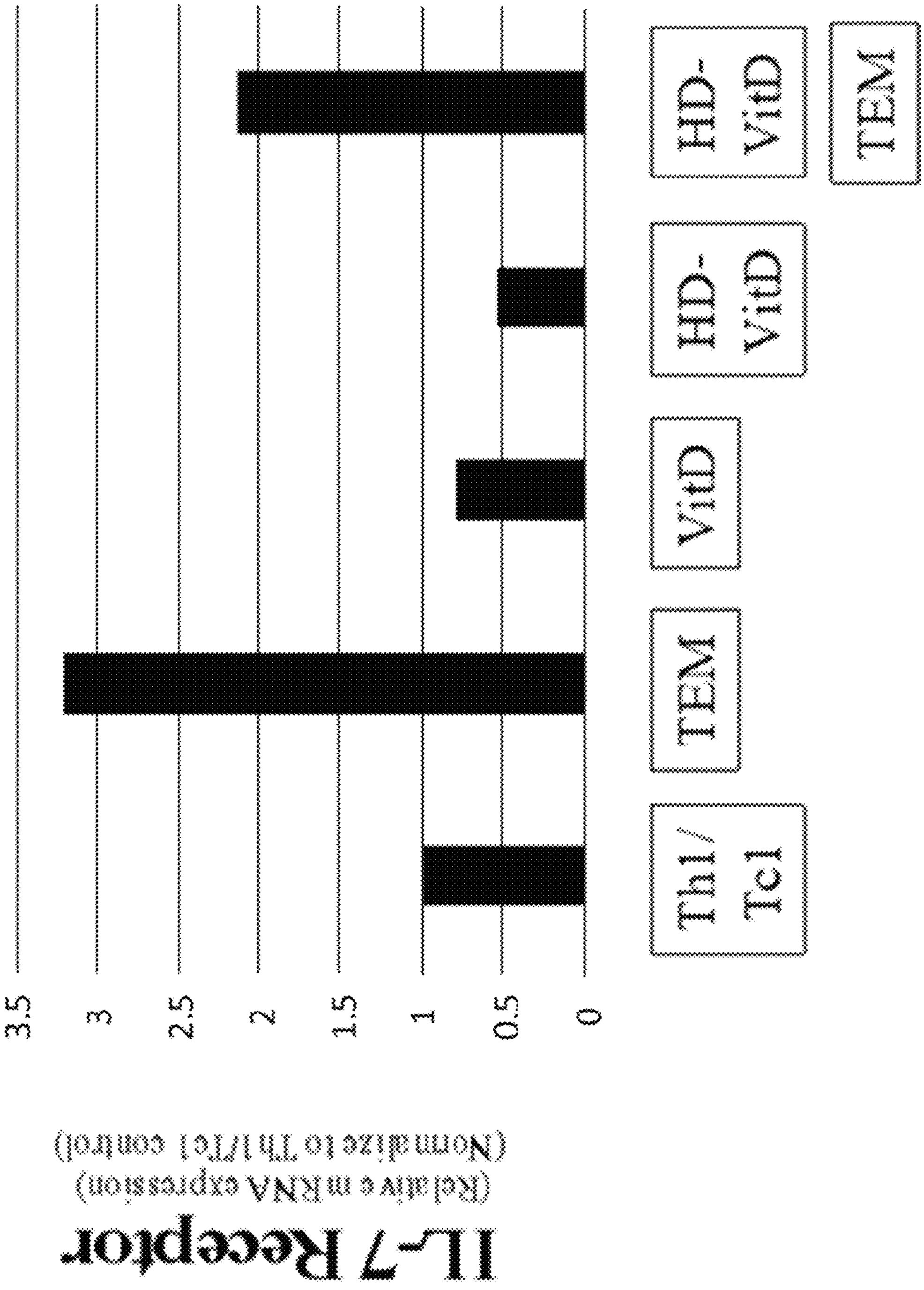
FIG. 2D depicts normalized IL-7 receptor mRNA expression for the control cells and cells treated under various conditions.

Finally, we evaluated cultured cells for RNA expression of IL-7 receptor alpha, which is up-regulated in T cells having a reduced differentiation status. Importantly, temsirolimus alone but not Vitamin D alone was capable of up-regulating IL-7 receptor alpha. Nonetheless, the combination of Vitamin D (1.0 nM) plus temsirolimus resulted in IL-7 receptor alpha up-regulation, as shown in FIG. 2D.

In sum, these data indicate that low-level co-stimulation combined with temsirolimus can be used to enforce T cell de-differentiation; preferably, culture should include temsirolimus plus Vitamin D for a more complete pattern of de-differentiation.

Example 3: Combination Vitamin D and Temsirolimus Reduces Key Transcription Factors Associated with Th1 Differentiation while Maintaining HIF-1-α Expression We also evaluated the effect of Vitamin D, temsirolimus, or the combination on the expression of key transcription factors associated with Th1-type differentiation, namely T-BET and STAT1.

Figure 3A:
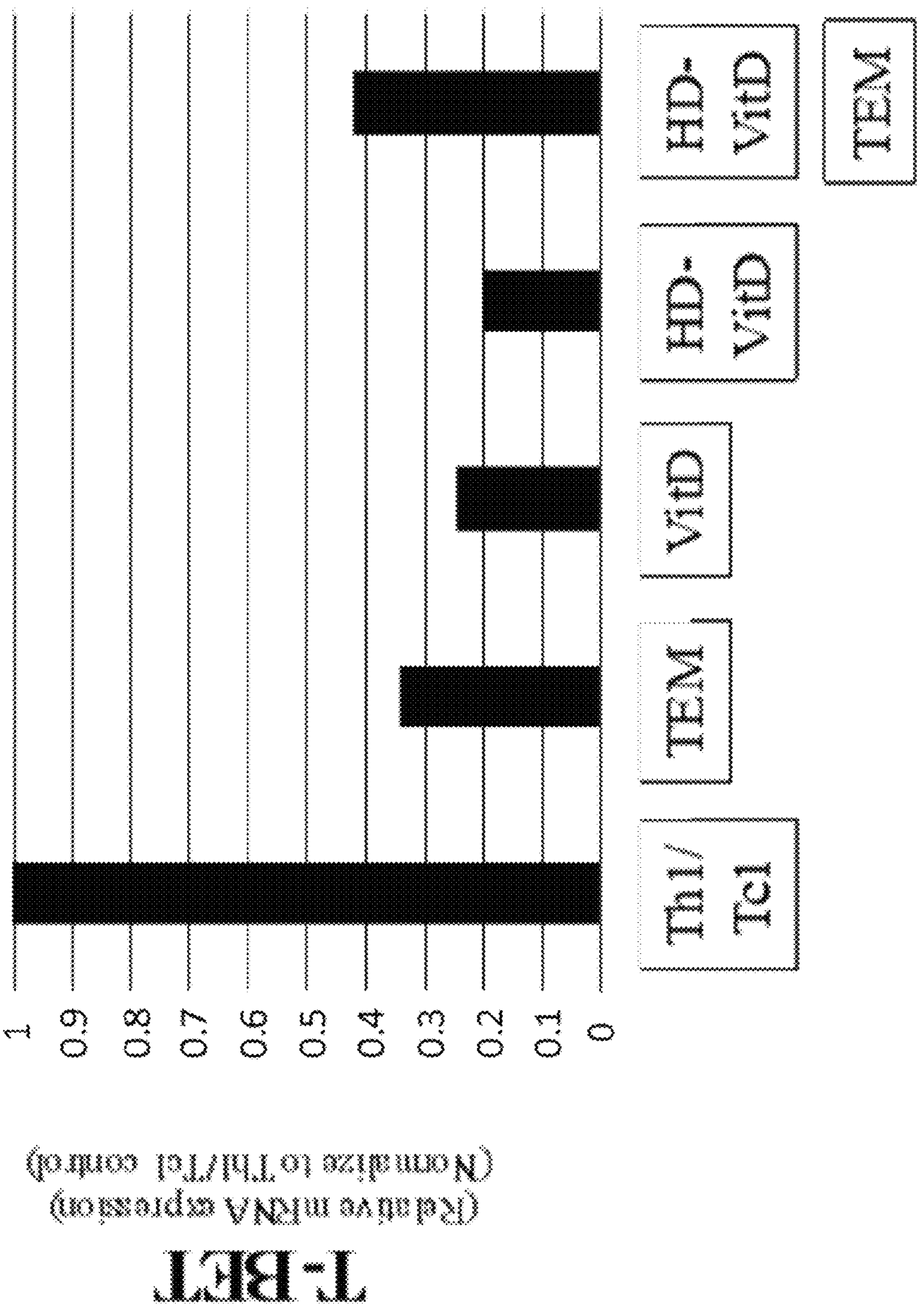
FIG. 3A depicts normalized T-BET mRNA expression for the control cells and cells treated under various conditions.
Figure 3B:
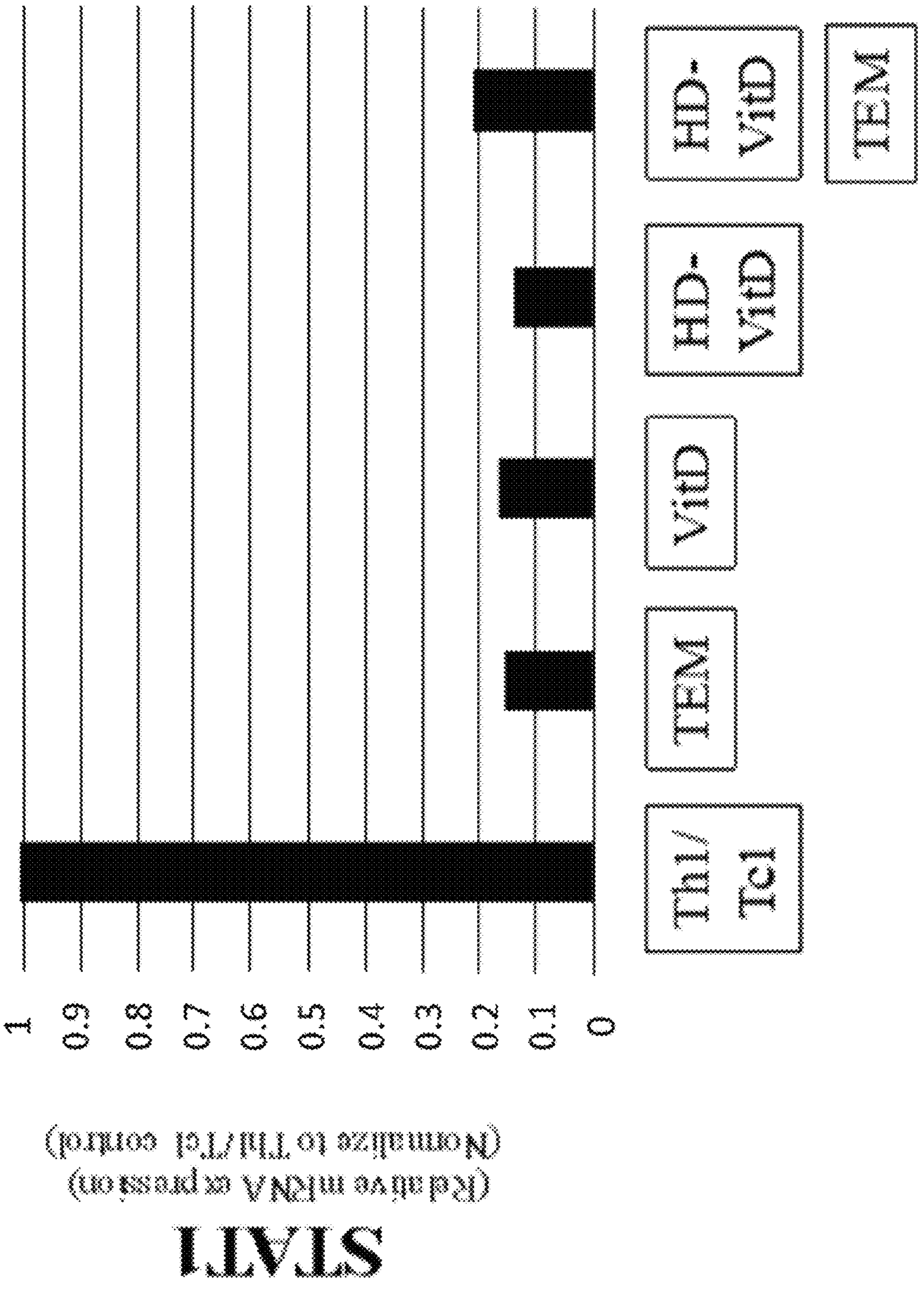
FIG. 3B depicts normalized STAT1 mRNA expression for the control cells and cells treated under various conditions.
Figure 3C:
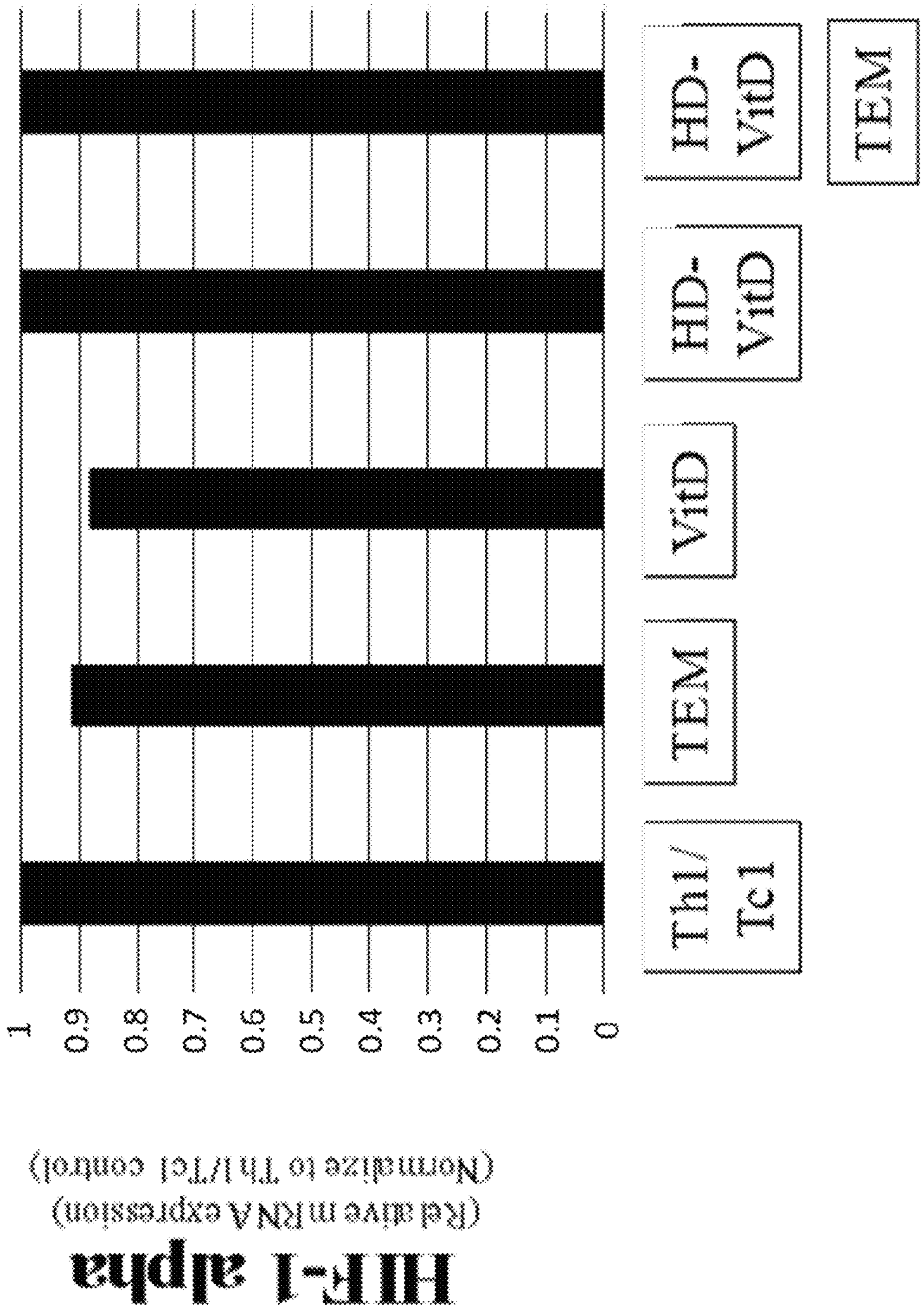
FIG. 3C depicts normalized HIF-1-α mRNA expression for the control cells and cells treated under various conditions.

FIG. 3A-3C illustrate that the combination of Vitamin D and temsirolimus reduces expression of transcription factors associated with effector Th1/Tc1 cells without reducing expression of a transcription factor associated with T cell survival, HIF-1-α. The combination of Vitamin D and temsirolimus reduces effector molecule expression in human $CD4^+$ and $CD8^+$ T cells. For columns #2 through #5, T cells were subjected to a 3-day de-differentiation interval that included a low-level of anti-CD3/anti-CD28 co-stimulation (bead-to-T cell ratio; 1:3); a high-dose of temsirolimus (1 μM); vitamin D (0.1 or 1.0 nM); and culture in X-Vivo 20 media. The first column represents a control culture (no temsirolimus, no Vitamin D, use of a bead-to-T cell ratio of 3:1; and inclusion of the type I polarizing cytokine IFN-α). The second column represents the culture that had the low bead-to-T cell ratio and temsirolimus but did not contain Vitamin D; in contrast, the third column represents the culture that had Vitamin D (0.1 nM) but no temsirolimus. The fourth column represents the culture with high-dose ("HD") vitamin D (1.0 nM) but no temsirolimus. The fifth column represents the culture that had both a high-dose of vitamin D (1.0 nM) combined with temsirolimus. At the end of the de-differentiation interval, cells were harvested, RNA was isolated, and RNA expression analysis was performed by Luminex Quantigene method. All results shown represent relative RNA expression, with results normalized to a value of 1.0 for the Th1/Tc1 control culture.

Importantly each agent or the combination of agents down-regulated both T-BET RNA (FIG. 3A) and STAT1 RNA (FIG. 3B). As shown in FIGS. 3A-3C, Vitamin D at a dose of 0.1 to 1.0 nM acts alone to beneficially down-regulate the differentiation molecules T-BET and STAT1. Temsirolimus at a dose of 1 μM does not detrimentally down-regulate the pro-survival transcription factor, HIF-1 alpha, even when combined with 1.0 nM Vitamin D. Yet, temsirolimus at a dose of 1 μM acts alone to beneficially down-regulate the differentiation molecules T-BET and STAT1; combination with Vitamin D yields a similar result (these two agents are not antagonistic).

In marked contrast, temsirolimus at a dose of 1 μM, Vitamin D at a dose of 0.1 to 1.0 nM, or the combination did not down-regulate the key transcription factor HIF-1-α (FIG. 3C), which is important as a T cell survival factor that is critical for anti-tumor effects.

In sum, these data indicate that the combination of low-level co-stimulation, temsirolimus, and Vitamin D can be used to reduce transcription factors required for Th1 generation without inhibiting a key transcription factor required for overall T cell survival, HIF-1-α.

Example 4: The Combination Vitamin D, Temsirolimus, and an Anti-IL-2 Receptor Monoclonal Antibody Increases an Autophagy Signature We also evaluated the effect of Vitamin D, temsirolimus, or the combination on the process of autophagy, which is critical for promotion of a stem-like, de-differentiated state. The level of autophagy can be determined in-part by the subsequent up-regulation of the autophagy substrate, p62, by western blot analysis.

Figure 4:
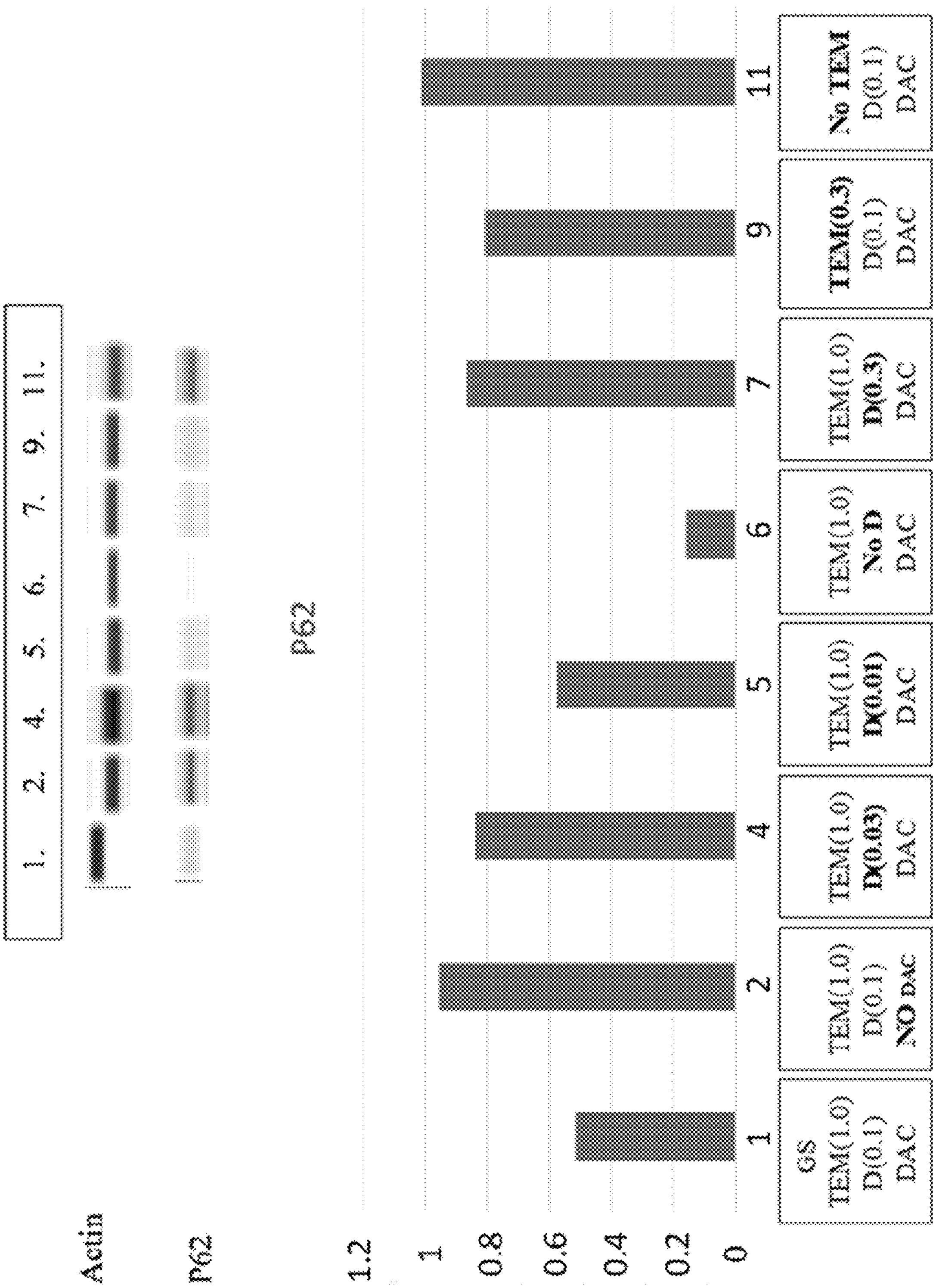
FIG. 4 depicts p62 expression normalized by actin expression for cells treated under various conditions and illustrates that the combination of Vitamin D, temsirolimus, and anti-IL-2 receptor blockade induces expression of the autophagy-related molecule, p62.

FIG. 4 illustrates that the combination of Vitamin D, temsirolimus, and anti-IL-2 receptor blockade induces expression of the autophagy-related molecule, p62. Human $CD4^+$ and $CD8^+$ T cells were subjected to the de-differentiation protocol, which involved a 3-day culture using low level co-stimulation (1:3 bead-to-T cell ratio), temsirolimus ("TEM", as indicated in FIG. 4; concentration of 1.0 or 0.3 μM), Vitamin D ("D", as indicated; concentration of 0.01, 0.03, 0.1, 0.3, or 1.0 nM), and an anti-IL-2 receptor monoclonal antibody (Daclizumab, 50 μg/ml; "DAC", as indicated). After the 3-day culture interval, the T cells were harvested, and protein was isolated and subjected to western blot analysis for the autophagy-related gene, p62, and the housekeeping gene, Actin.

As FIG. 4 demonstrates, inclusion of Vitamin D in the T cell culture was critical for increasing autophagy, as measured by up-regulated p62. Vitamin D at a dose of 0.01 to 0.1 nM works in concert with temsirolimus at a concentration of 0.3 to 1.0 μM to beneficially up-regulate the autophagy marker p62 during de-differentiation. That is, in FIG. 4, culture #6 (fifth column), there was very little p62 expression on western blot analysis, consistent with a low level of autophagy; as the figure legend indicates, this culture condition received a low-level of co-stimulation, temsirolimus, the anti-IL-2 receptor monoclonal antibody daclizumab, but did not receive Vitamin D.

In marked contrast, the other culture conditions each received Vitamin D supplementation and each had increased p62 expression (effective dose range of Vitamin D, 0.01 nM to 1.0 nM). This FIG. 4 also demonstrates that Vitamin D without anti-IL-2 receptor monoclonal antibody addition and Vitamin D without temsirolimus addition was sufficient for induction of T cell autophagy.

In sum, these data indicate that inclusion of Vitamin D with low-level co-stimulation is an efficient method for the induction of T cell autophagy either alone or in combination with other T cell inhibitors, namely the anti-IL-2 receptor reagents or the mTOR inhibitor temsirolimus.

Example 5: The Combination Vitamin D, Temsirolimus, and an Anti-IL-2 Receptor Monoclonal Antibody Results in Optimal Disruption of the mTORC1 Complex We also evaluated the effect of the various T cell culture conditions on expression of Raptor, which is a critical component of the mTORC1 signaling complex. Importantly, inhibition of mTORC1 has recently been discovered to be critical for somatic cell reprogramming to an iPSC state.

Figure 5:
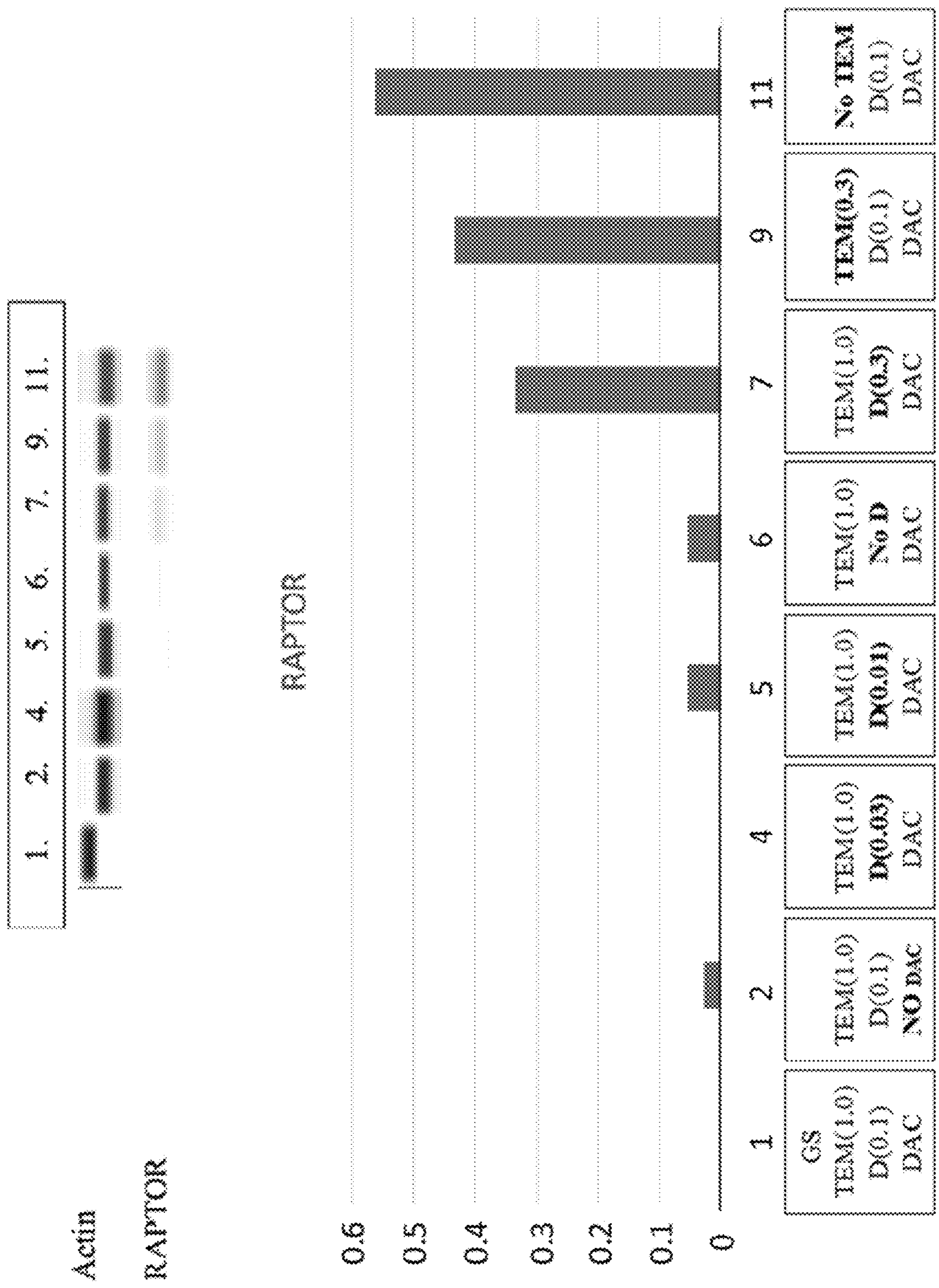
FIG. 5 depicts Raptor expression normalized by actin expression for cells treated under various conditions and illustrates that the combination of Vitamin D, temsirolimus, and anti-IL-2 receptor blockade reduces expression of the mTORC1-related molecule, Raptor.

FIG. 5 illustrates that the combination of Vitamin D, temsirolimus, and anti-IL-2 receptor blockade reduces expression of the mTORC1-related molecule, Raptor. Human $CD4^+$ and $CD8^+$ T cells were subjected to the de-differentiation protocol, which involved a 3-day culture using low level co-stimulation (1:3 bead-to-T cell ratio), temsirolimus ("TEM", as indicated in FIG. 5; concentration of 1.0 or 0.3 μM), Vitamin D ("D", as indicated; concentration of 0.01, 0.03, 0.1, 0.3, or 1.0 nM), and an anti-IL-2 receptor monoclonal antibody (Daclizumab, 50 ng/ml; "DAC", as indicated). After the 3-day culture interval, the T cells were harvested, and protein was isolated and subjected to western blot analysis for the mTORC1 complex protein, Raptor, and the housekeeping gene, Actin.

As FIG. 5 demonstrates, optimal inhibition of the mTORC1 complex, as indicated by reduction in Raptor expression, occurred when T cells were co-stimulated at a low bead-to-T cell ratio (1:3) in combination with temsirolimus (1.0 μM), Vitamin D (0.1 nM), and the anti-IL-2 receptor monoclonal antibody daclizumab (50 μg/nl) (first column shown; culture 1).

As FIG. 5 demonstrates, the omission of daclizumab resulted in a modest increase in Raptor expression, thereby indicating a role for an anti-IL-2 receptor reagent for optimal mTORC1 inhibition. Thus, anti-IL-2 receptor monoclonal antibody Daclizumab (dose, 50 μg/ml) plays a beneficial role in suppressing the mTORC1 sub-unit molecule, Raptor (column 2)

As FIG. 5 demonstrates, the optimal inhibition of mTORC1 sub-unit molecule Raptor by Vitamin D is a Vitamin D dose between 0.03 to 0.1 nM; concentrations lower than or higher than this range led to less optimal suppression of Raptor. Thus, levels of Vitamin D as low as 0.03 nM are sufficient for optimal inhibition of Raptor; reducing the Vitamin D level to 0.01 nM, however, results in a sub-optimal Raptor inhibition. Furthermore, increasing the Vitamin D level beyond the 0.1 nM concentration can be detrimental, as indicated by culture 7 (0.3 nM concentration of Vitamin D), which had a higher level of Raptor expression.

Furthermore, as FIG. 5 indicates, the optimal down-regulation of Raptor requires the combination of Vitamin D plus temsirolimus, with the temsirolimus dose optimally being 1.0 μM, as culture 9 that was supplemented with temsirolimus at the concentration of 0.3 μM had higher levels of Raptor expression.

Example 6: The Combination of Vitamin D, Temsirolimus, and an Anti-IL-2 Receptor Monoclonal Antibody Disrupts Both the mTORC1 Complex and the mTORC2 Complex We also evaluated the mTORC2 complex, which is not directly sensitive to the inhibitory effects of rapamycin but can be influenced by conditions that result in prolonged mTORC1 blockade. Importantly, inhibition of mTORC2 can promote a stem-like state.

Figure 6:
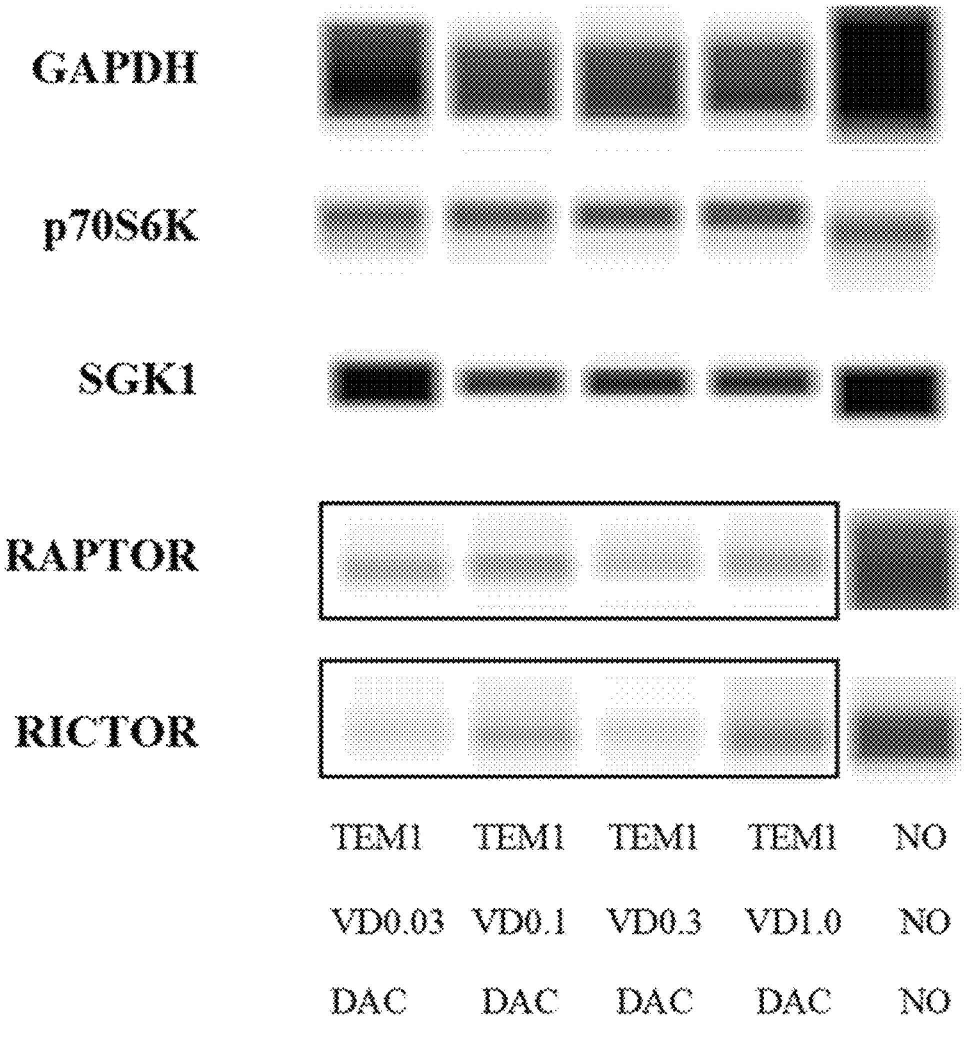
FIG. 6 depicts a Western blot of GAPDH, p70S6K, SGK1, Raptor and Rictor expression for cells treated under various conditions and illustrates that the combination of Vitamin D, temsirolimus, and anti-IL-2 receptor blockade reduces expression of the mTORC1-related molecule, Raptor, and the mTORC2-related molecule, Rictor.

FIG. 6 illustrates that the combination of Vitamin D, temsirolimus, and anti-IL-2 receptor blockade reduces expression of the mTORC1-related molecule, Raptor, and the mTORC2-related molecule, Rictor. Human $CD4^+$ and $CD8^+$ T cells were subjected to the de-differentiation protocol, which involved a 3-day culture using low level co-stimulation (1:3 bead-to-T cell ratio), temsirolimus ("TEM", as indicated in FIG. 6; concentration of 1.0 μM), Vitamin D ("D", as indicated; concentration of 0.03, 0.1, 0.3, or 1.0 nM), and an anti-IL-2 receptor monoclonal antibody (Daclizumab, 50 ng/ml; "DAC", as indicated). After the 3-day culture interval, the T cells were harvested, and protein was isolated and subjected to western blot analysis for the mTORC1 complex protein, Raptor; the mTORC2 complex protein, Rictor; the post-mTORC1 protein p70S6K; the post-mTORC2 protein, SGK1; and the housekeeping gene, GAPDH.

As FIG. 6 illustrates, relative to the control culture that did not contain any of the three inhibitors, T cell culture in media containing temsirolimus, Vitamin D, and the anti-IL-2 receptor antibody daclizumab had a reduction in both the mTORC1 molecule Raptor and the mTORC2 molecule Rictor. Levels of the post-mTORC1 molecule p70S6K and the post-mTORC2 molecule SGK1 were relatively preserved. Thus, Vitamin D (concentration between 0.03 and 1.0 nM) was effective during combination agent de-differentiation for down-regulation of the mTORC2 sub-unit, Rictor. And, temsirolimus at a concentration of 1 μM was effective during combination agent de-differentiation for down-regulation of the mTORC2 sub-unit, Rictor. Moreover, anti-IL-2 receptor monoclonal antibody Daclizumab (dose, 50 μg/ml) did not abrogate the ability of temsirolimus and Vitamin D to down-regulate the mTORC2 sub-unit Rictor.

As such, T cell culture using a low level of co-stimulation and a three-part inhibitory regimen of temsirolimus, Vitamin D, and anti-IL-2 receptor monoclonal antibody represents a novel method to reduce both Raptor and Rictor subunits.

Example 7: The Combination of Vitamin D), Temsirolimus, and an Anti-IL-2 Receptor Monoclonal Antibody Reduces Expression of the Pro-Apoptotic Bcl2-Family Member Gene, BIM As a result of autophagy at the level of the mitochondria (mitophagy), the quality of the mitochondrial proteins can be altered; in particular, with mitophagy, there can be an advantageous shift in the bcl2-family member genes from pro-apoptotic family members such as BIM towards anti-apoptotic family member genes. In addition, culture methods that reduce the apoptotic tendency are associated with an increased capacity for de-differentiation.

Figure 7:
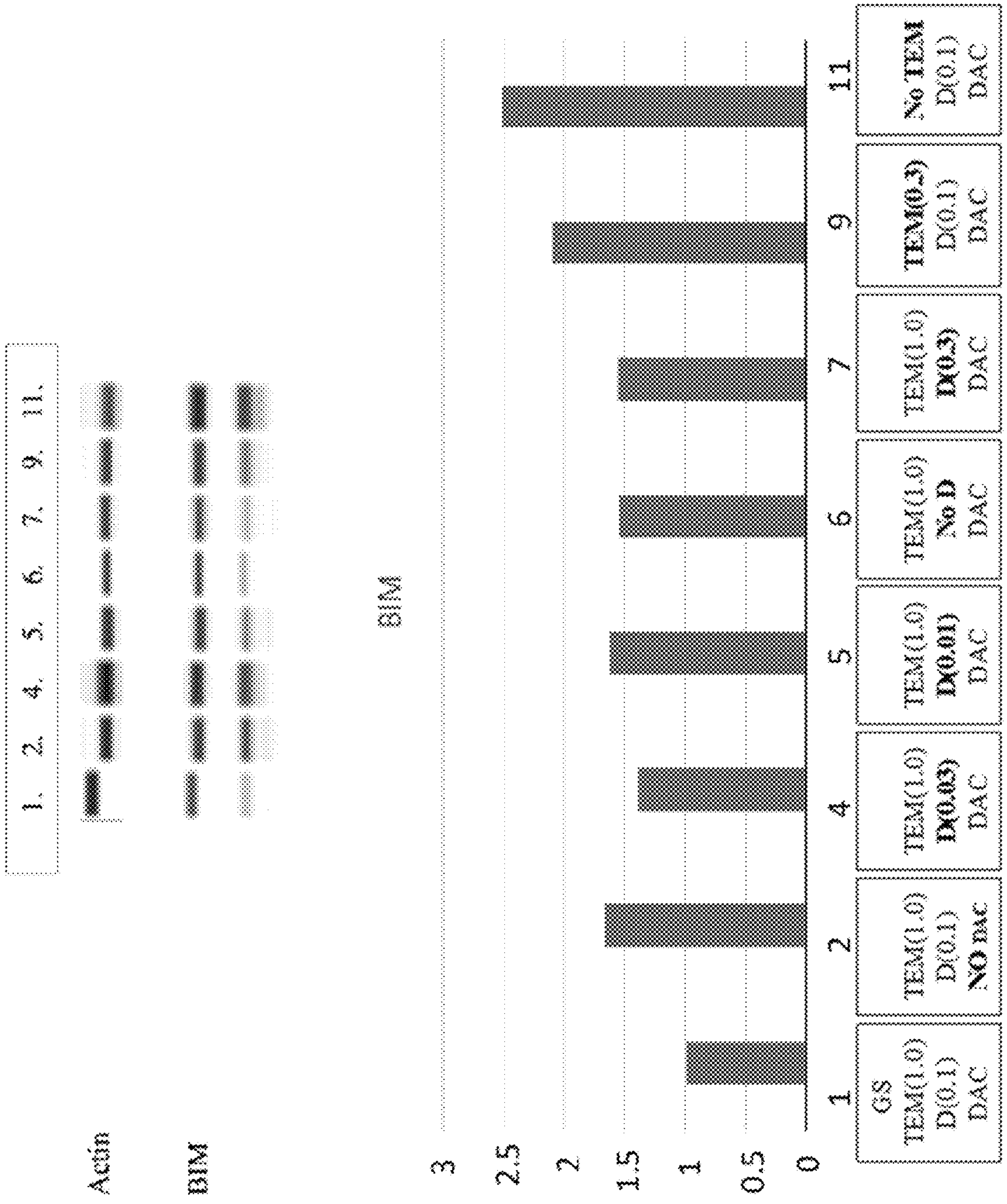
FIG. 7 depicts BIM expression normalized by actin expression for cells treated under various conditions and illustrates that the combination of Vitamin D, temsirolimus, and anti-IL-2 receptor blockade reduces expression of the pro-apoptosis molecule, BIM.

FIG. 7 illustrates that the combination of Vitamin D, temsirolimus, and anti-IL-2 receptor blockade reduces expression of the pro-apoptosis molecule, BIM. Human $CD4^+$ and $CD8^+$ T cells were subjected to the de-differentiation protocol, which involved a 3-day culture using low level co-stimulation (1:3 bead-to-T cell ratio), temsirolimus ("TEM", as indicated in FIG. 7; concentration of 1.0 or 0.3 μM), Vitamin D ("D", as indicated; concentration of 0.01, 0.03, 0.1, 0.3, or 1.0 nM), and an anti-IL-2 receptor monoclonal antibody (Daclizumab, 50 ng/ml; "DAC", as indicated). After the 3-day culture interval, the T cells were harvested, and protein was isolated and subjected to western blot analysis for the pro-apoptosis-related gene, BIM, and the housekeeping gene, Actin.

To assess this, we measured BIM levels in the T cells cultured with a low-strength of co-stimulation (1:3 bead-to-T cell ratio) and presence of the various inhibitors. As FIG. 7 illustrates, the T cell culture that contained the combination of temsirolimus, Vitamin D (0.1 nM), and the anti-IL-2 receptor monoclonal antibody daclizumab had the lowest level of BIM expression. But still, FIG. 7 shows that anti-IL-2 receptor monoclonal antibody Daclizumab (dose, 50 μg/ml) plays a beneficial role in suppressing the pro-apoptotic molecule, BIM (column 2). Each of the three inhibitors appeared to play a role in BIM inhibition because absence of any single inhibitor increased the BIM level.

As such, we conclude that the combination inhibitor regimen represents a method for inducing a favorable shift in the mitochondrial control of apoptotic tendency.

Example 8: The Three Inhibitor De-Differentiation Regimen Results in T Cells with Subsequent Proliferative Capacity after Removal of Inhibitors To demonstrate that the 3-day regimen comprised of a low-level of co-stimulation, temsirolimus, Vitamin D, and anti-IL-2 receptor monoclonal antibody resulted in a state of de-differentiation capable of re-differentiation, we performed experiments to re-stimulate the cells on day 3 of culture using a high-level of co-stimulation (3:1 bead-to-T cell ratio) after removal of the inhibitors from culture. After 10 days (13 days of total culture), the T cells were harvested, enumerated, and evaluated by flow cytometry.

Figure 8:
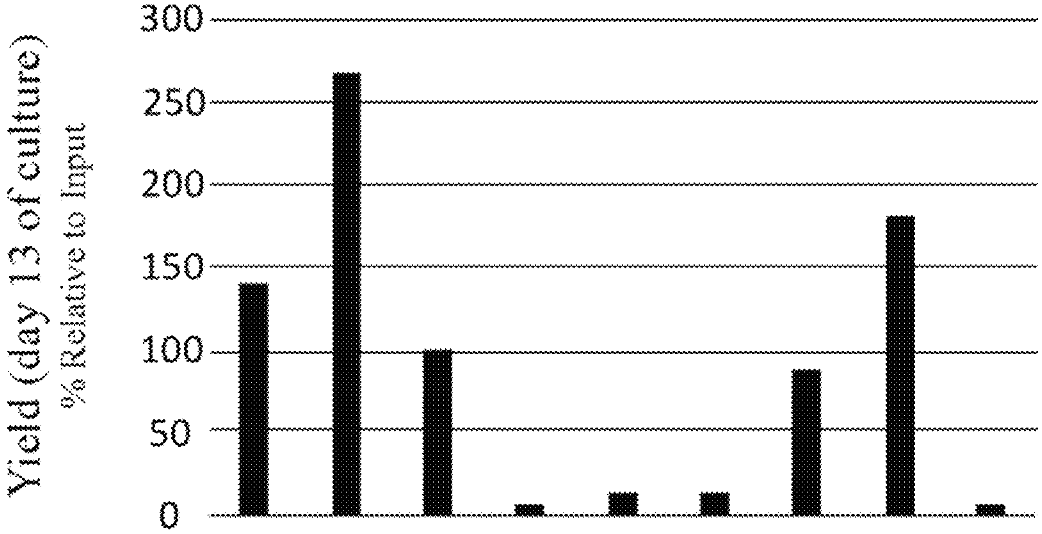
FIG. 8 illustrates the effect of culture components during the de-differentiation interval on subsequent T cell yield (at day 13 of culture).

FIG. 8 illustrates the effect of culture components during the de-differentiation interval on subsequent T cell yield (at day 13 of culture). Human $CD4^+$ and $CD8^+$ T cells were subjected to a 3-day de-differentiation interval that included a low-level of anti-CD3/anti-CD28 co-stimulation (bead-to-T cell ratio; 1:3 or 1:1, as indicated); a temsirolimus (1

μM; or, low-dose ["Lo"], 0.1 μM); vitamin D (0.1 nM; or, high-dose ["HD'] of 1.0 nM; or, low-dose of 0.01 nM); an anti-IL-2 receptor monoclonal antibody (daclizumab, 50 μg/ml); and culture in X-Vivo 20 media supplemented with 5% human AB serum. The first column represents a control culture (no temsirolimus, Vitamin D, or anti-IL-2R antibody). The second column represents the culture with no anti-IL-2R antibody; the fourth column represents the culture with no serum supplementation; the fifth column represents low-dose Vitamin D whereas the sixth column represents results using high-dose Vitamin D; the seventh column represents results using low-dose temsirolimus; and the eighth column represents the culture with no temsirolimus; and the ninth column represents results using the higher ratio of beads. After the 3-day interval, media was exchanged to fresh X-Vivo 20 without inhibitors, high-level co-stimulation was provided (3:1 bead-to-T cell ratio), and the T cell growth cytokines IL-2 (100 IU/ml) and IL-7 (10 ng/ml) were added. At day 13 of culture, viable T cells were enumerated and the overall yield is shown relative to day 0 input number.

FIG. 8 shows the T cell counts after the re-differentiation stage. As these data show (column #3), T cells that were initially maintained for the first 3-day de-differentiation interval using a low-level of co-stimulation, temsirolimus, Vitamin D, and anti-IL-2 receptor monoclonal antibody had a satisfactory T cell yield (more than 250% of culture input).

In marked contrast, a very low yield was observed in the culture represented in column #4, which did not receive serum supplementation during the initial 3-day culture interval; as such, this data demonstrates that the initial day 3 culture interval must include X-Vivo 20 culture media supplemented with 5% AB serum.

Also, reduction in the Vitamin D concentration to 0.01 nM or increase in the Vitamin D concentration to 1.0 nM resulted in a very low yield (data shown in column #5 and #6, respectively). As such, the preferable concentration of Vitamin D is 0.1 nM.

Furthermore, reduction of the temsirolimus concentration to 0.1 μM reduced the resultant T cell yield (column #7). As such, the preferable concentration of temsirolimus is 1.0 μM.

Finally, if the co-stimulation level was increased in the de-differentiation interval (change in bead-to-T cell ratio from 1:3 to 1:1; results shown in last column, column #9), then the resultant T cell count was very low. As shown in FIG. 8, it is necessary to use a low-level of co-stimulation during de-differentiation (1:3 co-stimulation bead-to-T cell ratio) as increasing ratio to 1:1 results in a greatly reduced ability to manufacture T cells from the de-differentiated state (last column). As such, the preferable bead-to-T cell ratio during the de-differentiation stage of culture is 1:3.

Example 9: The Initial Three-Component Culture Interval Results in the Generation of $CD4^+$ T Cells Expressing Cell Surface Molecules Consistent with Reduced Differentiation At various times during the re-differentiation stage of culture, the resultant CD4+ T cells were evaluated for expression of memory markers by flow cytometry.

Figure 9A:
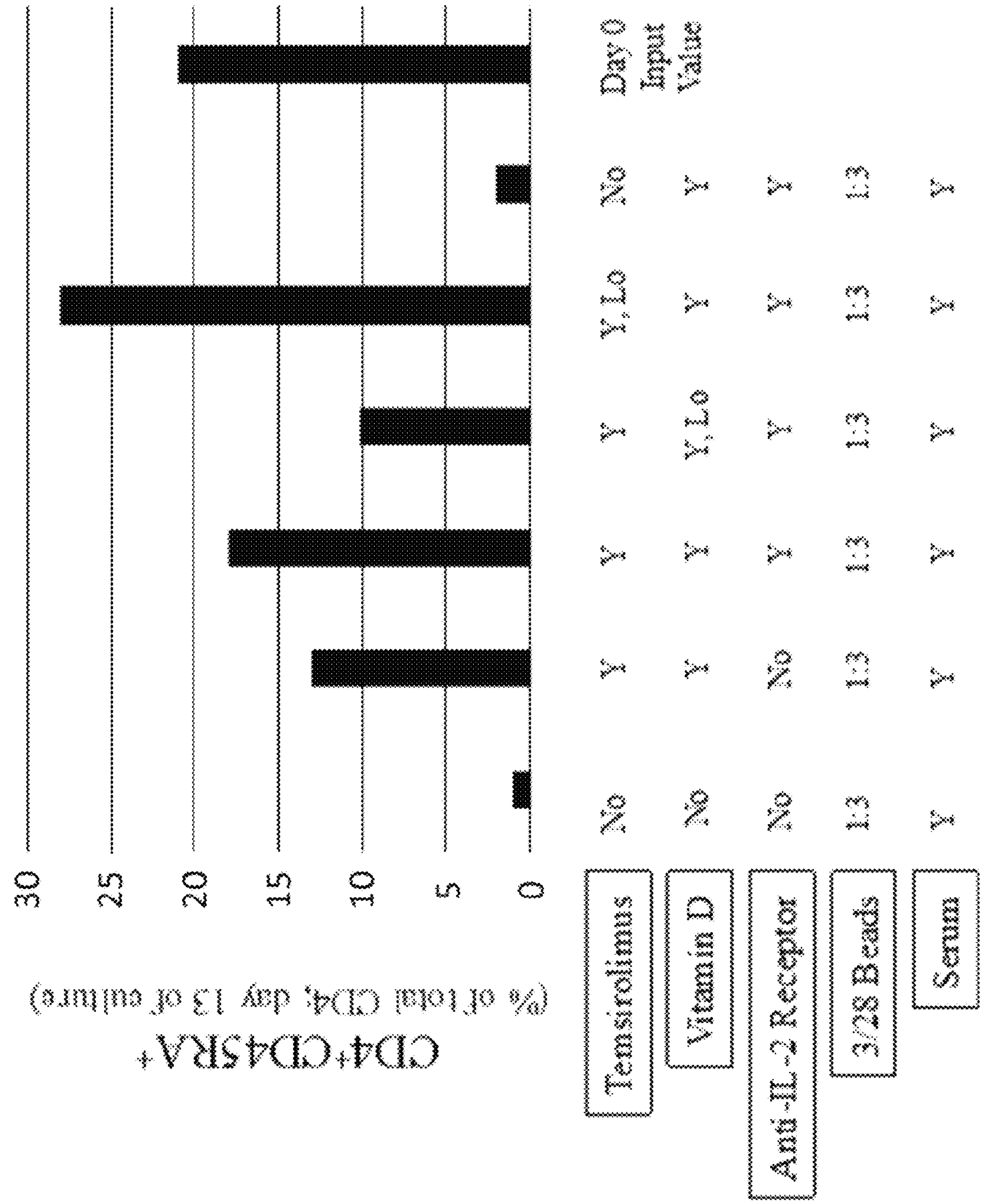
FIG. 9A depicts the percent of CD4 cells that are CD45RA+ for cells treated under various conditions.
Figure 9B:
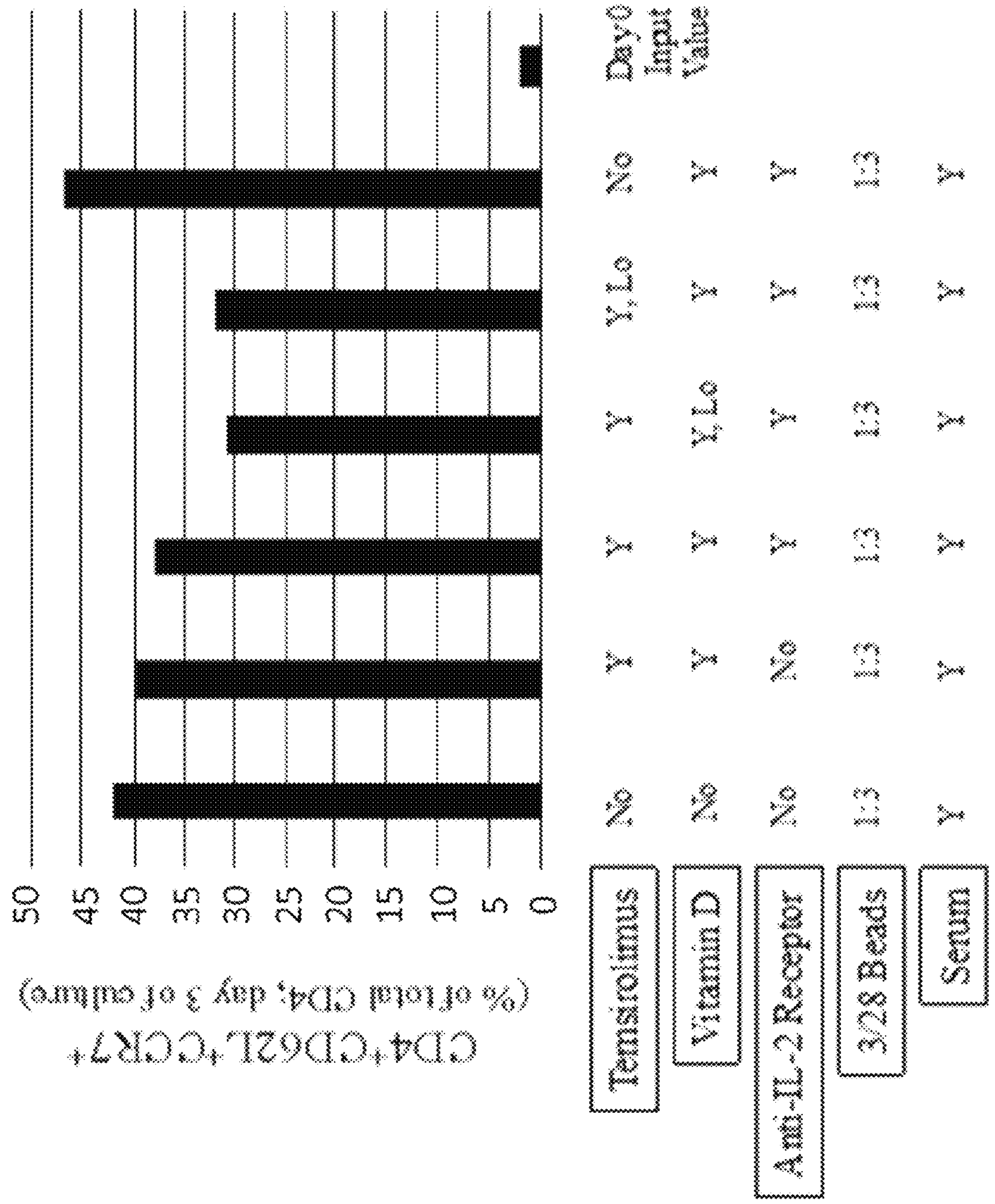
FIG. 9B depicts the percent of CD4 cells that are CD62L+ and CCR7+ for cells treated under various conditions.
Figure 9C:
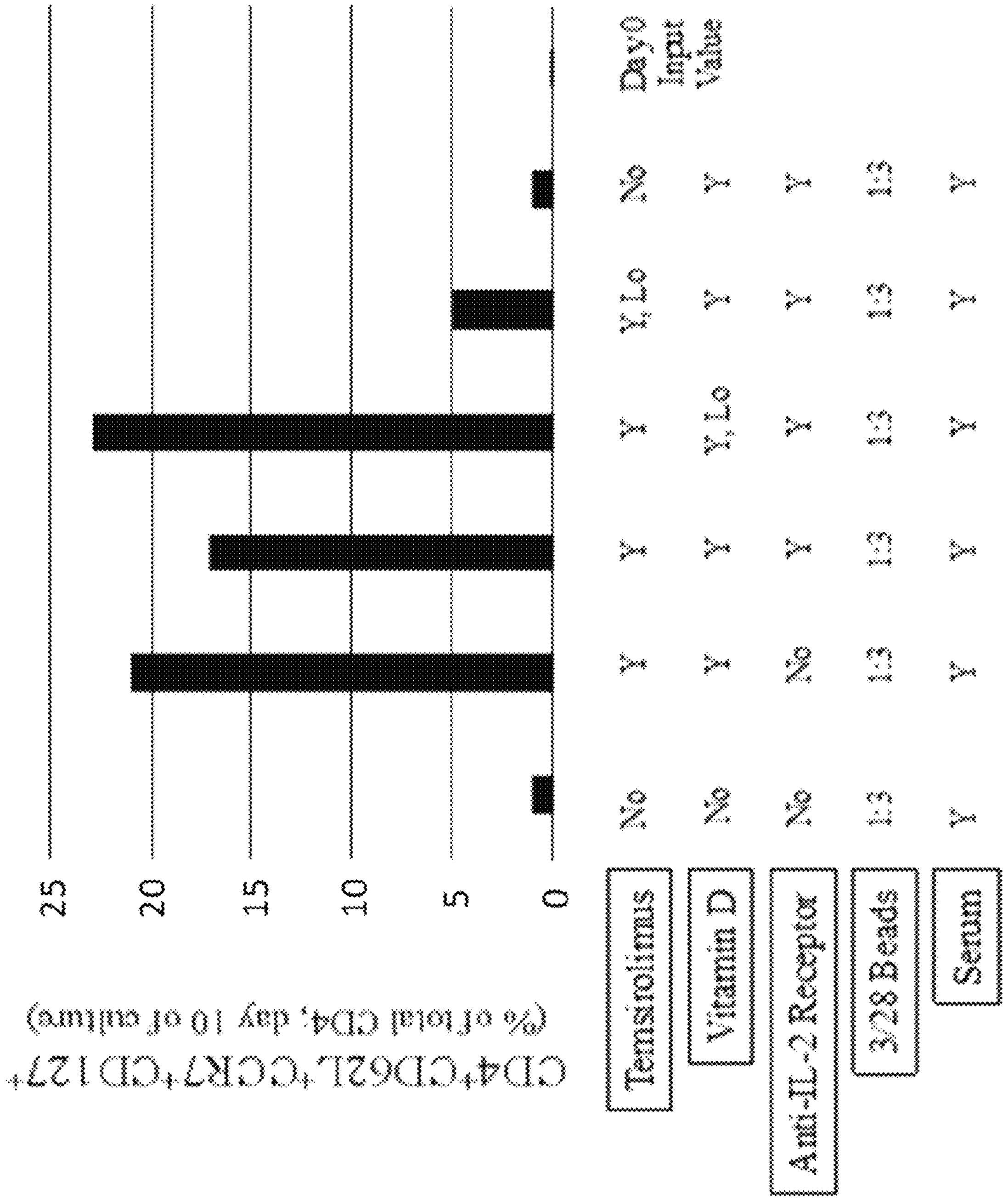
FIG. 9C depicts the percent of CD4 cells that are CD62L+, CCR7+, and CD127+ for cells treated under various conditions.

FIGS. 9A-9C illustrate the effect of culture components during the de-differentiation interval on $CD4^+$ T cell expression of memory markers (at day 13 of culture). Human $CD4^+$ and $CD8^+$ T cells were subjected to a 3-day de-differentiation interval that included (as indicated in above FIGS. 9A-9C) a low-level of anti-CD3/anti-CD28 co-stimulation (bead-to-T cell ratio; 1:3); temsirolimus (1 μM or 0.1 μM [low-dose; "Lo"]); Vitamin D (0.1 nM; or, 0.01 nM [low-dose; "Lo"]); an anti-IL-2 receptor monoclonal antibody (daclizumab, 50 μg/ml); and culture in X-Vivo 20 media supplemented with 5% human AB serum. After the 3-day interval, media was exchanged to fresh X-Vivo 20 without inhibitors, high-level co-stimulation was provided (3:1 bead-to-T cell ratio), and the T cell growth cytokines IL-2 (100 IU/ml) and IL-7 (10 ng/ml) were added. T cells were subjected to flow cytometry for evaluation of co-expression of $CD4^+$ and $CD45RA^+$ markers (results shown in top panel; evaluated at day 13 of culture); co-expression of $CD4^+$, $CD62L^+$, and $CCR7^+$ markers (bottom left panel; evaluated at day 3 of culture); and co-expression of $CD4^+$, $CD62L^+$, $CCR7^+$, and $CD127^+$ markers (bottom right panel; evaluated at day 10 of culture). All results are shown relative to the value of $CD4^+$ T cells at culture initiation (last column in FIGS. 9A-9C; "Day 0 Input Value").

As shown in FIG. 9A, relative to values from Day 0 input T cells, T cells initially propagated in the combination of temsirolimus, Vitamin D, and anti-IL-2 receptor monoclonal antibody had relatively preserved expression of the CD45RA marker that is expressed on naïve T cells (column #3). In marked contrast, absence of these three molecules during the initial culture interval resulted in depletion of the naïve T cell population (culture #1). Furthermore, elimination of temsirolimus during the initial culture interval resulted in depletion of the naïve T cell population (culture #6).

As shown in FIG. 9B, each of the T cell cultures that were initially propagated in the 3-day interval that incorporated a low-level of co-stimulation had an increase in T cell expression of the central memory molecules CD62L and CCR7.

Finally, as shown in FIG. 9C, T cells initially propagated in the combination of temsirolimus, Vitamin D, and anti-IL-2 receptor monoclonal antibody had greatly increased expression (relative to the Day 0 input cells) of T cells that were triple-positive for CD62L, CCR7, and IL-7 receptor alpha (CD127). Elimination of the three inhibitors during the initial 3-day culture (column #1) abrogated the ability of the initial culture interval to promote the expansion of this triple-positive population. In addition, reducing or eliminating only temsirolimus from the initial culture interval also greatly reduced the frequency of triple-positive T cells (columns #5 and 6).

In sum, these data indicate that the three-drug initial culture interval results in the conversion of $CD4^+$ T cells from primarily an end-stage, effector memory population towards a less-differentiated T cell population, including co-expression of CD62L, CCR7, and CD127, which is a state of very limited T cell differentiation.

Example 10: The Initial Three-Component Culture Interval Results in the Generation of $CD8^+$ T Cells Expressing Cell Surface Molecules Consistent with Reduced Differentiation At various times during the re-differentiation stage of culture, the resultant $CD8^+$ T cells were evaluated for expression of memory markers by flow cytometry.

Figure 10A:
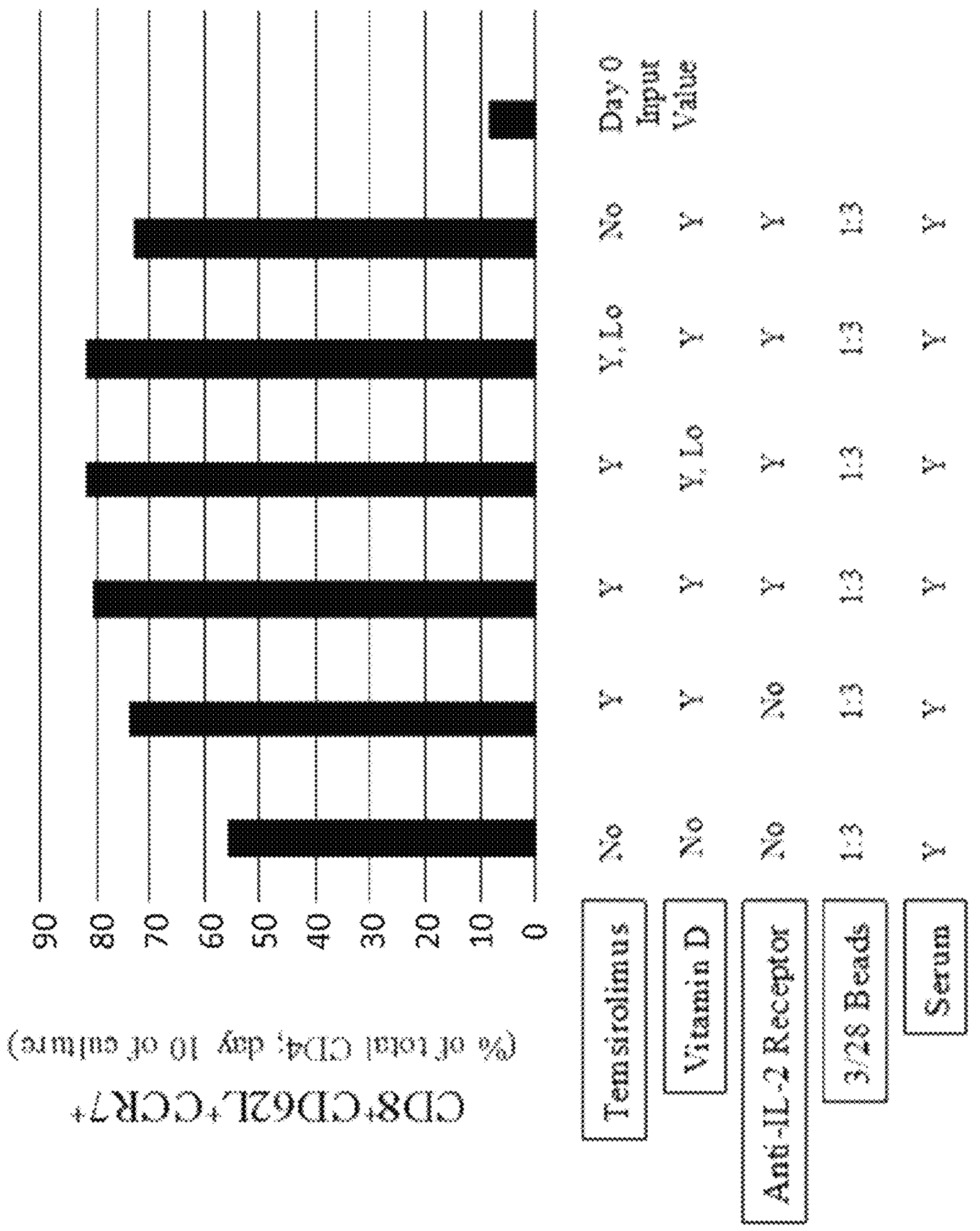
FIG. 10A depicts the percent of CD8 cells that are CD62L+ and CCR7+ for cells treated under various conditions.
Figure 10B:
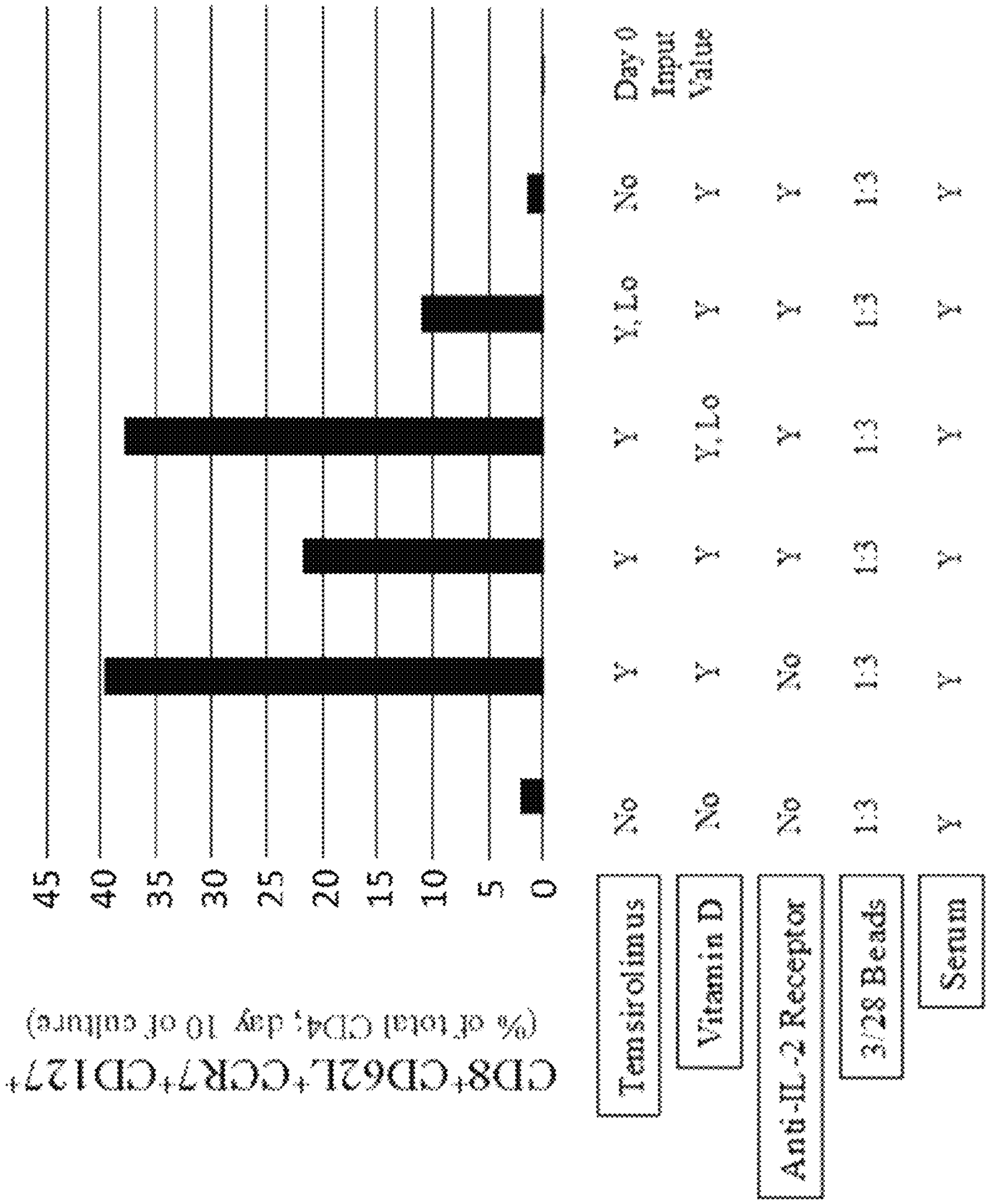
FIG. 10B depicts the percent of CD8 cells that are CD62L+, CCR7+, and CD127+ for cells treated under various conditions.
Figure 11A:
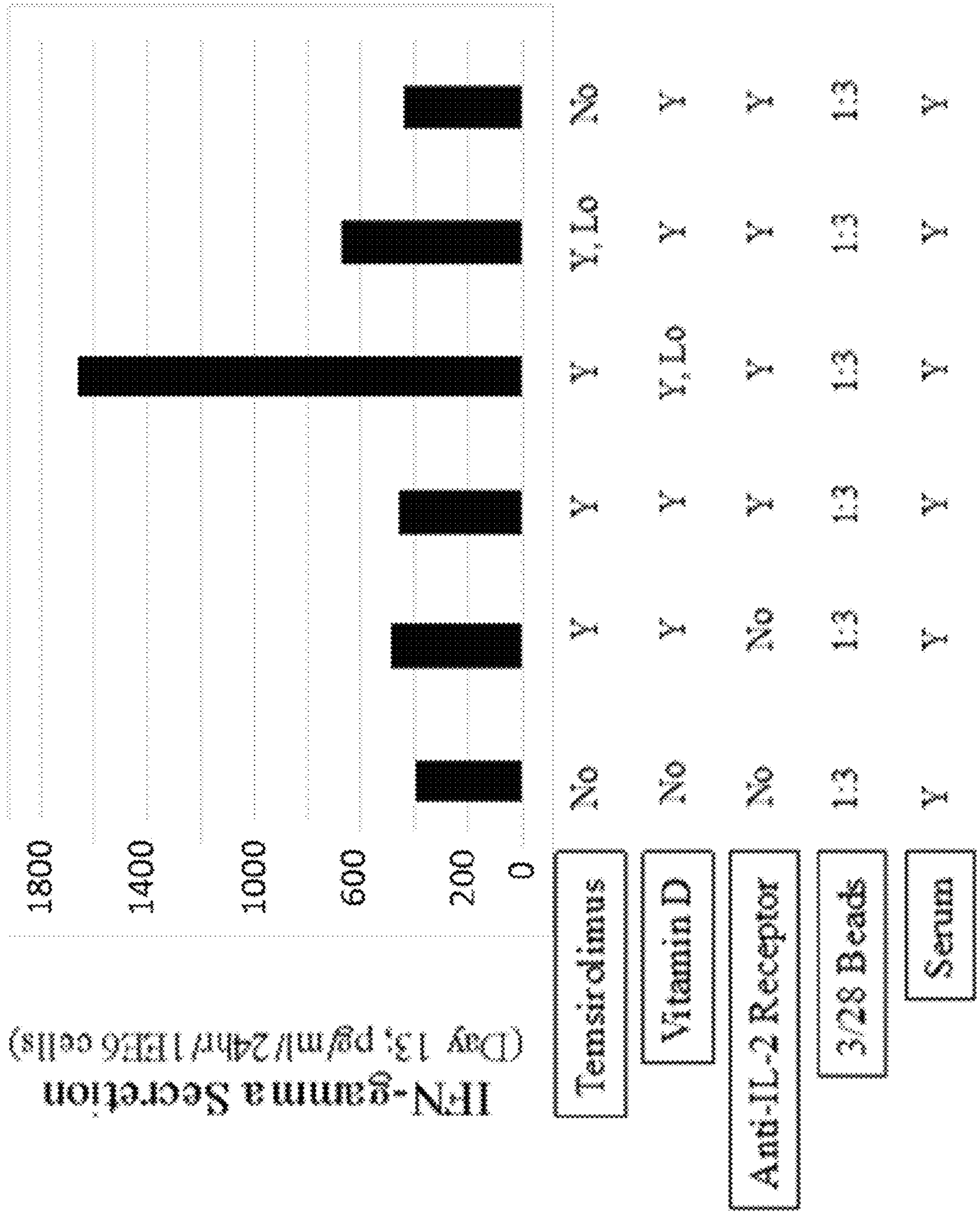
FIGS. 11A-11D depict the inflammatory Th1/Th17 cytokine analysis of cultured de-differentiated T cells in polarization-neutral media.
Figure 11B:
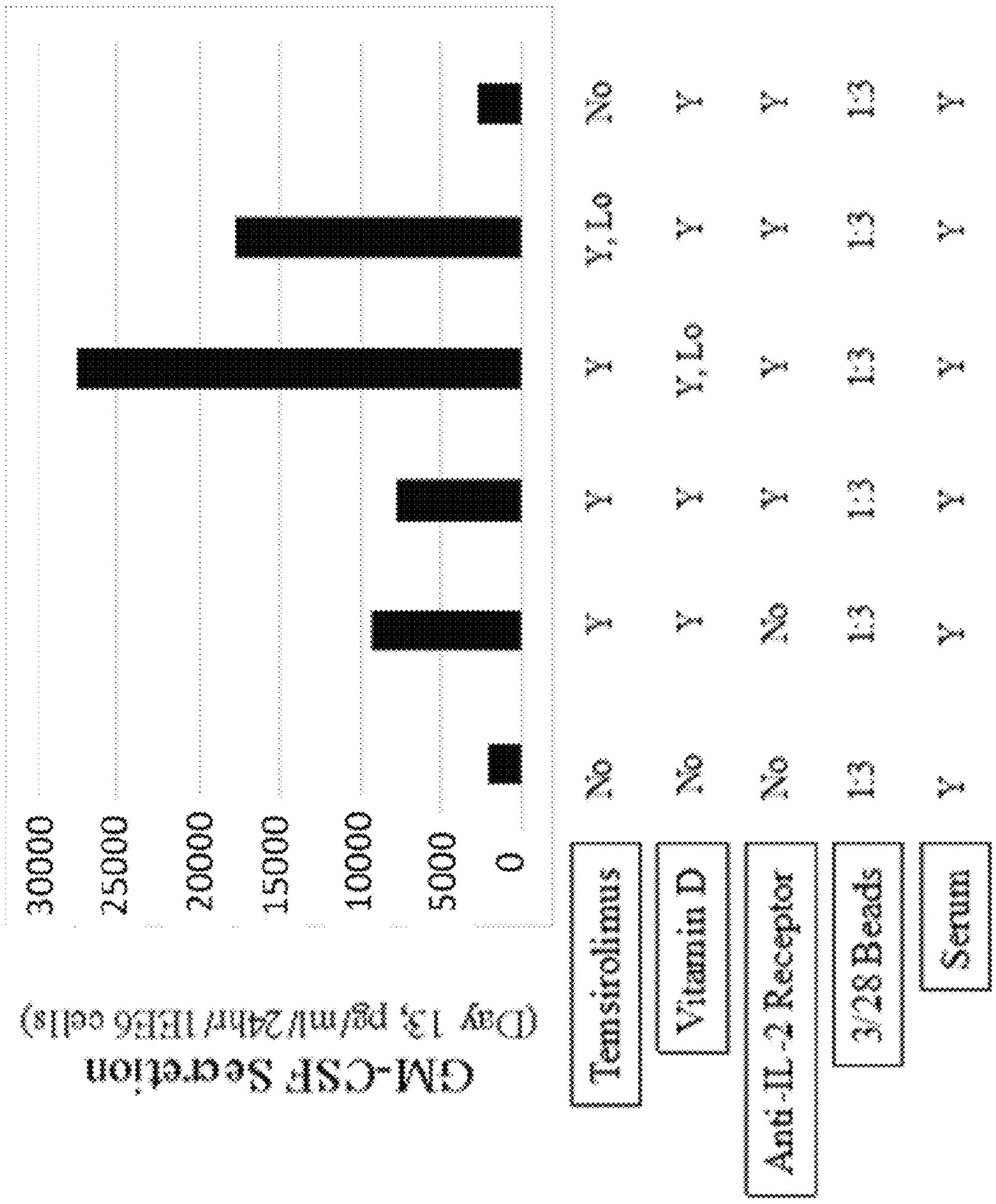
Figure 11C:
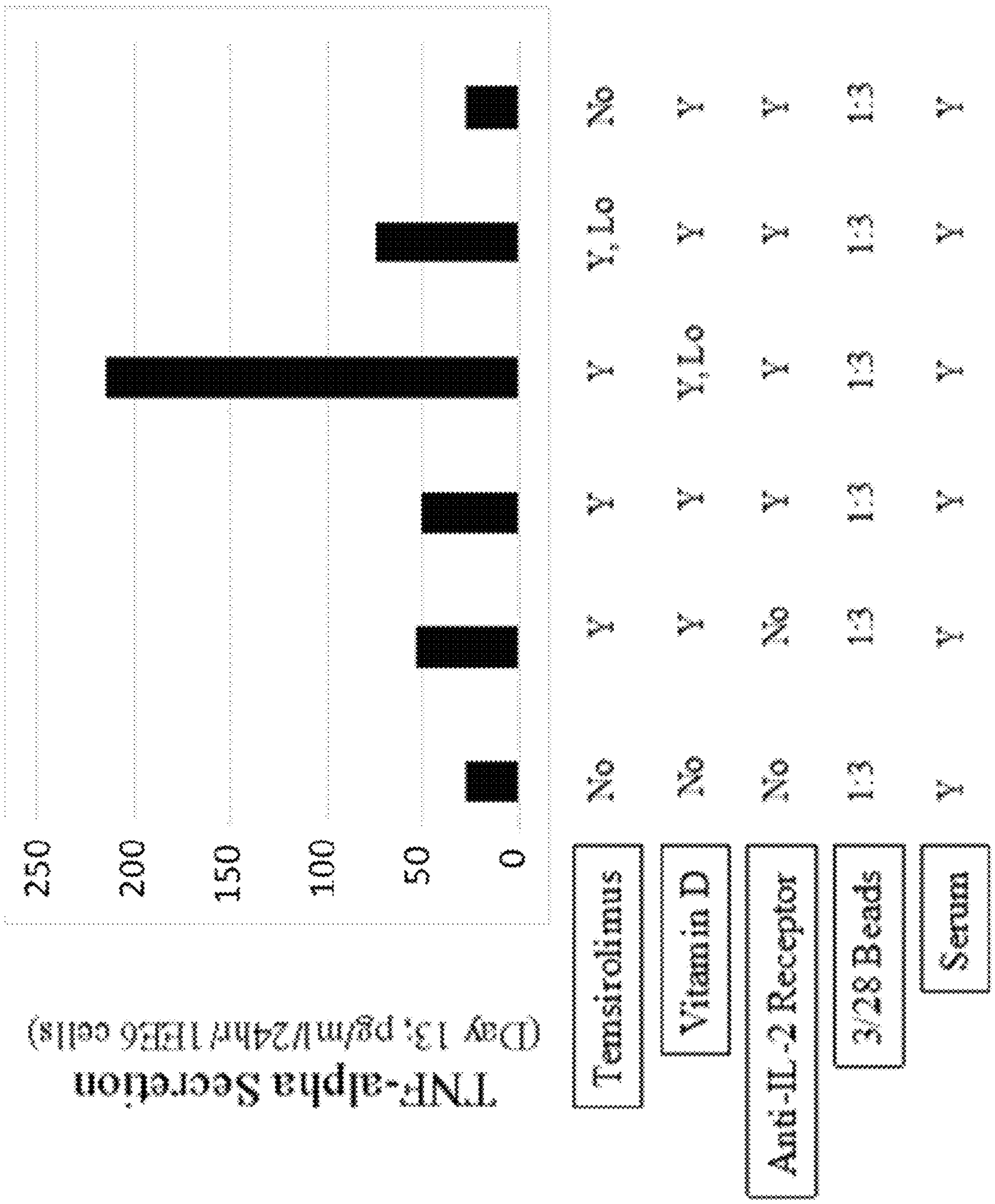
Figure 11D:
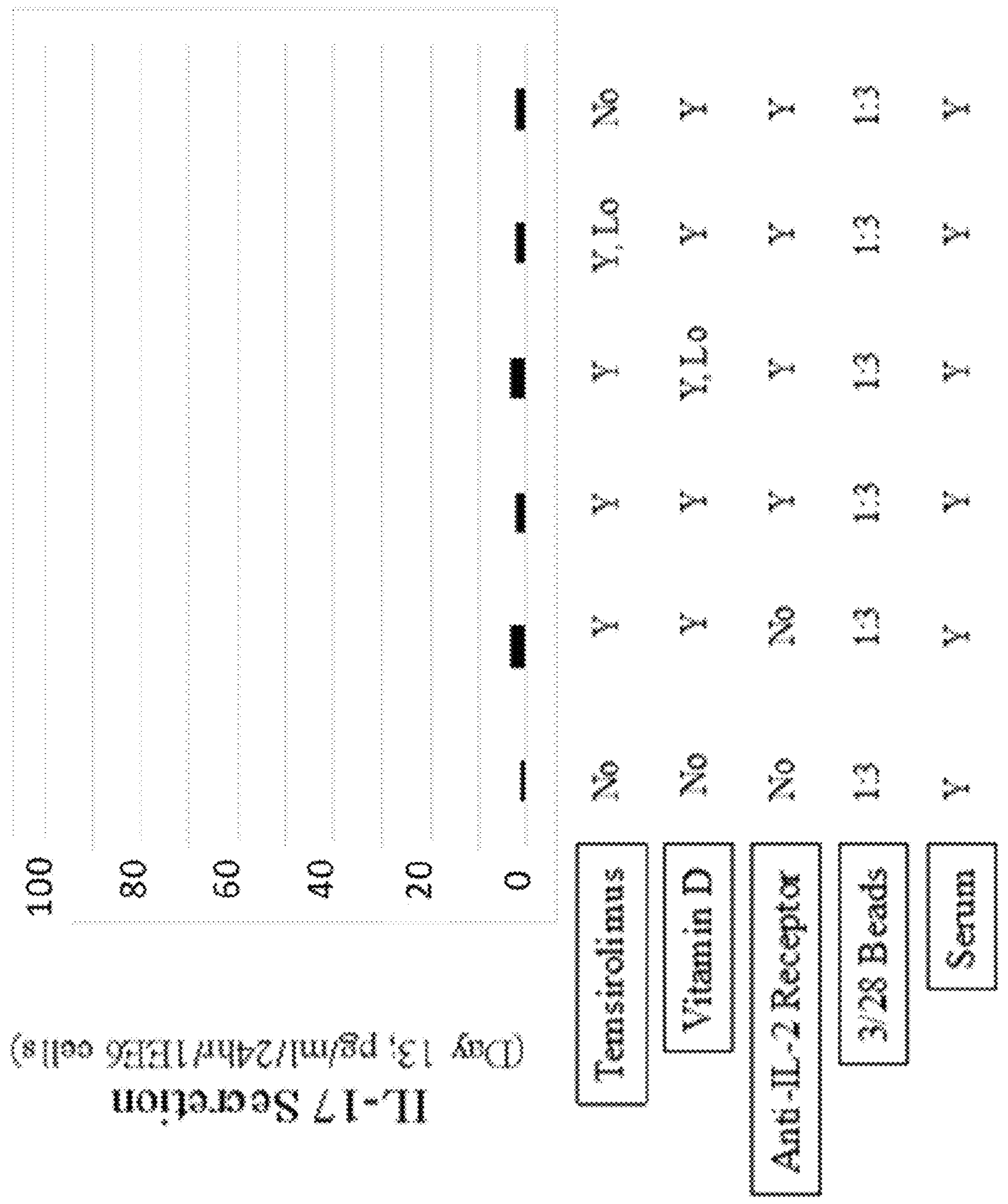
Figure 12A:
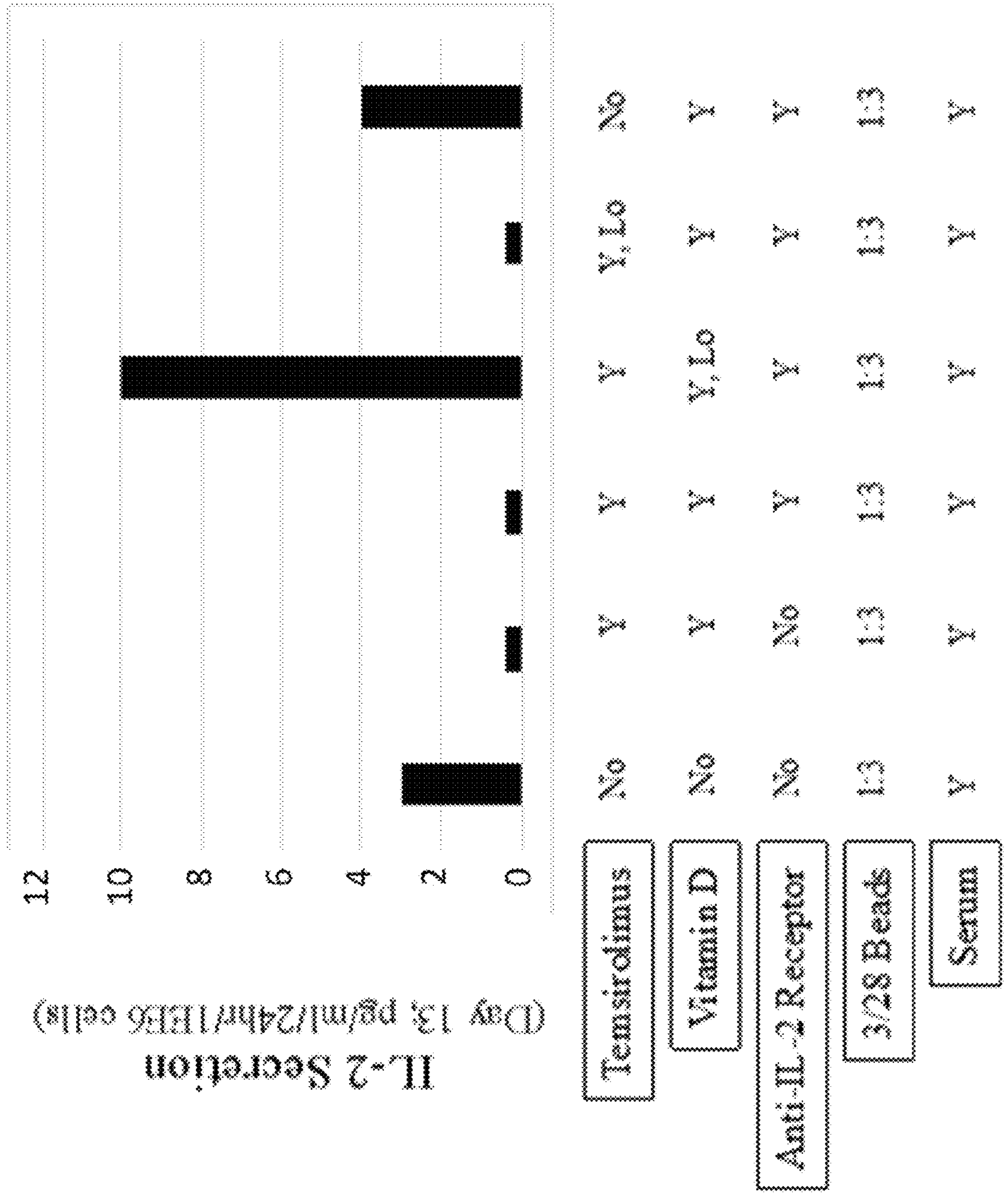
FIGS. 12A-12D depict the IL-2 and Th2-type cytokine analysis of cultured de-differentiated T cells in polarization-neutral media.
Figure 12B:
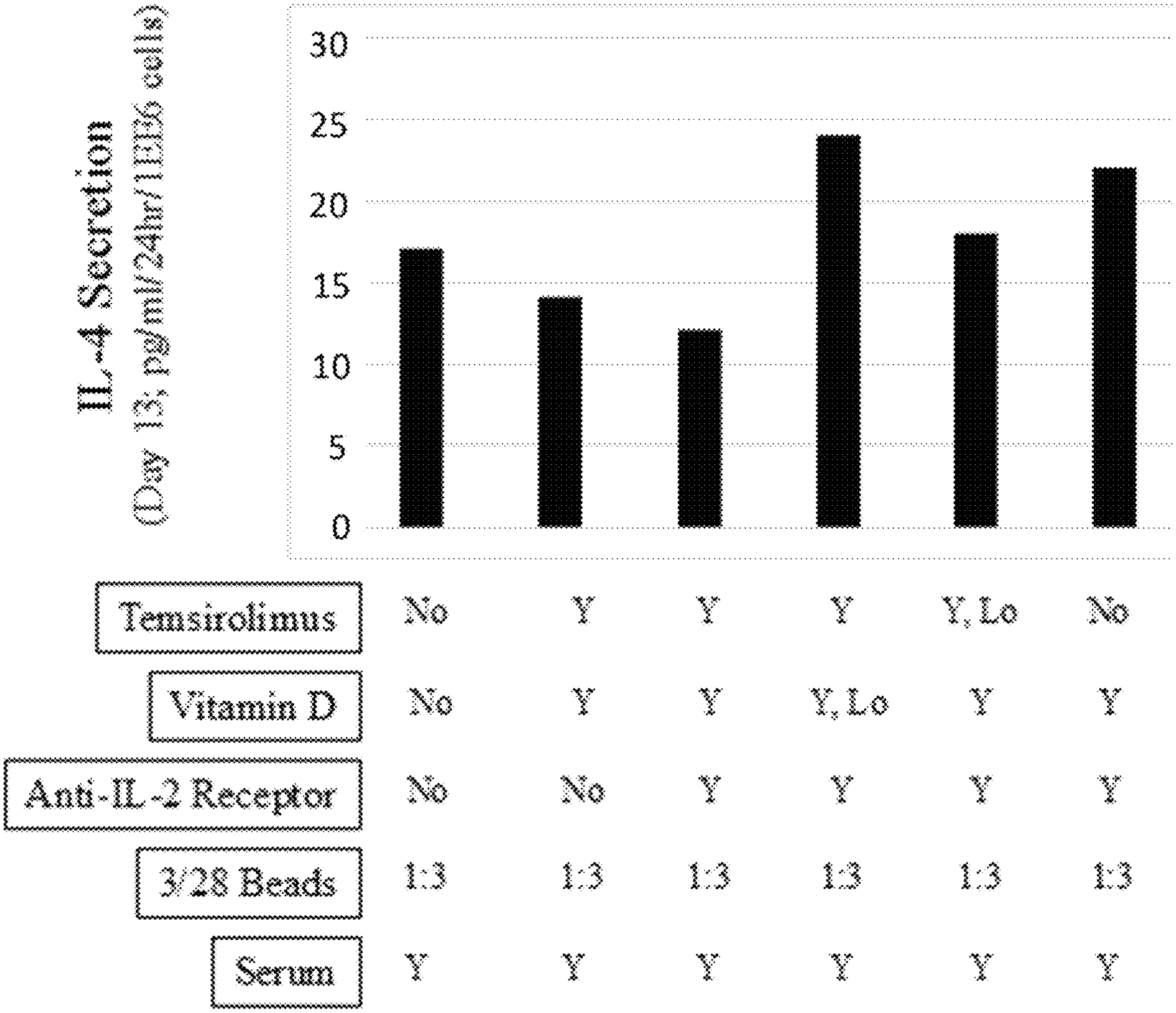
Figure 12C:
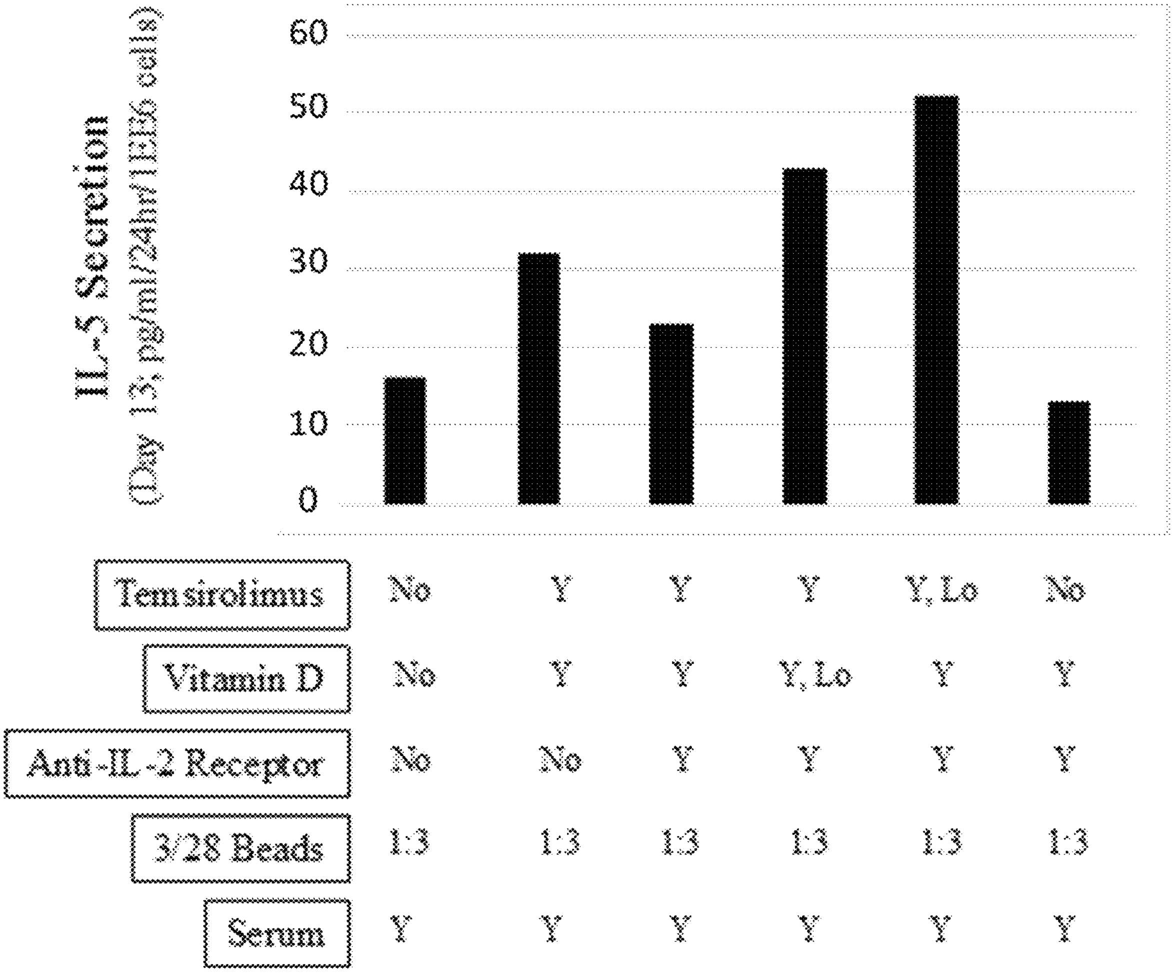
Figure 12D:
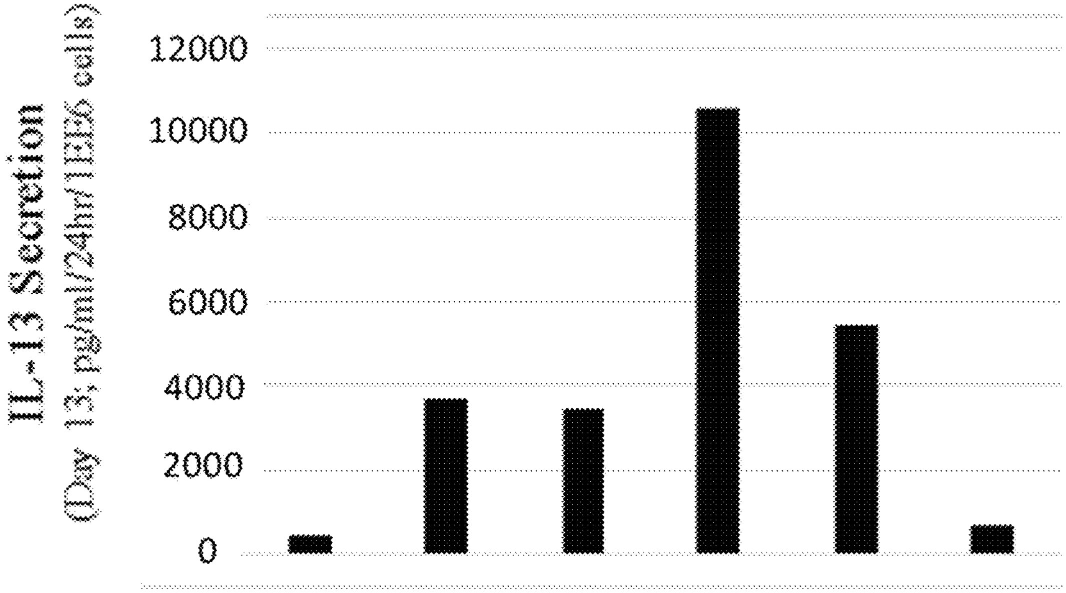

FIGS. 10A-10B illustrates the effect of culture components during the de-differentiation interval on $CD8^+$ T cell expression of memory markers. Human $CD4^+$ and $CD8^+$ T cells were subjected to a 3-day de-differentiation interval that included (as indicated in above FIGS. 10A-10B) a low-level of anti-CD3/anti-CD28 co-stimulation (bead-to-T cell ratio; 1:3); temsirolimus (1 μM or 0.1 μM [low-dose;

"Lo"]); Vitamin D (0.1 nM; or, 0.01 nM [low-dose; "Lo"]); an anti-IL-2 receptor monoclonal antibody (daclizumab, 50 μg/ml); and culture in X-Vivo 20 media supplemented with 5% human AB serum. After the 3-day interval, media was exchanged to fresh X-Vivo 20 without inhibitors, high-level co-stimulation was provided (3:1 bead-to-T cell ratio), and the T cell growth cytokines IL-2 (100 IU/ml) and IL-7 (10 ng/ml) were added. T cells were subjected to flow cytometry for evaluation of co-expression of $CD8^+$, $CD62L^+$, and $CCR7^+$ markers (left panel; evaluated at day 10 of culture); and co-expression of $CD8^+$, $CD62L^+$, $CCR7^+$, and $CD127^+$ markers (right panel; evaluated at day 10 of culture). All results are shown relative to the value of $CD8^+$ T cells at culture initiation (last column in FIGS. 10A-10B; "Day 0 Input Value").

As shown in FIG. 10A, each of the T cell cultures that were initially propagated in the 3-day interval that incorporated a low-level of co-stimulation had an increase in $CD8^+$ T cell expression of the central memory molecules CD62L and CCR7.

Finally, as shown in FIG. 10B, T cells initially propagated in the combination of temsirolimus, Vitamin D, and anti-IL-2 receptor monoclonal antibody had greatly increased expression (relative to the Day 0 input cells) of $CD8^+$ T cells that were triple-positive for CD62L, CCR7, and IL-7 receptor alpha (CD127). Elimination of the three inhibitors during the initial 3-day culture (column #1) abrogated the ability of the initial culture interval to promote the expansion of this triple-positive population. In addition, reducing or eliminating only temsirolimus from the initial culture interval also greatly reduced the frequency of triple-positive T cells (columns #5 and 6).

In sum, these data indicate that the three-drug initial culture interval results in the conversion of $CD8^+$ T cells from primarily an end-stage, effector memory population towards a less-differentiated T cell population, including co-expression of CD62L, CCR7, and CD127, which is a state of very limited T cell differentiation.

Example 11: De-Differentiated T Cells have an Inherent Bias Towards Low Cytokine Potential FIGS. 11A-11D highlight the components of the de-differentiation process, including use of: a low-level of co-stimulation (an anti-CD3/anti-CD28 bead to T cell ratio of 1:3, which is reduced relative to conventional methods as described in Kalamasz D, Long S A, Taniguchi R, Buckner J H, Berenson R J, Bonyhadi M. Optimization of human T-cell expansion ex vivo using magnetic beads conjugated with anti-CD3 and Anti-CD28 antibodies) Journal of immunotherapy (Hagerstown, Md: 1997). 2004; 27(5): 405-418; the mTOR inhibitor temsirolimus; vitamin D; and an anti-IL-2 receptor monoclonal antibody.

FIGS. 11A-11D depict the inflammatory Th1/Th17 cytokine analysis of cultured de-differentiated T cells in polarization-neutral media. Human $CD4^+$ and $CD8^+$ T cells were subjected to a 3-day de-differentiation procedure that included the following culture components, as indicated: temsirolimus (Y, indicates concentration of 1 μM; Y, Lo, indicates concentration of 0.1 μM); Vitamin D (Y, indicates concentration of 0.1 nM; Y, Lo, indicates concentration of 0.01 nM); an anti-IL-2 receptor monoclonal antibody (Daclizumab, 50 μg/ml); co-stimulation with anti-CD3/anti-CD28 (3/28) coated magnetic beads at a low ratio (bead-to-T cell ratio, 1:3), and supplementation with 5% human serum. After 3-days, the de-differentiated T cells were co-stimulated (typical bead-to-T cell ratio of 3:1) in media supplemented with the T cell growth cytokines rhu IL-2 (100 IU/ml) and rhu IL-7 (10 ng/ml), which are not potent in terms of inducing T cell polarization. After 10 days in culture (total, day 13 of culture), the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr.

To assess whether the de-differentiated T cell state manifested an inherent bias towards a particular cytokine secretion pattern, we cultured the de-differentiated T cells using a high-level of co-stimulation (bead-to-T cell ratio, 3:1) and maintenance in media that did not contain any inhibitor and only contained the T cell growth cytokines IL-2 and IL-7.

As FIGS. 11A-11D detail, the resultant T cells that were re-differentiated from each of the de-differentiated precursor states had very low levels of secretion of inflammatory cytokines, including IFN-γ (most values below 1000 pg/ml), TNF-α (most values below 100 pg/ml), and IL-17 (all values below 10 pg/ml). Of note, GM-CSF was secreted in some conditions at much higher levels, in some cases, greater than 10,000 pg/ml. The GM-CSF value was moderated in the de-differentiated condition that was comprised of higher dose temsirolimus (1.0 μM) and higher dose vitamin D (0.1 nM); as such, for resultant moderation of T cell cytokine secretion of GM-CSF, it is desirable to expand T cells from a de-differentiation method that incorporates these higher concentrations of temsirolimus and vitamin D.

Notably, inclusion of a low concentration of vitamin D (0.01 nM) during the de-differentiation interval also resulted in somewhat higher levels IFN-γ and TNF-α relative to use of a higher concentration of vitamin D (0.1 nM). As such, with respect to moderating resultant T cell secretion of the inflammatory cytokine IFN-γ, it is preferable to use a concentration of vitamin D that is approximately 0.1 nM.

Furthermore, as shown in FIGS. 12A-12D, the resultant T cells that were re-differentiated from each of the de-differentiated precursor state T cells had very low level secretion of IL-2, although again, the level was lower in the condition that incorporated the higher concentrations of temsirolimus and vitamin D relative to the conditions that used a lower concentration of these agents.

FIGS. 12A-12D depicts the IL-2 and Th2-type cytokine analysis of cultured de-differentiated T cells in polarization-neutral media. Human $CD4^+$ and $CD8^+$ T cells were subjected to a 3-day de-differentiation procedure that included the following culture components, as indicated: temsirolimus (Y, indicates concentration of 1 μM; Y, Lo, indicates concentration of 0.1 μM); Vitamin D (Y, indicates concentration of 0.1 nM; Y, Lo, indicates concentration of 0.01 nM); an anti-IL-2 receptor monoclonal antibody (Daclizumab, 50 μg/ml); co-stimulation with anti-CD3/anti-CD28 (3/28) coated magnetic beads at a low ratio (bead-to-T cell ratio, 1:3), and supplementation with 5% human serum. After 3-days, the de-differentiated T cells were co-stimulated (typical bead-to-T cell ratio of 3:1) in media supplemented with the T cell growth cytokines rhu IL-2 (100 IU/ml) and rhu IL-7 (10 ng/ml), which are not potent in terms of inducing T cell polarization. After 10 days in culture (total, day 13 of culture), the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr.

The resultant T cells also had very low level secretion of the Th2-type cytokine IL-4 (values less than 20 pg/ml) and the Th2-type cytokine IL-5 (values less than 60 pg/ml). However, the levels of IL-13 were elevated in several of the T cell culture conditions, with lower cytokine secretion detected in the condition that incorporated the higher concentrations of temsirolimus and vitamin D relative to the conditions that used a lower concentration of these agents.

In sum, these data indicate that re-differentiation of T cells in media that contains T cell growth cytokines (IL-2 and IL-7) without strong polarization signals (no addition of IFN-α, IL-4, or TGF-β) after a step 1 de-differentiation process has an inherent bias towards T cells of low cytokine potential; in particular, we demonstrated low levels of the deleterious cytokines IFN-γ, TNF-α, and IL-17. This observation is particularly strong if the de-differentiation step incorporates low-level co-stimulation and propagation in media that contains temsirolimus at a concentration of 1.0 μM, vitamin D at a concentration of 0.1 nM, and inclusion of an anti-IL-2 receptor monoclonal antibody.

Example 12: Favorable Expansion of De-Differentiated T Cells in a Hybrid $T_{REG}$ Th2 Polarization Condition and in the Presence of the Novel Pharmaceutical Agent Pemetrexed We evaluated the effect of de-differentiation components when T cell re-differentiation incorporated $T_{REG}$ polarizing cytokines IL-2 and TGF-β, or a Th1 polarizing cytokine, IFN-α.

Indeed, either TBET or GATA3 has been shown to maintain $T_{REG}$ cell capacity for maintaining immune tolerance. Nonetheless, in spite of this evidence for a role of either TBET or GATA3 in $T_{REG}$ cell function, we have elected to prioritize GATA3 expression in manufactured $T_{REG}$ cells because of the very strong linkage of TBET and consequent Th1-type pathways in autoimmunity. As such, we evaluated whether the step 1 de-differentiation process followed by a step 2 re-differentiation process that included both $T_{REG}$ polarizing signals (IL-2, TGF-β) and the main Th2 polarizing signal (IL-4) might generate a human "hybrid" $T_{REG}$-Th2 cell. Literature results from experimental murine models are mixed in this regard, as purposeful addition of IL-4 to a $T_{REG}$ cell ex vivo culture was shown to either promote or suppress the $T_{REG}$ phenotype. In addition to this conflicting murine literature pertaining to the role of exogenous IL-4 in $T_{REG}$ cell manufacturing, there is a paucity of information pertaining to the ex vivo role of IL-4 on human $T_{REG}$ cells, although one study found that IL-4 preserved human $T_{REG}$ cell function.

Human $iT_{REG}$ cells with a hybrid Th2 component may be favorable for adoptive T cell therapy because $iT_{REG}$ cells have been characterized as having a propensity to in vivo differentiation plasticity whereby an $iT_{REG}$ cells can convert to a pathogenic Th1-type or Th17-type subset. On the other hand, if differentiation towards a Th2-type phenotype is encoded within the $iT_{REG}$ manufacturing, the Th2 bias will predictably limit plasticity towards the Th1/Th17 phenotypes.

In addition, we evaluated whether the pharmaceutical agent pemetrexed might be beneficial for promoting an $iT_{REG}$ cell phenotype. There exists a precedent for the use of pharmaceutical agents for preferential $iT_{REG}$ cell generation; most notably, the mTOR inhibitor rapamycin has been associated with a shift towards $iT_{REG}$ cells. However, pemetrexed has not been characterized as having an $iT_{REG}$-promoting effect. Pemetrexed has a complex mechanism of action as a folate anti-metabolite.

Figure 13:
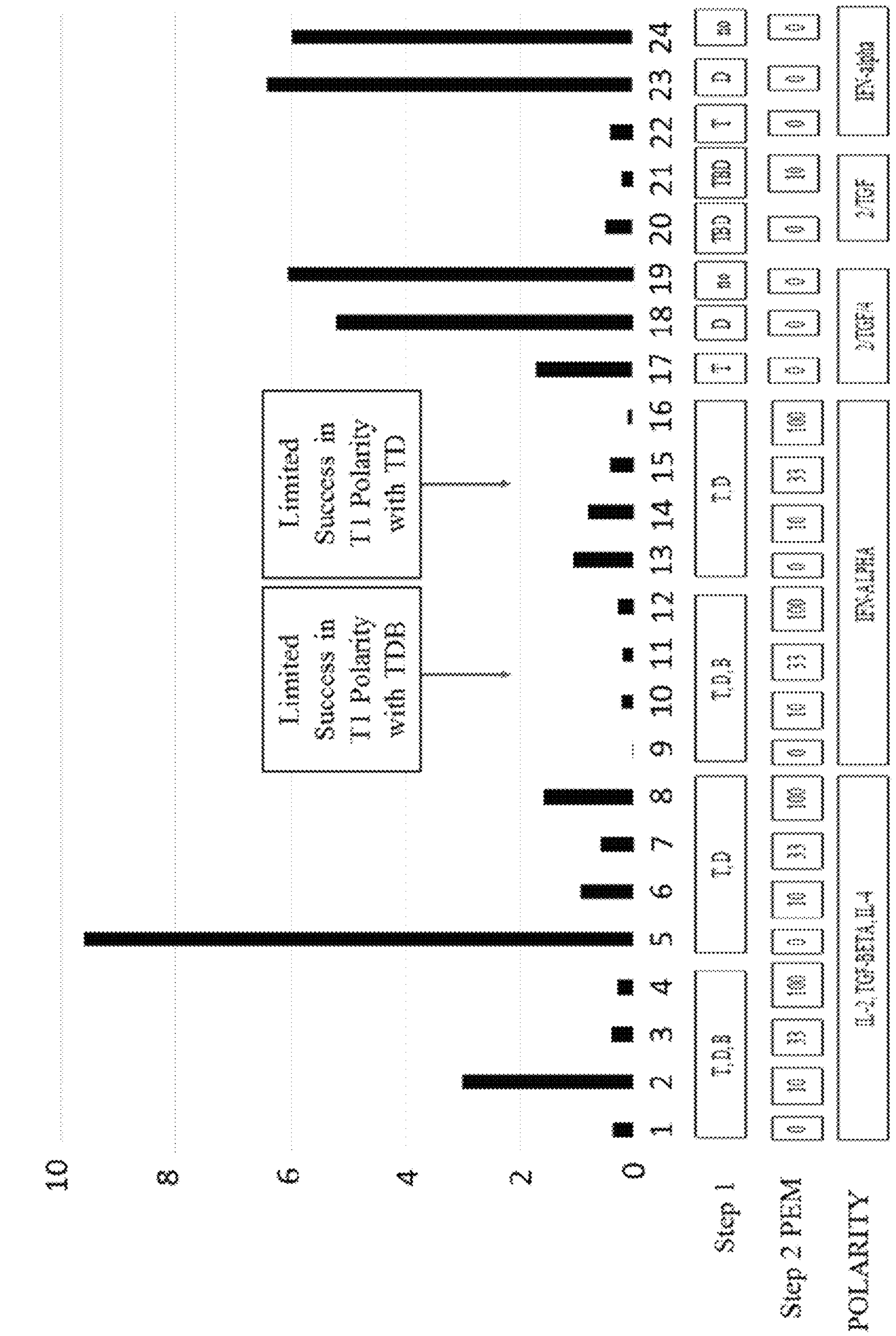
FIG. 13 depicts favorable expansion of de-differentiated T cells in hybrid Th2/$T_{REG}$ polarization condition relative to Th1 polarization condition.

FIG. 13 depicts favorable expansion of de-differentiated T cells in hybrid Th2/$T_{REG}$ polarization condition relative to Th1 polarization condition. Human $CD4^+$ and $CD8^+$ T cells were subjected to a 3-day de-differentiation procedure ("STEP 1"). As indicated in FIG. 13, this STEP 1 de-differentiation intervention variably included: no inhibitor ("no"); temsirolimus alone ("T"; 1.0 μM); Vitamin D alone ("D"; 0.1 nM); the anti-IL-R monoclonal antibody Basiliximab alone ("B"; 10 μg/ml); or various combinations of the inhibitors (T, D; or T, D, B) After 3-days, the de-differentiated T cells were co-stimulated (typical bead-to-T cell ratio of 3:1) in media variably supplemented with: Th1 polarization condition (rhu IFN-α; 10,000 IU/ml); $T_{REG}$ polarization (rhu IL-2, 100 IU/ml; rhu TGF-β, 10 ng/ml); or a hybrid Th2-$T_{REG}$ polarization condition (IL-2, TGF-β, plus addition of rhu IL-4 [1000 IU/ml]). In addition, the T cell culture in the presence of the variable polarization conditions was performed without the novel inhibitory molecule, pemetrexed ("0") or in the presence of variable concentrations of pemetrexed, as indicated (10 nM ["10"]; 33 nM ["33"]; or 100 nM ["100"]. After a total of 10 days of culture, the n=24 cultures were harvested and live cells were enumerated and graphed above (y-axis indicated number of cells$\times10^6$; input cell number was $1.5\times10^6$ cells).

As FIG. 13 shows, an ability to re-differentiate T cells after step 1 de-differentiation depended on: the specific components added during de-differentiation; the specific cytokines added during re-differentiation; and the presence of pemetrexed during re-differentiation.

Remarkably, attempts to re-differentiate a sufficient number of T cells after step 1 de-differentiation were unsuccessful in conditions of Th1-type polarization (see FIG. 13, cultures #9 through #16; all T cell yields below T cell input number). The greatly limited ability to re-differentiate along a Th1-type pathway was observed if the de-differentiation conditions included temsirolimus and vitamin D either alone or in combination with an anti-IL-2 receptor reagent and was also observed if pemetrexed was either not added during step 2 culture or added at concentrations ranging from 10 to 100 nM.

In marked contrast, attempts to re-differentiate a sufficient number of T cells after step 1 de-differentiation were successful in conditions of hybrid $T_{REG}$-Th2 polarization (see FIG. 13, cultures #2 and #5). Remarkably, in the most stringent de-differentiation condition (inclusion of temsirolimus, vitamin D, and anti-IL-2 receptor monoclonal antibody), sufficient T cells in the $T_{REG}$-Th2 polarization condition were only observed if pemetrexed was added to step 2 culture at a concentration of 10 nM.

Using this most stringent de-differentiation step 1 condition, attempts to re-differentiate a sufficient number of T cells during step 2 in a pure $T_{REG}$ polarizing condition (IL-2 plus TGF-β without IL-4) were unsuccessful, even in the presence of pemetrexed (cultures #20 and #21).

In sum, successful T cell re-differentiation, from a numerical perspective, is optimally performed using $T_{REG}$-Th2 hybrid polarization conditions (IL-2, TGF-β, and IL-4) AND using the pharmaceutical agent pemetrexed at a concentration of 10 nM.

Example 13: Culture of De-Differentiated T Cells in the Hybrid $T_{REG}$ Th2 Condition Results in the Generation of CD4 AND CD8 T Cells of Limited Differentiation Status We also evaluated the effect of this step 1 de-differentiation process followed by step 2 re-differentiation in various cytokine polarizing conditions/various pemetrexed conditions on T cell memory status. That is, studies show that T cells of limited differentiation status have improved therapeutic utility for adoptive cell therapy; thus, limited T cell differentiation would be a favorable feature of the step 1/step 2 T cell manufacturing method.

Figure 14A:
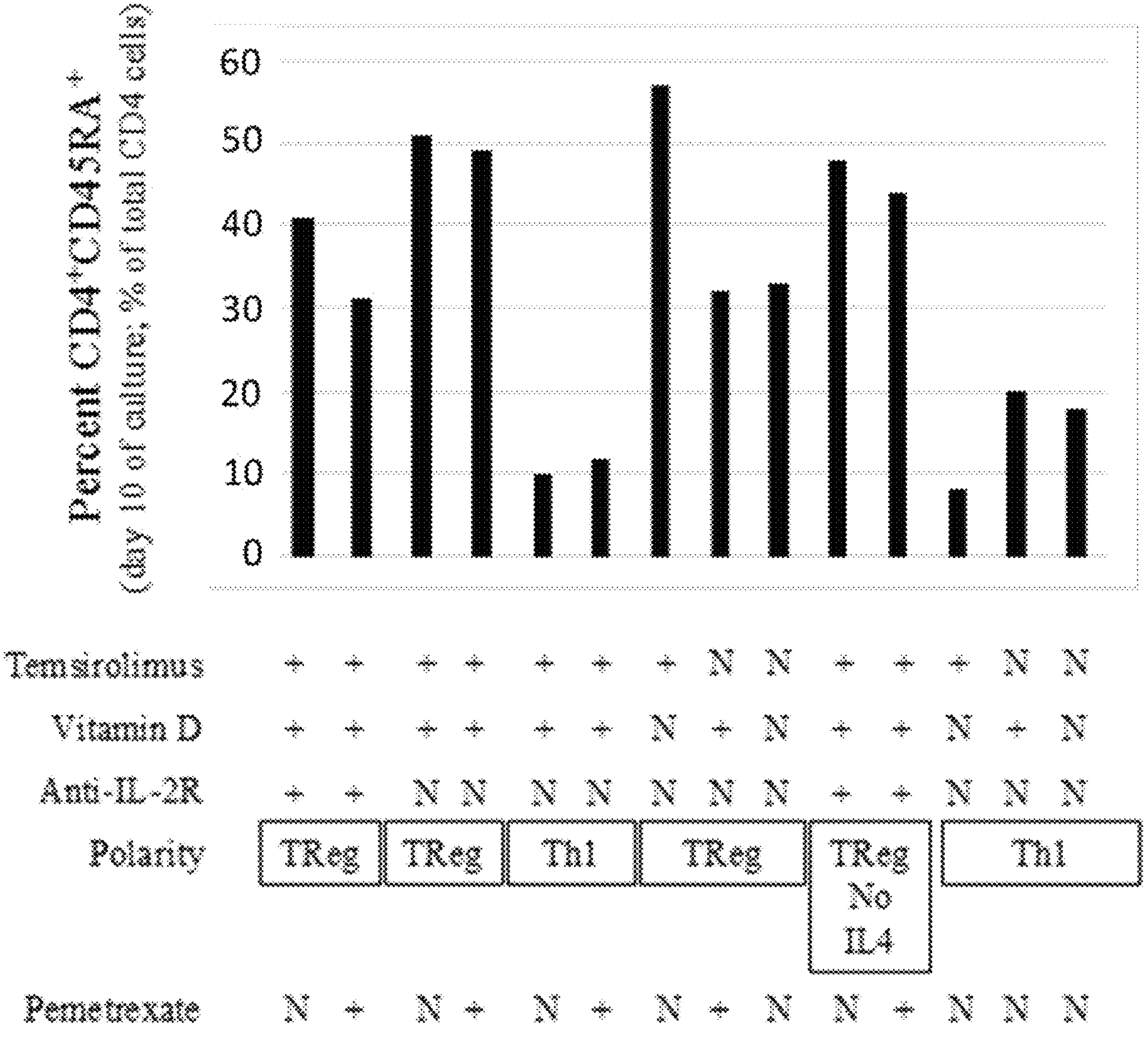
FIG. 14A depicts the percentage of CD4+CD45RA+ cells out of total CD4+ cells for cells treated under various conditions.
Figure 14B:
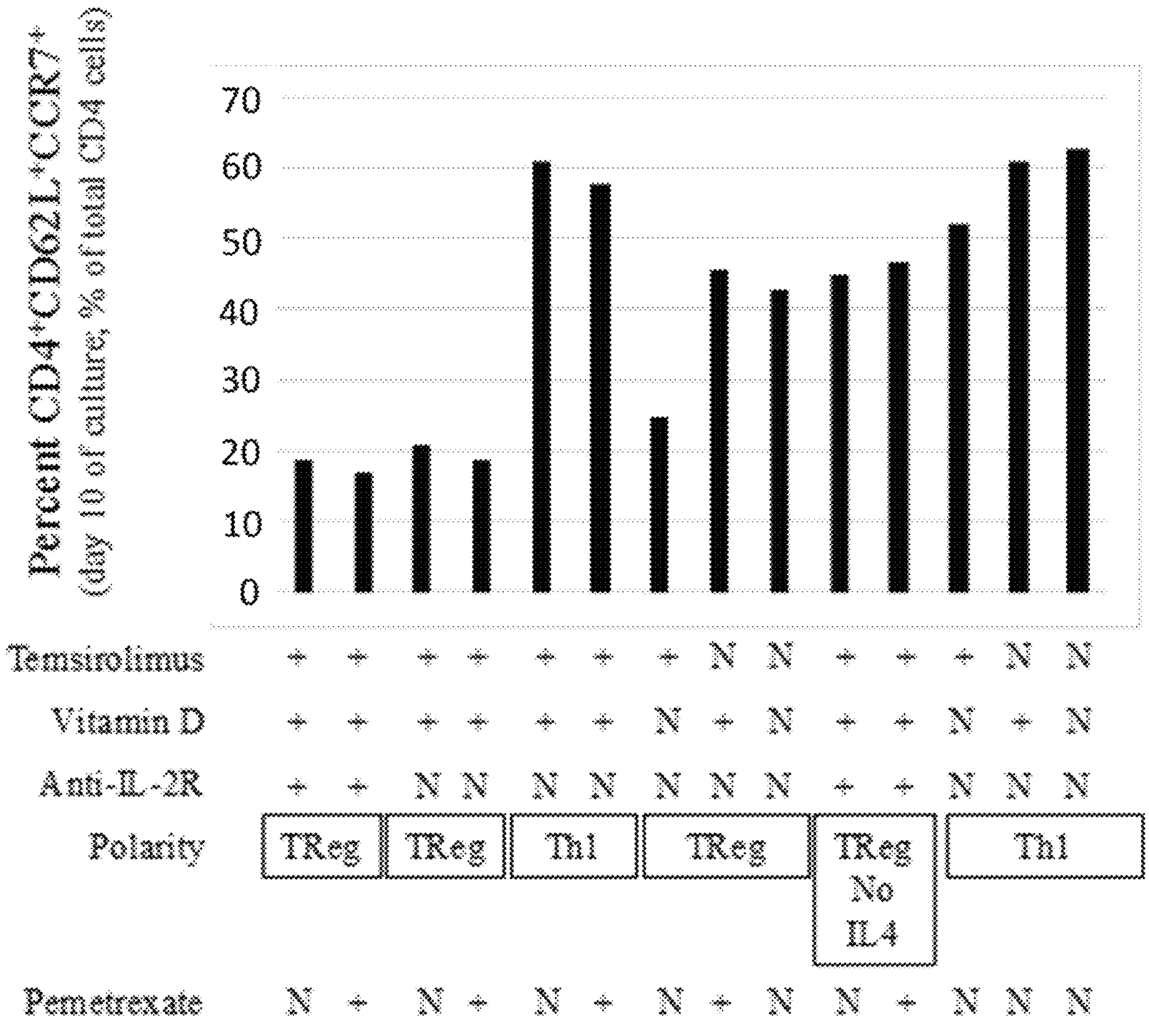
FIG. 14B depicts the percentage of CD4+CD62L+CCR7+ cells out of total CD4+ cells for cells treated under various conditions.
Figure 14C:
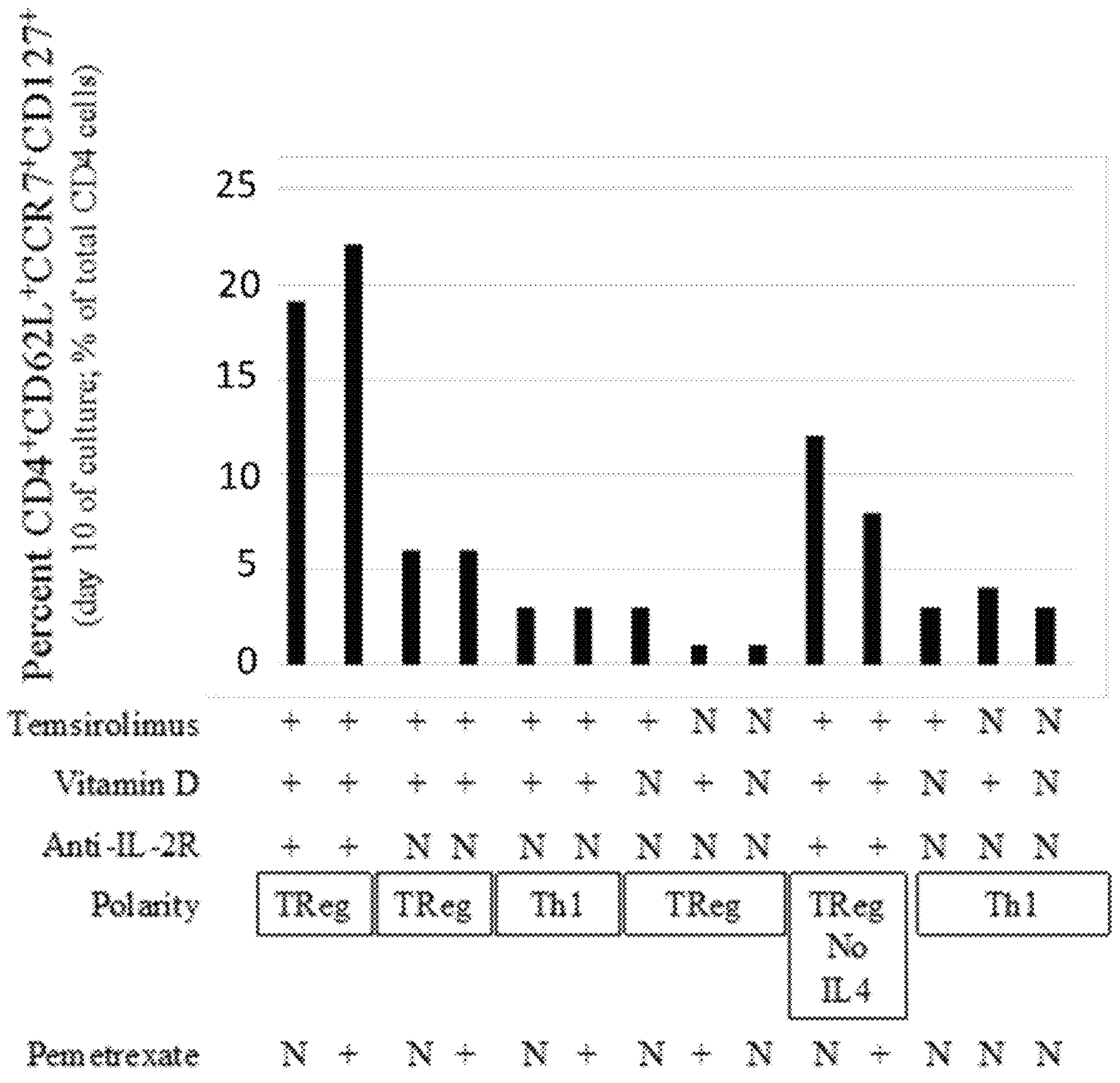
FIG. 14C depicts the percentage of CD4+CD62L+CCR7+ CD127+ cells out of total CD4+ cells for cells treated under various conditions.

FIGS. 14A-14C illustrates that the culture of de-differentiated T cells in hybrid Th2/$T_{REG}$ polarization condition results in the generation of naïve and triple-positive T central memory $CD4^+$ T cells. Human $CD4^+$ and $CD8^+$ T cells were subjected to a 3-day de-differentiation procedure and subsequent culture in media containing variable polarization culture conditions and variable presence of pemetrexed, as described in FIG. 13. Out of the total of n=24 culture conditions, only the cultures with favorable cell yields were further evaluated; all cultures shown that contained pemetrexed ("+") were at the concentration of 10 nM. The $T_{REG}$ conditions above all contained IL-2, TGF-β, and IL-4 ("TReg") unless indicated ("TReg, No IL4"). After a total of 10 days of culture, cultures were harvested and evaluated by flow cytometry for content of: naïve $CD4^+$ T cells (expressed as % of total $CD4^+$ T cells that co-expressed CD45RA; FIG. 14A); central-memory $CD4^+$ T cells (expressed % of total $CD4^+$ T cells that co-expressed both CD62L and CCR7; FIG. 14B); and triple-positive central-memory $CD4^+$ T cells (expressed % of total $CD4^+$ T cells that co-expressed CD62L, CCR7, and CD127; FIG. 14C).

As shown in FIG. 14A, step 2 re-differentiation in the hybrid $T_{REG}$-Th2 condition (with or without pemetrexed at the 10 nM concentration) resulted in a high frequency of the $CD4^+CD45RA^+$ naïve T cell subset that was favorable in experimental murine models of adoptive T cell therapy.

In addition, as shown in FIG. 14C, step 2 re-differentiation in the hybrid $T_{REG}$-Th2 condition (with or without pemetrexed at the 10 nM concentration) resulted in a high frequency of $CD4^+$ T cells that had triple positive co-expression of the memory markers CD62L, CCR7, and CD127. This triple-positive memory phenotype is a marker of T cells having a very primitive differentiation status.

As shown in FIG. 14C, the frequency of $CD4^+$ T cells that were triple positive for CD62L, CCR7, and CD127 was higher in the hybrid $T_{REG}$-Th2 polarizing condition relative to the pure $T_{REG}$ polarizing condition.

Also, as shown in FIG. 14C, use of the more stringent step 1 de-differentiation condition that included not only temsirolimus and vitamin D but also an anti-IL-2 receptor monoclonal antibody yielded the highest frequency of CD4 cells that were triple positive for CD62L, CCR7, and CD127 using the hybrid $T_{REG}$-Th2 polarizing condition.

Figure 15A:
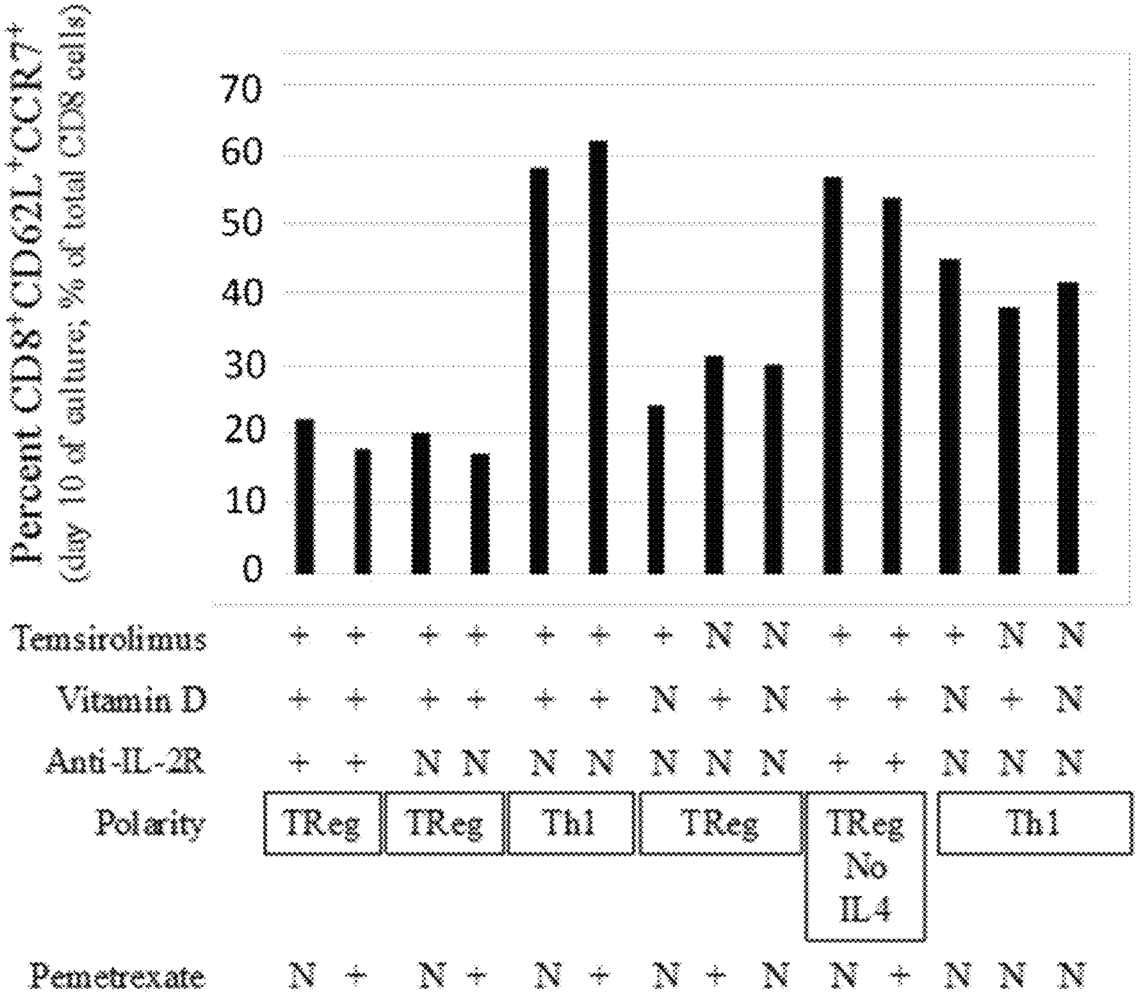
FIG. 15A depicts the percentage of CD8+CD62L+CCR7+ cells out of total CD8 cells for cells treated under various conditions.
Figure 15B:
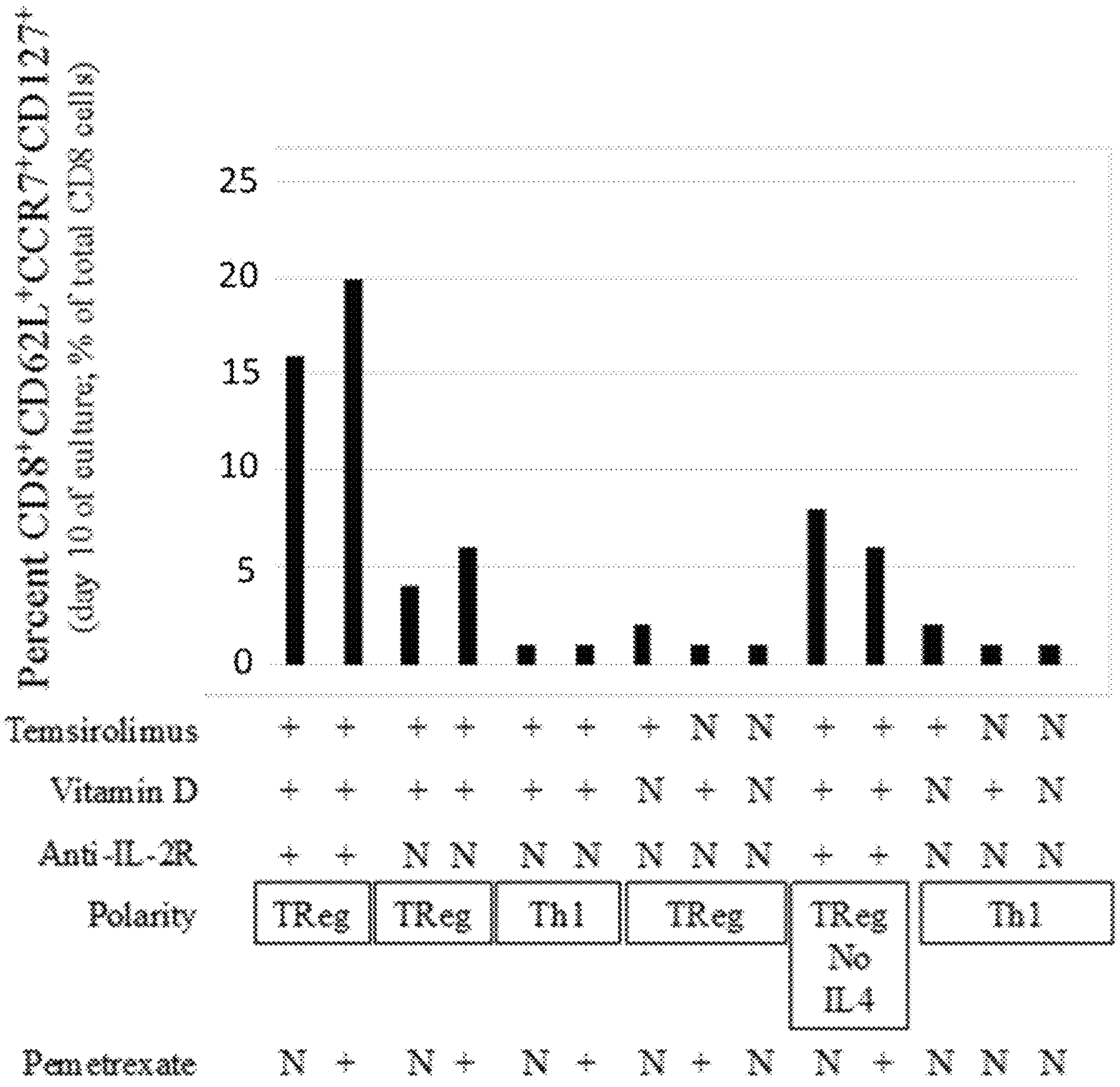

FIGS. 15A-15B illustrate that culture of de-differentiated T cells in hybrid Th2/TReg polarization condition results in the generation of triple-positive T central memory $CD8^+$ T cells. Human $CD4^+$ and $CD8^+$ T cells were subjected to a 3-day de-differentiation procedure and subsequent culture in media containing variable polarization culture conditions and variable presence of pemetrexed, as described in FIG. 13. Out of the total of n=24 culture conditions, only the cultures with favorable cell yields were further evaluated; all cultures shown that contained pemetrexed ("+") were at the concentration of 10 nM. The $T_{REG}$ conditions above all contained IL-2, TGF-β, and IL-4 ("TReg") unless indicated ("TReg, No IL4"). After a total of 10 days of culture, cultures were harvested and evaluated by flow cytometry for content of: central-memory $CD8^+$ T cells (expressed % of total $CD8^+$ T cells that co-expressed both CD62L and CCR7; FIG. 15A); and triple-positive central-memory $CD8^+$ T cells (expressed % of total $CD8^+$ T cells that co-expressed CD62L, CCR7, and CD127; FIG. 15B).

Also, as shown in FIG. 15B, the frequency of CD8 cells that were triple positive for CD62L, CCR7, and CD127 was higher in the hybrid $T_{REG}$-Th2 polarizing condition relative to the pure $T_{REG}$ polarizing condition. Furthermore, as shown in FIGS. 15A-15B, use of the more stringent step 1 de-differentiation condition that included not only temsirolimus and vitamin D but also an anti-IL-2 receptor monoclonal antibody yielded the highest frequency of $CD8^+$ T cells that were triple positive for CD62L, CCR7, and CD127 using the hybrid $T_{REG}$-Th2 polarizing condition.

In sum, these data indicate that T cell re-differentiation using hybrid $T_{REG}$-Th2 cytokine polarization (IL-2, TGF-β, and IL-4) AND using pemetrexed (10 nM) after step 1 de-differentiation results in $CD4^+$ and $CD8^+$ T cells of a favorable, limited differentiation status.

Example 14: Culture of De-Differentiated T Cells in the Hybrid $T_{REG}$ Th2 Polarizing Condition Results in T Cells with a Primitive Th2 Cell Cytokine Phenotype T cells re-differentiated in the step 2 culture conditions after step 1 de-differentiation were also evaluated for cytokine secretion pattern. Cytokine secretion is an indicator of T cell effector function, and as such, it is generally desirable that $T_{REG}$ cells have reduced cytokine secretion potential, particularly with respect to key inflammatory cytokines such as IL-17, IFN-γ and TNF-α. In the case of the proposed hybrid $T_{REG}$-Th2 cell population, it would be expected that such cells would also secrete some distribution of Th2 cytokines.

Figure 16A:
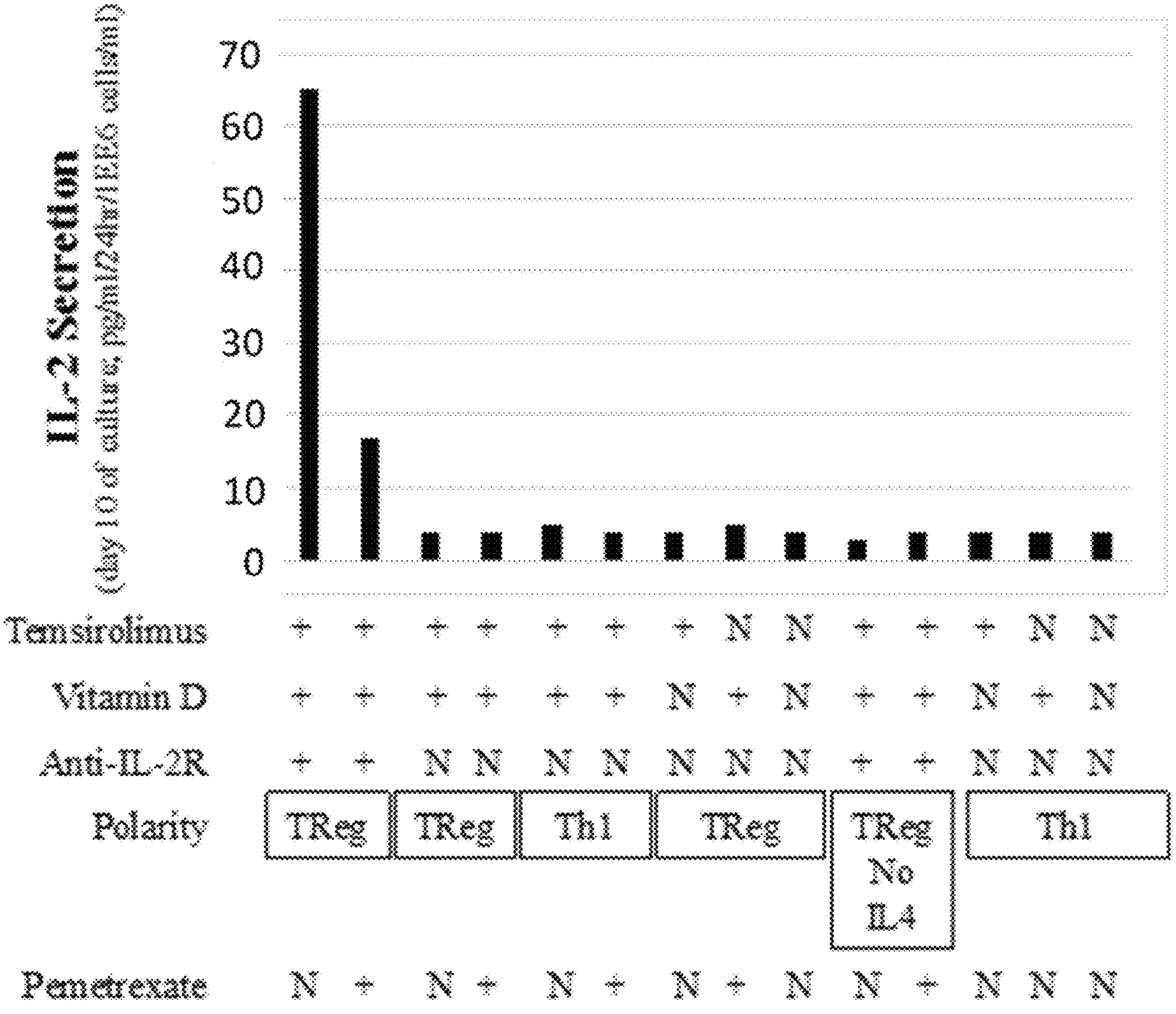
FIG. 16A depicts IL-2 secretion for cells treated under various conditions.
Figure 16B:
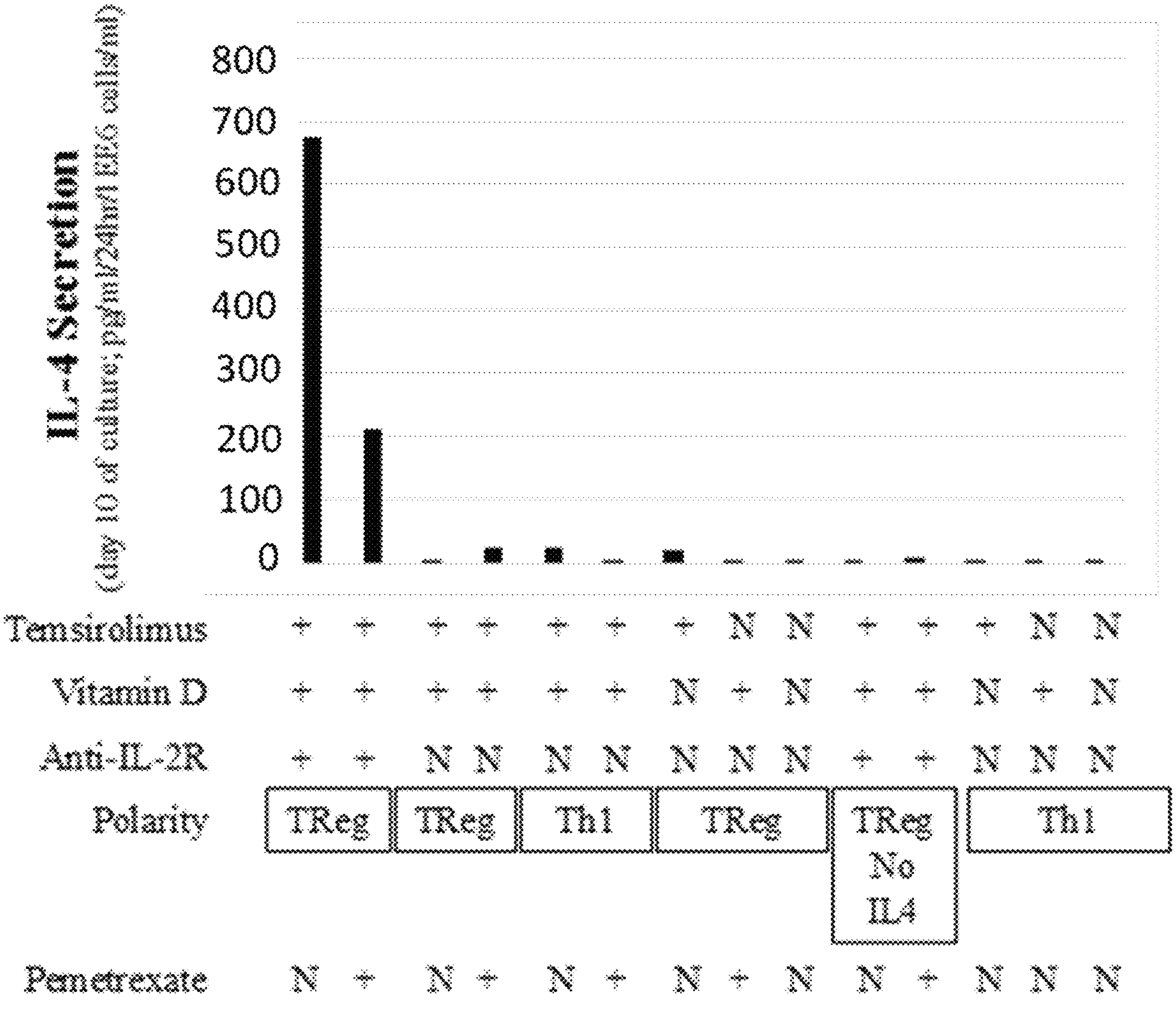
FIG. 16B depicts IL-4 secretion for cells treated under various conditions.
Figure 16C:
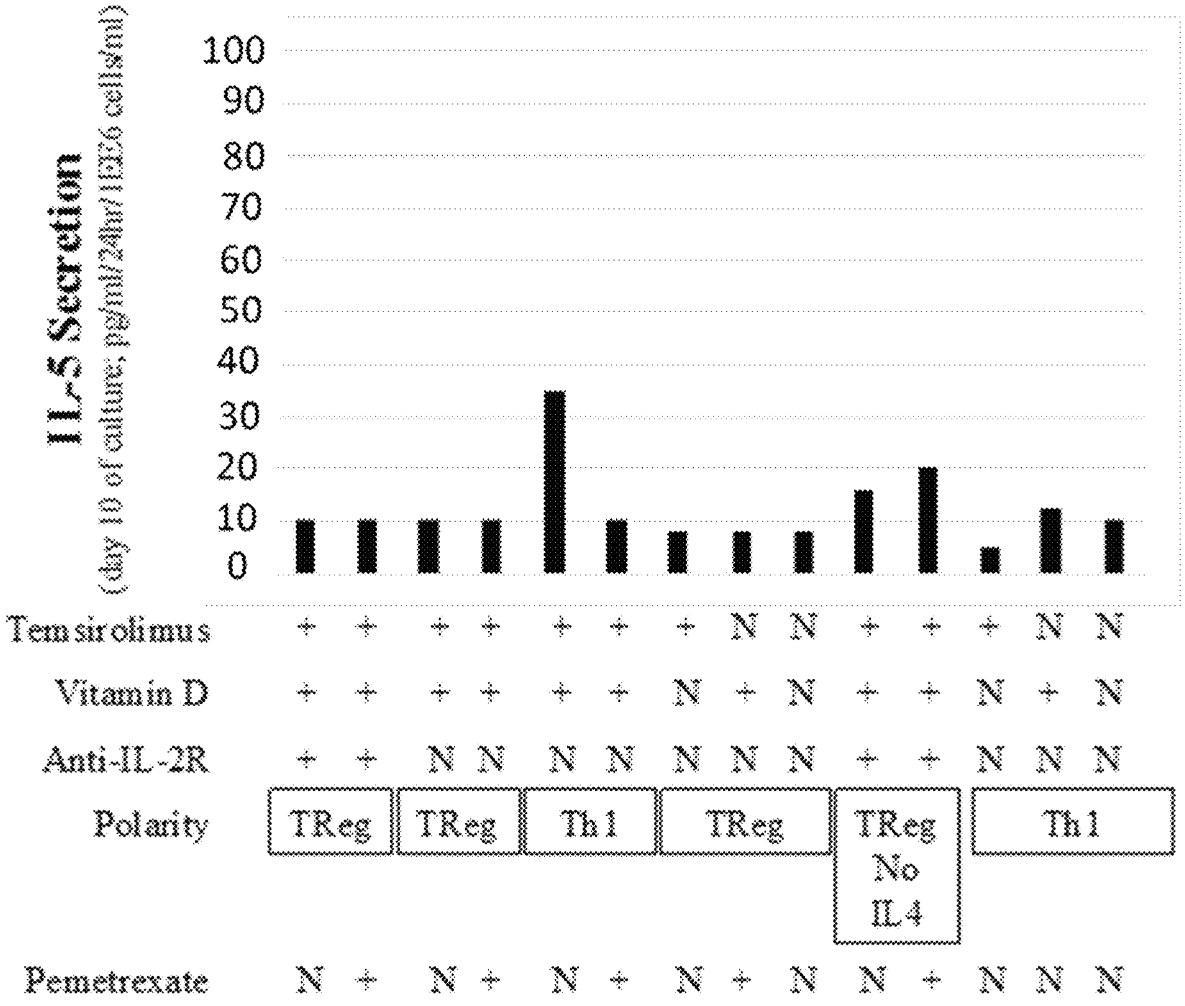
FIG. 16C depicts IL-5 secretion for cells treated under various conditions.

FIGS. 16A-16C illustrate that the culture of de-differentiated T cells in hybrid Th2/TReg polarization condition results in the generation of T cells with a primitive Th2 cell cytokine phenotype: as indicated by high levels of IL-2 and IL-4 secretion and a low level of IL-5 secretion. Human CD4+ and $CD8^+$ T cells were subjected to a 3-day de-differentiation procedure and subsequent culture in media containing variable polarization culture conditions and variable presence of pemetrexed, as described in FIG. 13. Out of the total of n=24 culture conditions, only the cultures with favorable cell yields were further evaluated; all cultures shown that contained pemetrexed ("+") were at the concentration of 10 nM. The $T_{REG}$ conditions above all contained IL-2, TGF-β, and IL-4 ("TReg") unless indicated ("TReg, No IL4"). After a total of 10 days of culture, the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr.

As shown in FIG. 16A, T cells re-differentiated in the hybrid $T_{REG}$-Th2 cytokine polarizing condition (IL-2, TGF-β, and IL-4) with or without pemetrexed added to culture had the highest values for IL-2 secretion. This result is consistent with the prior understanding that IL-2 secretion in T cells is a characteristic of T cells in an early state of differentiation, which T cells re-differentiated in the hybrid culture conditions possess.

Figure 17A:
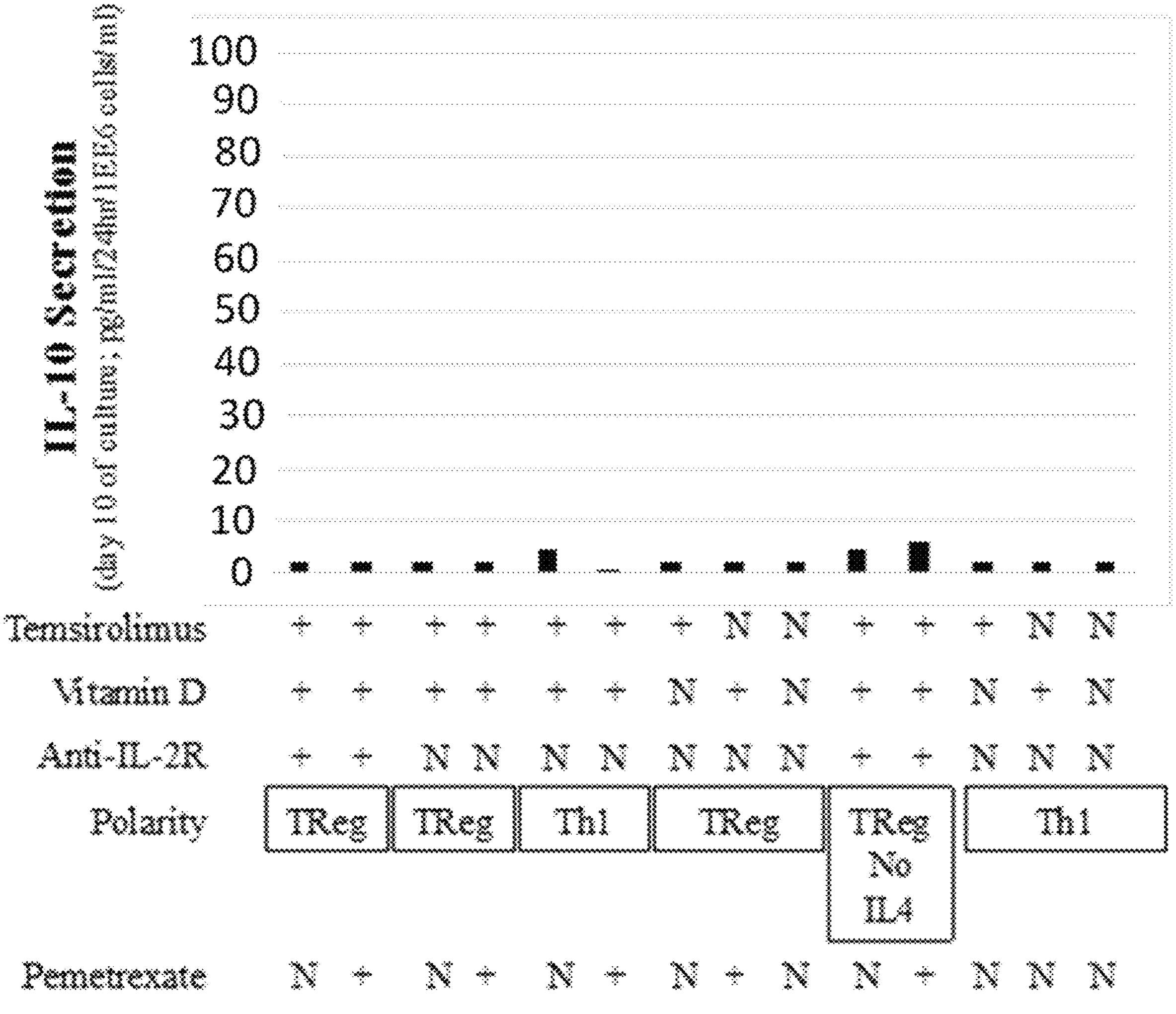
FIG. 17A depicts IL-10 secretion for cells treated under various conditions.
Figure 17B:
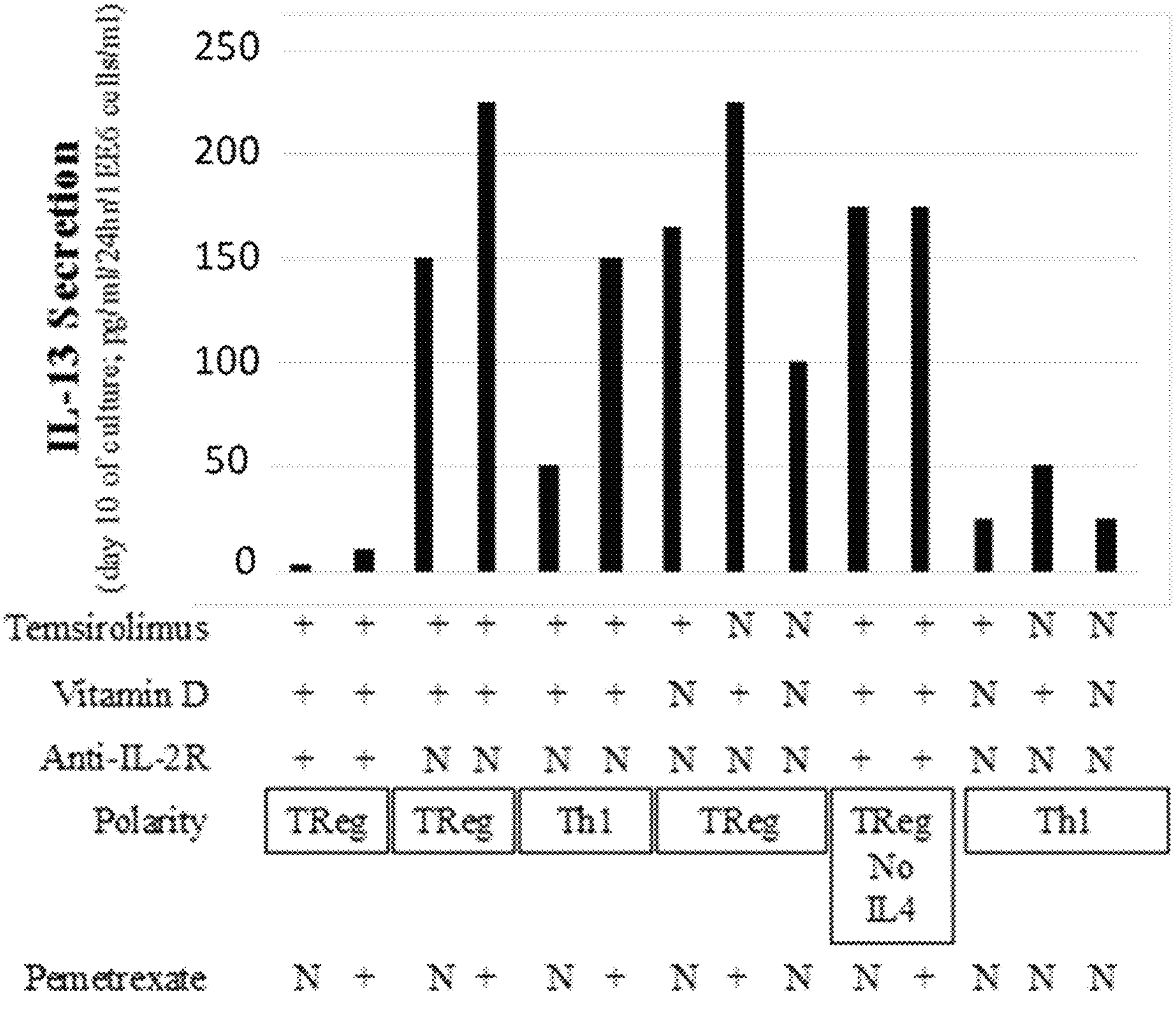
FIG. 17B depicts IL-13 secretion for cells treated under various conditions.
Figure 17C:
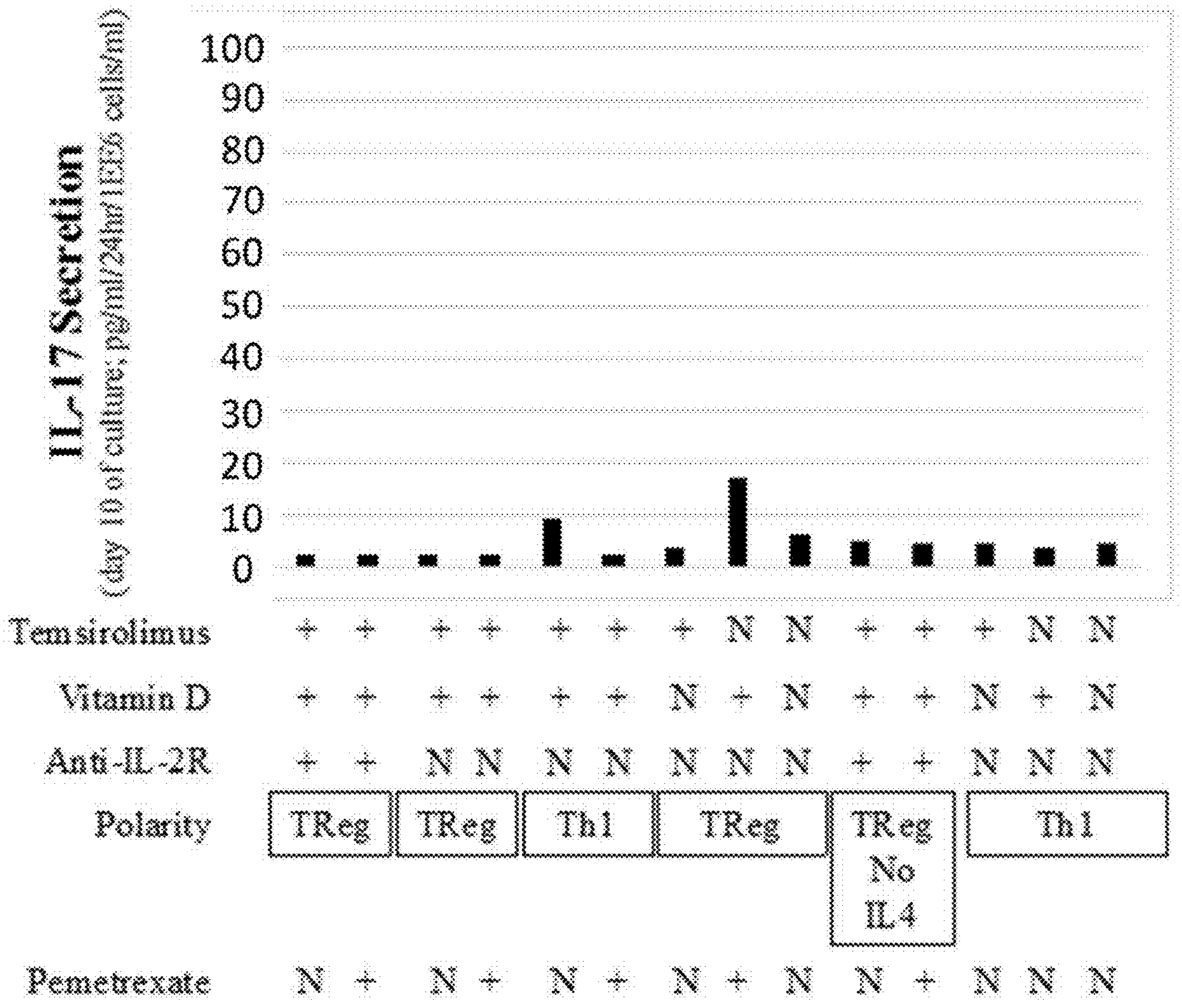
FIG. 17C depicts IL-17 secretion for cells treated under various conditions.

FIGS. 17A-17C illustrate that the culture of de-differentiated T cells in hybrid Th2/TReg polarization condition results in the generation of T cells with a primitive Th2 cell cytokine phenotype: as indicated by low levels of IL-10, IL-13, and IL-17 secretion. Human $CD4^+$ and $CD8^+$ T cells were subjected to a 3-day de-differentiation procedure and subsequent culture in media containing variable polarization culture conditions and variable presence of pemetrexed, as described in FIG. 13. Out of the total of n=24 culture conditions, only the cultures with favorable cell yields were further evaluated; all cultures shown that contained pemetrexed ("+") were at the concentration of 10 nM. The $T_{REG}$ conditions above all contained IL-2, TGF-β, and IL-4 ("TReg") unless indicated ("TReg, No IL4"). After a total of 10 days of culture, the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr.

Figure 18A:
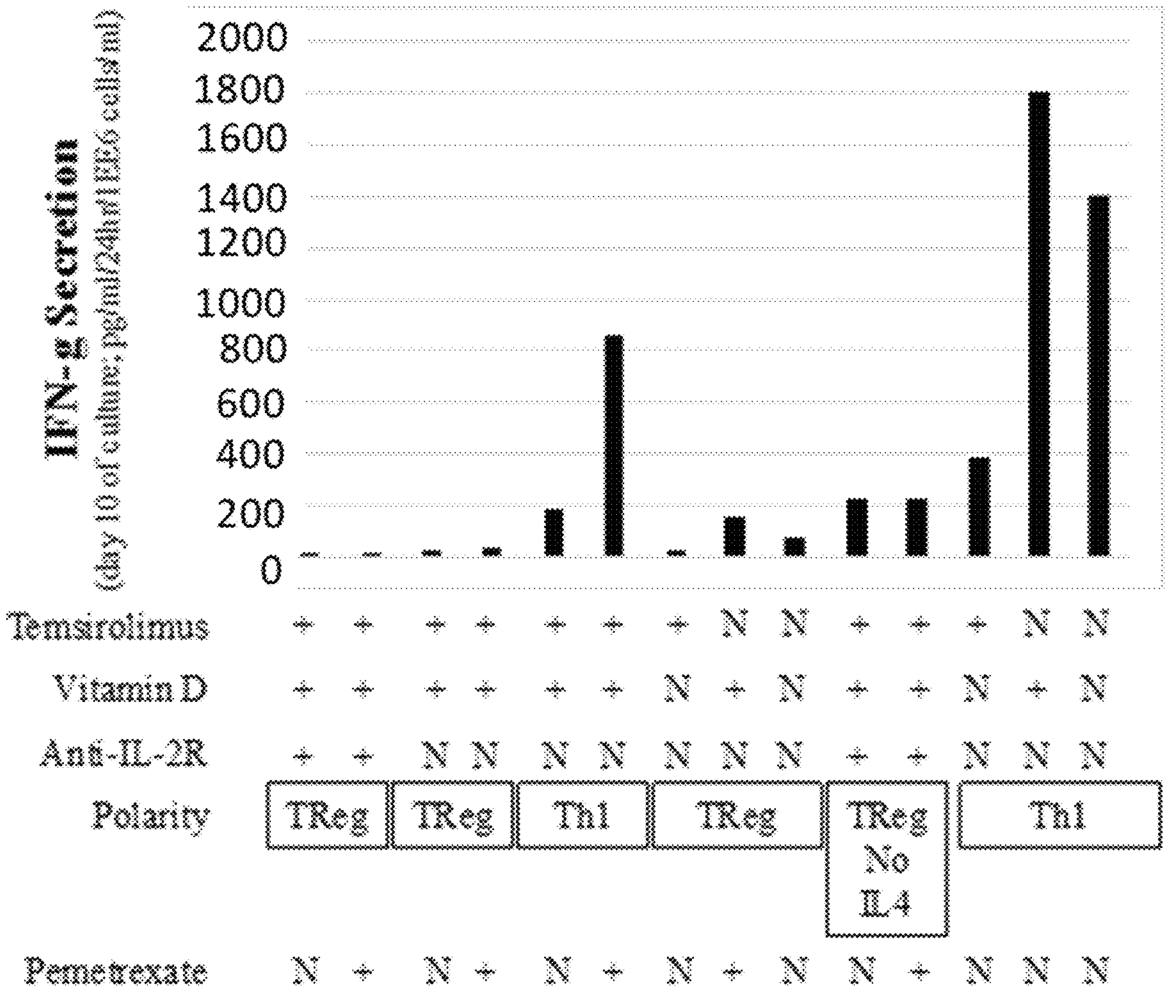
FIG. 18A depicts IFN-γ secretion for cells treated under various conditions.
Figure 18B:
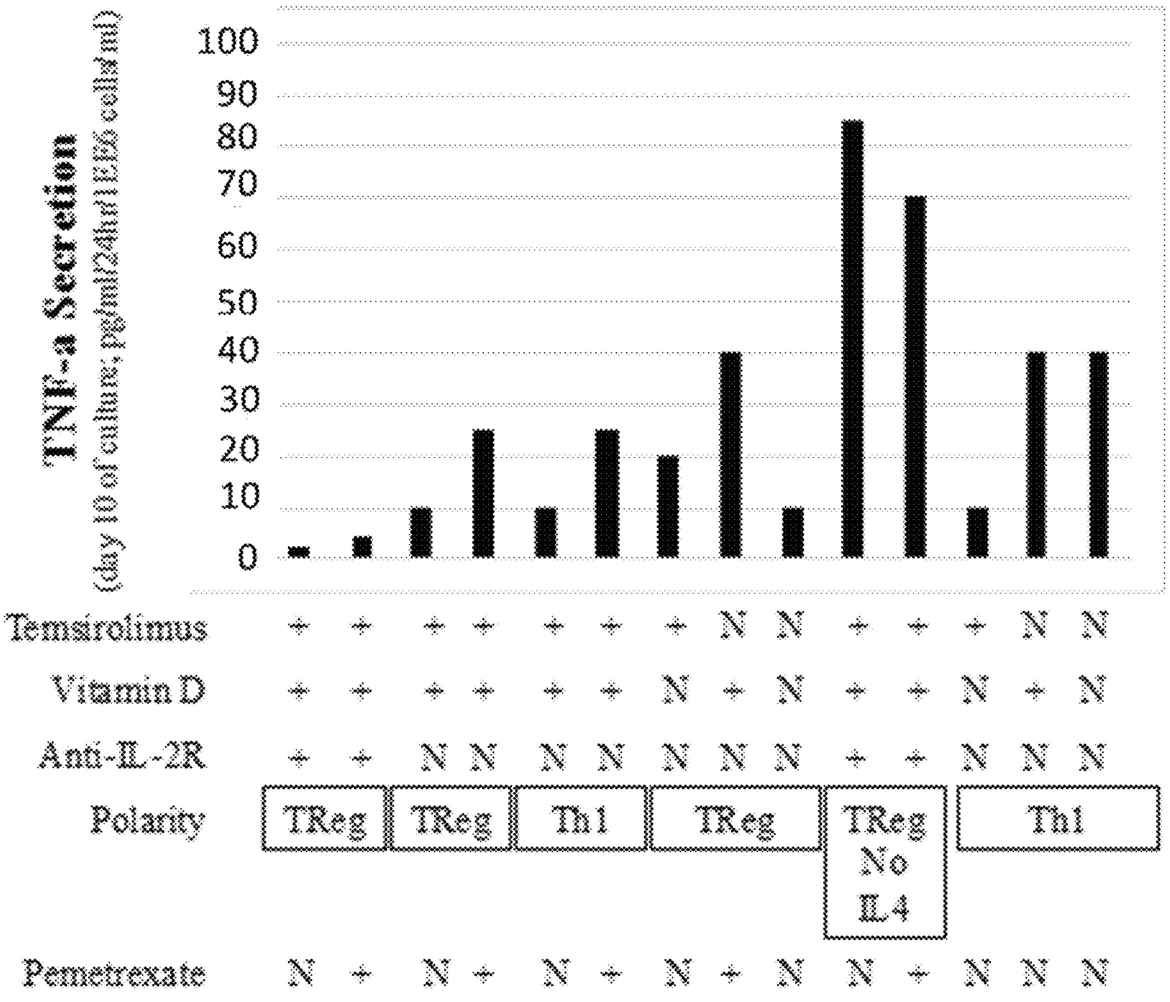
FIG. 18B depicts TNF-α secretion for cells treated under various conditions.
Figure 18C:
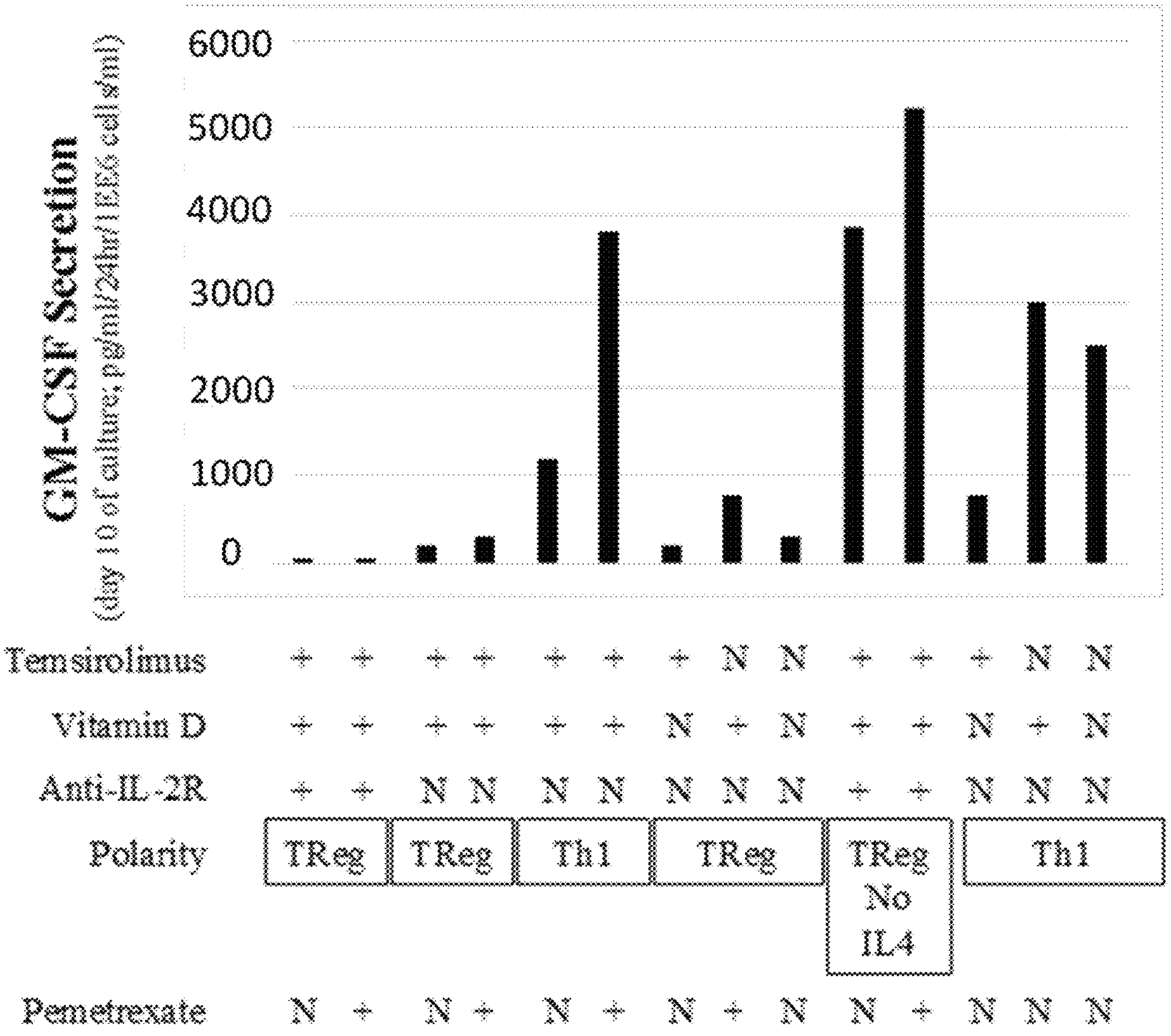
FIG. 18C depicts GM-CSF secretion for cells treated under various conditions.

FIGS. 18A-18C illustrates that the culture of de-differentiated T cells in hybrid Th2/$T_{REG}$ polarization condition results in the generation of T cells with a primitive Th2 cell cytokine phenotype: as indicated by low levels of IFN-gamma, TNF-alpha, and GM-CSF secretion. Human $CD4^+$ and $CD8^+$ T cells were subjected to a 3-day de-differentiation procedure and subsequent culture in media containing variable polarization culture conditions and variable presence of pemetrexed, as described in FIG. 13. Out of the total of n=24 culture conditions, only the cultures with favorable cell yields were further evaluated; all cultures shown that contained pemetrexed ("+") were at the concentration of 10 nM. The $T_{REG}$ conditions above all contained IL-2, TGF-β, and IL-4 ("TReg") unless indicated ("TReg, No IL4"). After a total of 10 days of culture, the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr.

Furthermore, as shown in FIG. 16B, T cells re-differentiated in the hybrid $T_{REG}$-Th2 condition (IL-2, TGF-β, and IL-4) with or without pemetrexed added to culture had the highest values for IL-4 secretion. Because IL-4 is the key cytokine that dictates Th2 polarization, T cells manufactured in the hybrid condition are indeed Th2 polarized. On the other hand, consistent with their limited differentiation state, cells re-differentiated in the hybrid condition did not secrete high levels of effector Th2 cytokine (IL-5, see FIG. 16C; IL-10, see FIG. 17A; IL-13, see FIG. 17B) or effector Th1/Th17 cytokines (IFN-γ, see FIG. 18A; TNF-alpha, see FIG. 18B; GM-CSF, see FIG. 18C; IL-17, see FIG. 17C).

Importantly, lack of IL-4 inclusion in the T cell re-differentiation process resulted in higher levels of the inflammatory cytokines IFN-γ, TNF-α, and GM-CSF (see FIGS. 18A-18C).

In sum, these data indicate that re-differentiation of T cells towards a $T_{REG}$ phenotype from step 1 de-differentiated cells optimally should utilize the hybrid $T_{REG}$-Th2 polarizing conditions because T cells emanating from this condition have a greatly reduced capacity for secretion of cytokines associated with inflammatory disease.

Example 15: Culture of De-Differentiated T Cells in the Hybrid $T_{REG}$ Th2 Condition Results in T Cells with an Enhanced Hybrid $T_{REG}$ Th2 Transcription Factor Profile T cell cytokine phenotype is determined by key transcription factors. The association of transcription factors with T cell subsets is as follows: FOXP3 dictates $T_{REG}$ cell development; TBET dictates Th1-type cell development; and GATA3 dictates Th2-type development.

To evaluate these transcription factors in our manufacturing method, T cells were first subjected to the step 1 de-differentiation procedure and then re-differentiated in the hybrid $T_{REG}$-Th2 culture condition (IL-2, TGF-β, and IL-4). In addition, we compared the effects of pemetrexed with a classical mTOR inhibitor. In our experiment, instead of using the oral formulation of the mTOR inhibitor (rapamycin; Sirolimus®), we utilized the water soluble parental form of the drug, temsirolimus (Toracel®).

The i$T_{REG}$ phenotype is considered to be unstable; as such, we evaluated the stability of T cells re-differentiated using the hybrid $T_{REG}$-Th2 culture condition at delayed time points, including days 20 and 32 of culture. In addition, to test phenotype stability in a rigorous manner, between day 24 and day 32 of culture, T cells received a high level of co-stimulation (3:1 bead-to-T cell ratio) and were propagated in media without cytokines or pharmacologic agents.

Figure 19A:
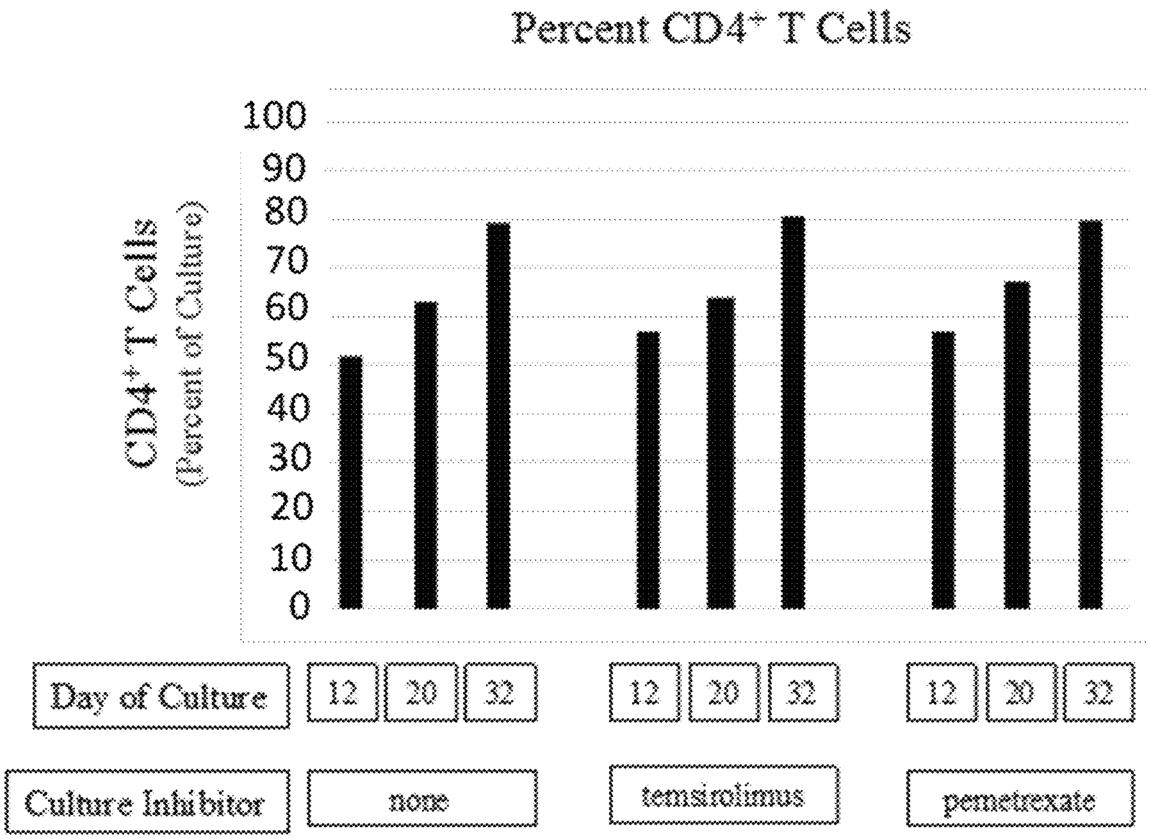
FIG. 19A depicts the percent of CD4+ T cells in culture by day and culture inhibitor.
Figure 19B:
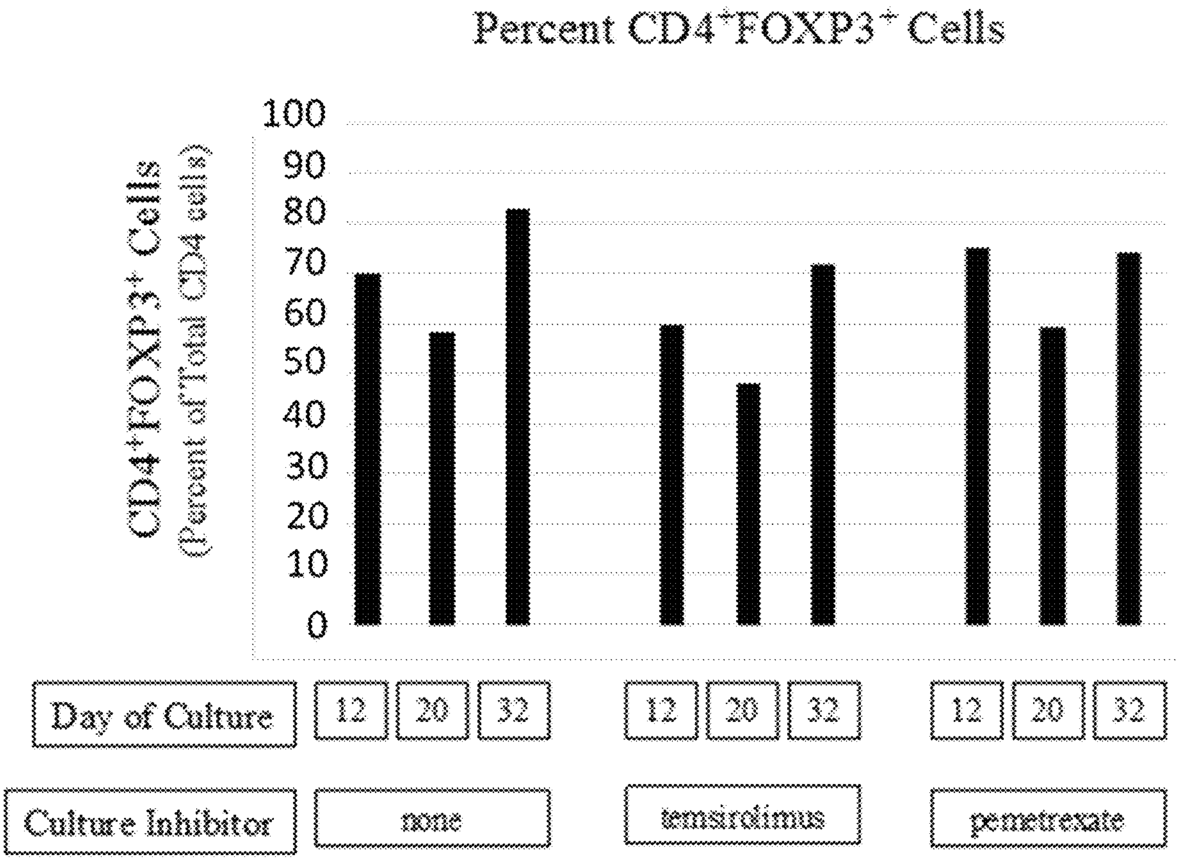
FIG. 19B depicts the percent of CD4+FOXP3+ T cells in culture by day and culture inhibitor.
Figure 19C:
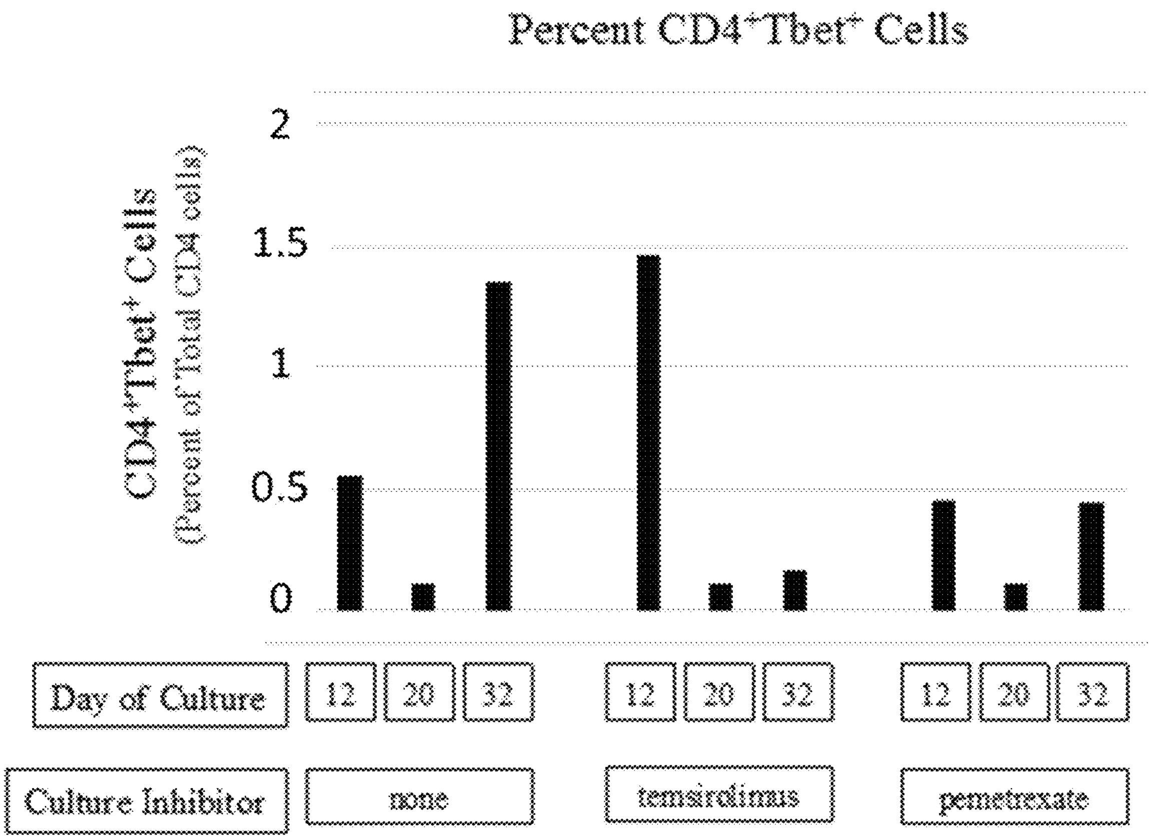
FIG. 19C depicts the percent of CD4+ Tbet+ T cells in culture by day and culture inhibitor.
Figure 19D:
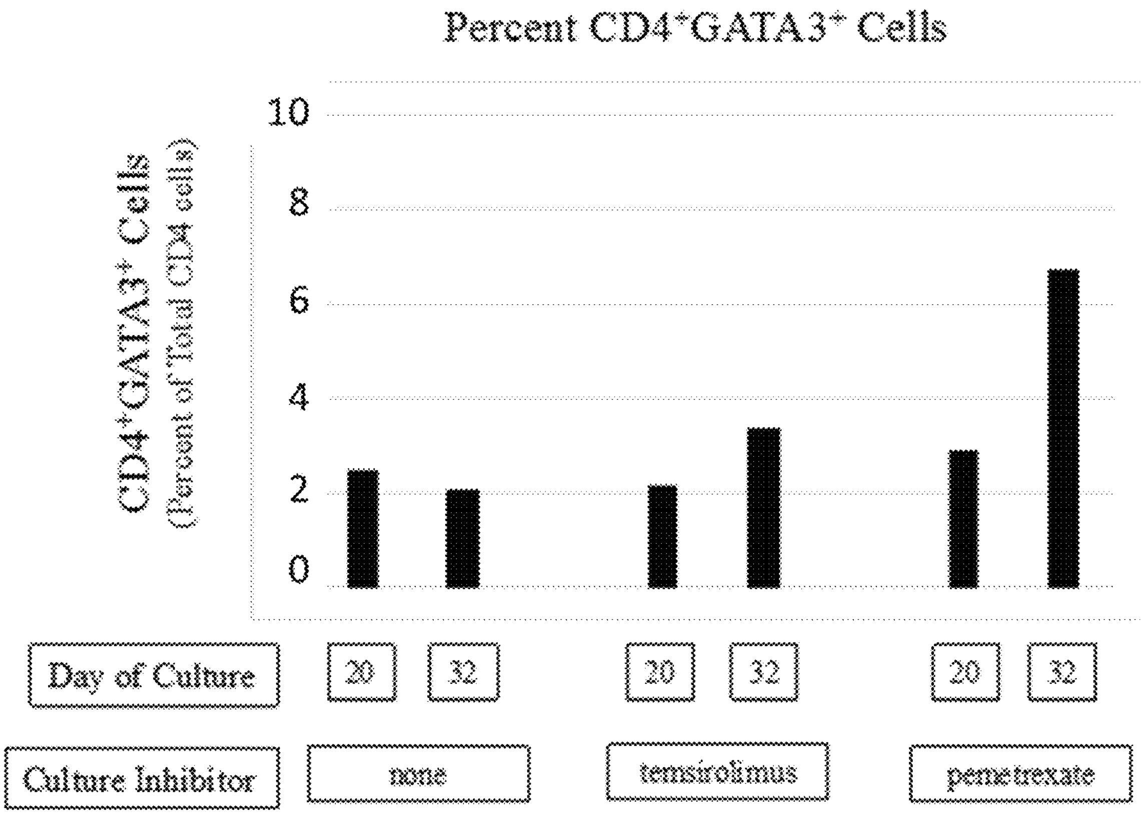
FIG. 19D depicts the percent of CD4+GATA3+ T cells in culture by day and culture inhibitor.

FIGS. 19A-19D illustrate that extended culture of de-differentiated T cells in the hybrid Th2/$T_{REG}$ polarization condition containing pemetrexed results in the generation of $CD4^+$ T cells expressing FOXP3 and GATA3 transcription factors. Human $CD4^+$ and $CD8^+$ T cells were subjected to a 3-day de-differentiation procedure and subsequently were co-stimulated (3:1 bead-to-T cell ratio) and propagated in media containing the hybrid Th2/$T_{REG}$ polarizing condition (IL-2; TGF-β; IL-4) either without or with the pharmacologic inhibitors temsirolimus (1.0 μM) or pemetrexed (10 nM). Cultures were restimulated with 3/28 beads at both day 14 and day 24 of culture; at day 24 of culture, to evaluate stability of the transcription factor expression, the culture media did not contain exogenous cytokines or pharmacologic inhibitors. At days 12, 20, and 32 of culture, T cells were harvested and subjected to surface flow cytometry (CD4 marker) and intra-cellular staining for the following transcription factors, FOXP3, Tbet, and GATA3. The data above show the percent CD4 cells out of the total cultured population (FIG. 19A); the percent of CD4 cells that expressed the $T_{REG}$ transcription factor FOXP3 (FIG. 19B); the percent of CD4 cells that expressed the Th1 transcription factor Tbet (FIG. 19C); and the percent of CD4 cells that expressed the Th2 transcription factor GATA3 (FIG. 19D).

As FIGS. 19A-19D detail, T cells re-differentiated in the $T_{REG}$-Th2 condition had a gradual shift towards CD4 cell predominance over time in culture (FIG. 19A). As shown in FIG. 19B, CD4 cells expressed FOXP3 at a high frequency and in a stable manner from day 12 through day 32 of culture independent of temsirolimus or pemetrexed presence in culture.

As FIG. 19C, there was a very low frequency of contamination with the Th1 transcription factor TBET even without pharmacologic inhibitor presence. However, the most consistently reduced TBET values were observed in the hybrid polarization conditions that also included pemetrexed. Finally, as shown in FIG. 19D, the highest end-of-culture Th2-associated GATA3 expression was observed in the T cells manufactured in the hybrid $T_{REG}$-Th2 condition that was supplemented with pemetrexed.

Figure 20A:
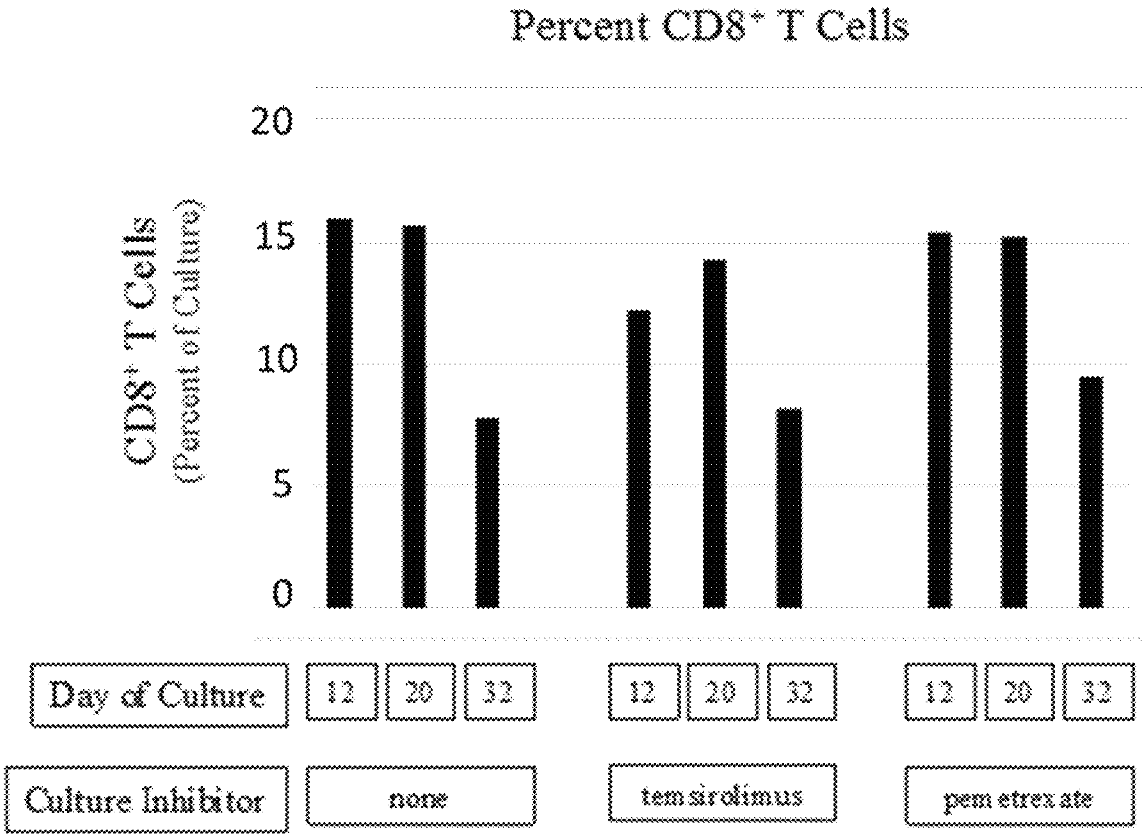
FIG. 20A depicts the percent of CD8+ T cells in culture by day and culture inhibitor.
Figure 20B:
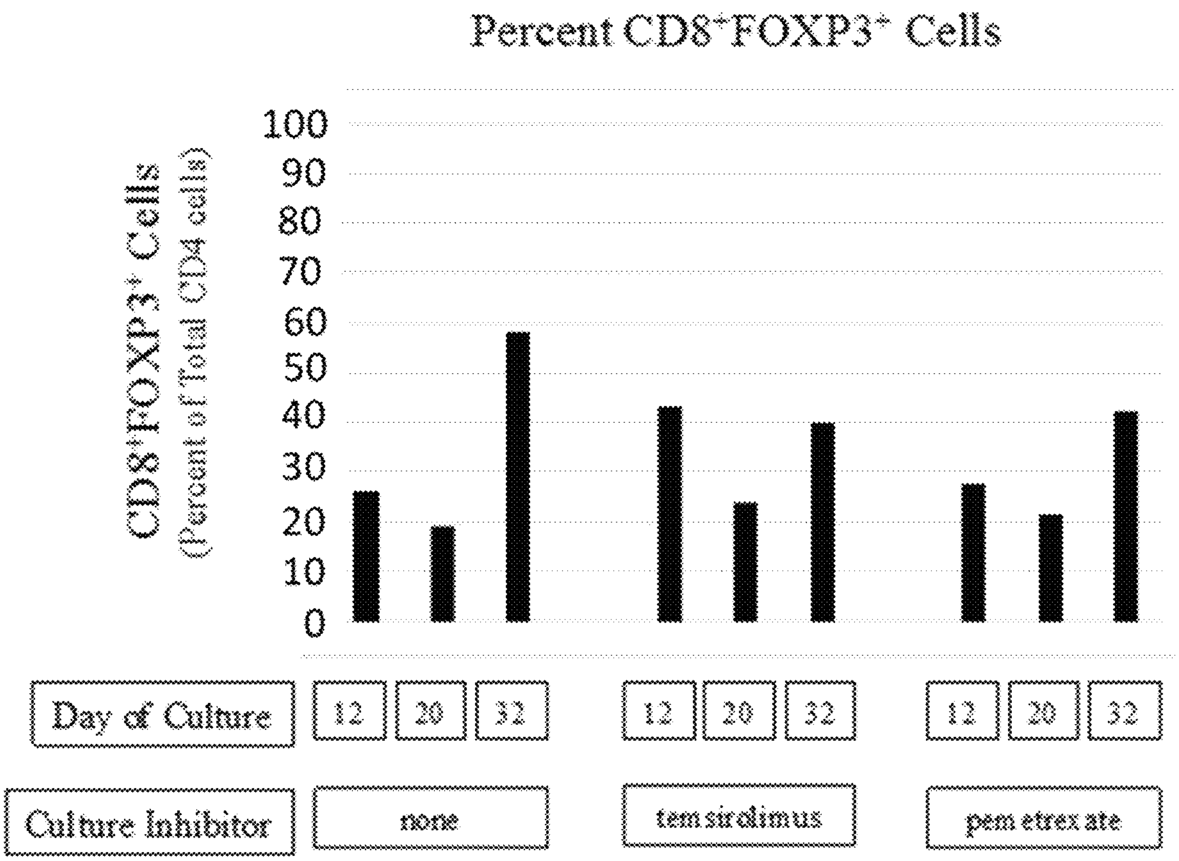
FIG. 20B depicts the percent of CD8+FOXP3+ T cells in culture by day and culture inhibitor.
Figure 20C:
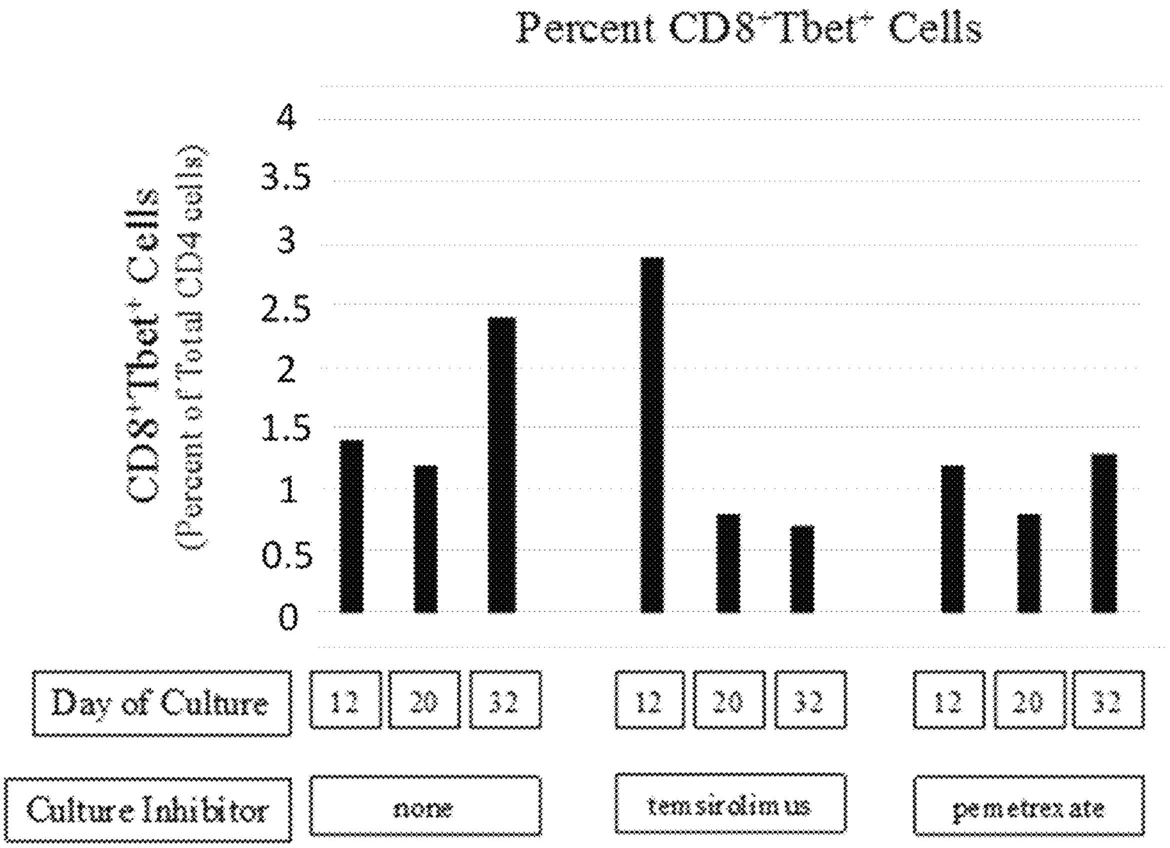
FIG. 20C depicts the percent of CD8+ Tbet+ T cells in culture by day and culture inhibitor.
Figure 20D:
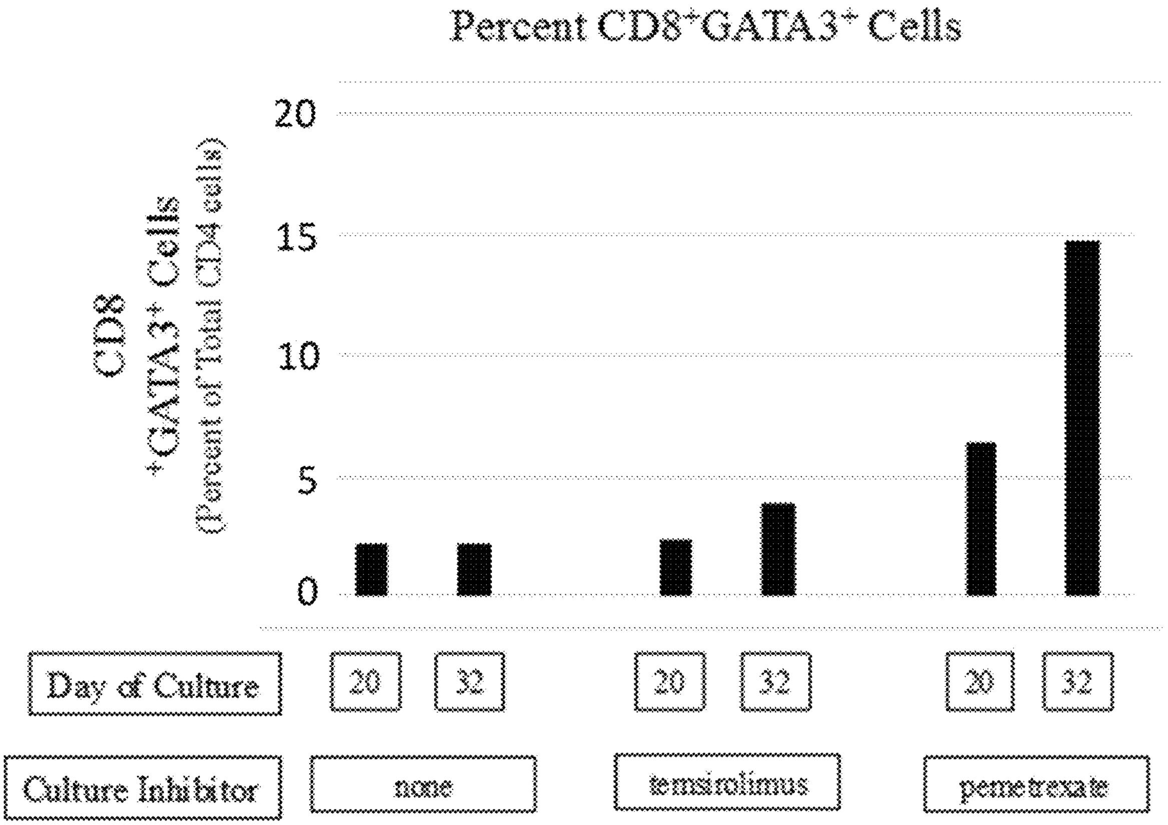
FIG. 20D depicts the percent of CD8+GATA3+ T cells in culture by day and culture inhibitor.
Figure 21A:
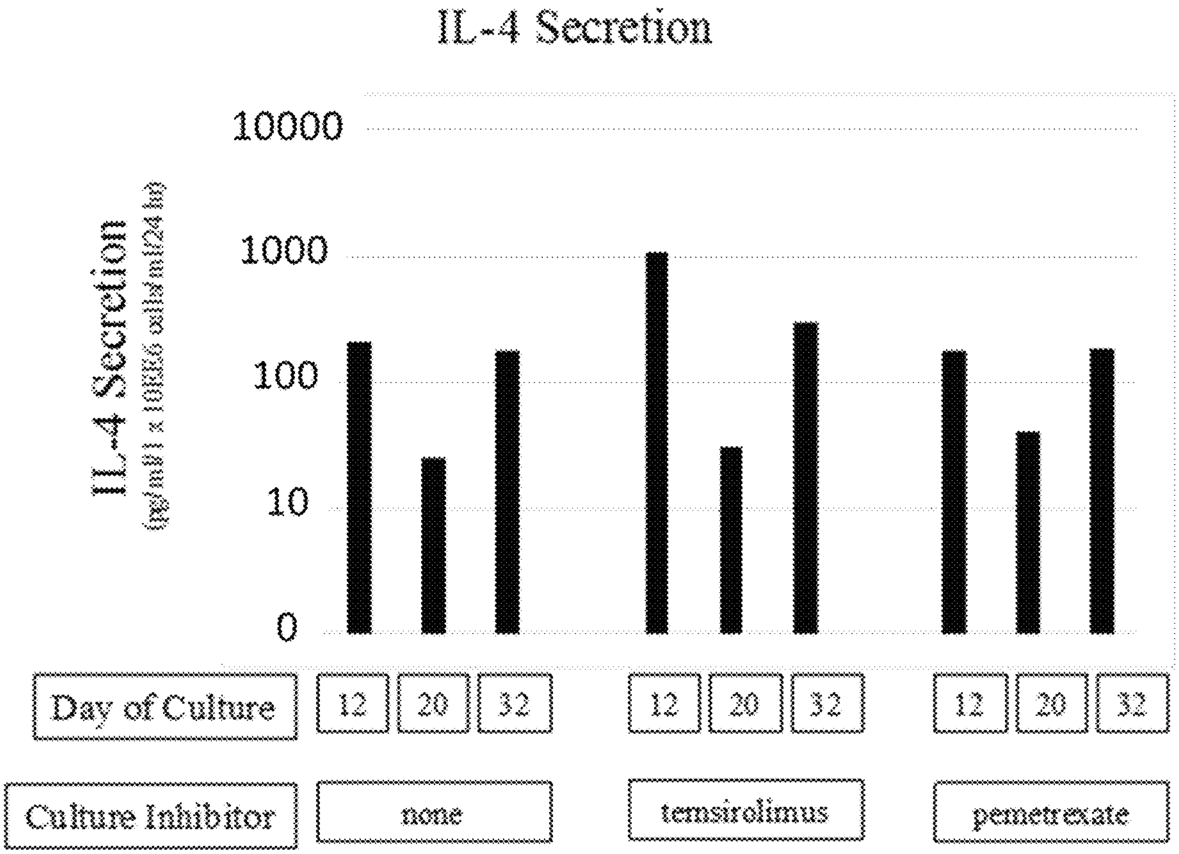
FIG. 21A depicts IL-4 secretion for cells in culture by day and culture inhibitor.
Figure 21B:
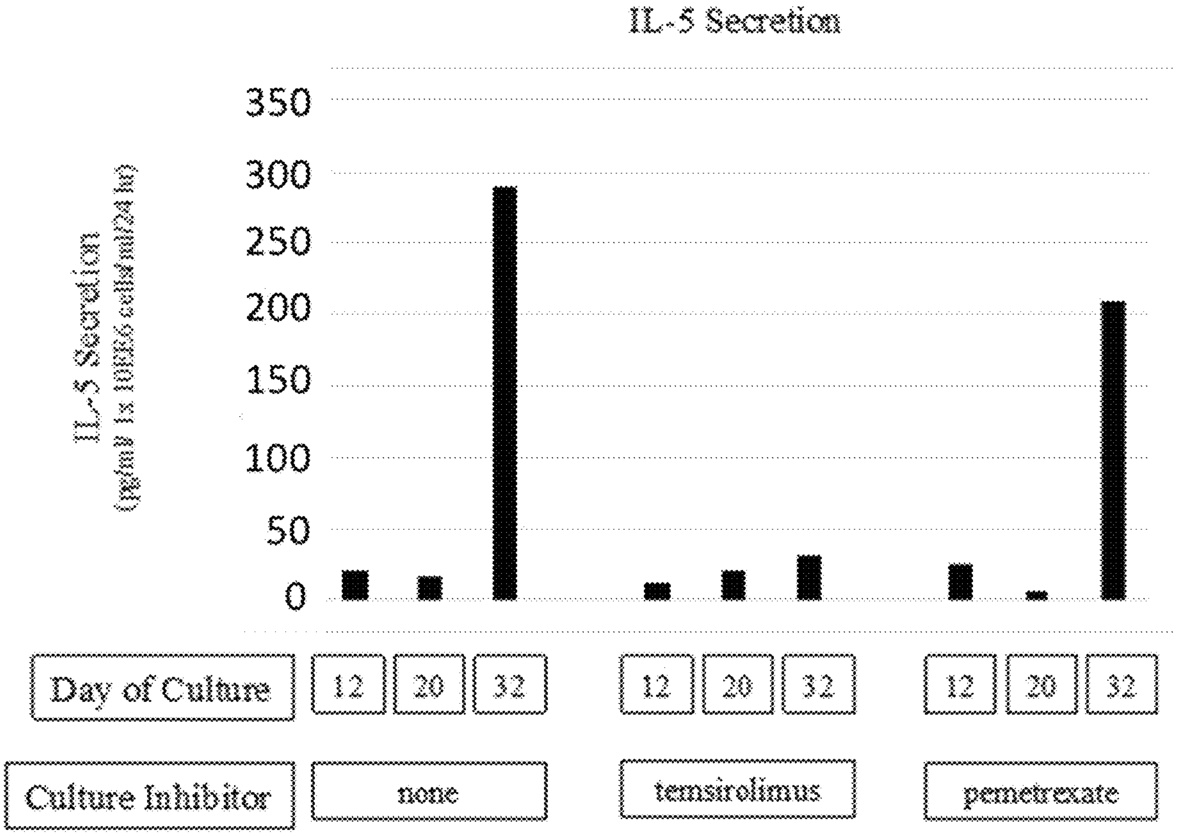
FIG. 21B depicts IL-5 secretion for cells in culture by day and culture inhibitor.
Figure 21C:
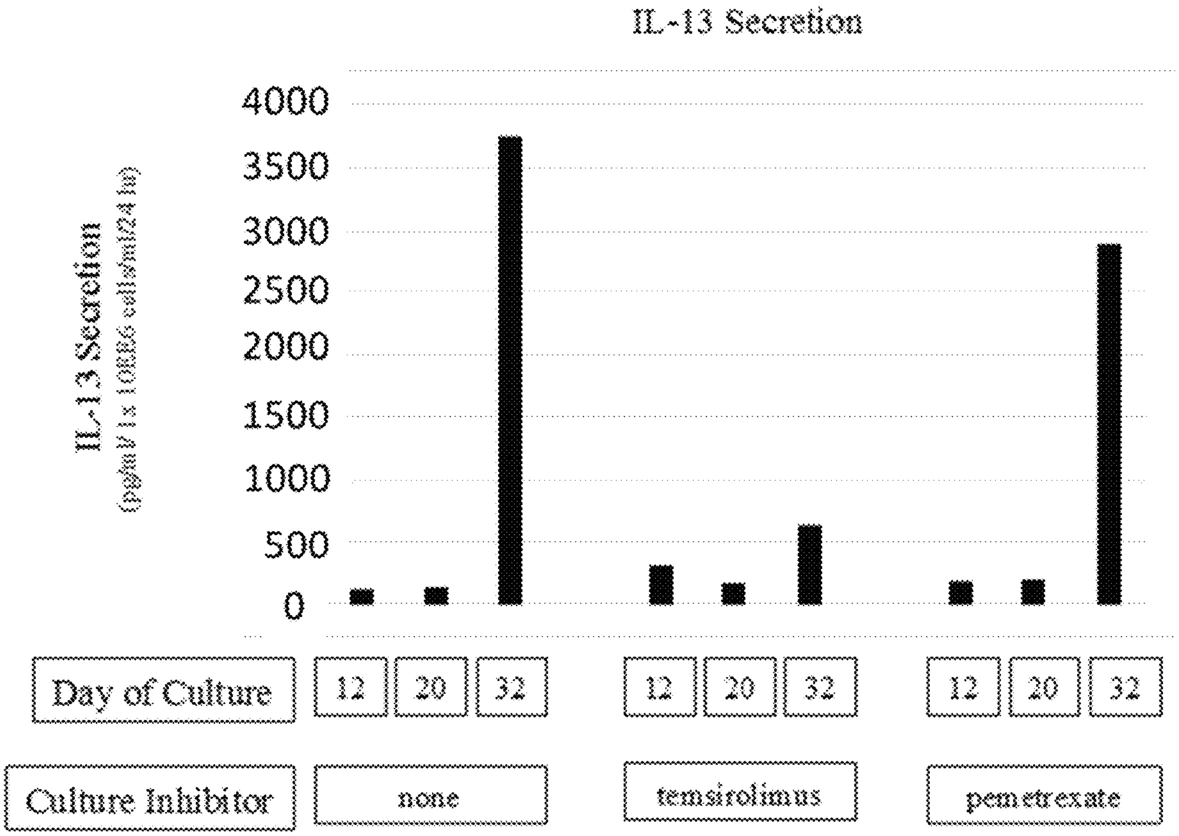
FIG. 21C depicts IL-13 secretion for cells in culture by day and culture inhibitor.

FIGS. 20A-20D illustrate that extended culture of de-differentiated T cells in the hybrid Th2/$T_{REG}$ polarization condition containing pemetrexed results in the generation of $CD8^+$ T cells expressing FOXP3 and GATA3 transcription factors. Human $CD4^+$ and $CD8^+$ T cells were subjected to a 3-day de-differentiation procedure and subsequently were co-stimulated (3:1 bead-to-T cell ratio) and propagated in media containing the hybrid Th2/$T_{REG}$ polarizing condition (IL-2; TGF-β; IL-4) either without or with the pharmacologic inhibitors temsirolimus (1.0 μM) or pemetrexed (10 nM). Cultures were restimulated with 3/28 beads at both day 14 and day 24 of culture; at day 24 of culture, to evaluate stability of the transcription factor expression, the culture media did not contain exogenous cytokines or pharmacologic inhibitors. At days 12, 20, and 32 of culture, T cells were harvested and subjected to surface flow cytometry (CD8 marker) and intra-cellular staining for the following transcription factors, FOXP3, Tbet, and GATA3. The data above show the percent CD8 cells out of the total cultured population (FIG. 20A); the percent of CD8 cells that expressed the $T_{REG}$ transcription factor FOXP3 (FIG. 20B); the percent of CD8 cells that expressed the Th1 transcription factor Tbet (FIG. 20C); and the percent of CD8 cells that expressed the Th2 transcription factor GATA3 (FIG. 20D).

As shown in FIG. 20A, CD8 cell content gradually and modestly diminished over time in culture. It should be noted that, although $T_{REG}$ cell function is generally attributed to the CD4 cell subset, CD8+ $T_{REG}$ cells have also been well described; it is possible that use of a $T_{REG}$ population that contains both $CD4^+$ and $CD8^+$ T cell subsets may be advantageous due to diversification of antigen-specificity. As such, the method we describe is potentially advantageous in-part because it generates both CD4- and CD8-type TREGS.

As FIG. 20B shows (upper right panel), the $CD8^+$ T cells manufactured using this method were indeed enriched for FOXP3 expression, which was stable over time in culture and stable independent of pharmacologic inhibitor presence.

As FIG. 20C shows (lower left panel), re-differentiation in the $T_{REG}$-Th2 polarization condition in general led to $CD8^+$ T cell expression of low levels of the Th1 transcription factor TBET; however, the lowest levels were observed most consistently in the presence of pemetrexed.

Finally, as FIG. 20D shows (lower right panel), re-differentiation in the $T_{REG}$-Th2 condition indeed resulted in $CD8^+$ T cells that were also shifted towards Th2-type differentiation, as indicated by increased expression of the GATA3 transcription factor.

Figure 40A:
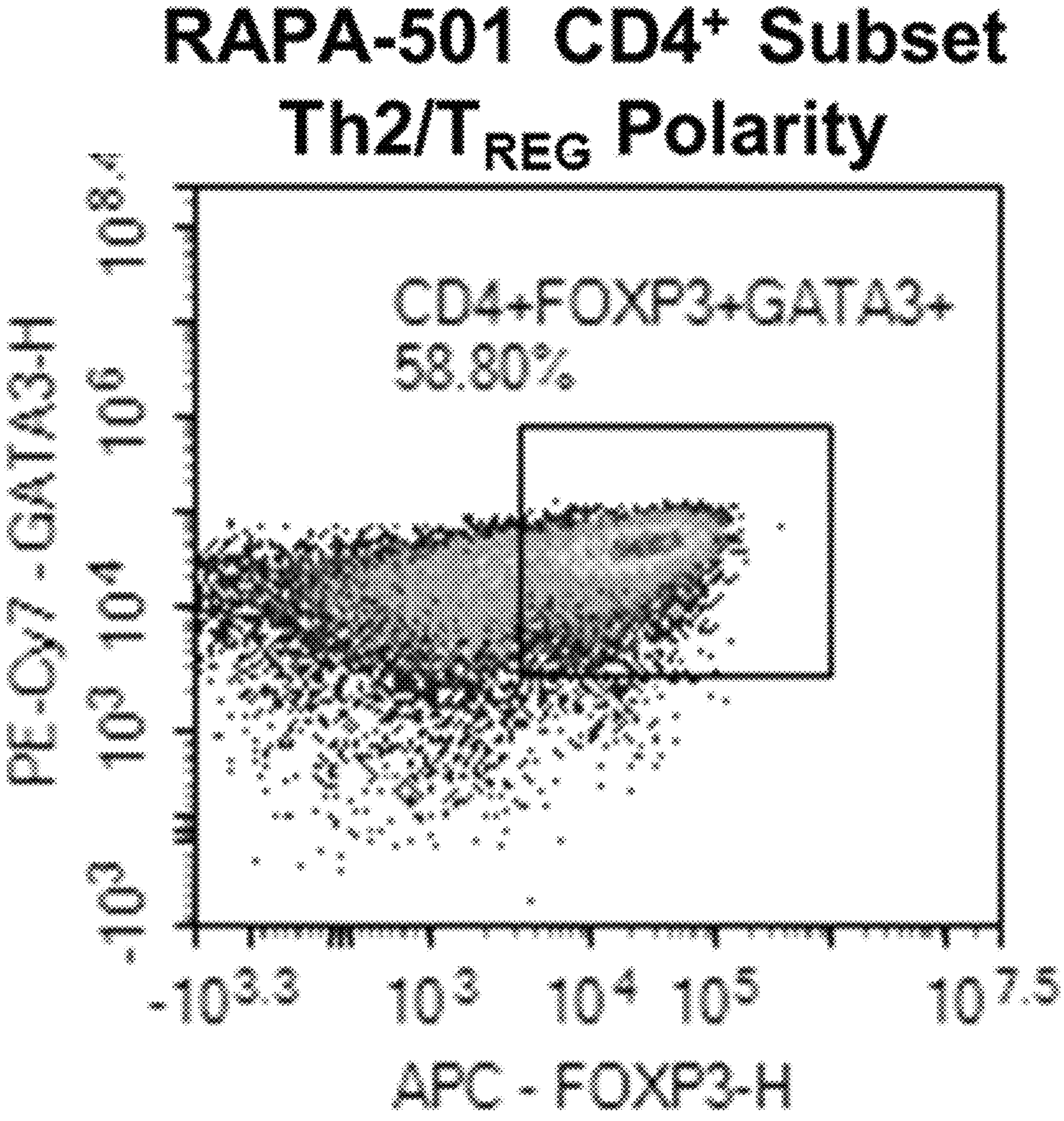
FIG. 40A depicts RAPA-501 GATA3 and FOXP3 as measured by flow cytometry for $CD4^+$ cells.
Figure 40B:
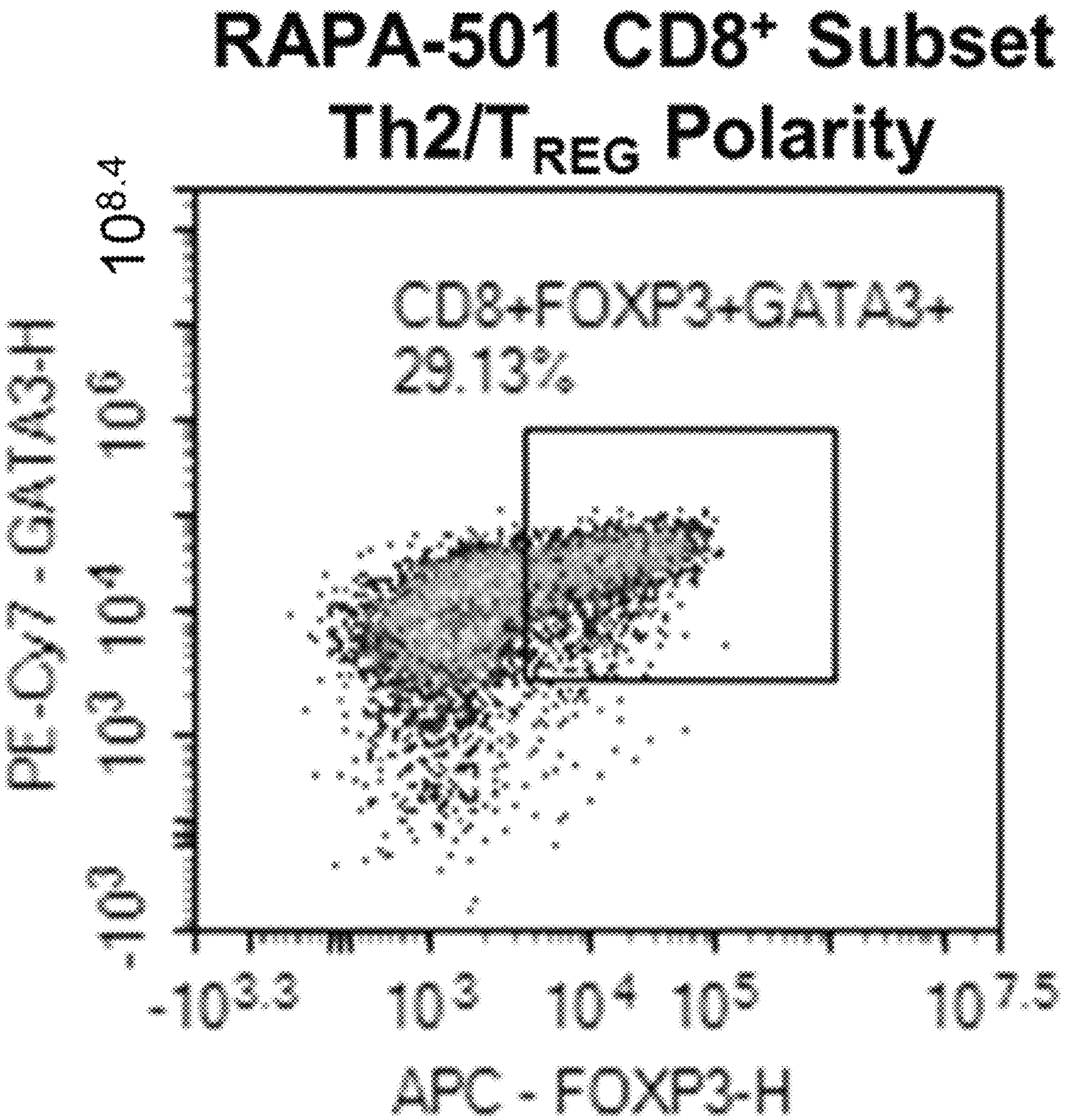
FIG. 40B depicts RAPA-501 GATA3 and FOXP3 as measured by flow cytometry for CD8+ cells.

FIGS. 40A-40B also depict flow cytometry of GATA3 and FOXP3 for the re-differentiated $T_{REG}$-Th2 cells in both the $CD4^+$ and $CD8^+$ subsets.

In sum, these transcription factor analyses indicate that re-differentiation in the hybrid $T_{REG}$-Th2 culture condition plus pemetrexed addition can be optimal because it can preserve both $CD4^+$ and $CD8^+$ T cells that express both FOXP3 and GATA3, with limited expression of TBET.

Example 16: Culture of De-Differentiated T Cells in the Hybrid $T_{REG}$ Th2 Condition Results in T Cells with an Enhanced Th2 Cytokine Secretion Profile In addition to transcription factor measurement, we also evaluated the T cells re-differentiated in the hybrid $T_{REG}$-Th2 polarizing condition for cytokine secretion capacity. As shown in FIGS. 21A-21D, all re-differentiation cultures propagated in the $T_{REG}$-Th2 polarization condition yielded T cells capable of IL-4 secretion, thereby demonstrating the inherent capability of this method to achieve Th2 polarity even in the absence of pharmacologic inhibitors.

FIGS. 21A-21D illustrates that extended culture of de-differentiated T cells in the hybrid Th2/$T_{REG}$ polarization condition results in the generation of T cells expressing with a predominant Th2 cytokine phenotype: IL-4, IL-5, and IL-13 secretion. Human $CD4^+$ and $CD8^+$ T cells were subjected to a 3-day de-differentiation procedure and subsequently were co-stimulated (3:1 bead-to-T cell ratio) and propagated in media containing the hybrid Th2/$T_{REG}$ polarizing condition (IL-2; TGF-β; IL-4) either without or with the pharmacologic inhibitors temsirolimus (1.0 μM) or pemetrexed (10 nM). Cultures were restimulated with 3/28 beads at both day 14 and day 24 of culture; at day 24 of culture, to evaluate stability of the transcription factor expression, the culture media did not contain exogenous cytokines or pharmacologic inhibitors. At days 12, 20, and 32 of culture, the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr. The Th2 cytokine IL-10 was also evaluated: all values were less than 20 pg/ml per $1\times10^6$ cells/ml/24 hr.

Of note, whereas temsirolimus blunted the ability of T cells re-differentiated in the $T_{REG}$-Th2 condition to secrete the effector Th2 cytokines IL-5 (FIG. 21B) and IL-13 (FIG. 21C), use of pemetrexed fully preserved the ability of T cells to secrete IL-5 and IL-13. As such, these data provide further evidence that the use of pemetrexed is favorable relative to use of conventional $T_{REG}$-promoting agents such as the mTOR inhibitor temsirolimus because pemetrexed is more compatible with the manufacture of the $T_{REG}$-Th2 hybrid subset.

Figure 22A:
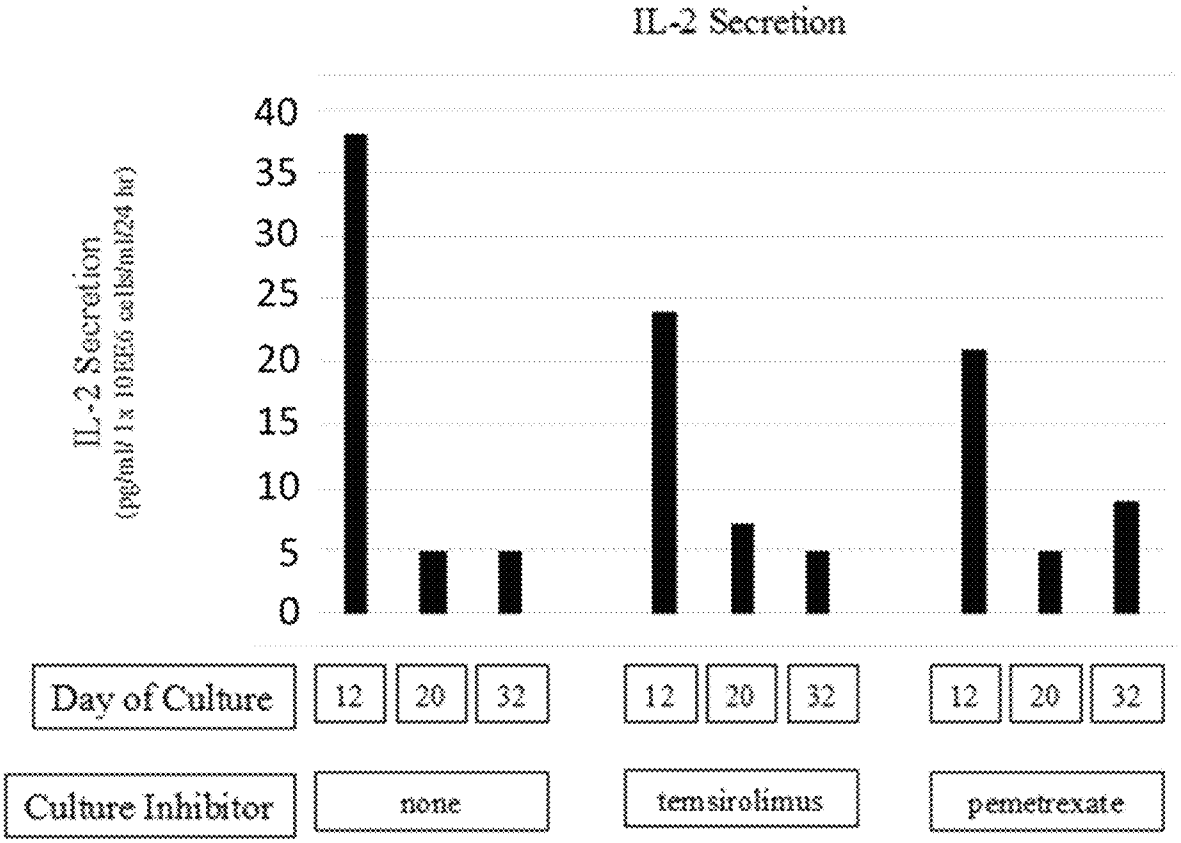
FIG. 22A depicts IL-2 secretion for cells in culture by day and culture inhibitor.
Figure 22B:
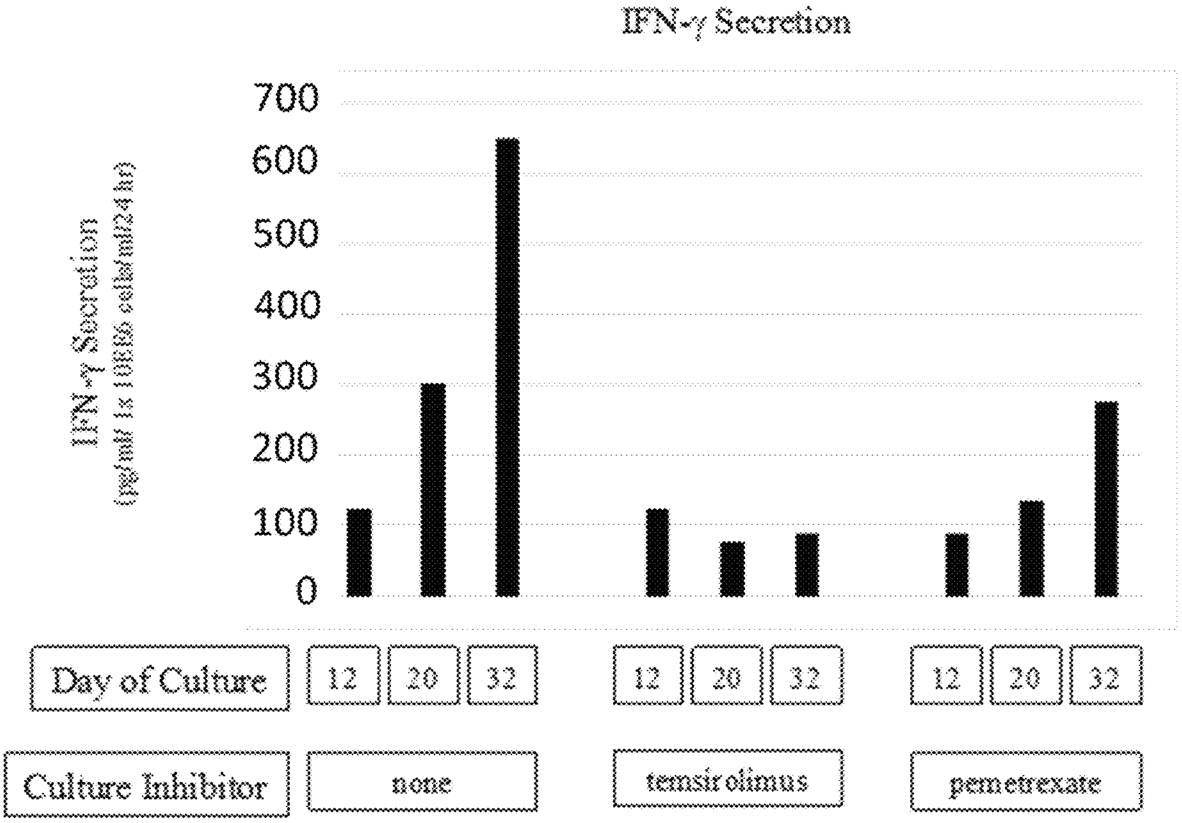
FIG. 22B depicts IFN-γ secretion for cells in culture by day and culture inhibitor.

Furthermore, all T cells re-differentiated in the $T_{REG}$-Th2 polarizing condition had relatively low level expression of IL-2 (FIG. 22A), IFN-γ, (FIG. 22B), IL-17 (all values less than 20 μg/ml), and TNF-α (all values less than 20 pg/ml).

FIGS. 22A-22D illustrate that extended culture of de-differentiated T cells in the hybrid Th2/$T_{REG}$ polarization condition results in the generation of T cells expressing with a predominant Th2 cytokine phenotype: IL-2, IFN-γ, and GM-CSF secretion. Human $CD4^+$ and $CD8^+$ T cells were subjected to a 3-day de-differentiation procedure and subsequently were co-stimulated (3:1 bead-to-T cell ratio) and propagated in media containing the hybrid Th2/$T_{REG}$ polarizing condition (IL-2; TGF-β; IL-4) either without or with the pharmacologic inhibitors temsirolimus (1.0 M) or pemetrexed (10 nM). Cultures were restimulated with 3/28 beads at both day 14 and day 24 of culture; at day 24 of culture, to evaluate stability of the transcription factor expression, the culture media did not contain exogenous cytokines or pharmacologic inhibitors. At days 12, 20, and 32 of culture, the T cells were harvested, washed, and re-stimulated with 3/28 beads (3:1 ratio) for 24 hr; the resultant supernatant was harvested and tested for cytokine content by Luminex multi-analyte method. All results shown are expressed as cytokine level in pg per ml per $1\times10^6$ cells/ml/24 hr. The inflammatory cytokines IL-17 and TNF-α were also evaluated: all values were less than 20 pg/ml per $1\times10^6$ cells/ml/24 hr.

Figure 22C:
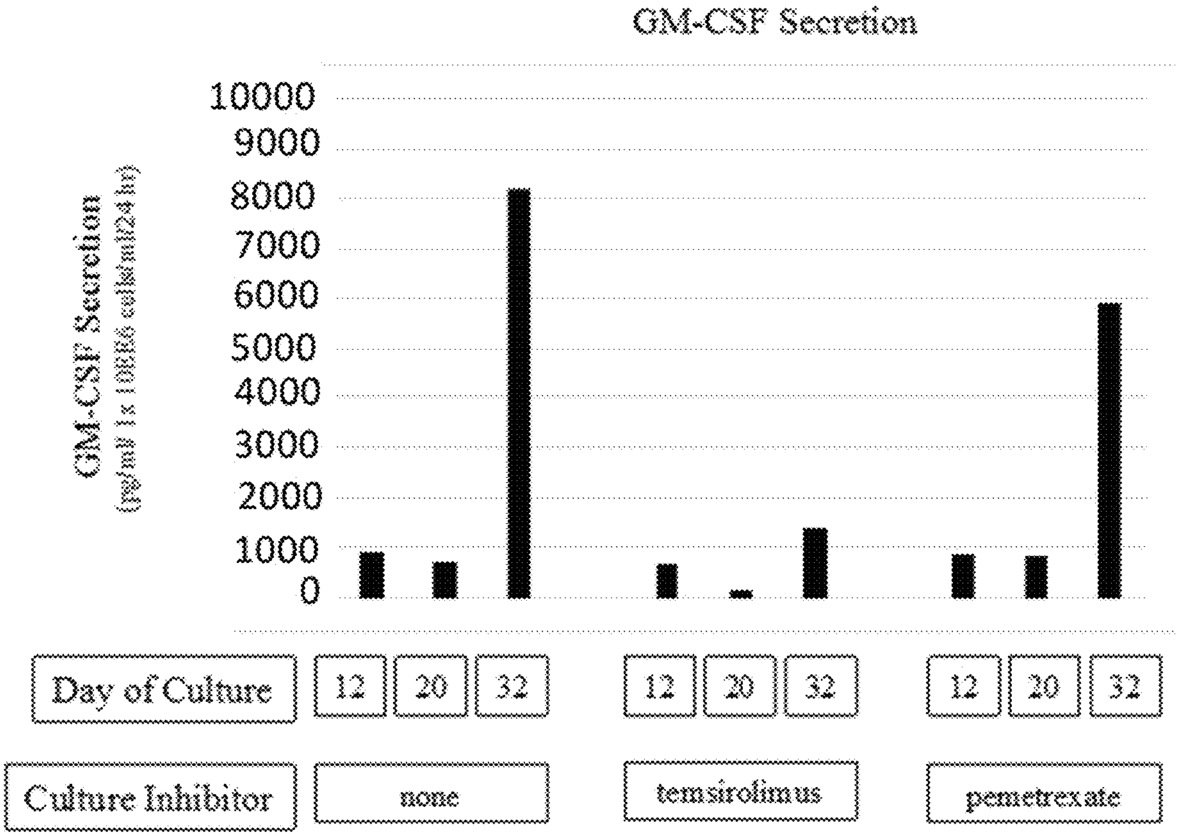
FIG. 22C depicts GM-CSF secretion for cells in culture by day and culture inhibitor.

Of note, GM-CSF secretion was observed to a higher degree in T cell re-differentiated in the $T_{REG}$-Th2 hybrid culture condition that was further supplemented with pemetrexed (10 nM; FIG. 22C). Extrapolating from experimental studies in the literature, it is not clear whether the capacity for enhanced GM-CSF within a $T_{REG}$-Th2 hybrid population would necessarily be either detrimental or beneficial.

In sum, these data indicate that T cell re-differentiation in the $T_{REG}$-Th2 polarizing condition is favorable because it results in T cells with a low level of capacity for secretion of the Th1- and Th17-type cytokines associated with inflammatory disease. Inclusion of pemetrexed to the hybrid $T_{REG}$-Th2 polarizing condition is advantageous because it results in an increased capacity for Th2 cytokine production, which will further provide a hedge against differentiation plasticity towards the Th1- and Th17-type subsets.

Figure 23A:
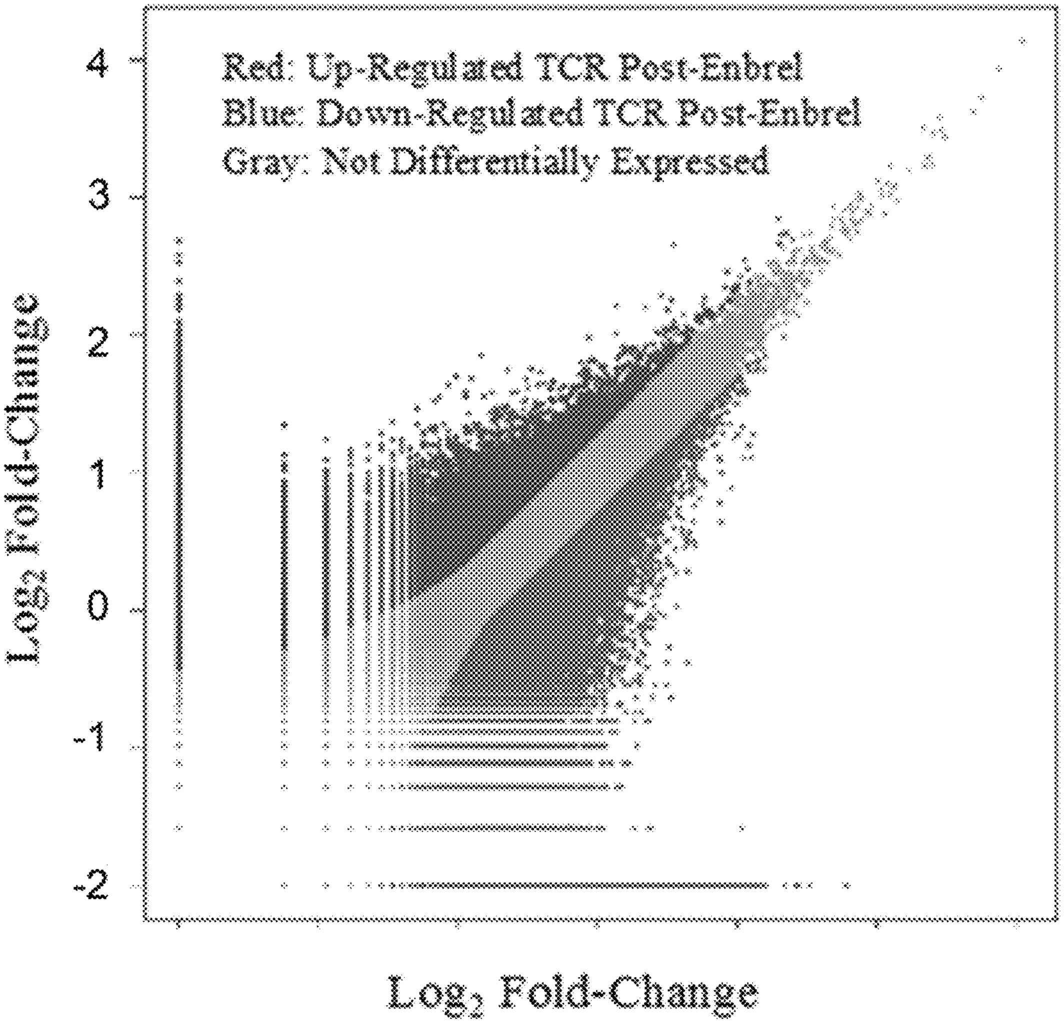

Example 17: Use of Select Anti-TNF-α Reagents Prior to Lymphocyte Collection by Apheresis to Beneficially Alter the Input T Cell TOR Repertoire FIGS. 23A & 23B depict the use of RNA-based T cell receptor sequencing to detect a widespread up- and down-regulation of T cell TCR specificities after therapy with the TNF-α inhibitor, etanercept. In FIG. 23, RNA was isolated from peripheral blood mononuclear cells from an ALS patient pre- and post-therapy with etanercept therapy. The RNA was subjected to TCR repertoire profiling, as previously described by Rosati E, Dowds C M, Liaskou E, Henriksen E K K, Karlsen T H, Franke A. Overview of methodologies for T-cell receptor repertoire analysis. BMC Biotechnol. 2017; 17(1): 61. In FIG. 23A it is demonstrated that approximately 25% of TCR specificities were up-regulated in the post-therapy sample (as indicated in red); in marked contrast, approximately 25% of TCR specificities were down-regulated in the post-therapy sample (as indicated in blue). As indicated in the upper right figure (B), etanercept therapy resulted in marked T cell clonal expansion, as several T cell clones increased from frequencies of 0.01 pre-etanercept (near the detection limit of the assay) to post-treatment values ranging from 247 to 486, thereby consistent with a more than 4-log T cell expansion. As indicated in the lower right FIG. 23B, etanercept therapy resulted in marked T cell clonal contraction, as several T cell clones decreased from frequencies of 259 to 598 pre-etanercept to post-treatment values of 0.01, thereby consistent with a more than 4-log T cell clonal contraction.

FIGS. 23A-B indicates that anti-TNF-α therapy with etanercept, which preferentially inhibits the serum, cell-free form of TNF-α that promotes TNFR1-expressing Th1-type cells, is associated with widespread changes in T cell receptor up- and down-regulation. These observations indicate that pre-treatment of a subject with etanercept or any other anti-TNF-α therapeutic that preferentially inhibits the serum, cell-free form of TNF-α (such as the monoclonal antibody, adalimumab) can be utilized to shift the T cell receptor repertoire away from T cells of Th1-type phenotype on an antigen-specific basis, thereby enriching for T cells of a $T_{REG}$ phenotype on an antigen-specific basis.

Example 18: Characterization of the TREG-Th2 Hybrid Population as a Cell Product Enriched for Expression of CD25, CD27, 2B4, BTLA, and CTLA4

Figure 24:
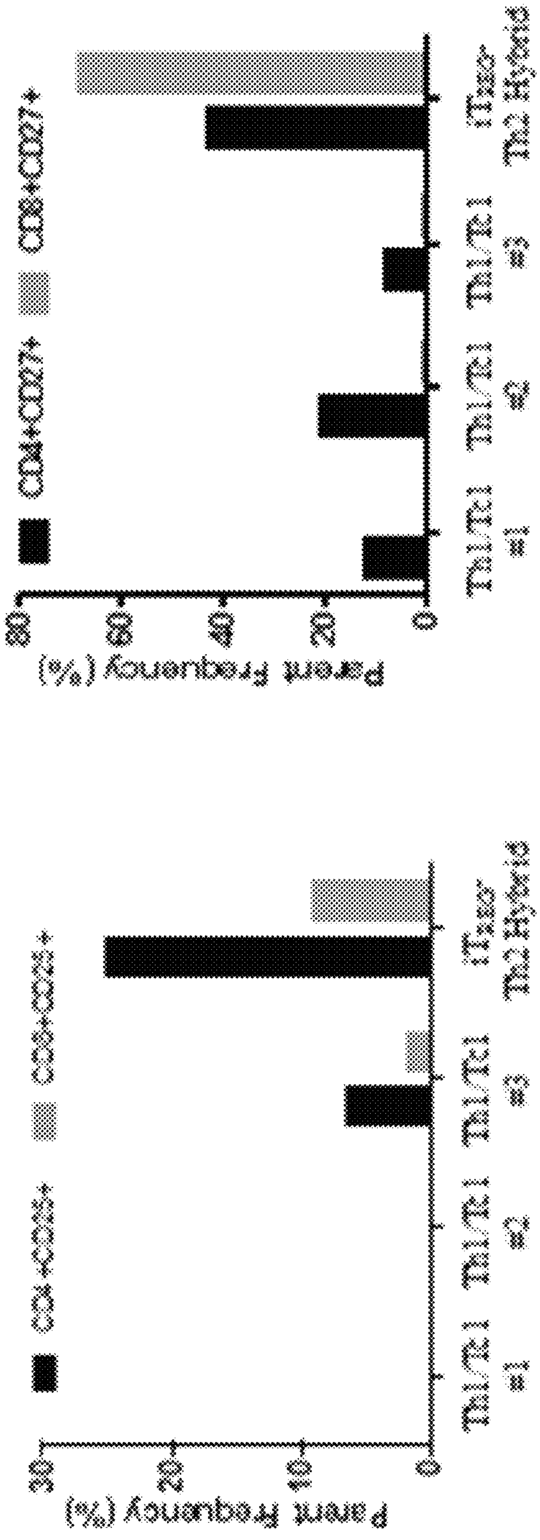
FIG. 24 illustrates that extended culture of de-differentiated T cells in the hybrid Th2/TREG polarization condition results in the generation of T cells expressing increased levels of the following molecules relative to control Th1/Tc1 cells: CD25, CD27, 2B4, BTLA, and CTLA.
Figure 24:
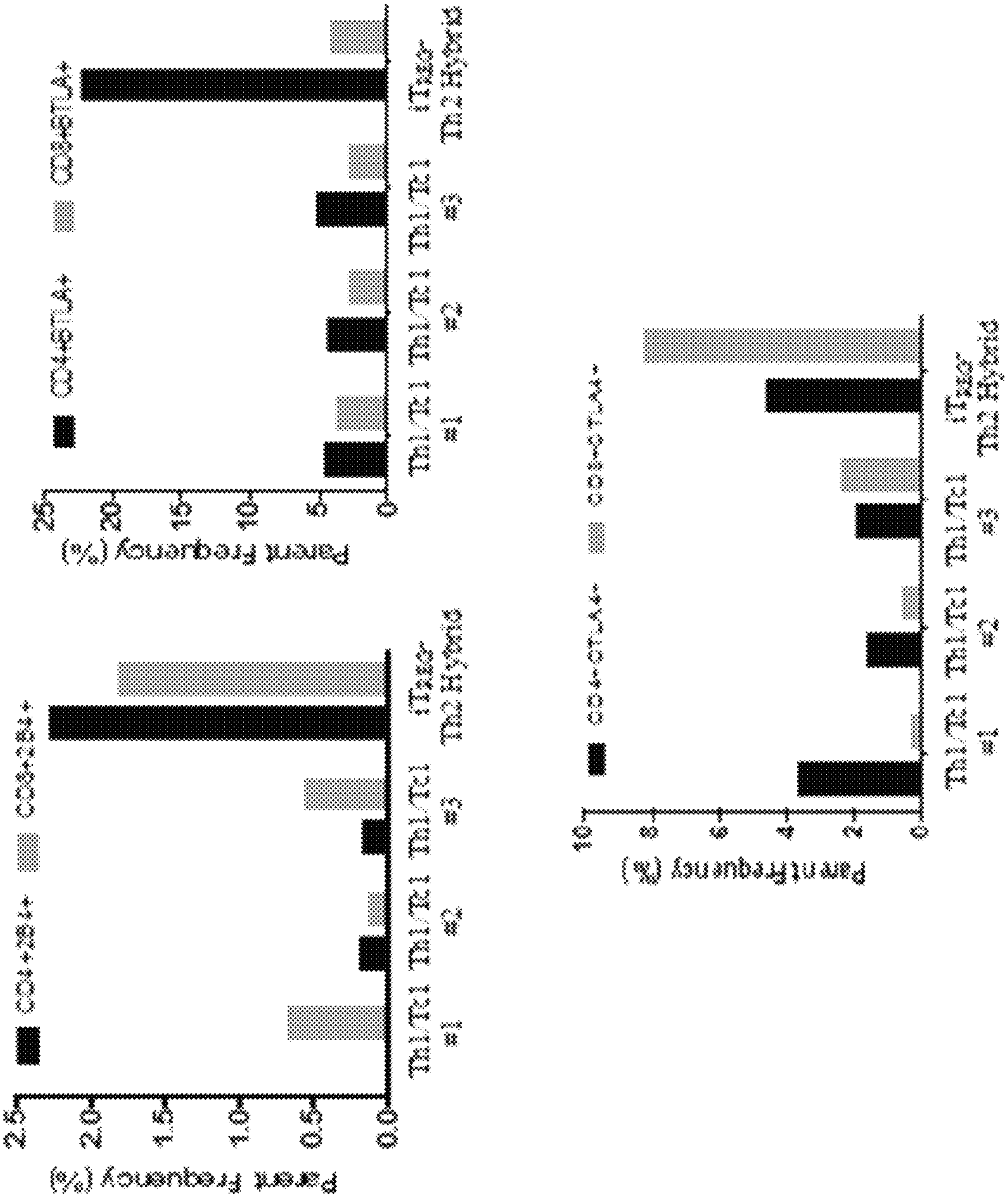

FIG. 24 illustrates that the manufactured iTREG/Th2 hybrid population has increased expression of CD25, CD27, 2B4, BTLA, and CTLA4 relative to control Th1/Tc1 cultures. In FIG. 24, the iTREG/Th2 hybrid population was generated by the method previously detailed using an initial phase of T cell de-differentiation followed by re-differentiation in media containing IL-2, TGF-β, and IL-4. At day 11 of iTREG/Th2 manufacturing, the cells were harvested and subjected to flow cytometry for assessment of CD4+ and CD8+ T cell expression of molecules of relevance, namely CD25, CD27, 2B4, BTLA, and CTLA4; comparison was made to three separate control conditions evaluating Th1/Tc1 polarization.

FIG. 24 indicates that hybrid TREG-Th2 cells manufactured according to the described conditions have increased expression of the following cell surface molecules by flow cytometry relative to control Th1/Tc1 cells: CD25, CD27, 2B4, BTLA, and CTLA4.

As FIG. 24 illustrates, the iTREG/Th2 hybrid cell product has CD4+ and CD8+ T cells that express at least 10% and more preferably 50% higher levels of CD25, CD27, 2B4, BTLA, and CTLA4 relative to control Th1/Tc1 cells.

CD25, the IL-2 receptor, is critical for the ability of TREG cells to control autoimmunity, in particular CD8+ T cell driven responses. Therefore, expression of CD25 on the iTREG/Th2 manufactured cell product is a desirable characteristic.

CD27, a co-stimulatory molecule with increased expression on TREG cells, has been shown to contribute to the inhibitory function of TREGS. Therefore, expression of CD27 on the iTREG/Th2 manufactured cell product is a desirable characteristic.

2B4 (CD244) has recently been shown to inhibit CD8+ T cell responses by attenuation of glycolysis and cell division. Therefore, expression of 2B4 on the iTREG/Th2 manufactured cell product is a desirable characteristic.

BTLA (CD272) is a co-inhibitory receptor, and the ligation of BTLA with the herpesvirus-entry mediator HVEM promotes TREG cell induction and inhibition of effector immune responses. Therefore, expression of BTLA on the iTREG/Th2 manufactured cell product is a desirable characteristic.

CTLA4 is a critical effector molecule of TREG cells, as recently evidenced by its ability to limit immunity to malarial infection. Therefore, expression of CTLA4 on the iTREG/Th2 manufactured cell product is a desirable characteristic.

Example 19: Characterization of the TREG-Th2 Hybrid Population as a Cell Product Enriched for Expression of TIGIT, TIM3, ICOS, LAIR1, and OX40

Figure 25:
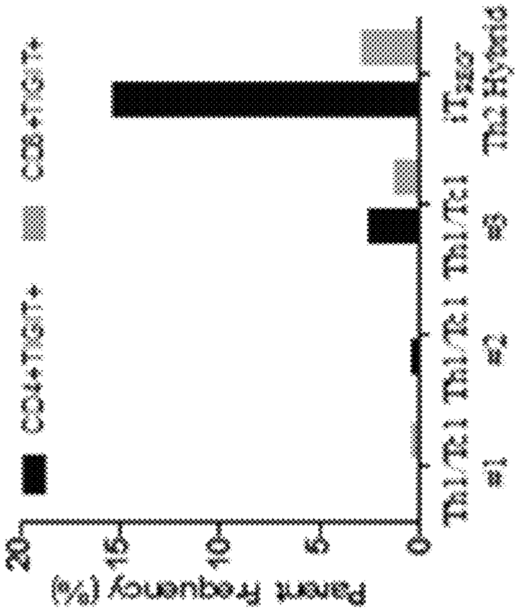
FIG. 25 illustrates that extended culture of de-differentiated T cells in the hybrid Th2/$T_{REG}$ polarization condition results in the generation of T cells expressing increased levels of the following molecules relative to control Th1/Tc1 cells: TIGIT, TIM3, ICOS, LAIR1, and OX40.
Figure 25:
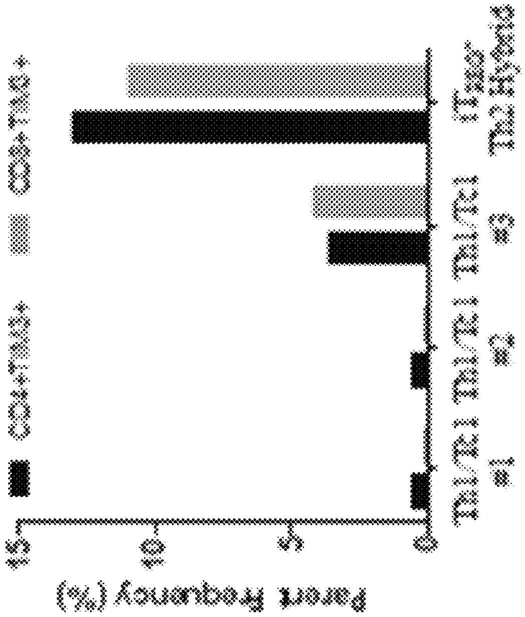
Figure 25:
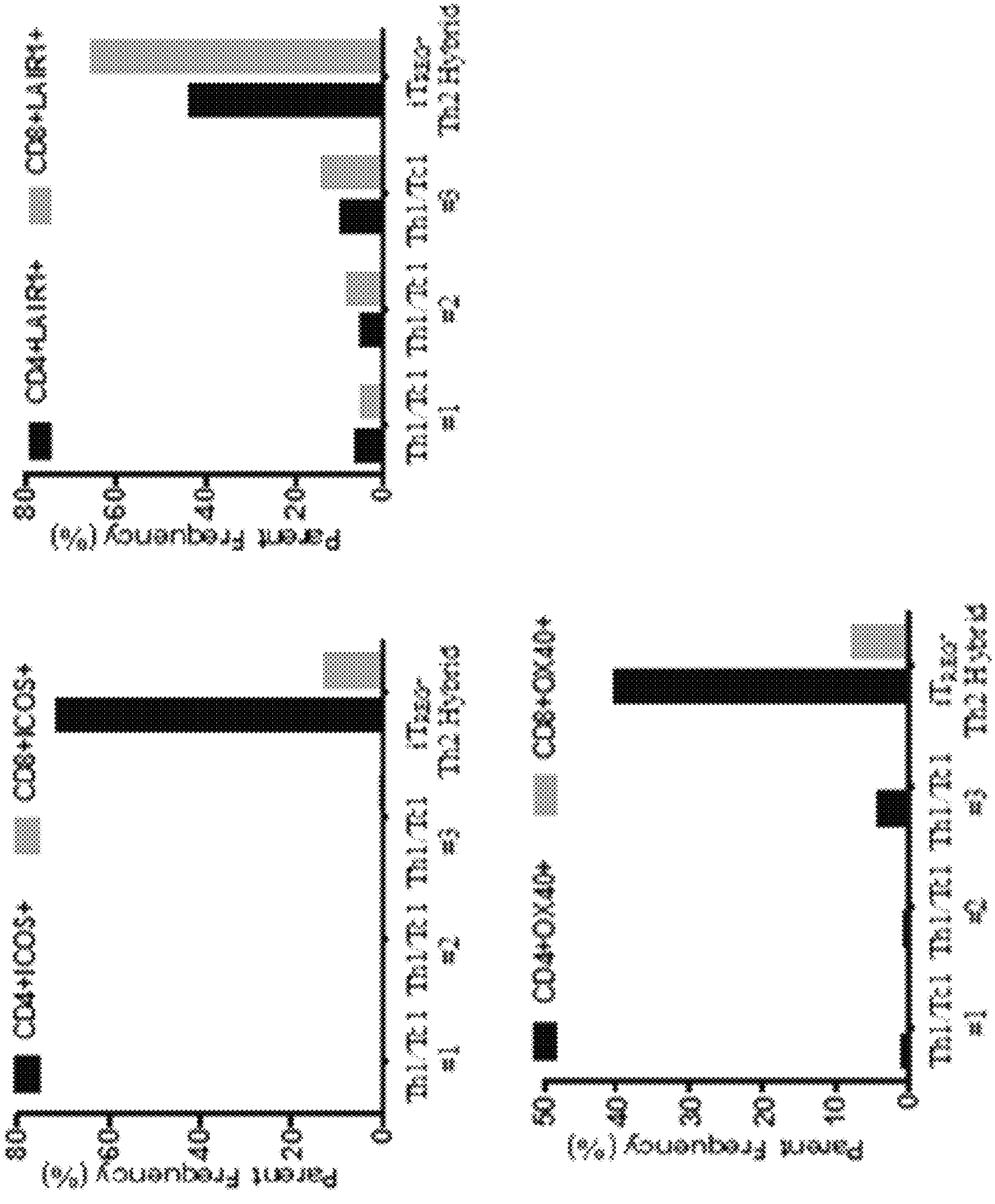

FIG. 25 illustrates that the manufactured iTREG/Th2 hybrid population has increased expression of TIGIT, TIM3, ICOS, LAIR1, and OX40 relative to control Th1/Tc1 cultures. In FIG. 25, the iTREG/Th2 hybrid population was generated by the method previously detailed using an initial phase of T cell de-differentiation followed by re-differentiation in media containing IL-2, TGF-β, and IL-4. At day 11 of iTREG/Th2 manufacturing, the cells were harvested and subjected to flow cytometry for assessment of CD4+ and CD8+ T cell expression of molecules of relevance, namely TIGIT, TIM3, ICOS, LAIR1, and OX40; comparison was made to three separate control conditions evaluating Th1/Tc1 polarization. FIG. 25 indicates that hybrid TREG-Th2 cells manufactured according to the described conditions have increased expression of the following cell surface molecules by flow cytometry relative to control Th1/Tc1 cells: TIGIT, TIM3, ICOS, LAIR1, and OX40.

As FIG. 25 illustrates, the iTREG/Th2 hybrid cell product has CD4+ and CD8+ T cells that express at least 10% and more preferably 50% higher levels of TIGIT, TIM3, ICOS, LAIR1, and OX40 relative to control Th1/Tc1 cells.

TIGIT is a cell surface co-inhibitory receptor molecule that associates with regulatory T cell function. Therefore, expression of TIGIT on the iTREG/Th2 manufactured cell product is a desirable characteristic.

TIM3 is a co-inhibitory receptor that mediates an inhibitory effect of TREG cells. Therefore, expression of TIM3 on the iTREG/Th2 manufactured cell product is a desirable characteristic.

ICOS is a co-stimulatory molecule that was recently determined to help maintain immune suppression by regulatory T cells for control of immune reactivity in the central nervous system. Therefore, expression of ICOS on the iTREG/Th2 manufactured cell product is a desirable characteristic.

LAIR1 (CD305) is a multi-faceted inhibitory molecule that can block inflammation at multiple steps, including the suppression of activated, effector memory T cells. Therefore, expression of LAIR1 on the iTREG/Th2 manufactured cell product is a desirable characteristic.

OX40 is a co-stimulatory molecule. Therefore, expression of OX40 on the iTREG/Th2 manufactured cell product is a desirable characteristic.

Figure 26A:
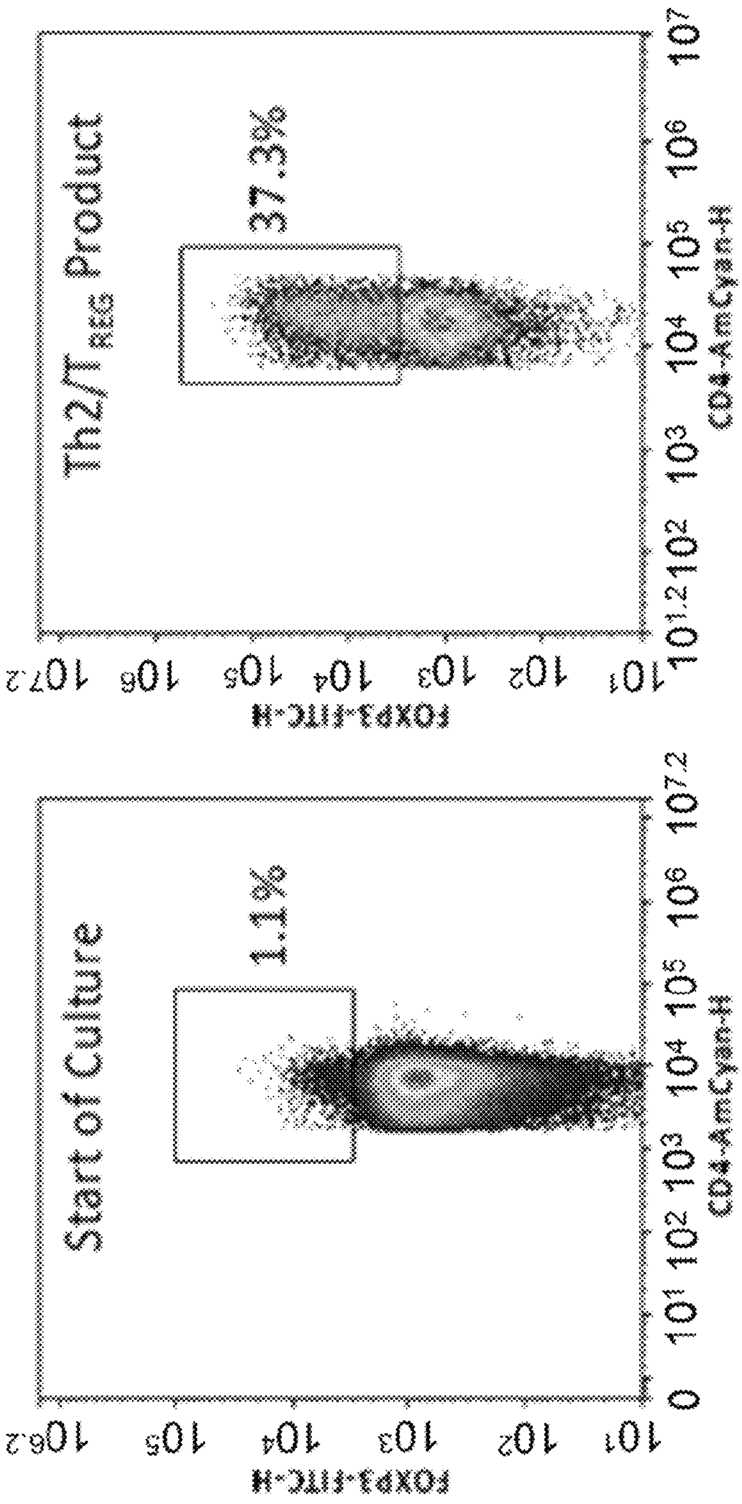
FIG. 26A depicts FOXP3 expression in CD4+ and CD8+ T cells at culture initiation and after culture as measured by flow cytometry.
Figure 26A:
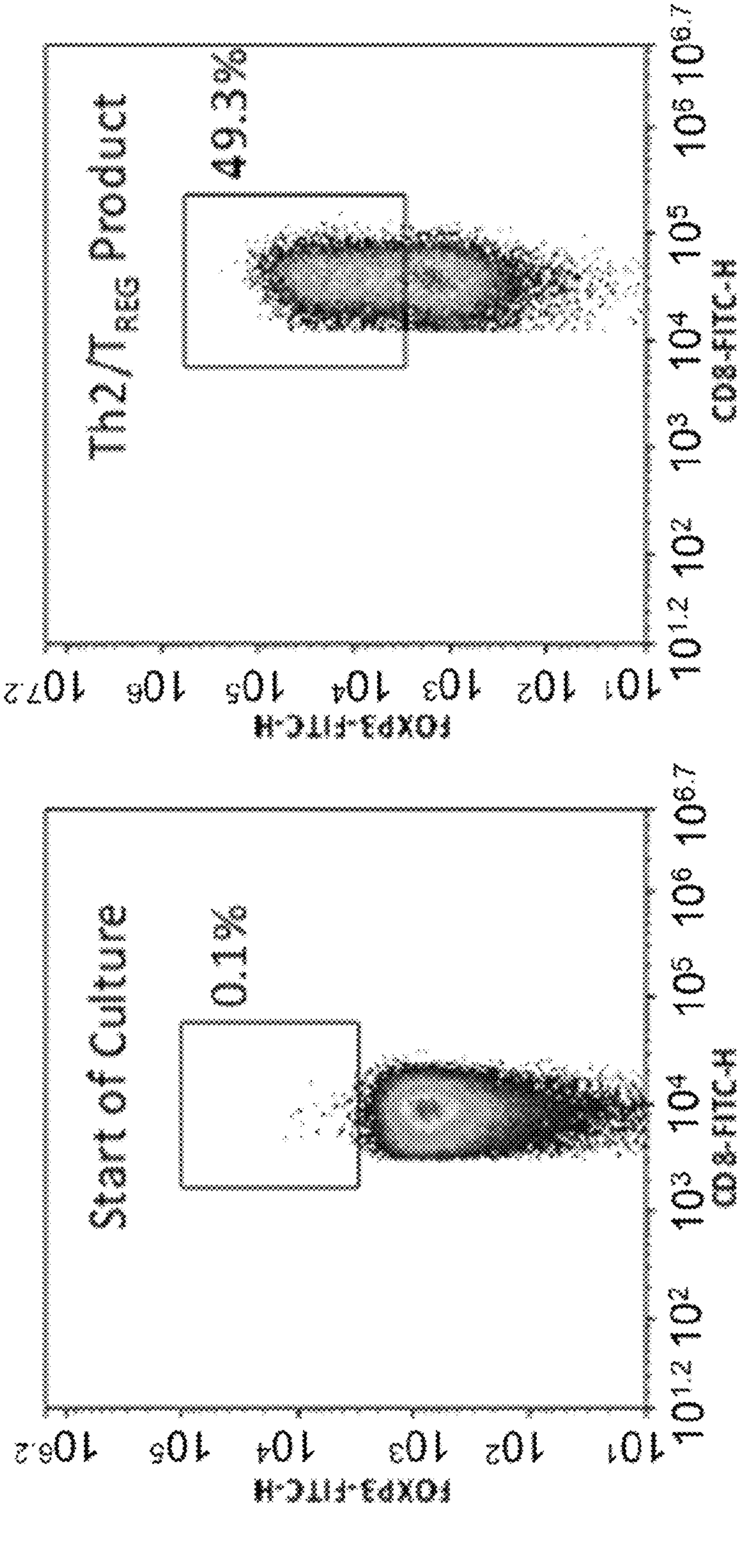
Figure 26B:
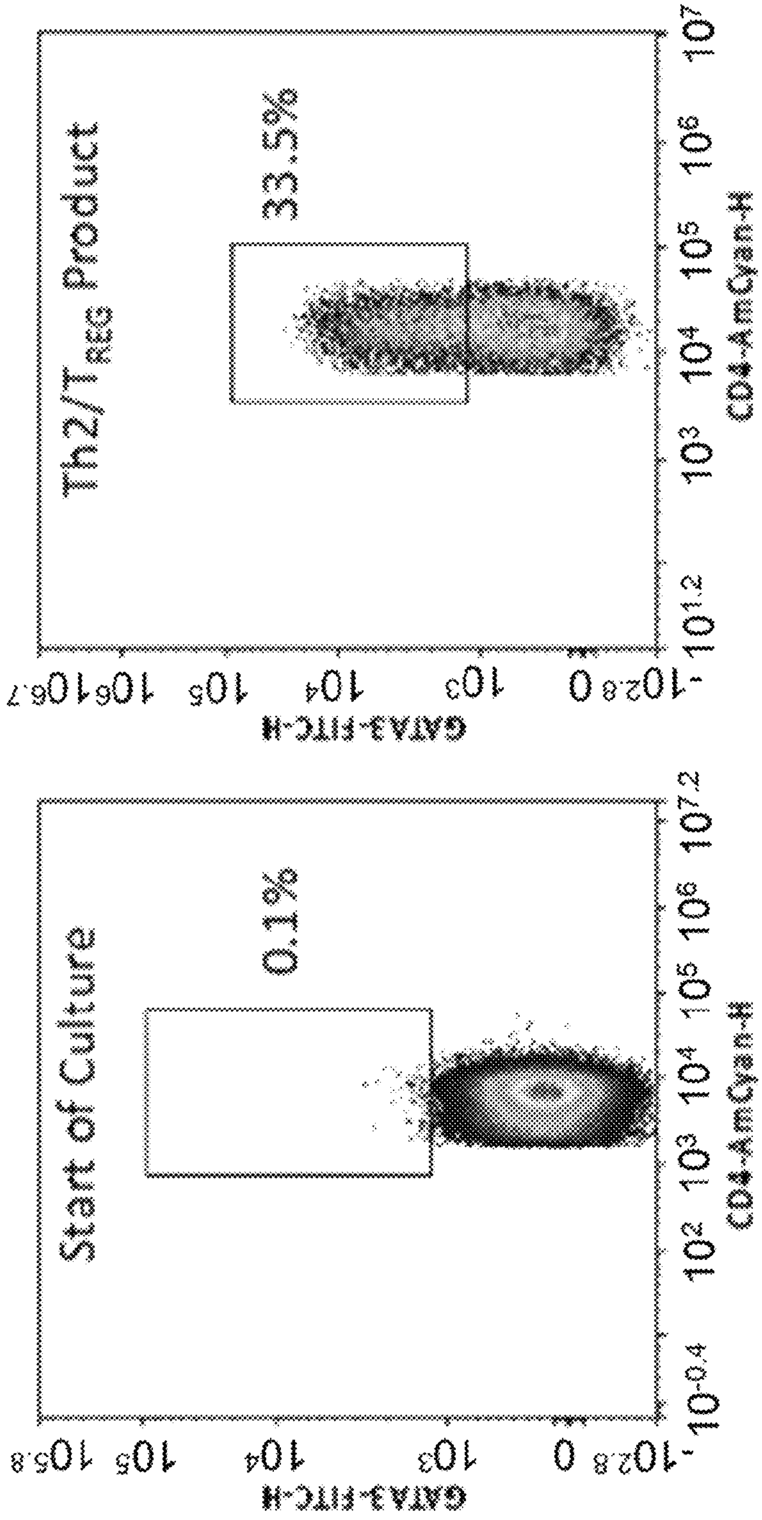
FIG. 26B depicts GATA3 expression in CD4+ and CD8+ T cells at culture initiation and after culture as measured by flow cytometry.
Figure 26B:
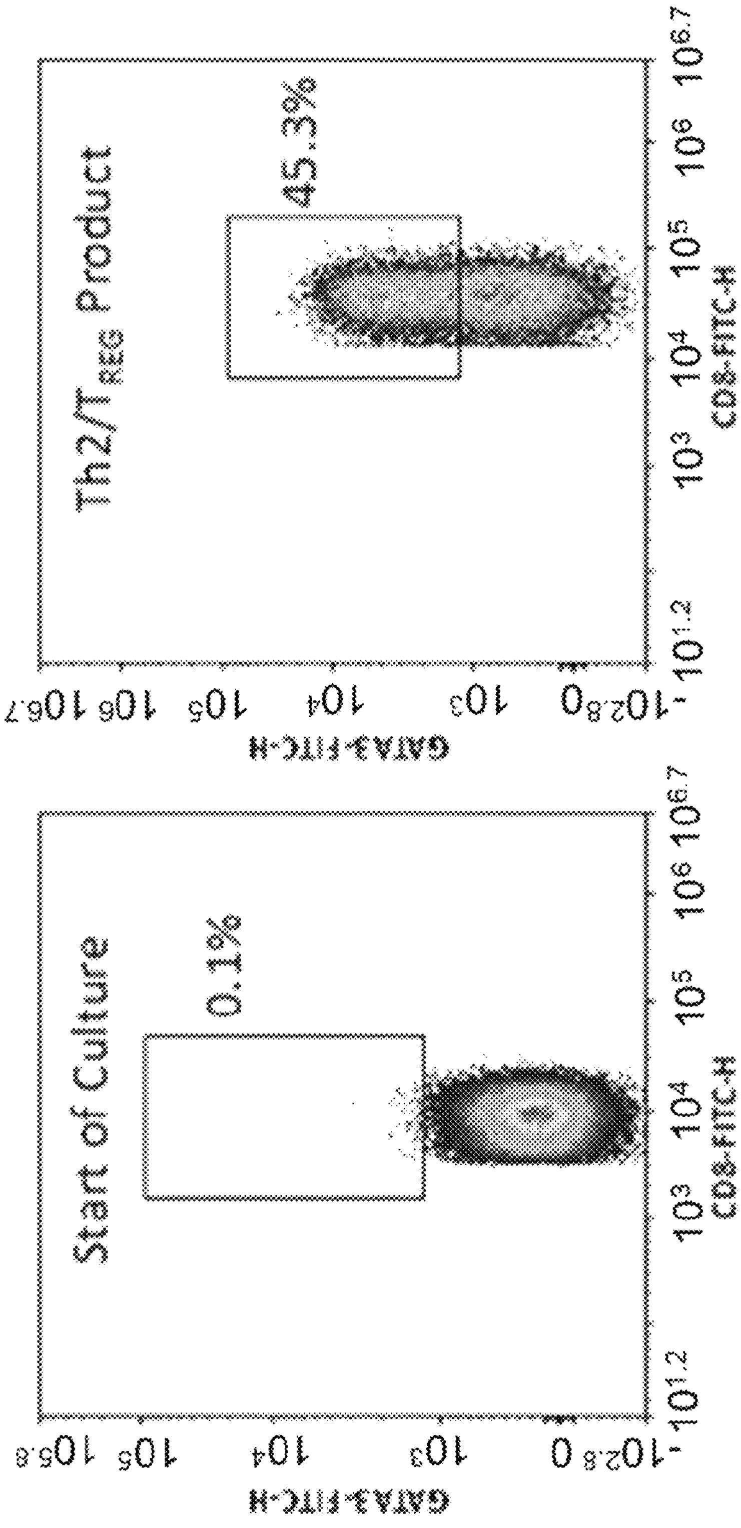

Example 20: Characterization of GATA3 and FOXP3 Expression of the TREG Th2 Hybrid Population A steady-state apheresis sample was obtained and enriched for lymphocytes by a Ficoll gradient and then plated in a G-Rex culture vessel and incubated in complete media containing Vitamin D (0.3 nM), temsirolimus (3.0 μM) and basiliximab (30 μg/mL). After an initial de-differentiation interval, the T cells were co-stimulated at a 3:1 bead-to-T cell ratio with anti-CD3/anti-CD28-coated magnetic beads and cytokines were added (IL-4 (1000 IU/mL), IL-2 (10,000 IU/mL) and TGF-β (100 ng/mL)). After the 6-day culture, the T cells were harvested, stained for surface markers (CD4 and CD8) and intracellular molecule expression (GATA3 and FOXP3) and evaluated by flow cytometry. Results in FIGS. 26A-B show the FOXP3 and GATA3 expression for CD4+ and CD8+ T cells at the start of culture and after culture (Th2/TREG) as measured by flow cytometry. The percentages provided indicate the amount of cells considered positive for CD4+ or CD8+ and the intracellular marker (shown in boxes).

The results shown in FIGS. 26A-B show results that are indicative of the phenotype of the manufactured Th2/TREG cell product. T cells of type II cytokine phenotype can be characterized in part by their expression of the transcription factor GATA3 whereas regulatory T cell populations can be identified in part by their expression of FoxP3 transcription factor. At culture initiation, a very low frequency of T cells expressed either GATA3 or FoxP3. In marked contrast, the T cell product manufactured in the Th2/TREG culture conditions expressed a high frequency of T cells that were either single-positive for GATA3, single-positive for FOXP3, or double-positive for both GATA3 and FOXP3 (not shown); importantly, as shown, this transcription factor profile was expressed in both manufactured CD4+ (top panels) and CD8+ (bottom panels) T cells. A control manufacturing culture that did not include IL-4 resulted in a greatly reduced frequency of GATA3-positive T cells, thereby demonstrating the important role of IL-4 in the manufacture of the Th2/TREG hybrid population (not shown).

The majority of the phenotype characterization of the T cell product manufactured according to the $T_{REG}$/Th2 method detailed in this disclosure can be ascertained at the end of culture. However, it is important to note that the T cell product can be cryopreserved, and as such, phenotypic characterization of T cells in the post-thaw state reflect the actual product to be adoptively transferred to the subject. The TREG/Th2 cells in the post-thaw state can be characterized by the following relative to control Th1/Tc1 cells: (a) increased expression of CD25, CD27, 2B4, BTLA, CTLA4, TIGIT, TIM3, ICOS, LAIR1, and OX40 by flow cytometry; (b) reduced IFN-g and TNF-α and increased secretion of IL-4 by Luminex cytokine secretion analysis; and (c) altered expression of T cell fate transcription factors, namely reduced TBET and increased FOXP3 and GATA3.

Figure 27A:
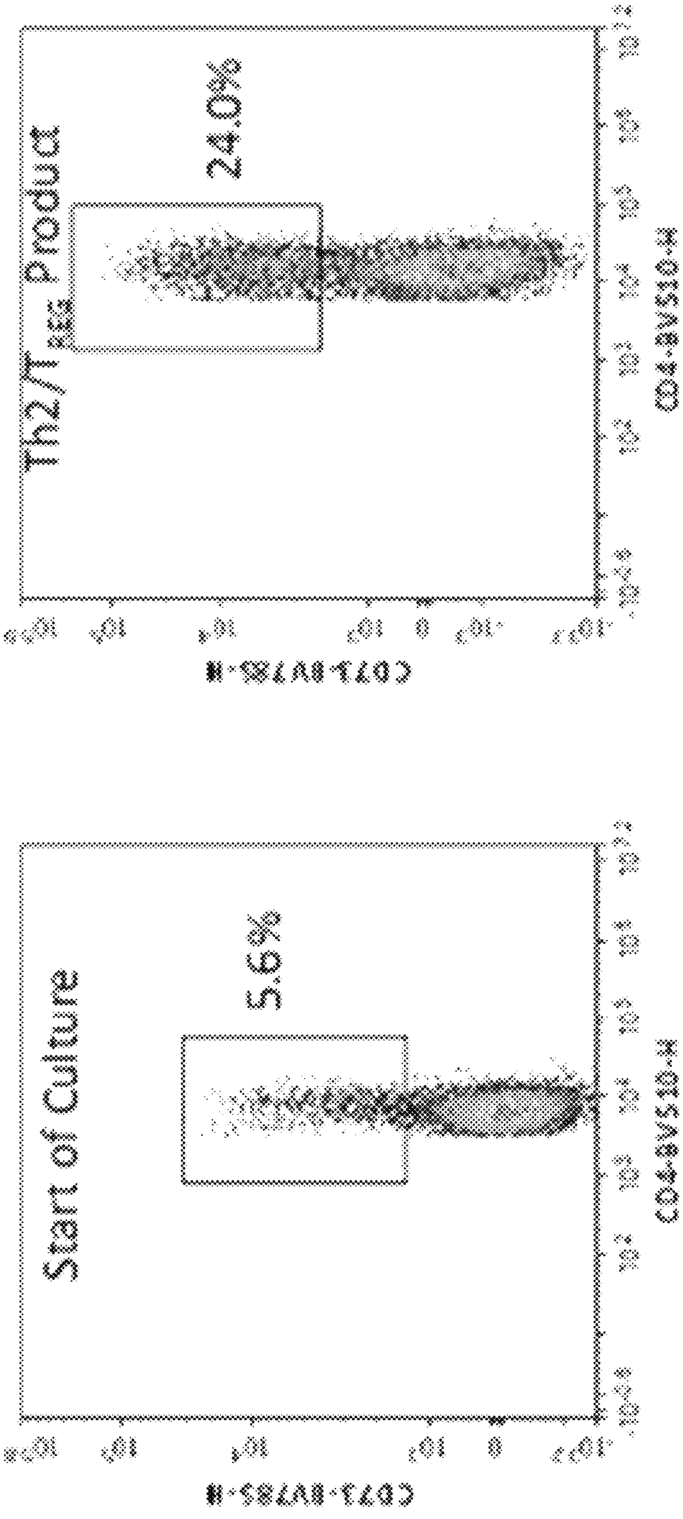
FIG. 27A depicts CD73 expression in CD4+ and CD8+ T cells at culture initiation and after culture as measured by flow cytometry.
Figure 27A:
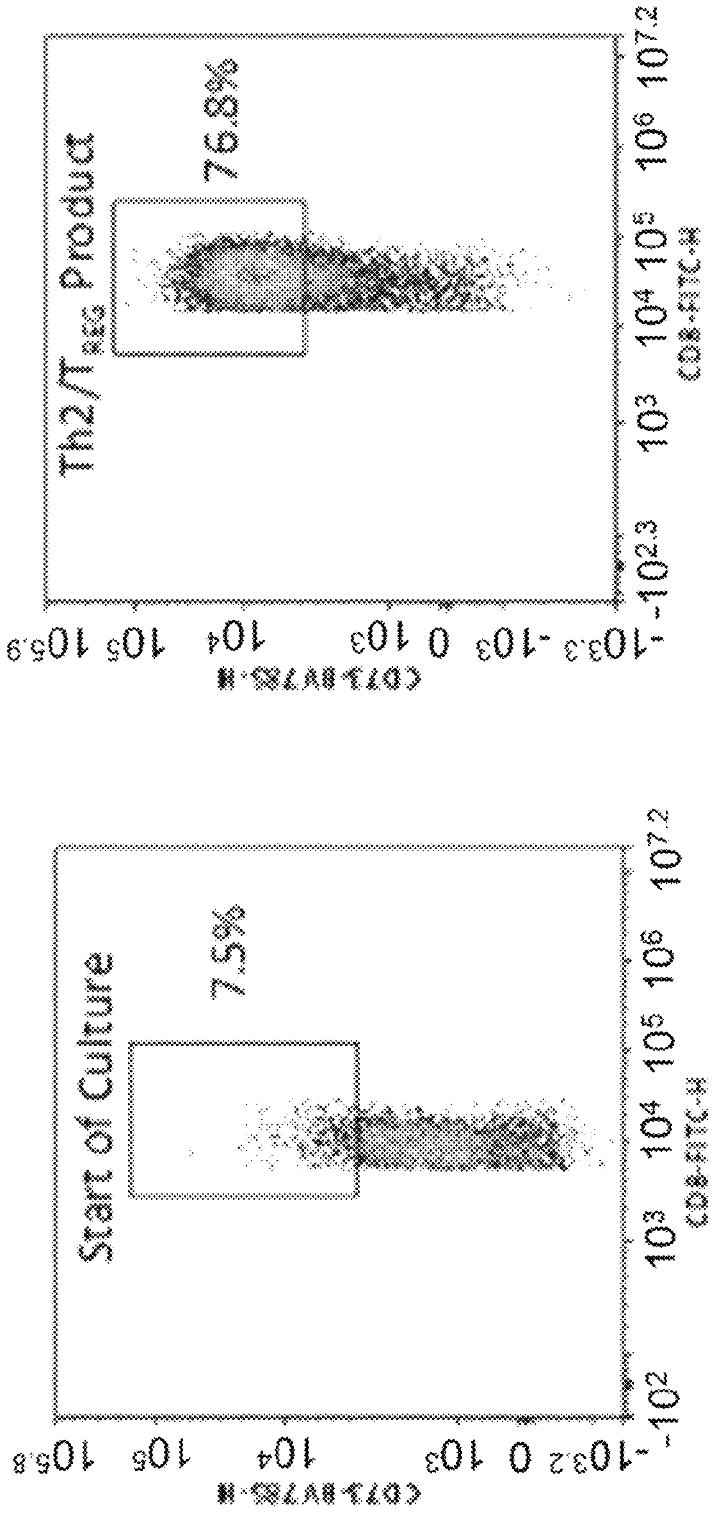
Figure 27B:
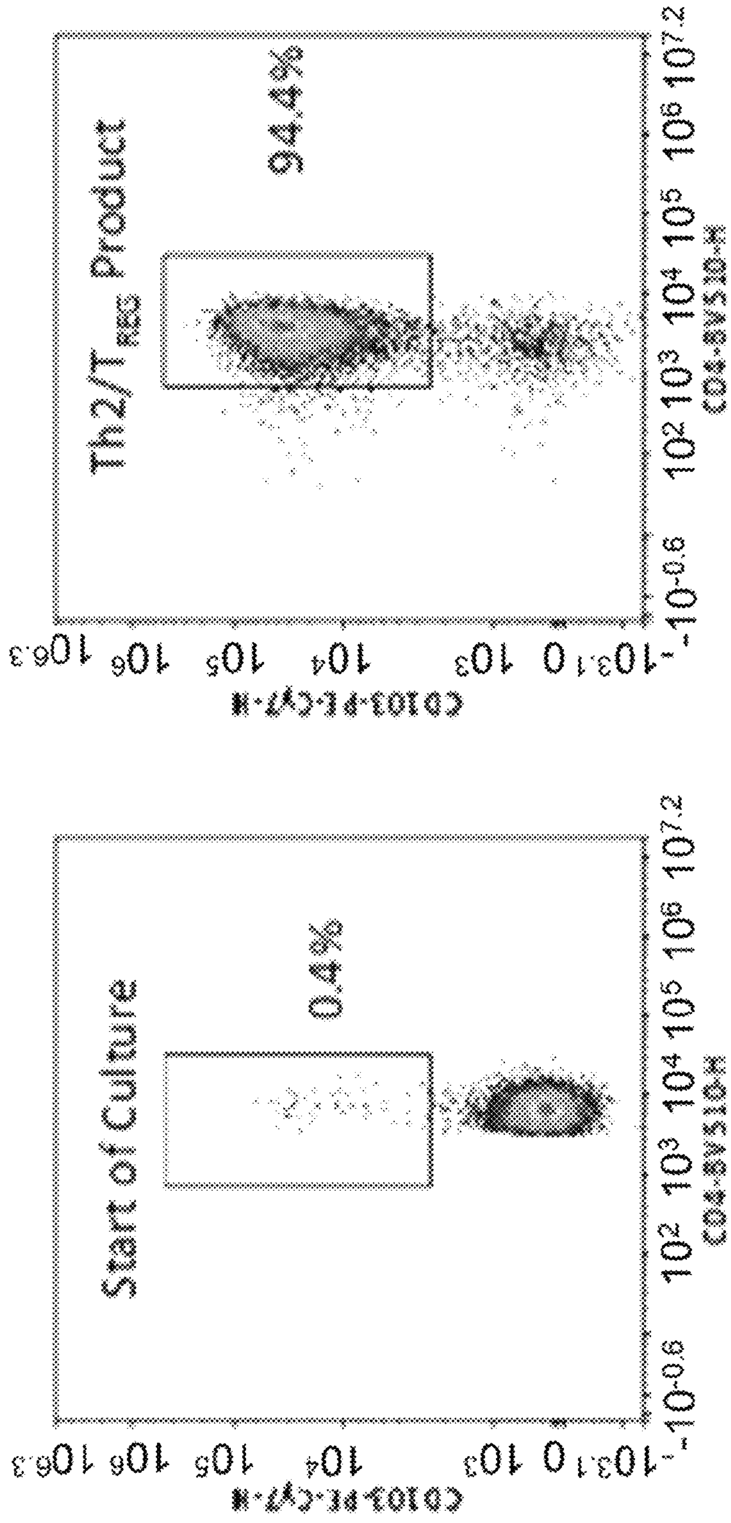
FIG. 27B depicts CD103 expression in CD4+ and CD8+ T cells at culture initiation and after culture as measured by flow cytometry.
Figure 27B:
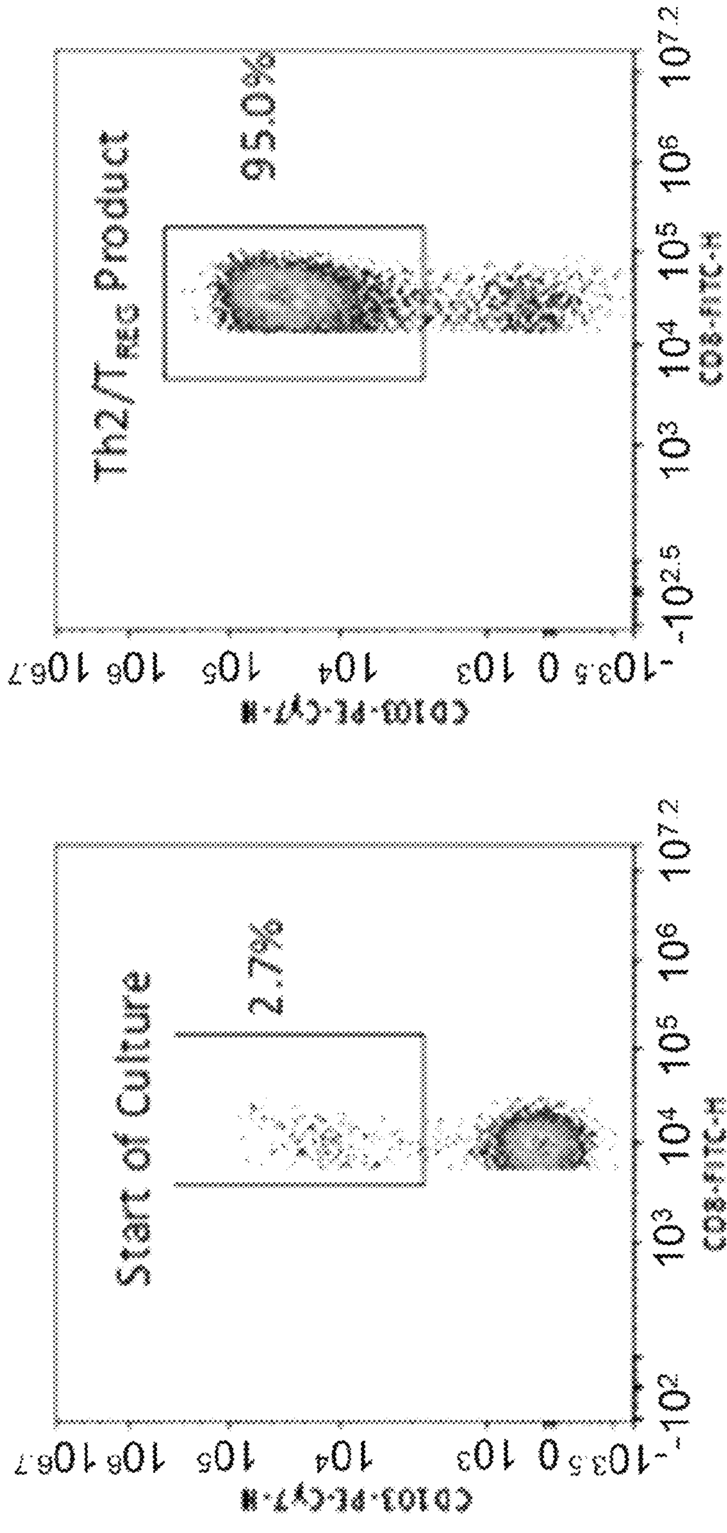

Example 21: Characterization of CD73 and CD103 Expression of the TREG Th2 Hybrid Population A steady-state apheresis sample was obtained and enriched for lymphocytes by a Ficoll gradient and then plated in a G-Rex culture vessel and incubated in complete media containing Vitamin D (0.3 nM), temsirolimus (3.0 μM) and basiliximab (30 μg/mL). After an initial de-differentiation interval, the T cells were co-stimulated at a 3:1 bead-to-T cell ratio with anti-CD3/anti-CD28-coated magnetic beads and cytokines were added (IL-4 (1000 IU/mL), IL-2 (10,000 IU/mL) and TGF-β (100 ng/mL)). After the 6-day culture, the T cells were harvested, stained for surface markers (CD4 and CD8) and the ectonucleotidase molecule, CD73, or the integrin molecule, CD103, and evaluated by flow cytometry. Results in FIGS. 27A-B show the CD73 and CD103 expression for CD4+ and CD8+ T cells at the start of culture and after culture (Th2/TREG) as measured by flow cytometry. The percentages provided indicate the amount of cells considered positive for CD4+ or CD8+ and the ectonucleotidase molecule or integrin molecule, respectively (shown in boxes).

Regulatory T cell populations can suppress pathogenic effector T cell populations by several defined mechanisms, including through expression of CD39 and CD73 ectonucleotidase molecules, which act to hydrolyse pro-inflammatory ATP towards the immune suppressive adenosine substrate. Indeed, TREG cells that express CD39 possess increased suppressive function and have been associated with resolution of inflammatory bowel disease. Furthermore, suppressive function of human TREG cells is mediated in part by CD73. As shown below in FIG. 27A, T cells manufactured in the Th2/TREG culture condition can have an increase in expression of the TREG-associated effector molecule, CD73; CD39 was also highly expressed on the TREG/Th2-manufactured T cells (not shown). In addition to the CD39/CD73 ectonucleotidases, TREG cell function has also been correlated with expression of CD103, which is an integrin that dictates epithelial lymphocyte localization Indeed, CD103 and IL-2 receptor signaling cooperate to maintain immune tolerance in the gut mucosa; furthermore, CD103-expressing TREG cells are critical for amelioration of experimental chronic GVHD. As shown below in FIG. 27B, T cells manufactured in the Th2/TREG culture condition can have an increase in expression of the TREG-associated effector molecule, CD103.

Figure 28A:
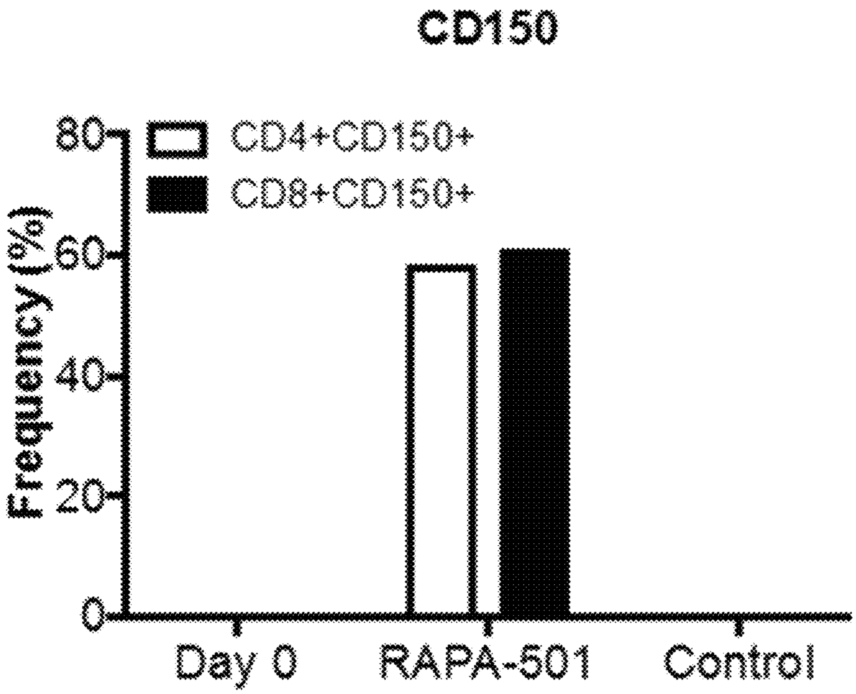
FIG. 28A depicts CD150 frequency as measured by flow cytometry in CD4+ and CD8+ T cells at culture initiation, after culture and for control T cells not exposed the mTOR inhibitors, as measured by flow cytometry.
Figure 28B:
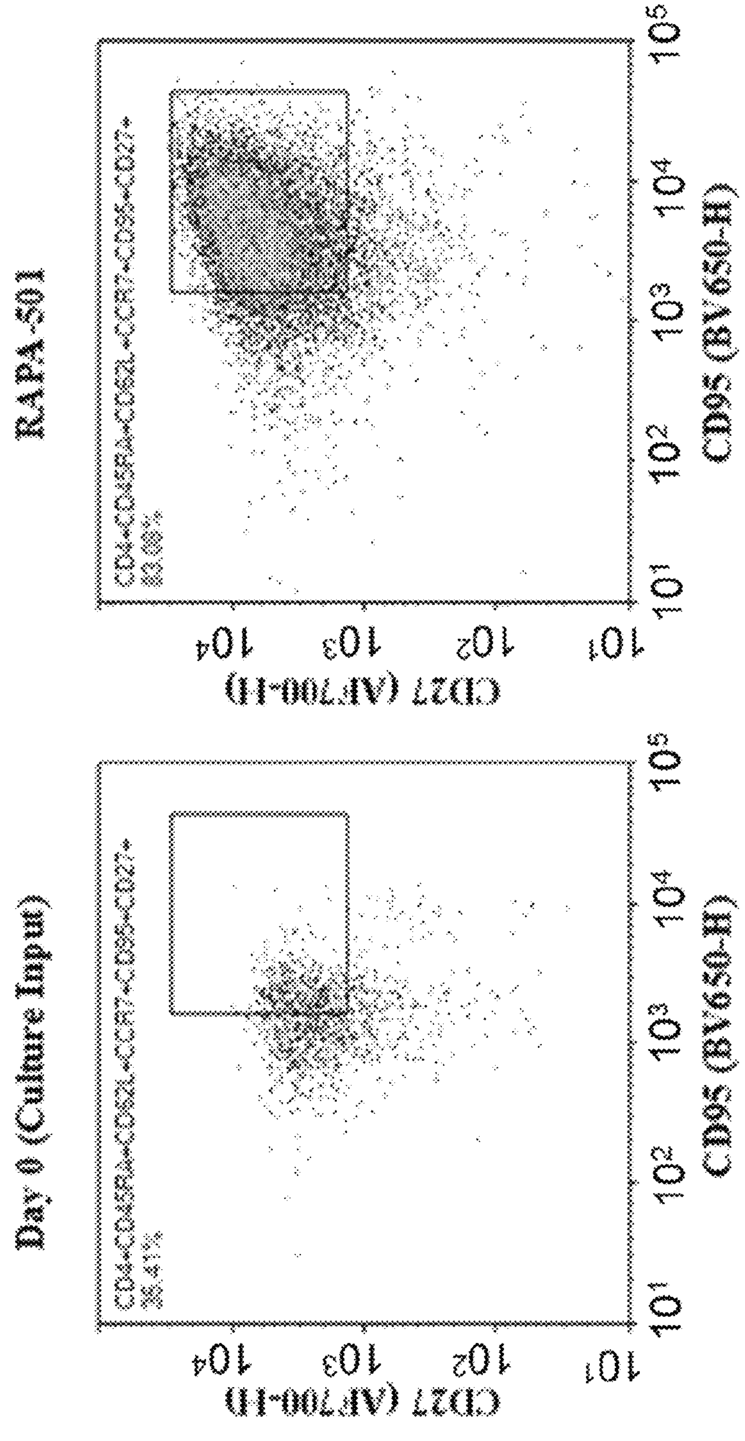
FIG. 28B depicts CD27 versus CD95 expression for CD4+ T cells at culture initiation and after culture as measured by flow cytometry.

Example 22: Characterization of CD150 and CD27 CD95 Expression of the TREG Th2 Hybrid Population A steady-state apheresis sample was enriched for lymphocytes by a Ficoll gradient, plated into a G-Rex culture vessel, and incubated in complete media containing Vitamin D (0.3 nM), temsirolimus (3.0 μM) and basiliximab (30 μg/mL). After this initial de-differentiation interval, the T cells were co-stimulated at a 3:1 bead:T cell ratio with anti-CD3/anti-CD28-coated magnetic beads and cytokines were added (IL-4 (1000 IU/mL), IL-2 (10,000 IU/mL) and TGF-β (100 ng/mL)). After the 6-day culture, the T cells were harvested, stained for surface markers, and subjected to multi-color flow cytometric analysis for CD4, CD8, CD150, CD27, CD95, CD45RA, CD62L, and CCR7. Results are shown in FIGS. 28A-B.

T cell cultured in the TREG (RAPA-501) condition were compared to the culture input T cells ("Day 0") and also compared to control culture T cells that were propagated without mTOR inhibitors ("Control"). As shown in FIG. 28A, both CD4+ and CD8+ T cell subsets contained within the RAPA-501 cell product had greatly increased expression of the stem cell marker CD150 relative to culture input T cells and relative to control cultured T cells. As shown in FIG. 28B, the RAPA-501 cell product was also enriched for a T stem cell memory (TSCM) phenotype relative to culture input cells; the control culture was devoid of this population, as the resultant T cells in this condition were effector memory, CD45RO+ (not shown). The left panel (culture input T cells) and the right panel (RAPA-501 cells) show expression of the TSCM markers CD95 and CD27 after gating on the TSCM markers CD45RA, CD62L, and CCR7; a similar difference in expression of these TSCM markers was observed for CD8+ T cells (not shown).

In experimental models, the efficacy of adoptive T cell therapy is dependent upon successful engraftment and in vivo persistence of the T cell population. Importantly, the T cell differentiation state helps dictate in vivo persistence, with less differentiated cells having increased persistence. In our initial studies, murine rapamycin-resistant T cells, which expressed a T central memory (TCM) phenotype, had increased in vivo engraftment potential relative to control T cells; in addition, human rapamycin-resistant T cells also had increased engraftment in a human-into-murine model of xenogeneic graft-versus-host disease. Other investigators have determined that T cells with reduced differentiation relative to the T effector memory (TEM) population have increased in vivo persistence and mediate increased in vivo effects, including the TCM subset, the naïve T cell subset, and more recently, the T stem cell memory (TSCM) subset. This relationship between T cell differentiation status and in vivo T cell function is operational relative to TREG cells, as: (1) TREG cells of TCM phenotype were more effective at reducing experimental GVHD relative to TREG cells of TEM phenotype; and (2) TREG cells that expressed the stem cell marker CD150 were highly effective for the prevention of stem cell graft rejection. As shown below in FIG. 28A, T cells manufactured in the Th2/TREG culture condition were enriched for cells a reduced differentiation state consistent with a T stem cell subset, including expression of the CD150 marker.

Example 23: Characterization of Cytokine Secretion of the TREG Th2 Hybrid Population A steady-state apheresis sample was enriched for lymphocytes by a Ficoll gradient, plated into a G-Rex culture vessel, and incubated in complete media containing Vitamin D (0.3 nM), temsirolimus (3.0 μM) and basiliximab (30 μg/mL). After an initial de-differentiation interval, the T cells were co-stimulated at a 3:1 bead:T cell ratio with anti-CD3/anti-CD28-coated magnetic beads and cytokines were added (IL-4 (1000 IU/mL), IL-2 (10,000 IU/mL) and TGF-β (100 ng/ml)). This culture is termed Condition "A." Condition "B" was the same culture condition but without IL-4 addition. Condition "C" reflects the standard $T_{REG}$ culture condition of rapamycin (1 μM), IL-2 (100 IU/mL), and TGF-β (10 ng/ml). Condition "D" reflects a Th1-type control culture manufactured in the presence of IFN-α without mTOR inhibitors. After culture, the T cells were harvested, stimulated with anti-CD3/anti-CD28 beads, and the resultant supernatant was tested for cytokine content by Luminex assay.

Figure 29:
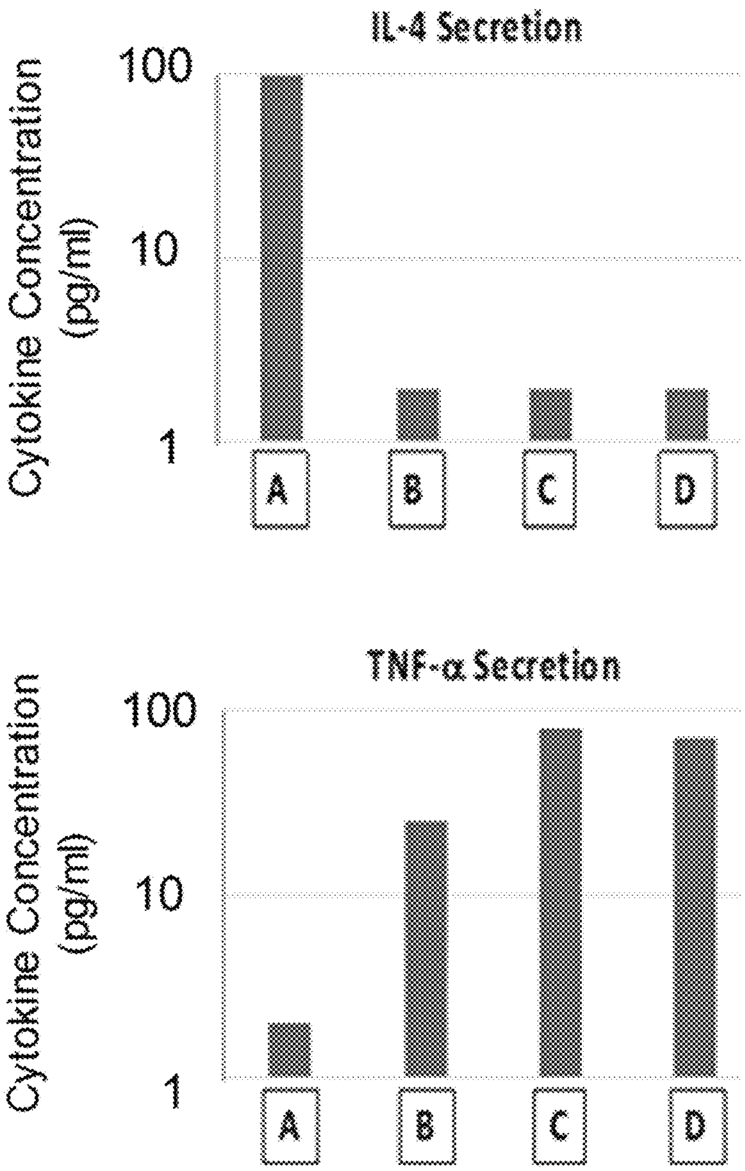
FIG. 29 depicts the IL-4, IL-2, IFN-γ, TNF-α, IL-17 and GM-CSF for differently cultured cells and control cells.
Figure 29:
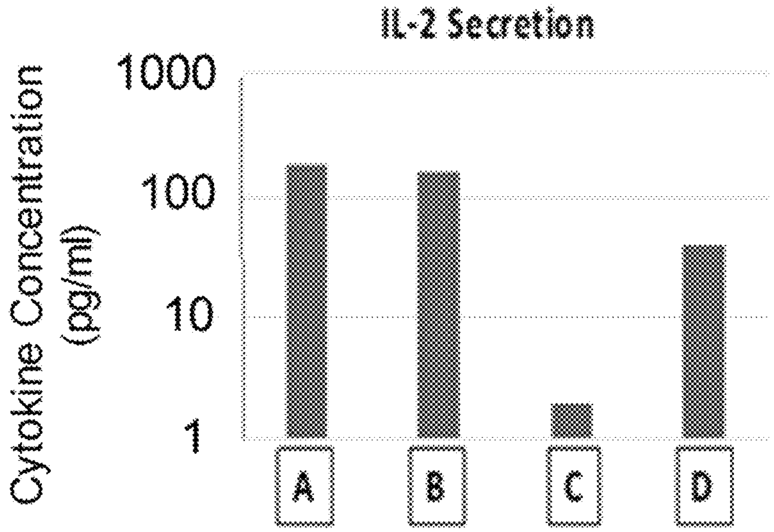
Figure 29:
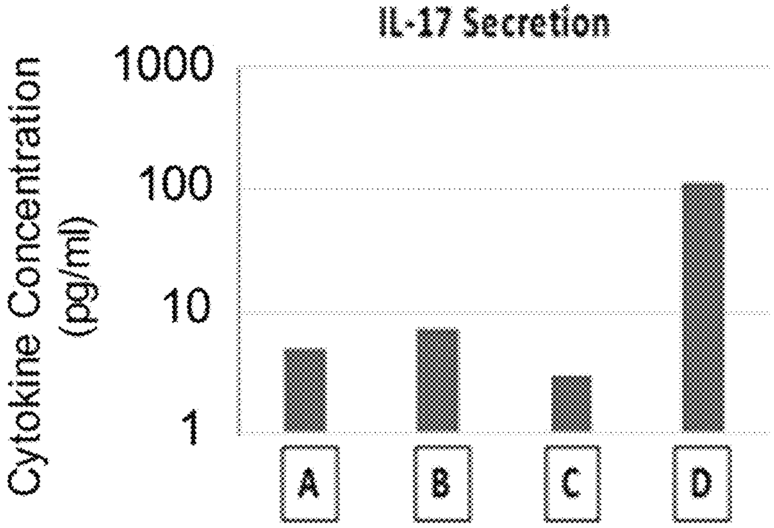
Figure 29:
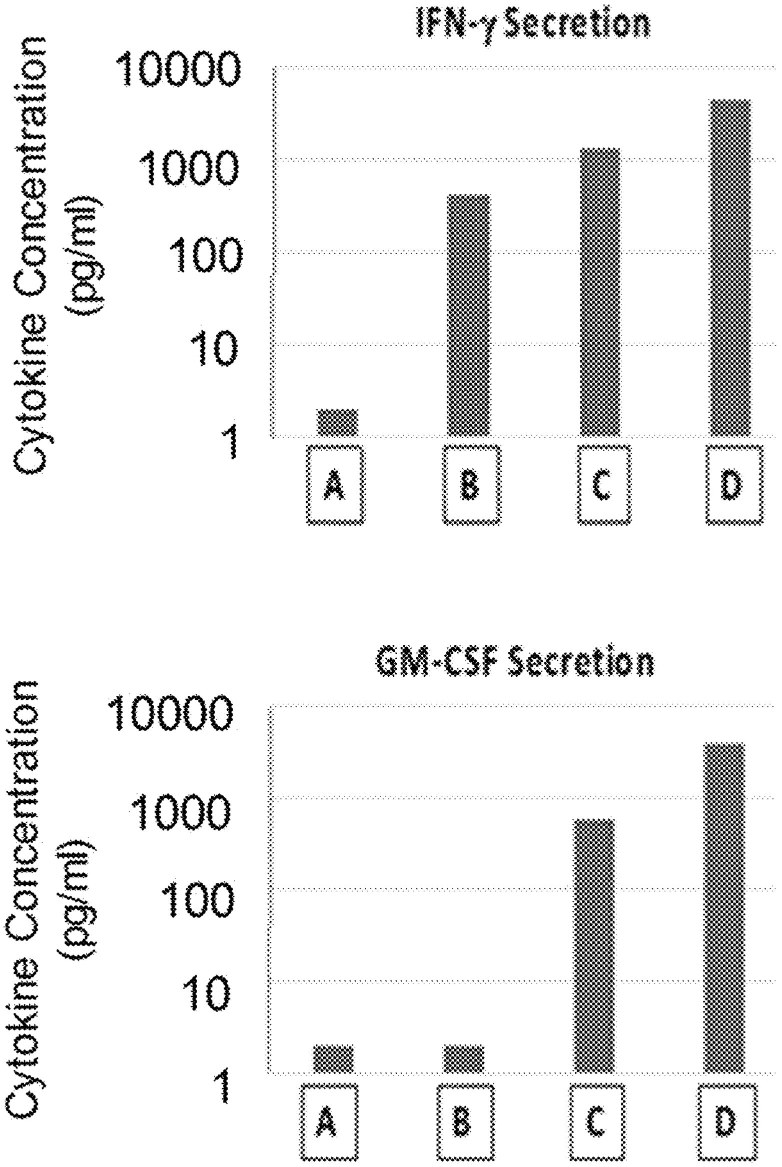

It can be important to assess cytokine secretion of the manufactured Th2/$T_{REG}$ cells. First, it is critical that the cell product can secrete IL-4, which is the driver cytokine for subsequent Th2 differentiation. Second, it is desirable that an adoptively transferred T cell population is capable of secreting IL-2, as this capacity indicates a progenitor function that permits T cells to expand more readily in vivo without the need for exogenous IL-2. Finally, it is important that the Th2/$T_{REG}$ cell population has reduced secretion of the Th1- or Th17-type cytokines IFN-α, TNF-α, IL-17, and GM-CSF. As FIG. 29 illustrates, the manufactured Th2/$T_{REG}$ cell product secreted IL-4 and IL-2 with minimal secretion of Th1- or Th17-type cytokines.

Example 24: Characterization of Th1 Tel Suppression by the $T_{REG}$ Th2 Hybrid Population A steady-state apheresis sample was enriched for lymphocytes by a Ficoll gradient, plated into a G-Rex culture vessel, and incubated in complete media containing Vitamin D (0.3 nM), temsirolimus (3.0 μM) and basiliximab (30 μg/mL). After an initial de-differentiation interval, the T cells were co-stimulated at a 3:1 bead:T cell ratio with anti-CD3/anti-CD28-coated magnetic beads and cytokines were added (IL-4 (1000 IU/mL), IL-2 (10,000 IU/mL) and TGF-β (100 ng/mL)) for ex vivo manufacture of Th2/$T_{REG}$ cells. In parallel, T cells were cultured in the presence of the type I polarizing cytokine IFN-α to generate effector Th1/Tc1 cells; the Th1/Tc1 culture was generated from the same donor as the RAPA-501 cell culture (autologous; "AUTO") or from an unrelated donor (allogeneic; "ALLO"). After ex vivo culture, the Th1/Tc1 effector T cells were plated in the bottom chamber of a transwell plate and co-stimulated with anti-CD3/anti-CD28 coated beads at a bead-to-T cell ratio of 3:1. After 24 hours of Th1/Tc1 cell co-stimulation, RAPA-501 cells were added to the top chamber of the transwell plate at a Th1/Tc1-to-RAPA 501 ratio of 1:1. (A) RAPA-501 modulation of cytokine content. At 24 hours (prior to addition of RAPA-501 cells to the upper chamber) and at 48 hours of culture (either with or without addition of RAPA-501 cells), the culture supernatant was harvested and tested for cytokine content by Luminex assay. Results are expressed for IL-2, IFN-γ, GM-CSF, and TNF-α content in pg/ml/24 hours/1×106 cells/ml. (B) RAPA-501 cell modulation of Th1/Tc1 cell expression of PD1 occurs in an antigen-independent manner. At 48 hours, the autologous or allogeneic Th1/Tc1 cells were harvested after either addition or no addition of RAPA-501 cells at the 24-hour time point; the Th1/Tc1 cells were then subjected to flow cytometry for evaluation of PD1 expression.

Figure 30A:
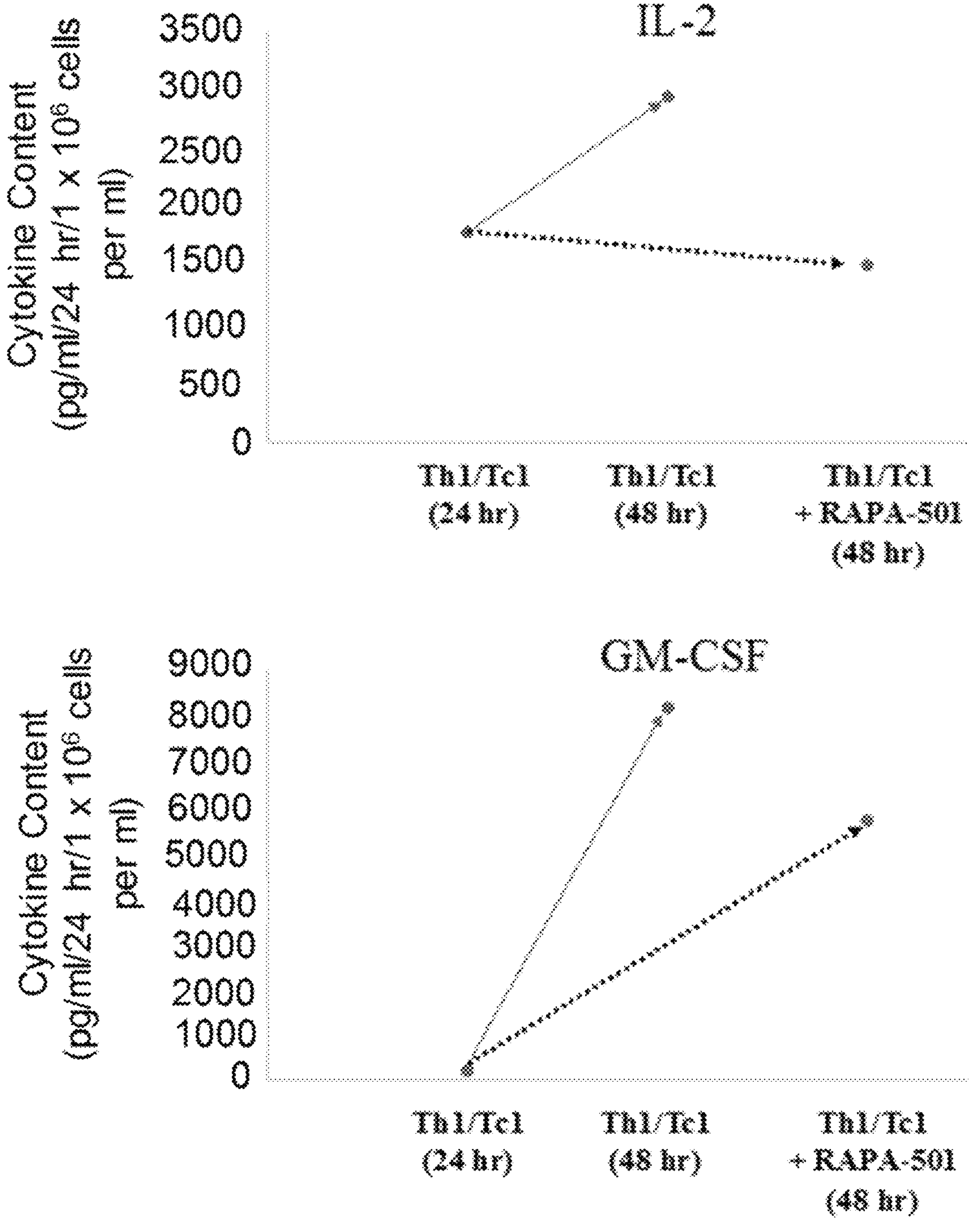
FIG. 30A depicts the cytokine content for a transwell assay of Th1/Tc1 cells with or without RAPA-501 cells.
Figure 30A:
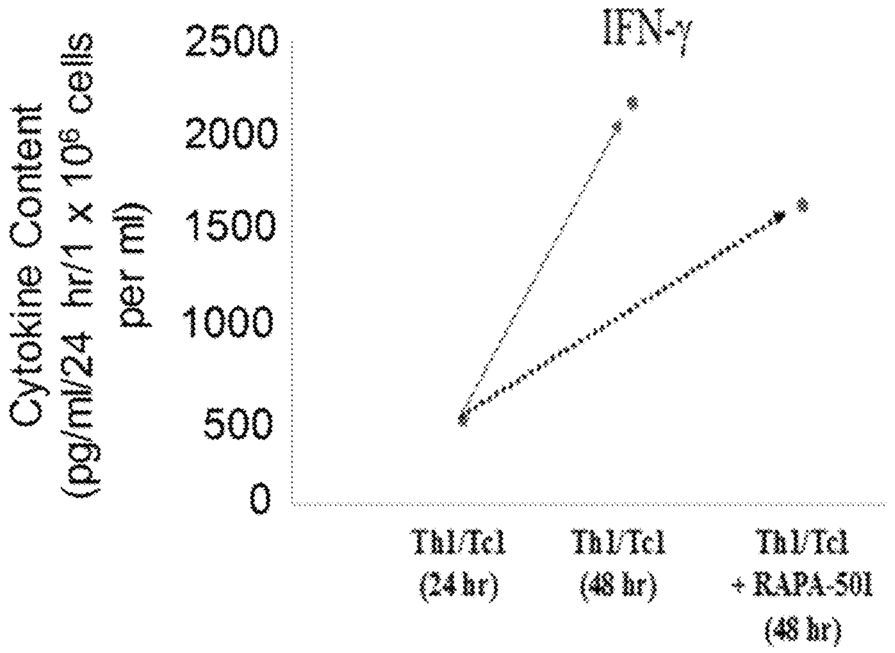
Figure 30A:
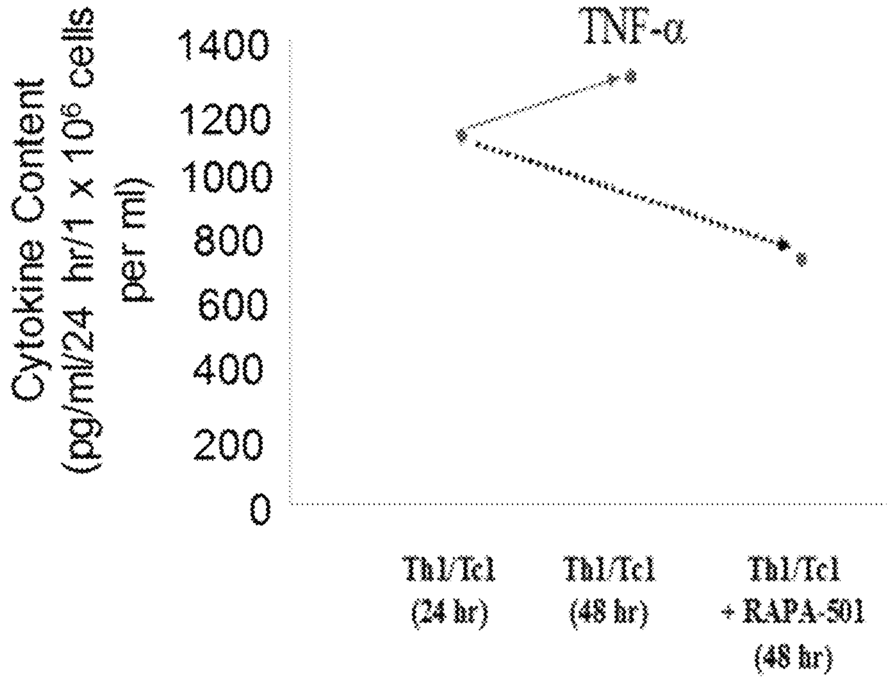
Figure 30B:
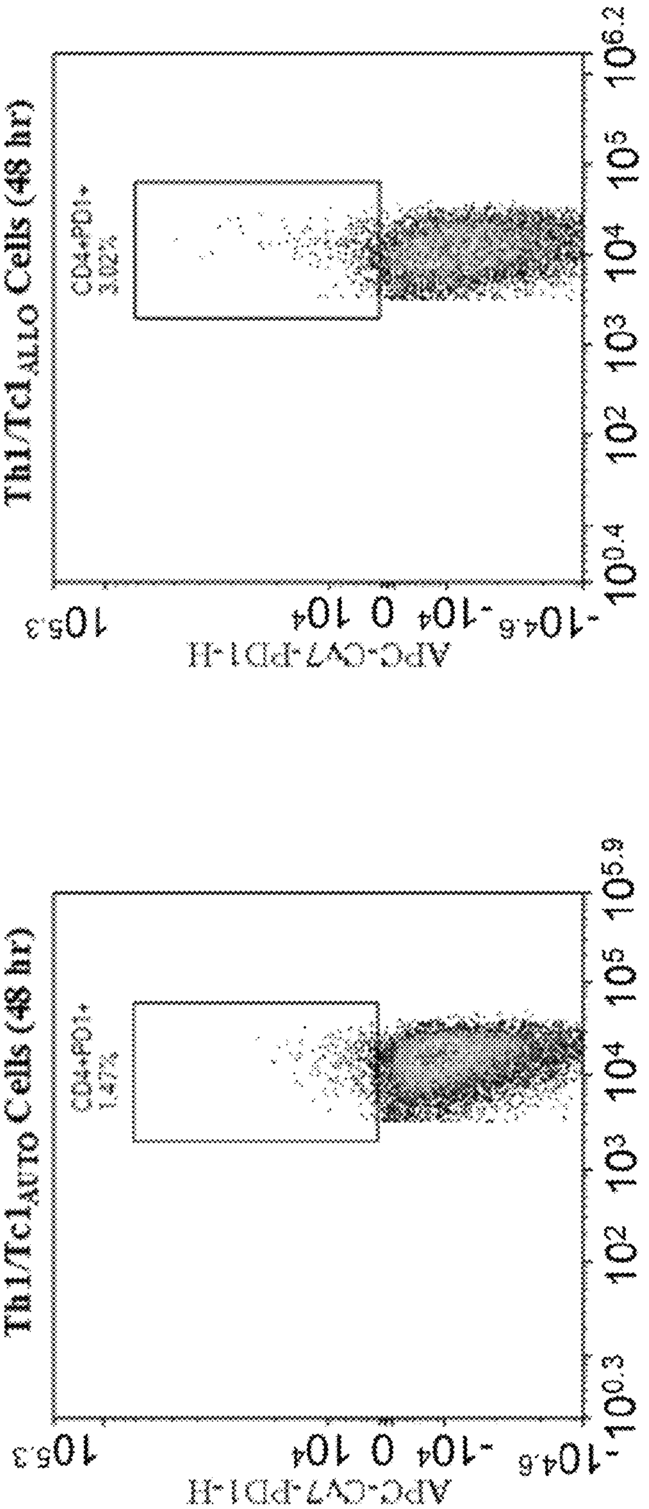
FIG. 30B depicts the flow cytometry results for assays of CD4 and PD1 in Example 24.
Figure 30B:
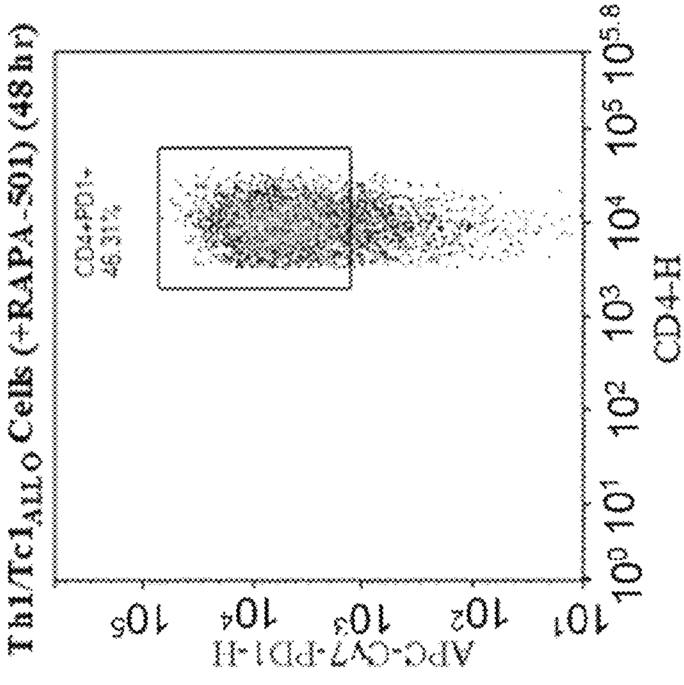
Figure 30B:
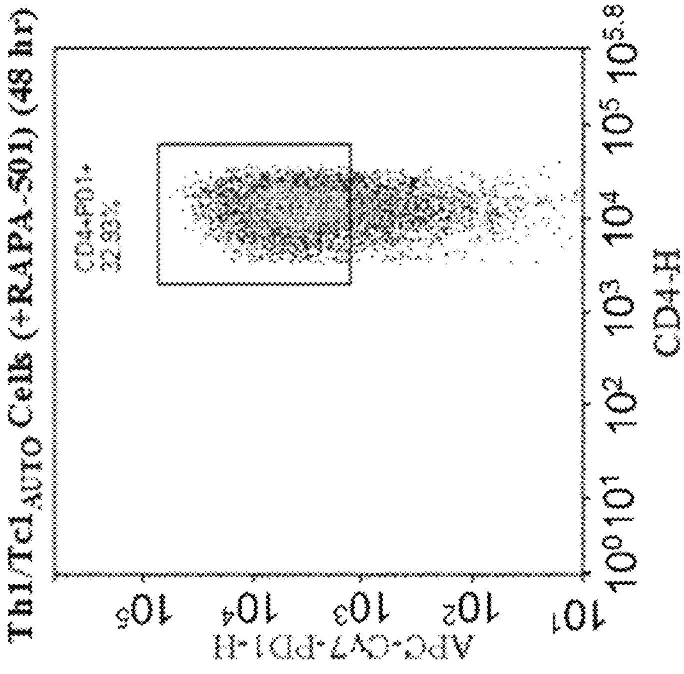

During development of the RAPA-501 cell product, we performed experiments to characterize the molecular mechanism of the observed T cell suppression. One method to evaluate potential mechanisms is the transwell assay, whereby effector T cells and RAPA-501 cells are separated by a filter that prevents cell-to-cell contact but allows cell communication by small soluble mediators such as cytokines. FIGS. 30A-B illustrate that the RAPA-501 cells modulate effector T cells in a contact-independent manner (experiments performed in a transwell vessel). RAPA-501 cells acted in a T cell receptor independent manner to suppress the cytokine secretion capacity of effector T cells; that is, because no co-stimulation beads were added to the transwell chamber containing the RAPA-501 cells, RAPA-501 cells did not require co-stimulation in order to modulate inflammatory cytokine levels, including IL-2, IFN-γ, GM-CSF, and TNF-α (FIG. 30A). The ability of TREG cells to consume IL-2 is a commonly described phenomenon, although previous studies identified the requirement of cell-to-cell contact for IL-2 consumption. As such, RAPA-501 cells appear to be somewhat uniquely capable of modulating the level of multiple inflammatory cytokines in a contact-independent manner. These results suggest that RAPA-501 cells represent a suitable candidate for neutralization of cytokines. Second, we found that RAPA-501 cells modulated additional aspects of effector T cell biology in a contact-independent manner (use of transwell experiments), namely, the promotion of programmed death-1 (PD-1) checkpoint molecule expression on the effector T cells. Importantly, as shown in FIG. 30B, RAPA-501 cells up-regulated PD1 expression on both autologous and allogeneic Th1/Tc1 cells, thereby further clarifying that one mechanism of RAPA-501 cell suppressive function occurs in a TCR-independent manner by soluble mediators.

Figure 31A:
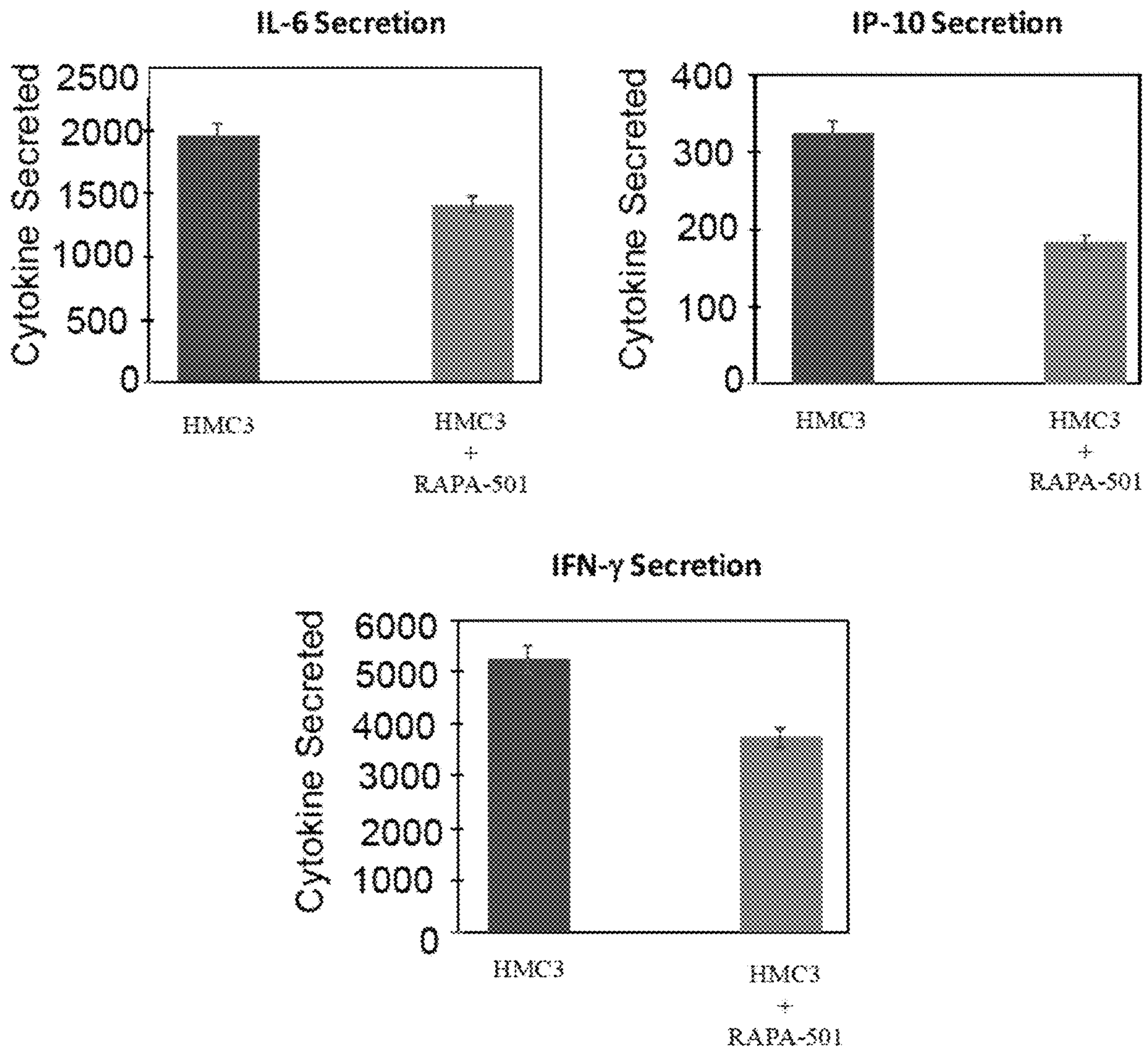
FIG. 31A depicts IL-6, IP-10, and IFN-γ secretion for human microglial cells with or without exposure to RAPA-501 cells.
Figure 31B:
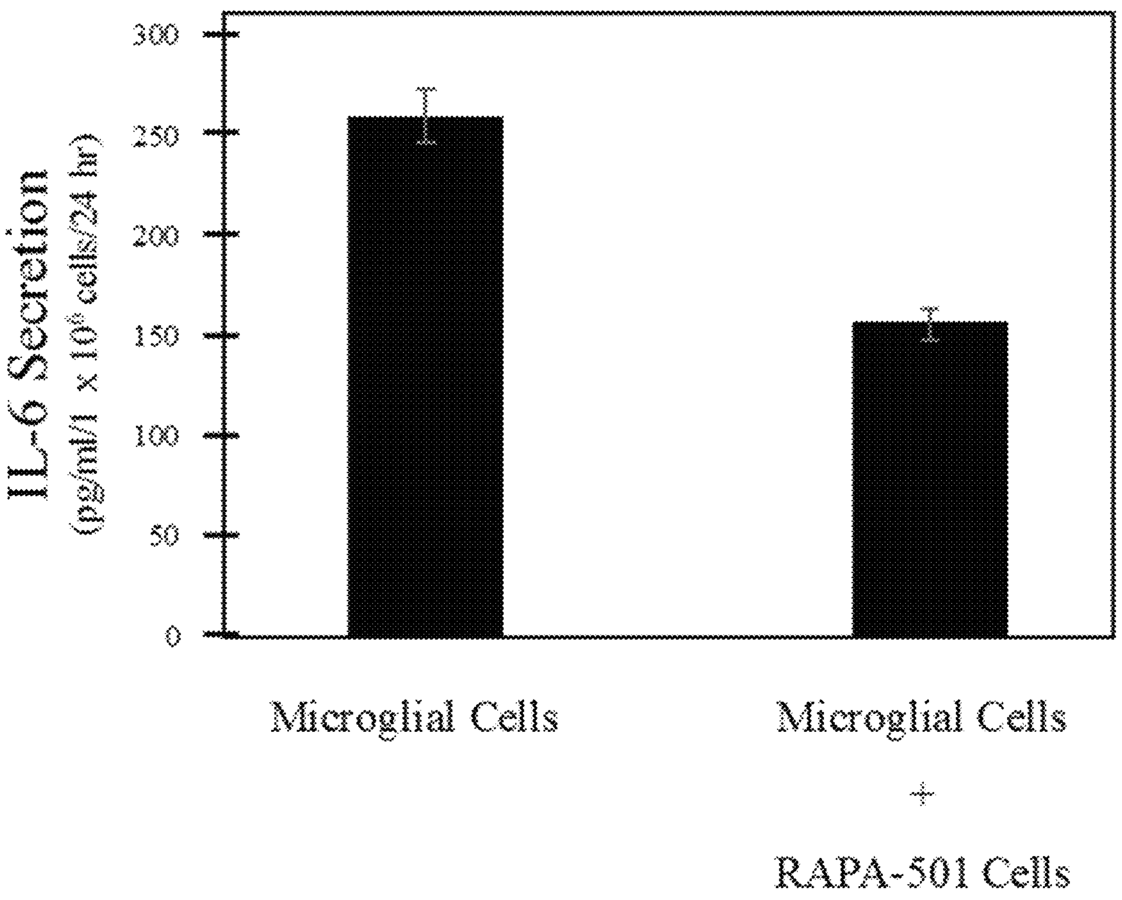
FIG. 31B depicts IL-6, IP-10, and IFN-γ secretion for human microglial cells with or without exposure to RAPA-501 cells.

Example 25: Characterization of ONS Microglial Cell Cytokine Secretion Suppression by the $T_{REG}$ Th2 Hybrid Population Human microglial cells (HMC3 cell line) were first activated with IFN-γ (10 ng/ml; 24 hr) and then activated with LPS (10 ng/ml; 3 hr); the treated HMC3 cells were then plated into the lower chamber of a transwell, either without (left panel) or with (right panel) addition of RAPA-501 cells, made as previously described, into the upper chamber (RAPA-501 to HMC3 ratio, 1:40). The RAPA-501 cells were generated using methods described in the patent application to generate T cells of a hybrid Th2/$T_{REG}$ phenotype. After 24 hours, cell free supernatants were harvested and evaluated for content of IL-6, IFN-γ, and IP-10 by Luminex assay (cytokine secretion measured in pg/ml/1×106 cell per ml/24 hr). Results are shown in FIG. 31.

Microglial cells are CNS-resident antigen-presenting-cells that can develop into pro-inflammatory factors in ALS. The ability of a manufactured human Th2/$T_{REG}$ cell to suppress human microglial cell inflammation has not been previously reported to our knowledge. To address this, we induced a human microglial cell line HMC3 into a pro-inflammatory state by sequential culture in IFN-γ followed by LPS endotoxin. As FIGS. 31A-31B demonstrate, the addition of the RAPA-501 Th2/TREG cell product to the pro-inflammatory microglial cells reduced the culture supernatant content of the pro-inflammatory cytokines IL-6, IP-10, and IFN-γ. In this experiment, the observed immune suppressive effect occurred in a transwell vessel and at a very dilute TREG to inflammatory microglial cell ratio of 1-to-40, thereby indicated that the RAPA-501 cells can reduce CNS inflammation in a contact independent manner (as indicated by the transwell design) and with a high degree of potency (as indicated by the 1:40 TREG-to-microglial cell ratio).

Figure 32:
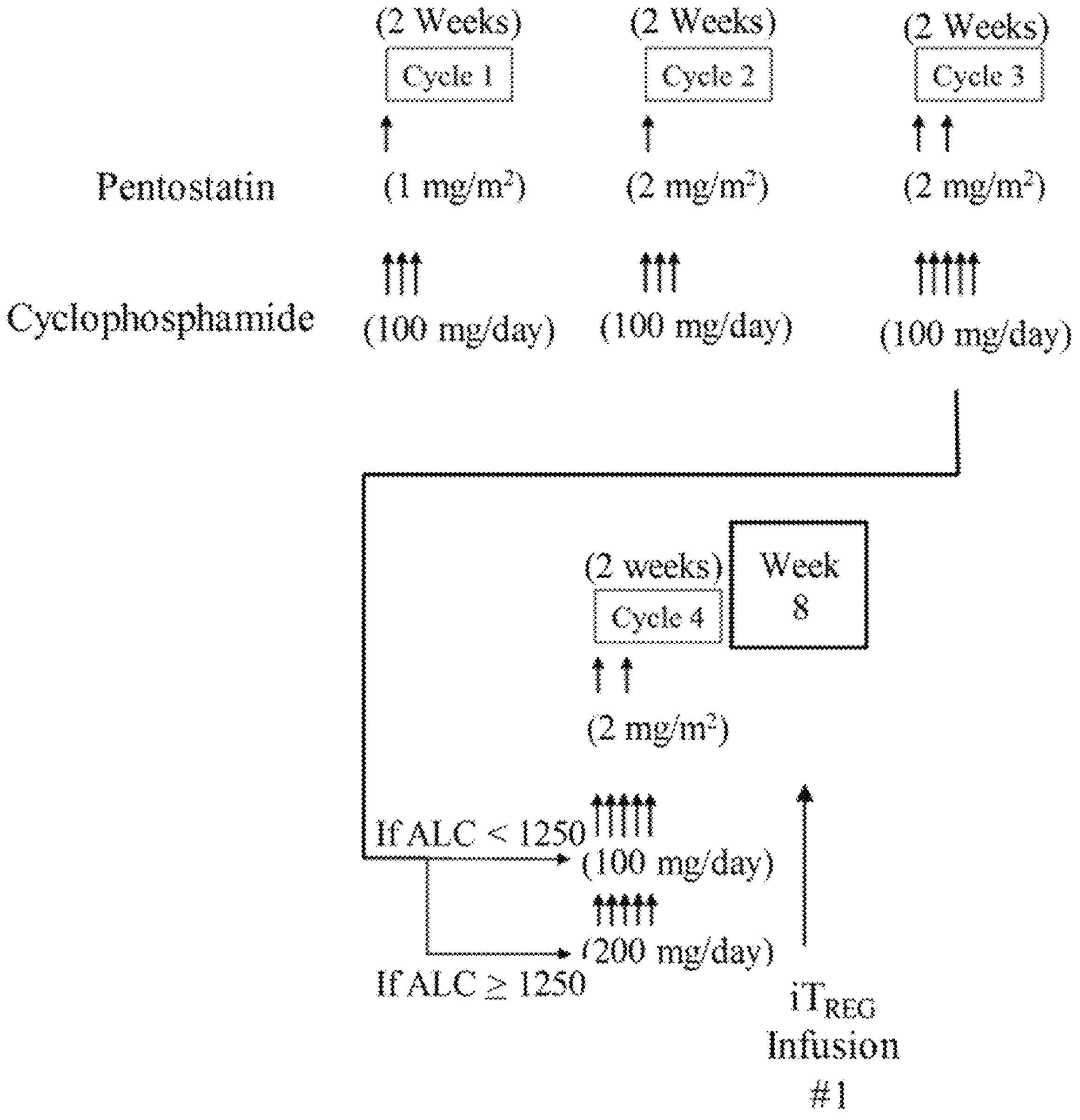
FIG. 32 schematically depicts the PC Regimen and the overall therapeutic approach.

Example 26: $iT_{REG}$ Cell Therapy of ALS Using the Pentostatin, Cyclophosphamide, and Lamivudine Host Conditioning Platform FIG. 32 details the PC Regimen and the overall therapeutic approach. The PC regimen will be administered in 2-week cycles, with escalating doses of pentostatin or cyclophosphamide over cycles 1 to 4, as indicated (8 weeks total duration of the PC regimen). Pentostatin is administered either on day 1 or on days 1 and 4 of the 14-day cycle; cyclophosphamide (Cy) is administered either on days 1, 2, and 3 or on days 1, 2, 3, 4, and 5 of the 14-day cycle. For cycle 4, if the ALC is <1250 cells per microliter, the Cy dose will be increased to 200 mg per day. After immune depletion and immune suppression is realized through administration of the PC regimen, the first $iT_{REG}$ cell infusion will occur at week 8 of therapy. The inflammasome inhibitor lamivudine will be administered continuously at a dose of 150 mg BID from protocol week 8 to week 26.

Figure 33:
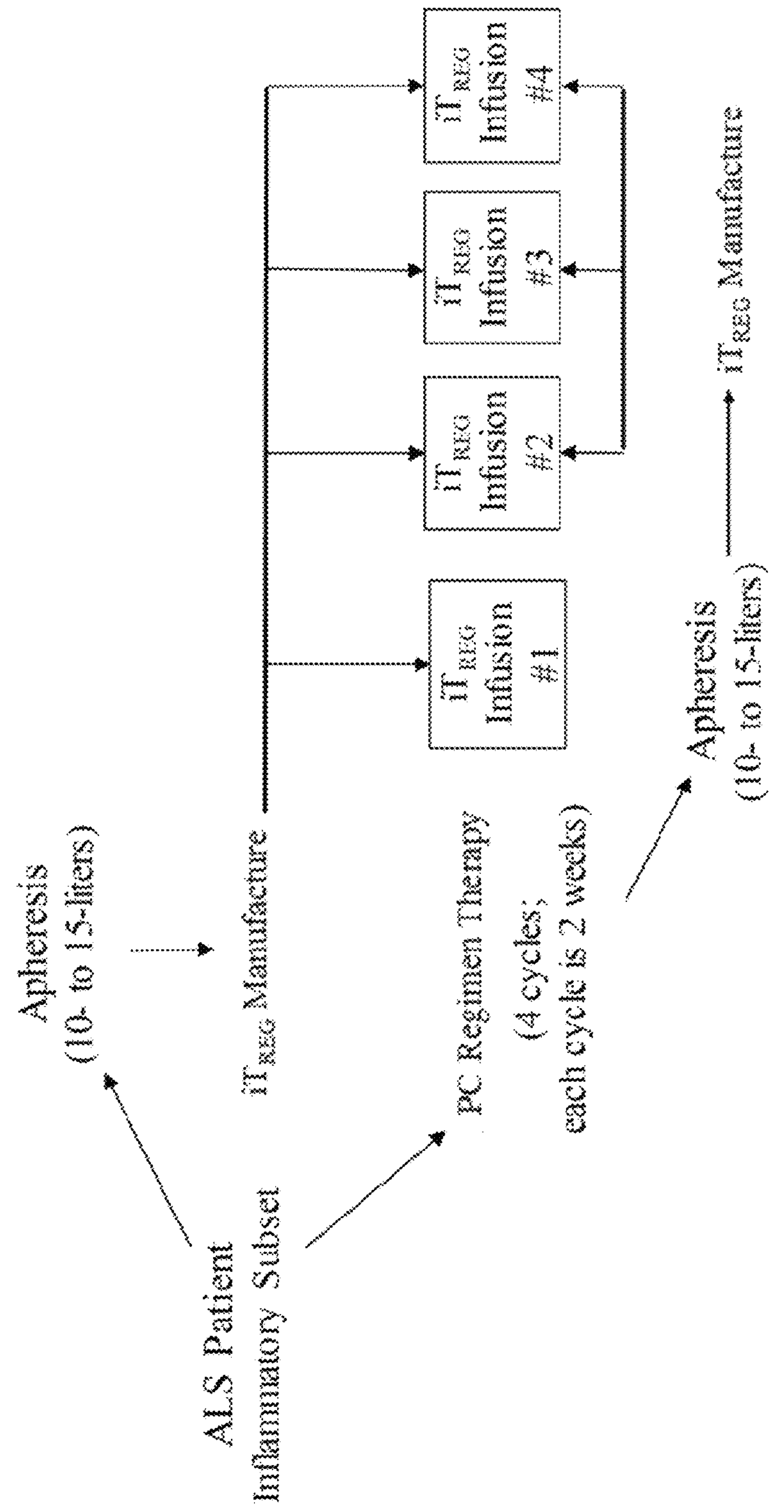
FIG. 33 schematically depicts lymphocyte collection by apheresis pre- and post-PC regimen.

FIG. 33 provides further details regarding the $iT_{REG}$ cell manufacturing, depicting lymphocyte collection by apheresis pre- and post-PC regimen. Lymphocytes from ALS patients will be collected by steady-state apheresis (10- to 15-liter collection), which will be performed either just before or just after the PC regimen. The collection prior to the PC regimen may be more advantageous for $iT_{REG}$ manufacturing because the T cells will be found in higher numbers and will not be immune suppressed; by comparison, the collection after the PC regimen may be advantageous because inflammatory Th1/Tc1 cells that will contaminate the $iT_{REG}$ culture will be depleted in vivo prior to manufacturing. After $iT_{REG}$ manufacturing, the product will be cryopreserved in therapeutic doses to allow repetitive dosing of $iT_{REG}$ cells, as indicated by infusions #2, #3, and #4.

Figure 34:
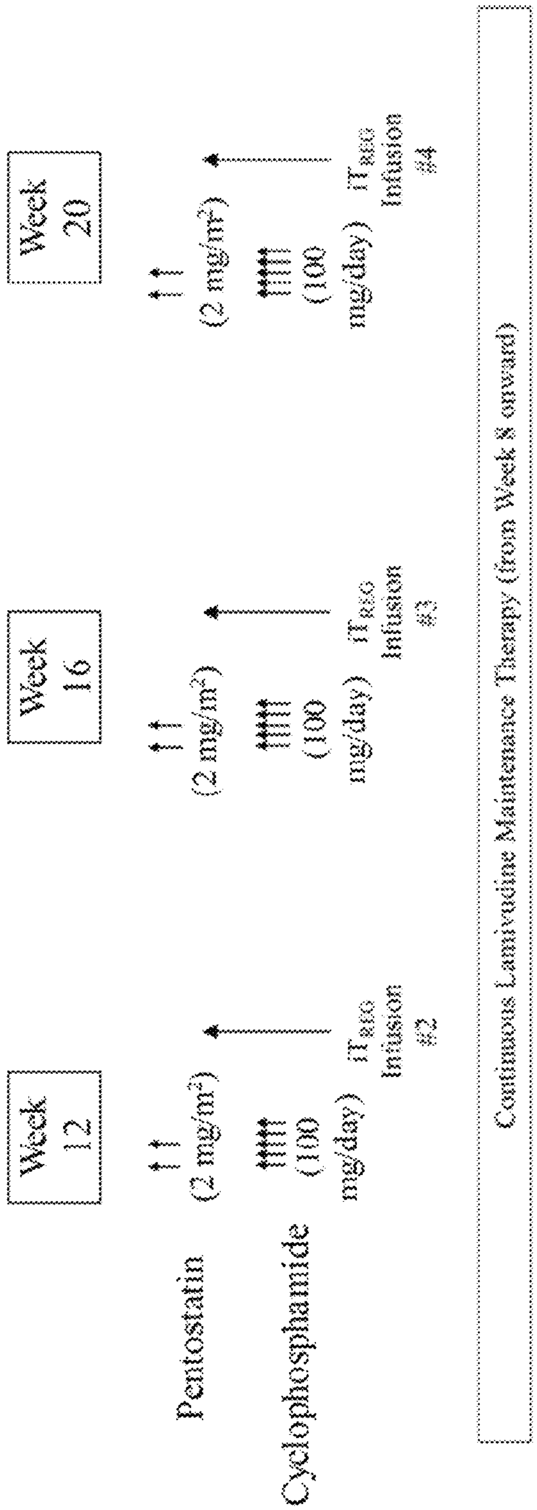
FIG. 34 schematically depicts the PC regimen prior to each of the repetitive doses of $iT_{REG}$ cells.

FIG. 34 further details the strategy of multiple $iT_{REG}$ cell infusions, depicting sequencing of the PC regimen prior to each of the repetitive doses of $iT_{REG}$ cells. The PC regimen will be administered prior to each $iT_{REG}$ infusion to: (1) deplete and suppress inflammatory Th1/Tc1 cells that contribute to disease pathogenesis; and (2) increase the in vivo levels of homeostatic cytokines such as IL-7 and IL-15, which will allow in vivo expansion of the adoptively transferred $iT_{REG}$ populations. The PC regimen will consist of pentostatin at a dose of 2 mg/$m^2$ on days 1 and 4 combined with cyclophosphamide at a flat dose of 100 mg per day on days 1 through 5. After two days of rest, the $iT_{REG}$ cells will be administered (day 8 of the regimen). The inflammasome inhibitor lamivudine will be continuously administered from week 8 onward to limit the inflammatory drive during $iT_{REG}$ cell therapy.

Figure 35:
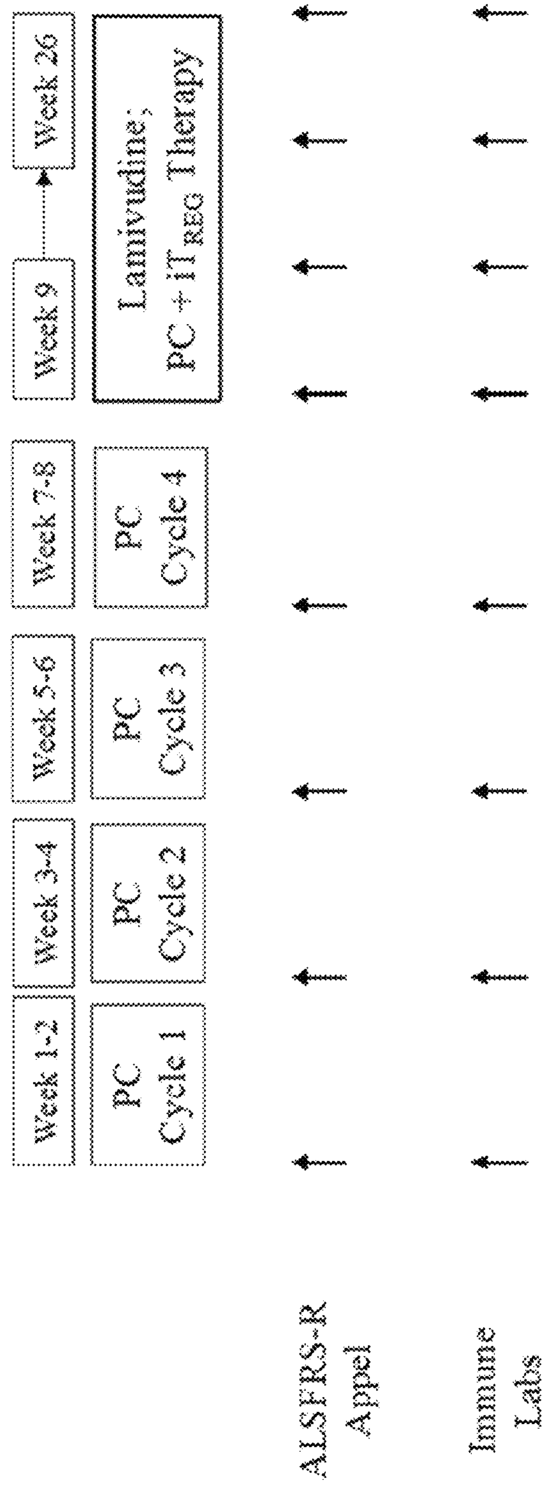
FIG. 35 schematically depicts monitoring of patients treated with $iT_{REG}$ cells.

FIG. 35 provides further details regarding monitoring of patients treated with $iT_{REG}$ cells, illustrating that monitoring of ALS will be by both patient-reported ALSFRS-R and clinician-reported Appel scores approximately monthly, as indicated. Immune labs to monitor the ALS patient inflammatory state will be assessed approximately monthly, as indicated.

Figure 36A:
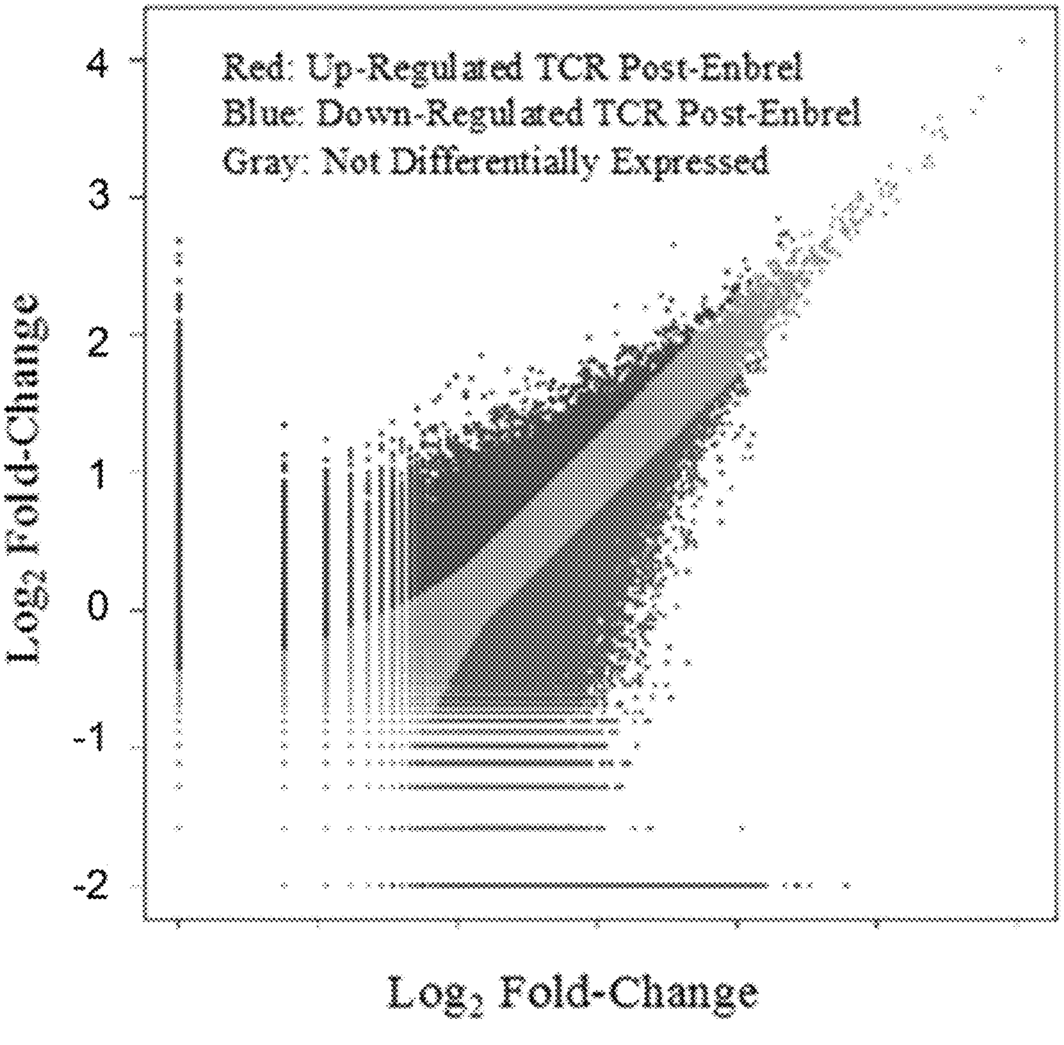

Example 27: Use of Select Anti-TNF-α Reagents Prior to Lymphocyte Collection by Apheresis to Beneficially Alter the Input T Cell TOR Repertoire FIGS. 36A-36B indicate that anti-TNF-α therapy with etanercept, which preferentially inhibits the serum, cell-free form of TNF-α that promotes TNFR1-expressing Th1-type cells, is associated with widespread changes in T cell receptor up- and down-regulation. FIGS. 36A-36B depict use of RNA-based T cell receptor sequencing to detect a widespread up- and down-regulation of T cell TCR specificities after therapy with the TNF-α inhibitor, etanercept. In FIGS. 36A-36B, RNA was isolated from peripheral blood mononuclear cells from an ALS patient pre- and post-therapy with etanercept therapy. The RNA was subjected to TCR repertoire profiling, as previously described by Rosati E, Dowds C M, Liaskou E, Henriksen E K K, Karlsen T H, Franke A.

Overview of methodologies for T-cell receptor repertoire analysis. BMC Biotechnol. 2017; 17(1): 61. As shown in FIG. 36A, it is demonstrated that approximately 25% of TCR specificities were up-regulated in the post-therapy sample (as indicated in red); in marked contrast, approximately 25% of TCR specificities were down-regulated in the post-therapy sample (as indicated in blue). As indicated in FIG. 36B, etanercept therapy resulted in marked T cell clonal expansion, as several T cell clones increased from frequencies of 0.01 pre-etanercept (near the detection limit of the assay) to post-treatment values ranging from 247 to 486, thereby consistent with a more than 4-log T cell expansion. As indicated in FIG. 36B, etanercept therapy resulted in marked T cell clonal contraction, as several T cell clones decreased from frequencies of 259 to 598 pre-etanercept to post-treatment values of 0.01, thereby consistent with a more than 4-log T cell clonal contraction These observations indicate that pre-treatment of a subject with etanercept or any other anti-TNF-α therapeutic that preferentially inhibits the serum, cell-free form of TNF-α (such as the monoclonal antibody, adalimumab) can be utilized to shift the T cell receptor repertoire away from T cells of Th1-type phenotype on an antigen-specific basis, thereby enriching for T cells of a $T_{REG}$ phenotype on an antigen-specific basis.

Example 28: Characterization of the $T_{REG}$-Th2 Hybrid Population as a Cell Product Enriched for Expression of CD25, CD27, 2B4, BTLA, and CTLA4

Figure 37:
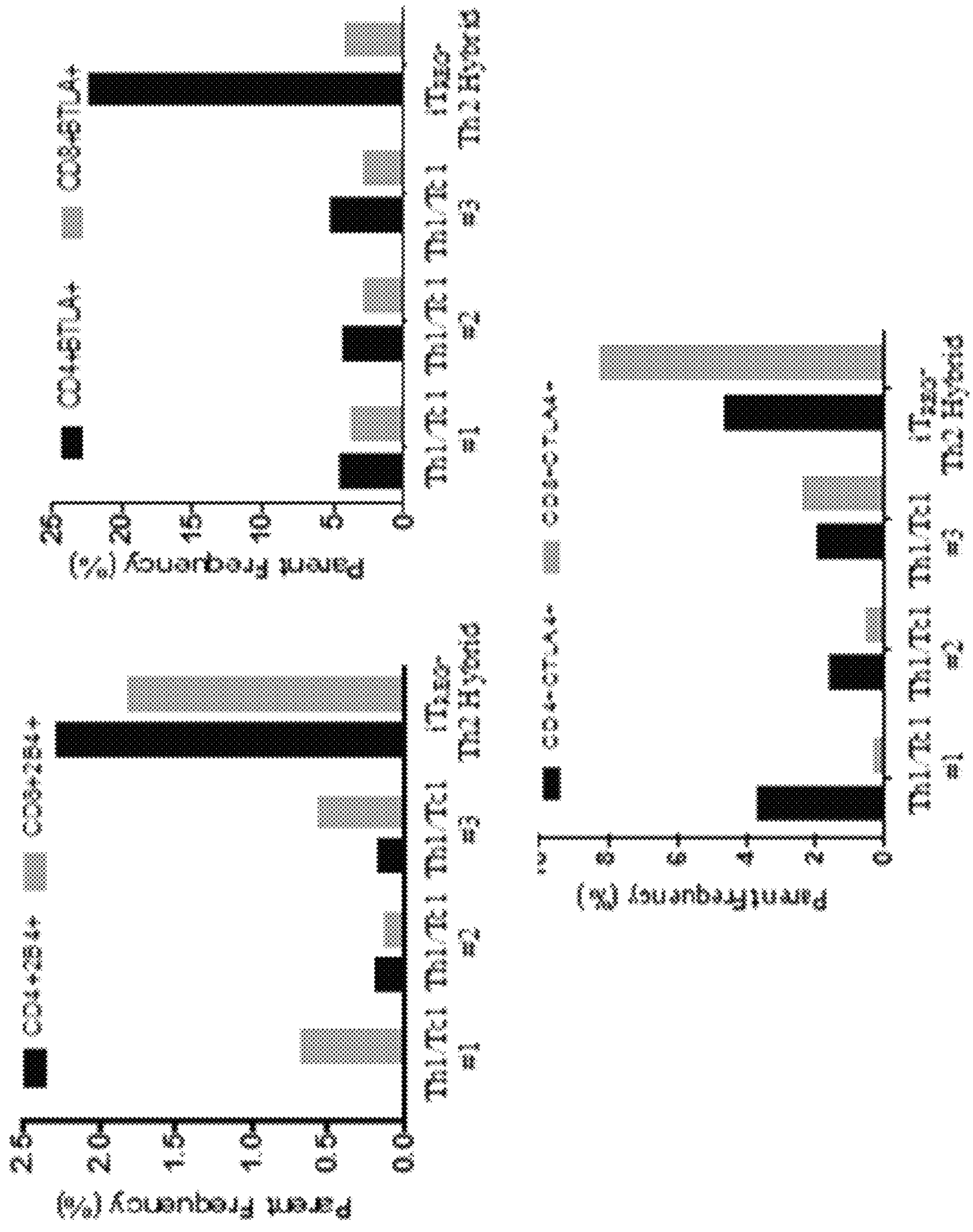
FIG. 37 illustrates that extended culture of de-differentiated T cells in the hybrid Th2/$T_{REG}$ polarization condition results in the generation of T cells expressing increased levels of the following molecules relative to control Th1/Tc1 cells: CD25, CD27, 2B4, BTLA, and CTLA.

FIG. 37 indicates that hybrid $T_{REG}$-Th2 cells manufactured according to the described conditions have increased expression of the following cell surface molecules by flow cytometry relative to control Th1/Tc1 cells: CD25, CD27, 2B4, BTLA, and CTLA4. In FIG. 37, The i$T_{REG}$/Th2 hybrid population was generated by the method previously detailed using an initial phase of T cell de-differentiation followed by re-differentiation in the hybrid $T_{REG}$/Th2 media containing IL-2, TGF-β, and IL-4; the cells were harvested and subjected to flow cytometry for assessment of $CD4^+$ and $CD8^+$ T cell expression of molecules of relevance, namely CD25, CD27, 2B4, BTLA, and CTLA4; comparison was made to three separate control conditions evaluating Th1/Tc1 polarization.

As FIG. 37 illustrates, the i$T_{REG}$/Th2 hybrid cell product has $CD4^+$ and $CD8^+$ T cells that express at least 10% and more preferably 50% higher levels of CD25, CD27, 2B4, BTLA, and CTLA4 relative to control Th1/Tc1 cells.

CD25, the IL-2 receptor, is critical for the ability of $T_{REG}$ cells to control autoimmunity, in particular $CD8^+$ T cell driven responses. Therefore, expression of CD25 on the i$T_{REG}$/Th2 manufactured cell product is a desirable characteristic.

CD27, a co-stimulatory molecule with increased expression on $T_{REG}$ cells, has been shown to contribute to the inhibitory function of TREGS. Therefore, expression of CD27 on the i$T_{REG}$/Th2 manufactured cell product is a desirable characteristic.

2B4 (CD244) has recently been shown to inhibit CD8+ T cell responses by attenuation of glycolysis and cell division. Therefore, expression of 2B4 on the i$T_{REG}$/Th2 manufactured cell product is a desirable characteristic.

BTLA (CD272) is a co-inhibitory receptor, and the ligation of BTLA with the herpesvirus-entry mediator HVEM promotes $T_{REG}$ cell induction and inhibition of effector immune responses. Therefore, expression of BTLA on the i$T_{REG}$/Th2 manufactured cell product is a desirable characteristic.

CTLA4 is a critical effector molecule of $T_{REG}$ cells, as recently evidenced by its ability to limit immunity to malarial infection. Therefore, expression of CTLA4 on the i$T_{REG}$/Th2 manufactured cell product is a desirable characteristic.

Example 29: Characterization of the $T_{REG}$-Th2 Hybrid Population as a Cell Product Enriched for Expression of TIGIT, TIM3, ICOS, LAIR1, and OX40

Figure 38:
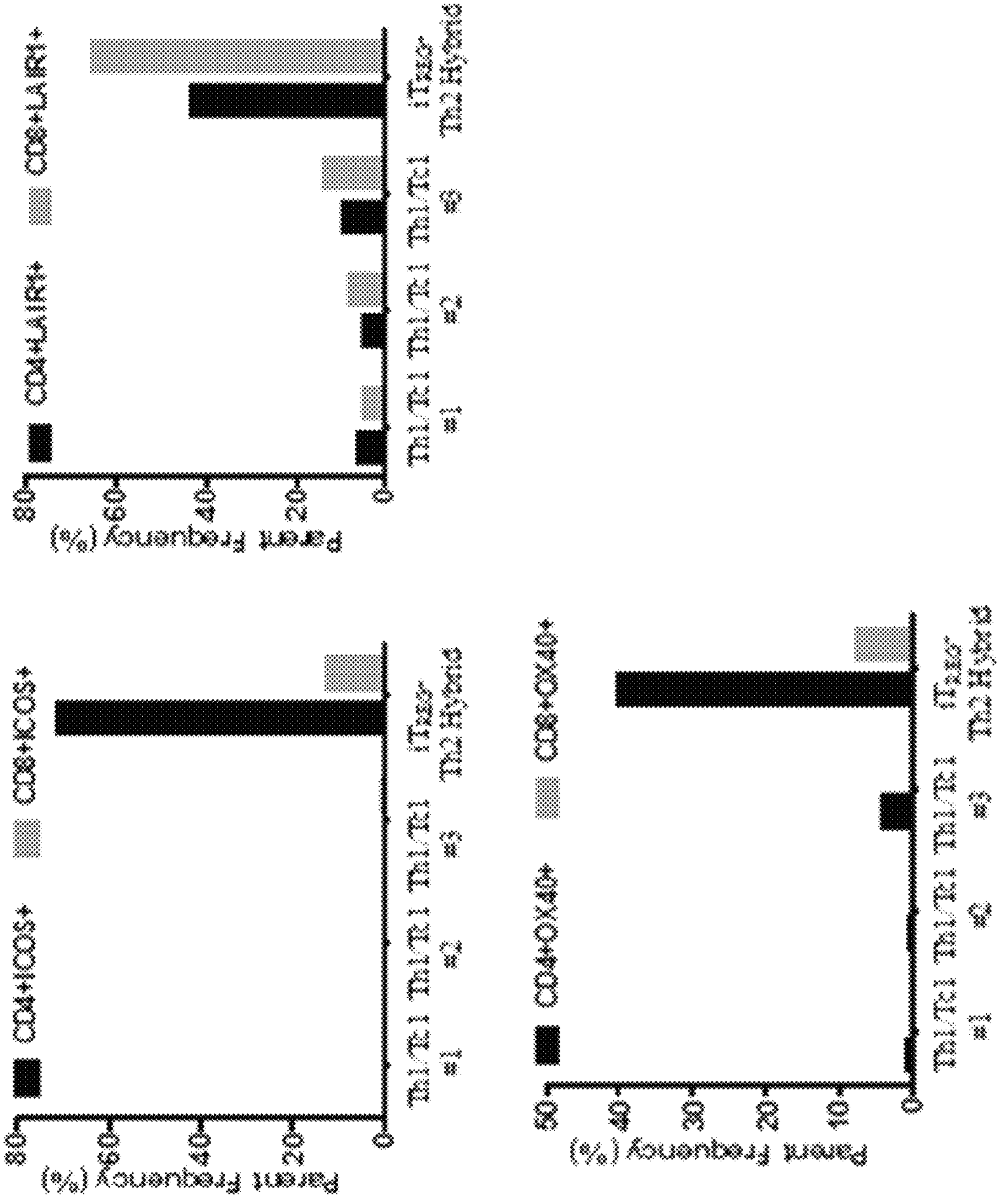
FIG. 38 illustrates that extended culture of de-differentiated T cells in the hybrid Th2/$T_{REG}$ polarization condition results in the generation of T cells expressing increased levels of the following molecules relative to control Th1/Tc1 cells: TIGIT, TIM3, ICOS, LAIR1, and OX40.

FIG. 38 indicates that hybrid $T_{REG}$-Th2 cells manufactured according to the described conditions have increased expression of the following cell surface molecules by flow cytometry relative to control Th1/Tc1 cells: TIGIT, TIM3, ICOS, LAIR1, and OX40. In FIG. 38, the i$T_{REG}$/Th2 hybrid population was generated by the method previously detailed using an initial phase of T cell de-differentiation followed by re-differentiation in media containing IL-2, TGF-β, and IL-4. At day 11 of i$T_{REG}$/Th2 manufacturing, the cells were harvested and subjected to flow cytometry for assessment of $CD4^+$ and $CD8^+$ T cell expression of molecules of relevance, namely TIGIT, TIM3, ICOS, LAIR1, and OX40; comparison was made to three separate control conditions evaluating Th1/Tc1 polarization.

As FIG. 38 illustrates, the i$T_{REG}$/Th2 hybrid cell product has $CD4^+$ and $CD8^+$ T cells that express at least 10% and more preferably 50% higher levels of TIGIT, TIM3, ICOS, LAIR1, and OX40 relative to control Th1/Tc1 cells.

TIGIT is a cell surface co-inhibitory receptor molecule that associates with regulatory T cell function, including for example, contribution to the immunosuppressive environment in B cell non-Hodgkin lymphoma. Therefore, expression of TIGIT on the i$T_{REG}$/Th2 manufactured cell product is a desirable characteristic.

TIM3 is a co-inhibitory receptor that mediates an inhibitory effect of $T_{REG}$ cells, including for example, suppression of T cells that infiltrate head and neck squamous cell carcinoma. Therefore, expression of TIM3 on the i$T_{REG}$/Th2 manufactured cell product is a desirable characteristic.

ICOS is a co-stimulatory molecule that was recently determined to help maintain immune suppression by regulatory T cells for control of immune reactivity in the central nervous system. Therefore, expression of ICOS on the i$T_{REG}$/Th2 manufactured cell product is a desirable characteristic.

LAIR1 (CD305) is a multi-faceted inhibitory molecule that can block inflammation at multiple steps, including the suppression of activated, effector memory T cells. Therefore, expression of LAIR1 on the i$T_{REG}$/Th2 manufactured cell product is a desirable characteristic.

OX40 is a co-stimulatory molecule. Therefore, expression of OX40 on the i$T_{REG}$/Th2 manufactured cell product is a desirable characteristic.

The majority of the phenotype characterization of the T cell product manufactured according to the $T_{REG}$/Th2 method detailed in this disclosure can be ascertained at the end of culture. However, it is important to note that the T cell product can be cryopreserved, and as such, phenotypic characterization of T cells in the post-thaw state reflect the actual product to be adoptively transferred to the subject. The $T_{REG}$/Th2 cells in the post-thaw state can be characterized by the following relative to control Th1/Tc1 cells: (a) increased expression of CD25, CD27, 2B4, BTLA, CTLA4, TIGIT, TIM3, ICOS, LAIR1, and OX40 by flow cytometry; (b) reduced IFN-g and TNF-α and increased secretion of IL-4 by Luminex cytokine secretion analysis; and (c) altered expression of T cell fate transcription factors, namely reduced TBET and increased FOXP3 and GATA3.

Apheresis for $iT_{REG}$ Generation.

Prior to therapy with the pentostatin/cyclophosphamide regimen, subjects will undergo a lymphocyte apheresis procedure. The purpose of this peripheral lymphocyte collection will be to manufacture $iT_{REG}$ cells for adoptive T cell therapy.

Apheresis will consist of a 10- to 15-liter collection on CS-3000 or equivalent machine. The apheresis product will be sent to the protocol sponsor, Rapa Therapeutics, and the $iT_{REG}$ cells will be manufactured by ex vivo culture using specialized culture conditions.

Study Objectives

Primary Objectives. Determine the safety of $iT_{REG}$ cell infusion in the context of the PC regimen and maintenance lamivudine therapy in the inflammatory subset of ALS patients.

Secondary Objectives. Determine the ability of the $iT_{REG}$ therapy to inhibit inflammatory markers in ALS patients. In a preliminary manner, determine the effect of $iT_{REG}$ therapy on patient-reported and clinician-reported ALS scores.

Eligibility Criteria.

Subjects with sporadic or familial ALS diagnosed as laboratory-supported suspected, probable, or definite according to the World Federation of Neurology El Escorial Criteria. Age≥18 years and less than or equal to 75 years. Karnofsky performance status of 70% or greater. Ejection fraction by MUGA or 2-D echocardiogram within institution normal limits. Serum creatinine less than or equal to 2.0 mg/dl. AST and ALT less than or equal to 3 times the upper limit of normal. Bilirubin less than or equal to 1.5 (except if due to Gilbert's disease). Corrected DLCO greater than or equal to 50% on Pulmonary Function Tests.

To assess secondary study endpoints, patient must have evidence of inflammatory markers in peripheral blood cell populations after evaluation of at least two separate blood samples during the screening interval. The assays used to assess the inflammatory status of a potential patient will include: flow cytometry; cytokine secretion analysis; and cell signaling events by Western Blot analysis. Other tests may include tests of T cell receptor repertoire or in vitro sensitization to potential self-antigens such as motor neuron proteins or ALS-related protein aggregates. Cytokine secretion will be evaluated without stimulation (autonomous cytokine secretion) and with stimulation from various modalities, including but not limited to: anti-CD3/anti-CD28 co-stimulation; LPS endotoxin exposure; CD40 ligand exposure; adenosine $A2_A$ and A3 receptor agonism and antagonism; T cell (PD1, TIM-3) and monocyte (CD47, CD200) checkpoint inhibition; and assessment of T cell receptor clonality by RNA sequencing. The decision as to whether a potential subject will be considered to have sufficient inflammation to warrant inclusion in the study will be based on a matrix analysis of all of these tests, with the decision being made by the study PI or Lead Associate Investigator in consultation with the Medical Director of the Rapa Therapeutics Lab where the immune assays will be performed.

Exclusion criteria include patient actively taking riluzole (Rilutek®) or edaravone (Radicava®) therapy (except if on a stable dose for more than one month). The following will also represent exclusion criteria: receipt of any investigational intervention within 30 days of protocol; pulmonary vital capacity measurement<60% of predicted; active uncontrolled infection; hypertension not adequately controlled by 3 or less medications; history of cerebro-vascular accident within 6 months of enrollment; history of documented pulmonary embolus within 6 months of enrollment; or clinically significant cardiac pathology (as defined by myocardial infarction within 6 months prior to enrollment; Class III or IV heart failure according to NYHY; uncontrolled angina; severe uncontrolled ventricular arrhythmias; or electrocardiographic of acute ischemia or active conduction system abnormalities). Patients with a history of coronary artery bypass grafting or angioplasty will receive a cardiology evaluation and will be considered on a case-by-case basis. Patients who are seropositive for HIV, hepatitis B, or hepatitis C will be excluded. Patients known or found to be pregnant will be excluded, as will be patients of childbearing age who are unwilling to practice contraception. Patients may be excluded at the discretion of the PI or if it is deemed that allowing participation would represent an unacceptable medical or psychiatric risk.

Treatment of ALS Patients with the PC Regimen.

The purpose of the 8-week PC regimen is to cause a partial depletion and suppress the Th1/Tc1 cells that contribute to ALS disease pathogenesis. In addition, at week 8 and at later time points when the PC regimen is immediately followed by $iT_{REG}$ cell infusion, the PC regimen is also intended to acutely result in the creation of an increase in T cell homeostatic cytokines, in particular, IL-7 and IL-15.

The PC Regimen will be administered as 14-day cycles; however, up to a two-week additional delay between cycles may be permitted in the event of logistical obstacles or additional time is required to evaluate and/or treat any adverse events. For cycle #1, pentostatin (1 $mg/m^2$ i.v. on day 1) will be administered in combination with cyclophosphamide (100 mg p.o. daily on days 1, 2, and 3). Cycle #2, which will be administered as long as no dose limiting toxicity has occurred, will consist of an increased dose of pentostatin (2 $mg/m^2$ i.v. on day 1) in combination with the same dose of cyclophosphamide (100 mg p.o. daily on days 1, 2, and 3). Cycles #3 and #4, which will be administered as long as no dose limiting toxicity has occurred AND the absolute lymphocyte count is greater than 750 cells per microliter, will consist of two doses of pentostatin (2 $mg/m^2$ i.v. on day 1 and day 4) in combination with five days of cyclophosphamide (100 mg p.o. daily on days 1, 2, 3, 4, and 5).

If the ALC count is 750 cells per microliter or less prior to cycle #3 or cycle #4, then no further cycles will be administered and the patient will proceed to maintenance therapy with lamivudine. In the event that the absolute lymphocyte count is greater than 1250 cells per microliter prior to cycle #4, then the dose of cyclophosphamide will be doubled (200 mg p.o. daily on days 1, 2, 3, 4, and 5).

Specifics relating to pentostatin administration: (a) Preparation: pentostatin will be reconstituted by the Pharmacy Department to a concentration of 2 mg/ml as per vial instructions. The appropriate patient specific dose will then be added to 0.9% sodium chloride to make up a total volume of 50 mL; (b) Dose and Administration: pentostatin dosing will be adjusted for renal dysfunction (see below); each dose of pentostatin will be administered intravenously over 30-60 minutes; (c) Premedication and Anti-emetic therapy: prior to infusion, infuse 1 liter of 0.9% sodium chloride over 30-60 minutes. Pentostatin can be emetogenic. Anti-emetic regimen guidelines are as follows (variations are allowed at the discretion of the PI): (1) Dexamethasone 12 mg by IV infusion 60 minutes prior to each dose of pentostatin; (2) In addition, oral dexamethasone may be administered in the first five days of each cycle, if needed for emesis control; (3) Ondansetron may be administered at a dose of 8 mg by IV infusion 60 minutes prior to each dose of pentostatin; (4) For the remainder of treatment, ondansetron may be administered at an oral dose of 8 mg (tablets) every 12 hours for as long as required during the cycle on Days 1 through 14; and (5) Aprepitant may be added as needed to the anti-emetic regimen in patients with uncontrolled nausea and vomiting.

Specifics relating to pentostatin dose reductions: serum creatinine levels will be obtained prior to each scheduled dose of pentostatin and CrCl calculated. The CrCl will be obtained either by 24-hour urine or calculated by the Cockcroft-Gault formula. If a subject experiences an increase in creatinine level during the pentostatin and cyclophosphamide therapy, subsequent dosing will be modified as follows: for CrCl≥60 (mL/min/1.73 $m^2$): administer 100% of intended pentostatin dose (1 mg/$m^2$ of pentostatin for cycles #1, #2; 2 mg/$m^2$ for cycles #3, #4); for CrCl<60 but ≥30: administer 50% of intended pentostatin dose (0.5 mg/$m^2$ of pentostatin for cycles #1, #2; 1 mg/$m^2$ for cycles #3, #4); for CrCl<30: hold pentostatin.

Because pentostatin is rarely associated with neurologic toxicity (seizure, coma), special attention should be paid towards evaluating CNS toxicity. If the PC regimen is associated with any new neurologic toxicity of grade 2 or greater severity or worsening of any pre-existing neurologic toxicity, the institutional PI should be contacted to discuss whether further pentostatin therapy and further protocol therapy is warranted.

Specific aspects of cyclophosphamide administration: hydration. Because cyclophosphamide can cause cystitis, it is important for patients to stay well hydrated. At a minimum, patients should drink at least 2 to 4 liters of fluid per day to maintain a clear color to the urine. It is also especially important to void the bladder prior to sleeping. Oral cyclophosphamide will be given at a fixed dose of 100 mg per day on days 1, 2, and 3 (for cycles #1 and #2) or on days 1, 2, 3, 4, and 5 (for cycles #3 and #4). However, for patients who do not have substantial reduction in the ALC prior to cycle #4 (as defined by an ALC greater than 1250 cells per microliter), the cyclophosphamide dose for cycle #4 will be increased to 200 mg per day for days 1, 2, 3, 4, and 5. IV infusion of cyclophosphamide will be allowed if a patient is unable to tolerate oral therapy; the IV dose will be the same as the intended oral dose. For IV infusion, cyclophosphamide will be reconstituted by the HUMC Pharmacy Department to a concentration of 20 mg/ml as per vial instructions. The appropriate dose (100 mg or 200 mg) will then be diluted in 100 ml of D5W or 0.9% sodium chloride and infused intravenously over 30 minutes.

It is not anticipated that the PC cycles will result in substantial reductions in the absolute neutrophil count. However, if the ANC below certain values at the determination just prior to the next cycle, then the dose of cyclophosphamide will be adjusted as follows: (1) for an ANC value of 1000 or greater cells per microliter, 100% of the intended dose will be administered; (2) for an ANC value of between 500 and 999 cells per microliter, 50% of the intended dose will be administered; and (3) if the ANC value is less than 500 cells per microliter, then the cyclophosphamide will not be administered. In addition, for ANC values less than 500 cells per microliter, the decision to start G-CSF therapy may be considered by the PI.

The quantitative goal of the 8-week PC regimen is to reduce the ALC value to approximately 750 cells per microliter. It is our hypothesis that this degree of depletion and suppression of the T cells contributing to disease pathogenesis will allow for successful engraftment and biologic activity of the i$T_{REG}$ cells to control the neuro-inflammatory process. However, it is possible that more stringent reductions in the host Th1/Tc1 cells might be required to allow the i$T_{REG}$ cells to exert their fully suppressive function; in such a case, the PC regimen can be intensified or prolonged in order to target lower ALC values prior to i$T_{REG}$ cell therapy, such as 500, 250, or 0 ALC per microliter. On the other hand, it is possible that the i$T_{REG}$ cell therapy will be so effective that even an ALC value of 750 cells per microliter might be considered too stringent; in such cases, the PC regimen can be de-intensified or shortened in duration to target higher ALC values such as 1000, 1250, or 1500 cells per microliter.

Implementation Relating to Lamivudine Maintenance Therapy.

Upon completion of the PC regimen, patients will proceed to maintenance therapy with lamivudine, which will continue until the end-of-study date at 6-months of the protocol. Lamivudine (oral tablets) will be administered at a dose of 150 mg p.o BID. In the event that the estimated creatinine clearance is reduced below 50 ml/min, lamuvidine will be reduced to a dose of 150 mg p.o. once daily; lamivudine will be discontinued for estimated creatine clearance values below 30 ml/min.

As stated previously, the stated objective of the lamivudine is to down-regulate the NLRP3 inflammasome that represents a proximal event in ALS pathogenesis. As such, we envision that other inflammasome inhibitors will be suitable or perhaps preferable for use on our protocol platform; for example, inflammasome inhibitors with a potentially improved risk:benefit ratio have been developed.

It is important to note that lamivudine is not predicted to be antagonistic to i$T_{REG}$ cell therapy because their mechanisms of action in fact are complimentary. This complimentary contrasts to other interventions proposed for $T_{REG}$ cell therapy, such as rapamycin (which can inhibit a wide variety of T cell responses) and IL-2 (which has a narrow therapeutic window in terms of promoting $T_{REG}$ expansion in vivo and can promote inflammatory T cell populations).

Supportive Care Therapy.

Patients will not be required to be on systematic antibiotic prophylaxis if neutropenic. The decision to initiate antibiotics will reside with the protocol PI.

All patients will be placed on oral anti-viral prophylaxis for HSV or VZV with Acyclovir (or its pro-drug Valacyclovir) at the time of initiation of protocol therapy through end-of-study.

All patients will be placed on oral anti-fungal prophylaxis (first line: fluconazole) at the time of initiation of protocol therapy through the end-of-study visit. Substitutions are allowed, as per the protocol PI approval.

All patients will initiate pneumocystis PJP prophylaxis at study entry (continued to end-of-study visit). Patients will be placed on oral Cotrimoxazole (Trimethoprim 160 mg/Sulfamethoxazole 800 mg): one tablet po on Mondays, Wednesday and Fridays; alternative schedules or substitutions are allowed, as per the protocol PI approval.

Treatment of ALS Patients with I$T_{REG}$ Cells: Manufacturing and Phenotype of the Product.

As previously detailed, the i$T_{REG}$ cell product will be manufactured from autologous T cells that are collected by apheresis either at the time of study entry prior to the PC regimen or at the completion of the 8-week PC regimen. Each apheresis collection may have inherent advantages: the initial collection will have a higher T cell yield whereas the post-PC collection will be comprised of a T cell population that is relatively depleted of Th1/Tc1 cells.

Because the $iT_{REG}$ cells are manufactured based on the principles of effector T cell conversion from an inflammatory phenotype to an anti-inflammatory $T_{REG}$ phenotype, there will be no need for expensive and laborious natural $T_{REG}$ purification steps that require either monoclonal antibody/column selection methods or flow cytometry to obtain the relatively rare $nT_{REG}$ population that is typically characterized as $CD4^+$, $CD25^+$, and low expression of CD127. In addition, there will be no need to eliminate $CD8^+$ T cells from the $iT_{REG}$ cell population because $CD8^+$ $T_{REG}$ cells have been shown to mediate immune suppression and may be beneficial in terms of providing increased diversity to the $iT_{REG}$ cell therapy.

It has been shown that $T_{REG}$ cells of limited differentiation status, which can be defined as being of central memory type based on expression of cell surface markers such as CD62L and CCR7, have increased in vivo regulatory function. On the other hand, it is also known that $T_{REG}$ cell acquisition of a more differentiated effector memory status allows up-regulation of molecules that mediate suppressive function such as: IL-10; CTLA-4; the ecto-nucleotidase molecules CD39 and CD73; and cytolytic molecules such as perforin and fas ligand. These data indicate that it will be beneficial to infuse an $iT_{REG}$ cell product that contains populations of both central and effector memory subsets, and as such, the $iT_{REG}$ cell product that we will utilize will have representation from both subsets.

In addition, it is necessary that the $iT_{REG}$ cells express FoxP3, which is the transcription factor that dictates the regulatory T cell differentiation program. Furthermore, because it has been shown that FoxP3 expression and consequent regulatory function can deteriorate over time, the $iT_{REG}$ cell product must have stable FoxP3 expression over extended periods of time in culture.

Furthermore, it has been shown in humans that FoxP3 alone is not sufficient for identification of a regulatory T cell phenotype because it can be transiently expressed by bona fide inflammatory T cell subsets. As such, it is critical to manufacture an $iT_{REG}$ cell product that expresses FoxP3 but also is relatively devoid of co-expression of molecules associated with inflammatory T cell subsets, such as the Th1/Tc1-type transcription factor TBET or Th1-type cytokines IL-2 or IFN-γ.

Finally, it is important that the $iT_{REG}$ cell product have reduced capacity for differentiation plasticity from a regulatory phenotype towards an inflammatory phenotype. That is, it has been well documented that $T_{REG}$ cells can be relatively unstable in their suppressive phenotype, which can result in transformation to an inflammatory T cell subset that can actually contribute to the mediation of neurodegenerative disease. As such, the $iT_{REG}$ cell product must stably express FoxP3 and also show a reduced propensity to conversion to the Th1/Tc1 subsets. As an additional safeguard against $T_{REG}$ cell differentiation plasticity into the Th1-type subset, we will purposefully incorporate IL-4 into the $iT_{REG}$ cell manufacturing process such that any such differentiation will be directed towards the Th2-type lineage, which: appears to be important of $T_{REG}$ cell maintenance and $T_{REG}$ cell suppressor function; has been described as a default pathway for $T_{REG}$ cells; and can mediate anti-inflammatory effects in the setting of ALS. In spite of this evidence for the potentially beneficial role of a Th2-like state of regulatory T cells, manufacturing methods for $T_{REG}$ cell therapy have not included the purposeful addition of exogenous IL-4 during culture (as illustrated in a recent example of $T_{REG}$ manufacturing).

At the end of manufacturing, the $iT_{REG}$ cell product will be cryopreserved into at least four single-use aliquots at the therapeutic cellular dose (between 1 and 5×106 cells/kg).

Treatment of ALS Patients with $IT_{REG}$ Cells: Combination of $T_{REG}$ Cell Populations.

The $iT_{REG}$ cell populations will be infused at a dose of between 1 and 5×106 cells per kg recipient body weight. This dosage of $T_{REG}$ cell therapy, which is relatively low compared to previous studies, is facilitated by several factors: the PC regimen will provide sufficient immunologic space for engraftment of the $iT_{REG}$ cells; the $iT_{REG}$ cells will express a memory profile that is associated with cellular persistence after adoptive transfer; and the $iT_{REG}$ cell product will be cryopreserved into at least four clinically-relevant therapeutic doses, thereby permitting multiple cycles of therapy.

As previously detailed, the $iT_{REG}$ cell product will contain a diversity of memory differentiation status (central memory [CM] plus effector memory [EM]), thereby allowing both long-term and immediate control of neuro-inflammation, respectively. It will be possible to control the ratio of such central and effector memory populations for optimal results, depending on the clinical situation; that is, based on clinical parameters, the $iT_{REG}$ distribution of CM:EM cells might be 1:1, 3:1, 10:1, 1:3, or 1:10.

In a similar manner, depending on the clinical situation, it will be possible to control the ratio of $CD4^+iT_{REG}$ cells to $CD8^+IT_{REG}$ cells for improved therapeutic effect.

Finally, because $iT_{REG}$ and $nT_{REG}$ cells express different T cell receptor repertoires and therefore can be complimentary in terms of mediating immune suppression, we envision that optimal therapy using $iT_{REG}$ cells might be attained by co-administration of $nT_{REG}$ cells.

Treatment of ALS Patients with $IT_{REG}$ Cells: Combination with Pharmaceutical Agents It is possible that the $iT_{REG}$ cell therapy, when combined with a platform that includes the immune modulation effect of the PC regimen and the inflammasome inhibitory effect of lamivudine, may be sufficient to control neuro-inflammation.

However, we envision that $iT_{REG}$ cell therapy might be optimized by alteration of the platform. By way of example but not limitation, the therapy could be optimized by changing the intensity of the PC regimen; substitution of cyclophosphamide with another agent to work in synergy with pentostatin; or addition of a third component to the PC regimen, for example, low-dose IL-2 therapy after anti-TNF therapy, which we reason will predictably increase $T_{REG}$ cells in vivo. By way of example but not limitation, low-dose IL-2 therapy as described in Pham MN, von Herrath M G, Vela J L. Antigen-Specific Regulatory T Cells and Low Dose of IL-2 in Treatment of Type 1 Diabetes. Frontiers in Immunology. 2015; 6:651.

Furthermore, we envision that the lamivudine might be replaced with a more potent or more specific inflammasome inhibitor similar to molecules that have recently been synthesized.

Ultimately, the drive for inflammation in ALS is initiated by more proximal events, such as the build-up of mis-folded RNA elements and insufficient autophagy. To this extent, there exists a rationale to utilize drugs in ALS therapy that can promote autophagy, most notably rapamycin. However, clinical trials of rapamycin for therapy of ALS are only now being initiated (ClinicalTrials.gov Identifier:

NCT03359538); furthermore, this protocol is evaluating continuous therapy of rapamycin (which can associate with substantial toxicity), a fixed dose of rapamycin (which can result in a large degree of inter-patient drug variability), and a relatively low dose of rapamycin (which will not ensure the high drug levels necessary for potent inhibition of the mTOR pathway and consequent promotion of autophagy). To circumvent these limitations, we will combine $iT_{REG}$ cell therapy with rapamycin for promotion of autophagy using the following parameters: use of intermittent rapamycin therapy to limit drug toxicity and to limit the potential for rapamycin inhibition of $iT_{REG}$ cells (by way of example but not limitation, one week on mTOR inhibition therapy plus three weeks of recovery off of mTOR therapy); use of variable dosing of rapamycin, including a loading dose of rapamycin, in combination serum testing of rapamycin levels to ensure homogenous drug levels for more consistent inhibition of the mTOR pathway; and use of high-dose rapamycin therapy to achieve serum rapamycin levels of 30 ng/ml in preference to the typical target of ~5 to 12 ng/ml. See Mossoba M E, Halverson D C, Kurlander R, et al. High-Dose Sirolimus And Immune Selective Pentostatin Plus Cyclophosphamide Conditioning Yields Stable Mixed Chimerism and Insufficient Graft-Versus-Tumor Responses. Clinical cancer research. 2015; 21(19): 4312-4320.

Furthermore, it is likely that rapamycin therapy may be sub-optimal for promotion of autophagy in neurodegenerative due to insufficient penetration of the drug into the central nervous system; to this point, even intravenous therapy with the rapamycin analog temsirolimus did not result in significant levels of drug in the cerebrospinal fluid. To overcome this limitation, we envision that we will administer temsirolimus through an indwelling Ommaya reservoir, in a manner similar to that utilized for therapy of lysosomal storage disease, to achieve consistent CSF drug levels of the mTOR inhibitor for optimal promotion of autophagy in the setting of neurodegenerative disease.

Treatment of ALS Patients with $IT_{REG}$ Cells: Immune Monitoring.

In the context of $iT_{REG}$ cell therapy of ALS, it will be important to quantify the success of the cellular therapy in terms of its ability to modulate the neuro-inflammatory pathways associated with the disease. That is, monitoring of the clinical course of neurodegenerative disease is insufficient given the wide degree of variability in disease progression across patient cohorts. An ability to optimally treat the neuro-inflammation will require multiple infusions of $iT_{REG}$ cells, including in combination with a variety of pharmacologic agents; as such, it will be critical to utilize immune biomarkers to assist in the guidance of therapeutic decisions.

Therapeutic decisions pertaining repetitive dosing of $iT_{REG}$ cell infusions and associated pharmacologic agents will be based upon specialized testing of peripheral blood mononuclear cells that we have developed. These tests address several key issues relating to inflammatory monitoring, including: spontaneous cytokine measurement; T cell and monocyte cooperativity in cytokine measurement; role of recombinant human CD40 ligand, T cell checkpoint inhibitor pathways, and monocyte checkpoint pathways in the unmasking of cytokine secretion; assessment of inflammasome activation by various techniques such as protein quantification by Western Blot; evaluation of adenosine receptor biology of peripheral T cells as an indicator for inflammatory events; use of flow cytometry to assess FoxP3 transcription factor co-expression with the Th1-related molecules TBET, IL-2, or IFN-γ; characterization of the T cell receptor repertoire by RNA sequencing; and detection of antigen-specific T cell responses against potential neurologic auto-antigens, such as the protein aggregates that develop during disease pathogenesis.

Protocol Evaluation.

Clinical evaluation by a physician or mid-level provider will be conducted on day 1 of each cycle of the PC regimen, which are intended to be 14-day cycles. Patients will also be seen by their local provider once during the 14-day PC cycles (ideally, around day 8 of the cycle). On these visits, a CBC with differential and complete metabolic panel (complete metabolic panel typically includes approximately 14 tests, including electrolytes, creatinine, liver transaminases, and bilirubin; specific panel to be used is not protocol-mandated) will be obtained and laboratory results will be sent to the protocol investigators.

At the completion of the interval encompassing the PC regimen (approximately month 2), the patient will then be seen monthly at months 3, 4, 5, and 6; the visit at month 6 will represent the end-of-study visit. Tests to be performed at the time of these clinical evaluations will include: (1) interim history and physical examination; (2) CBC with differential and platelet count; (3) complete metabolic panel; and (4) immune subset enumeration (TBNK panel).

To monitor research immune parameters, a peripheral blood sample will be sent to Rapa Therapeutics to allow for centralized monitoring and more in-depth analyses. Blood samples will consist of 30 ml in a green top heparinized tube (for cellular assays) and 5 ml in a red top tube (for serum assays) sent to Rapa Therapeutics.

Using the same samples sent to Rapa Therapeutics, we will investigate the effect of the PC regimen and the lamivudine maintenance therapy on: pro-inflammatory or anti-inflammatory cytokines or cellular subsets as measured by RNA expression, supernatant/Luminex assay, flow cytometry, and cell signaling events by phosphorylation analysis by Western Blot.

Serum will be evaluated for potential bio-markers of ALS. By way of example but not limitation, such as those biomarkers described in Beach T G. A Review of Biomarkers for Neurodegenerative Disease: Will They Swing Us Across the Valley? Neurology and Therapy. 2017; 6(Suppl 1): 5-13.

We will characterize the TCR repertoire of patients and evaluate whether the therapeutic interventions influence the repertoire.

In vitro studies will fall under the general category of "Immune Characterization Studies". They will focus on separation of distinct cell subsets by multi-parameter FACS analysis or separation by magnetic beads with subsequent characterization. Specifically, peripheral blood mononuclear cells (PBMC) will be analyzed by flow cytometry for expression of markers indicative of hematopoietic lineage, immune functional subsets, cytokine production, and activation state. Cell subsets will be analyzed for T cell receptor repertoire diversity. Cells may be activated in vitro with a number of different stimuli including specific antigens and mitogens which are known to activate distinct pathways of T lymphocyte or monocyte function. Assays may include T cell proliferation, cytokine production and gene expression. The specific assays to be used for the on-going data analyses are subject to be modified, deleted or replaced as technology and knowledge in the field evolve during the course of the study without constituting a change in research aims.

Response Criteria.

The patient-reported ALSFS-R score and the clinician-reported Appel score will be measured at various time points, as indicated previously.

Toxicity Criteria

Toxicity will be graded according to the Common Terminology Criteria for Adverse Events (CTCAE) of the NCI. A copy of the CTCAE version 4.0 can be downloaded from the CTEP home page. All treatment areas and personnel involved in the study should have access to a copy of the CTCAE version 4.0.

Any grade 4 or 5 toxicity (CTCAE version 4.0) with the attributions of probably or definitely related to the study drugs (pentostatin, cyclophosphamide, lamivudine) will be considered a dose limiting toxicity (DLT). The following toxicities will not be considered DLTs: biochemical grade 4 toxicity (except for renal and hepatic values); grade 4 emesis; grade 4 fever; and grade 4 toxicity related to infection that resolves within 7 days.

Statistical Considerations.

The study design incorporates a standard 3+3 method to evaluate safety of the pentostatin and cyclophosphamide regimen and maintenance lamivudine therapy (the platform). In the first three patients, if no patient develops a DLT through completion of the pentostatin/cyclophosphamide regimen, then the regimen will be determined safe for expansion of the cohort to a total of n=10 patients. On the other hand, if one out of three of the first patients develops a DLT, then accrual will be increased to a total of n=6 patients. In such a case, accrual to the n=10 number in the cohort can proceed if no more than 1 out of the first 6 patients develops a DLT.

Once this platform is successfully developed, we will evaluate the safety and potential efficacy of $iT_{REG}$ cell infusion. Initially, a pilot study will be performed to assess the ability of multiple infusions of $iT_{REG}$ cells to inhibit the neuro-inflammatory pathways associated with disease.

Once an ability to effectively modulate the biomarkers associated with neurodegeneration has been documented, we will perform phase II clinical trials (using either historical control data or a randomized cohort design) to assess whether the $iT_{REG}$ cell therapy can improve the clinical outcome in ALS patients.

Risk Benefit Analysis.

The estimated survival of patients accrued to this study are anticipated to be approximately two to four years from study entry.

The first protocol component consists of four cycles of an immune depletion and immune suppression regimen consisting of pentostatin and cyclophosphamide (PC regimen). We hypothesize that the PC regimen will eliminate and suppress pathogenic immune cells that contribute to ALS progression; as such, it is possible that patient's may benefit from this effect in the form of improved quality of life or ultimately, decreased progression of disease. However, there may be unexpected toxicities of the PC regimen in terms of the central nervous system. Although dosing modifications are being made to help ensure that the PC regimen will be relatively safe in this new ALS patient population, it is possible that the PC regimen may have a paradoxical effect and actually increase the rate of ALS progression or cause some other neurologic toxicity. Pentostatin in rare cases can also cause toxicity in other organs such as the heart or kidney. The most common toxicity to be expected from the PC regimen will be lymphocyte depletion, although this effect is part of the therapeutic rationale; on the other hand, the PC regimen may eliminate myeloid cells, thereby increasing the chance of bacterial or fungal infection. The PC regimen is anticipated to be associated with T cell immune suppression, and as such, opportunistic viral infections may occur.

The second protocol component consists of maintenance therapy with the anti-viral drug, lamivudine. Patients may benefit from this therapy if the drug works as hypothesized to reduce inflammation emanating from the central nervous system. Lamivudine is generally a very well tolerated drug outside of primarily gastro-intestinal side effect and pancreatitis.

The third protocol component consists of multiple infusions of $iT_{REG}$ cells. Patients may benefit from this therapy because cellular therapy to control inflammation occurs directly in the microenvironment where inflammation is initiated, because cellular therapy operates through multiple molecular mechanisms of action that cannot be easily replicated through drug therapy, and because the effects of cellular therapy can be long-lasting due to memory cell effects.

Alternative Protocol Design

Figure 39:
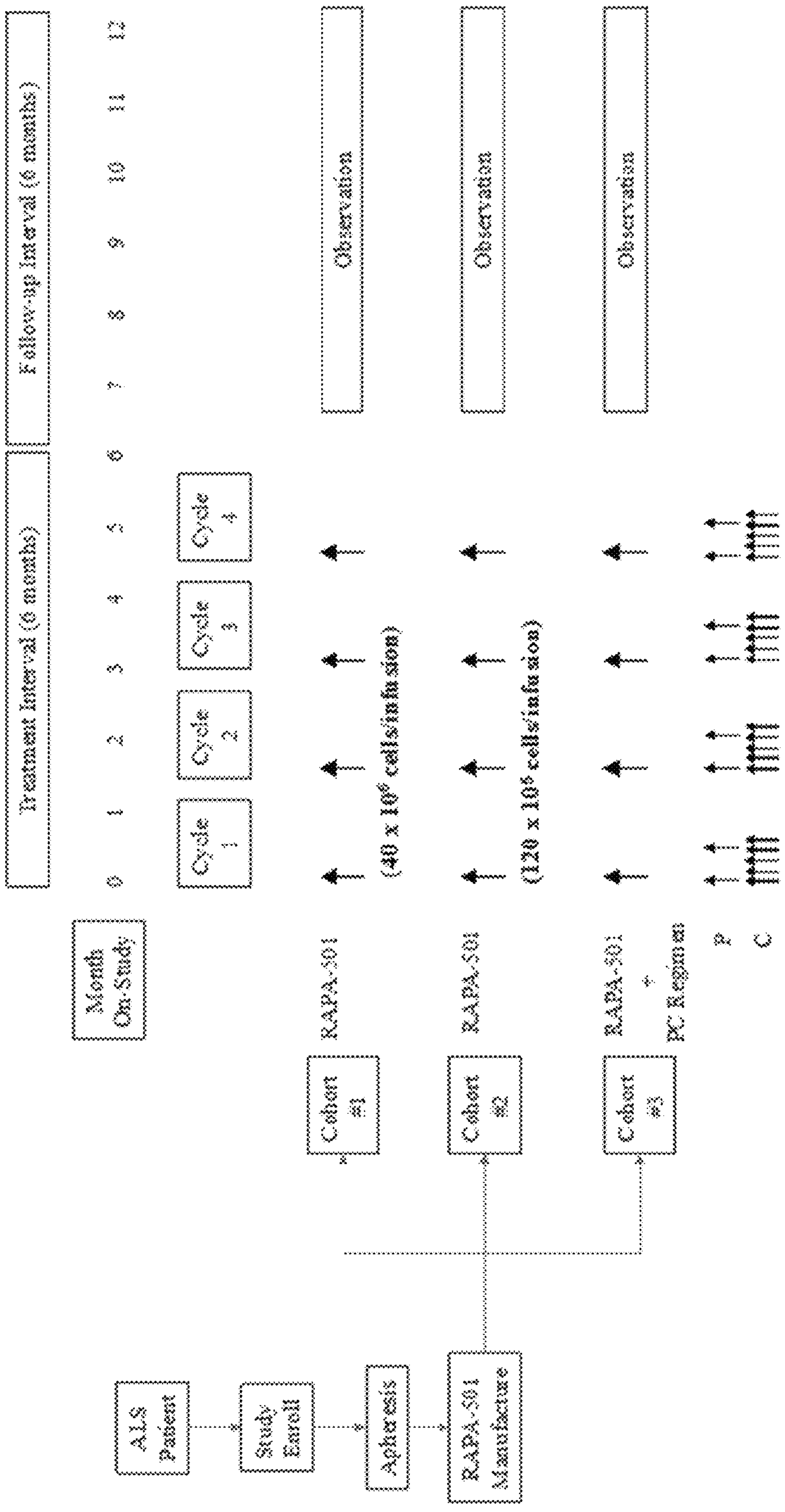
FIG. 39 depicts an alternative protocol design.

FIG. 39 provides an alternative protocol design. Lymphocytes will be collected by steady-state apheresis; the apheresis product will be shipped to the Rapa Therapeutics (Rockville, MD). After RAPA-501 cell manufacturing, n=4 doses of RAPA-501 cells will be cryopreserved in single-use infusion bags at the clinically-indicated cell dose. The treatment interval will be 6-months, followed by a 6-month observation interval. Cohort #1 will receive RAPA-501 cells, administered over 4 cycles at a dose of 40×106 cells/infusion. Cohort #1 represents a safety cohort and will utilize a standard 3+3 design; advancement to Cohort #2 will occur if 0/3 or not more than 1/6 patients experience a dose-limiting toxicity (DLT). Cohort #2 will receive the same four cycles of RAPA-501 cells as in the previously discussed study protocol except that the T cell dose will be increased to 120×106 cells/infusion. Cohort #3 will evaluate the highest dose of RAPA-501 cells that can be safely administered as a single-agent (as per Cohorts #1 or #2, either 40 or 120×106 cells/infusion, respectively) plus host conditioning with the PC regimen prior to each of the four RAPA-501 cell infusions. The PC regimen will consist of pentostatin (2 $mg/m^2$ on days 1 and 4), cyclophosphamide (100 mg per day, days 1 through 5), no therapy on days 6 and 7, and RAPA-501 cell infusion on day 8.

De-Differentiation Embodiments

1. A method for de-differentiation of T cells, comprising:
   - inoculating a culture input population of cells comprising T cells from a subject at a cell density in a culture medium comprising vitamin D, temsirolimus and an IL-2 signaling inhibitor;
   - adding anti-CD3/anti-CD28 coated magnetic beads to said T cells and culture medium at a bead:T cell ratio of 1:1 to 1:12;
   - incubating said culture input population of cells and culture medium for a period of time to yield de-differentiated T cells.
2. The method of embodiment 1, further comprising:
   - harvesting said de-differentiated T cells.
3. The method of embodiment 2, further comprising, after harvesting said de-differentiated T cells:
   - packaging at least a portion of said de-differentiated T cells in a package; and
   - freezing said package containing said portion of said de-differentiated T cells.
4. The method of any one of embodiments 1-3, further comprising, before inoculating said culture input population of cells into said culture medium:

harvesting said culture input population of cells from said subject.

5. The method of any one of embodiments 1-4, wherein said culture medium does not contain IL-2 and no IL-2 is added to said culture medium.

6. The method of any one of embodiments 1-5, wherein said cell density is at least 1.5×106 T cells per mL.

7. The method of any one of embodiments 1-6, wherein said temsirolimus is present in said culture medium at a concentration of about 0.3 μM to about 1 μM.

8. The method of any one of embodiments 1-6, wherein said temsirolimus is present in said culture medium at a concentration of about 1 μM.

9. The method of any one of embodiments 1-8, wherein said IL-2 signaling inhibitor is an anti-IL-2 receptor antibody or fragment thereof.

10. The method of embodiment 9, wherein said IL-2 signaling inhibitor is basiliximab or daclizumab.

11. The method of any one of embodiments 1-10, wherein said IL-2 signaling inhibitor is present in said culture medium at a concentration of 5 to 50 μg/mL.

12. The method of any one of embodiments 1-11, wherein said period of time is about 3 days.

13. The method of any one of embodiments 1-12, wherein said bead:T cell ratio is 1:3.

14. The method of any one of embodiments 1-13, wherein said culture medium further comprises 5% human serum.

15. The method of any one of embodiments 1-14, wherein said culture medium comprises X-Vivo 20 medium.

16. The method of any one of embodiments 1-15, wherein said vitamin D is present in said culture medium at about 0.03 nM to about 1 nM.

17. The method of any one of embodiments 1-15, wherein said vitamin D is present in said culture medium at about 0.1 nM.

18. The method of any one of embodiments 1-11 and 13-17, further comprising:

measuring an expression level of RAPTOR or RICTOR in said culture input population of cells, wherein said period of time lasts until the expression level of RAPTOR or RICTOR in the culture input population of cells is at least 50% and more preferably 90% reduced relative to a control population of T cells manufactured under the same conditions as the culture input population of cells without temsirolimus, IL-2 signaling inhibitor and Vitamin D.

19. The method of any one of embodiments 1-11 and 13-17, further comprising:

measuring an expression level of RAPTOR or RICTOR and a housekeeping protein in said culture input population of cells, wherein said period of time lasts until the expression level of RAPTOR or RICTOR, respectively, in said culture input population of cells is reduced at least 50% relative to control population of T cells manufactured under the same conditions as the culture input population of cells without temsirolimus, IL-2 signaling inhibitor and Vitamin D, after normalizing for expression level of a housekeeping protein.

20. The method of embodiment 19, wherein said housekeeping protein is actin or GAPDH.

21. The method of any one of embodiments 18-20, wherein said step of measuring the expression level is performed by Western blot analysis.

22. The method of any one of embodiments 1-11 and 13-17, further comprising:

measuring an expression level of RAPTOR or RICTOR in said culture input population of cells, wherein said period of time lasts until the expression level of RAPTOR or RICTOR in the culture input population of cells is reduced by at least 50% and more preferably by 90% relative to a control population of T cells manufactured under the same conditions as the culture input population of cells without temsirolimus, IL-2 signaling inhibitor and Vitamin D.

23. A de-differentiated T cell produced by the method of any one of embodiments 1-22.

24. A composition comprising a population of de-differentiated T cells, wherein at least a portion of said population of said de-differentiated T cells express less than 50% of both RAPTOR or RICTOR as compared to a control population of T cells, wherein the control population of T cells is manufactured under the same conditions as the culture input population of cells without temsirolimus, IL-2 signaling inhibitor and Vitamin D.

25. A method for de-differentiation of T cells, comprising:

inoculating a culture input population of cells comprising T cells from a subject at a cell density in a culture medium comprising vitamin D and temsirolimus;

adding anti-CD3/anti-CD28 coated magnetic beads to said T cells and culture medium at a bead:T cell ratio of 1:1 or less to stimulate said T cells;

incubating said culture input population of cells and culture medium for a period of time to yield de-differentiated T cells.

26. The method of embodiment 25, further comprising:

harvesting said de-differentiated T cells.

27. The method of embodiment 26, further comprising, after harvesting said de-differentiated T cells:

packaging at least a portion of said de-differentiated T cells in a package; and freezing said package containing said portion of said de-differentiated T cells.

28. The method of any one of embodiments 25-27, further comprising, before inoculating said culture input population of cells into said culture medium:

harvesting said culture input population of cells from said subject.

29. The method of any one of embodiments 25-28, wherein said culture medium does not contain IL-2 and no IL-2 is added to said culture medium.

30. The method of any one of embodiments 25-29, wherein said cell density is 1.5×106 T cells per mL.

31. The method of any one of embodiments 25-30, wherein said temsirolimus is present in said culture medium at a concentration of about 0.3 μM to about 1 μM.

32. The method of any one of embodiments 25-30, wherein said temsirolimus is present in said culture medium at a concentration of about 1 μM.

33. The method of any one of embodiments 25-32, wherein said period of time is about 3 days.

34. The method of any one of embodiments 25-33, wherein said bead:T cell ratio is 1:3.

35. The method of any one of embodiments 25-34, wherein said culture medium further comprises 5% human serum.

36. The method of any one of embodiments 25-35, wherein said culture medium comprises X-Vivo 20 medium.

37. The method of any one of embodiments 25-36, wherein said vitamin D is present in said culture medium at about 0.03 nM to about 1 nM.

38. The method of any one of embodiments 25-37, wherein said vitamin D is present in said culture medium at about 0.1 nM.

39. The method of any one of embodiments 25-32 and 34-38, further comprising:

measuring an expression level of RAPTOR or RICTOR in said culture input population of cells, wherein said period of time lasts until the expression level of RAPTOR or RICTOR in said culture input population of cells is reduced by at least 50% relative to a control population of T cells manufactured under the same conditions as the culture input population of cells without temsirolimus, IL-2 signaling inhibitor and Vitamin D.

40. The method of any one of embodiments 25-32 and 34-38, further comprising:

measuring an expression level of RAPTOR, RICTOR and a housekeeping protein in said culture input population of cells, wherein said period of time lasts until the expression level of RAPTOR or RICTOR in the culture input population of cells is reduced by 50% or more preferably by 90% relative to a control population of T cells manufactured under the same conditions as the culture input population of cells without temsirolimus, IL-2 signaling inhibitor and Vitamin D after normalizing for housekeeping protein expression.

41. The method of embodiment 40, wherein said housekeeping protein is actin or GAPDH.

42. The method of any one of embodiments 39-41, wherein said step of measuring the expression level is performed by Western blot analysis.

43. The method of any one of embodiments 25-32 and 34-38, further comprising:

measuring an expression level of RAPTOR or RICTOR in said culture input population of cells, wherein said period of time lasts until the expression level of RAPTOR or RICTOR in the culture input population of cells are reduced by at least 50% and more preferably by 90% relative to a control population of T cells manufactured under the same conditions as the culture input population of cells without temsirolimus, IL-2 signaling inhibitor and Vitamin D.

44. A de-differentiated T cell produced by the method of any one of embodiments 25-43.

45. A de-differentiated T cell population characterized by at least a 10% reduction and more preferably a 50% reduction in expression of RNA for the following T cell differentiation molecules relative to a control population of T cells cultured without the culture additives specified in these methods: cytolytic molecules, including but not limited to granzyme B; and cytokine molecules, including but not limited to IFN-γ.

46. A de-differentiated T cell population characterized by at least a 10% increase and more preferably a 50% increase in expression of RNA for the following T cell differentiation molecules relative to a control population of T cells cultured without the culture additives specified in these methods: transcription factors associated with induced pluripotent stem cells, including but not limited to Nanog, KLF4, and KLF10; and molecules associated with naïve T cells, including but not limited to the IL-7 receptor, CD127.

47. A de-differentiated T cell population characterized by at least a 10% decrease and more preferably a 50% decrease in expression of RNA for the following T cell differentiation molecules relative to a control population of T cells cultured without the culture additives specified in these methods: transcription factors associated with Th1 effector T cells, including but not limited to T-Bet and STAT1; however, concomitantly, the manufactured T cells will have equivalent expression of transcription factors associated with cell survival, including but not limited to HIF-1-alpha.

48. A de-differentiated T cell population characterized by at least a 10% increase and more preferably a 50% increase in expression of molecular markers of autophagy relative to a control population of T cells cultured without the culture additives specified in these methods, including but not limited to: an increase in protein level by Western Blot analysis of the autophagy-related molecule, p62.

49. The method of any one of embodiments 1-22, wherein said step of adding anti-CD3/anti-CD28 coated magnetic beads to said T cells and culture medium at a bead:T cell ratio of 1:1 to 1:12 is not performed.

50. The method of any one of embodiments 25-43, wherein said step of adding anti-CD3/anti-CD28 coated magnetic beads to said T cells and culture medium at a bead:T cell ratio of 1:1 or less to stimulate said T cells is not performed.

51. A population of de-differentiated T cells characterized by one or more of the following properties:

at least a 10% decrease, and more preferably, a 50% decrease in mRNA expression of one or more of granzyme B, IL-10, and IFN-γ relative to a control T cell population incubated under the same conditions without temsirolimus, vitamin D and the IL-2 signaling inhibitor;

at least a 10% increase, and more preferably, a 50% increase in mRNA expression of one or more of Nanog, KLF4, KLF10 and CD127 relative to a control T cell population incubated under the same conditions without temsirolimus, vitamin D and the IL-2 signaling inhibitor;

at least a 10% decrease, and more preferably a 50% decrease in mRNA expression of one or more of T-Bet and STAT1 relative to a control T cell population incubated under the same conditions without temsirolimus, vitamin D and the IL-2 signaling inhibitor;

HIF-1-α expression within about 20% of a control T cell population incubated under the same conditions without temsirolimus, vitamin D and the IL-2 signaling inhibitor;

at least a 10% increase, and more preferably a 50% increase, in p62 expression relative to a control T cell population incubated under the same conditions without temsirolimus, vitamin D and the IL-2 signaling inhibitor;

an expression level of RAPTOR or RICTOR reduced by at least 50% and more preferably by 90% relative to a control population of T cells manufactured under the same conditions as the culture input population of cells without temsirolimus, IL-2 signaling inhibitor and Vitamin D;

an expression level of RAPTOR or RICTOR normalized by a housekeeping protein is reduced by at least 50% and more preferably by 90% relative to a control population of T cells manufactured under the same conditions as the culture input population of cells without temsirolimus, IL-2 signaling inhibitor and Vitamin D; and combinations thereof.

52. A de-differentiated T cell characterized by one or more of the following properties:

at least a 10% decrease, and more preferably, a 50% decrease in mRNA expression of one or more of granzyme B, IL-10, and IFN-γ relative to a control T cell incubated under the same conditions without temsirolimus, vitamin D and the IL-2 signaling inhibitor;

at least a 10% increase, and more preferably, a 50% increase in mRNA expression of one or more of Nanog, KLF4, KLF10 and CD127 relative to relative to a control T cell incubated under the same conditions without temsirolimus, vitamin D and the IL-2 signaling inhibitor;

at least a 10% decrease, and more preferably a 50% decrease in mRNA expression of one or more of T-Bet and STAT1 relative to a control T cell incubated under the same conditions without temsirolimus, vitamin D and the IL-2 signaling inhibitor;

HIF-1-α expression within about 20% of a control T cell incubated under the same conditions without temsirolimus, vitamin D and the IL-2 signaling inhibitor;

at least a 10% increase, and more preferably a 50% increase, in p62 expression relative to a control T cell population incubated under the same conditions without temsirolimus, vitamin D and the IL-2 signaling inhibitor;

an expression level of RAPTOR or RICTOR reduced by at least 50% and more preferably by 90% relative to a control T cell manufactured under the same conditions as the culture input population of cells without temsirolimus, IL-2 signaling inhibitor and Vitamin D;

an expression level of RAPTOR or RICTOR normalized by a housekeeping protein is reduced by at least 50% and more preferably by 90% relative to a control T cell manufactured under the same conditions as the culture input population of cells without temsirolimus, IL-2 signaling inhibitor and Vitamin D; and combinations thereof.

Re-Differentiation Embodiments

1. A method for differentiating de-differentiated T cells to TREG/Th2 cells, comprising:

culturing de-differentiated T cells in a culture medium comprising IL-2, IL-4 and TGF-β; adding anti-CD3/anti-CD28 coated magnetic beads at a ratio of 3:1 (bead:T cell ratio); incubating said de-differentiated T cells for a period of time to yield TREG/Th2 cells.

2. The method of embodiment 1, wherein said culture medium further comprises pemetrexed.

3. The method of any one of embodiments 1-2, wherein said IL-2 is present in said culture medium at a concentration of about 100 IU/mL.

4. The method of any one of embodiments 1-3, wherein said IL-4 is present in said culture medium at a concentration of about 1000 IU/mL.

5. The method of any one of embodiments 1-4, wherein said TGF-β is present in said culture medium at a concentration of about 10 ng/mL.

6. The method of embodiment 2, wherein said pemetrexed is present in said culture medium at a concentration of up to 100 nM.

7. The method of embodiment 2, wherein said pemetrexed is present in said culture medium at a concentration of about 10 nM.

8. The method of any one of embodiments 6-7, wherein said IL-2 is present in said culture medium at a concentration of about 100 IU/mL.

9. The method of any one of embodiments 6-8, wherein said IL-4 is present in said culture medium at a concentration of about 1000 IU/mL.

10. The method of any one of embodiments 6-9, wherein said TGF-β is present in said culture medium at a concentration of about 10 ng/mL.

11. A method for differentiating de-differentiated T cells to TREG/Th2 cells, comprising:

culturing de-differentiated T cells, wherein said de-differentiated T cells express RAPTOR and RICTOR at a level that is at least 10% reduced relative to control T cells in a culture medium comprising IL-2, IL-4 and TGF-β;

adding anti-CD3/anti-CD28 coated magnetic beads at a ratio of 3:1 (bead:T cell ratio);

incubating said de-differentiated T cells for a period of time to yield TREG/Th2 cells.

12. The method of embodiment 11, wherein said culture medium further comprises pemetrexed.

13. The method of any one of embodiments 11-12, wherein said IL-2 is present in said culture medium at a concentration of about 100 IU/mL.

14. The method of any one of embodiments 11-13, wherein said IL-4 is present in said culture medium at a concentration of about 1000 IU/mL.

15. The method of any one of embodiments 11-14, wherein said TGF-β is present in said culture medium at a concentration of about 10 ng/ml.

16. The method of embodiment 12, wherein said pemetrexed is present in said culture medium at a concentration of up to 100 nM.

17. The method of embodiment 12, wherein said pemetrexed is present in said culture medium at a concentration of about 10 nM.

18. The method of any one of embodiments 16-17, wherein said IL-2 is present in said culture medium at a concentration of about 100 IU/mL.

19. The method of any one of embodiments 16-18, wherein said IL-4 is present in said culture medium at a concentration of about 1000 IU/mL.

20. The method of any one of embodiments 16-19, wherein said TGF-β is present in said culture medium at a concentration of about 10 ng/mL.

21. The method of any one of embodiments 1-20, wherein said culture medium is X-Vivo 20 supplemented with 5% human AB serum.

22. The method of any one of embodiments 1-21, wherein said period of time is between 3 days and 40 days.

23. A TREG/Th2 cell produced by the method of any one of embodiments 1-22.

24. A method for differentiating de-differentiated T cells to $T_{REG}$ cells, comprising:

culturing de-differentiated T cells having reduced expression of RAPTOR and RICTOR relative to a control population of T cells in a culture medium comprising IL-2 and TGF-β; adding anti-CD3/anti-CD28 coated magnetic beads at a ratio of 3:1 (bead:T cell ratio); incubating said de-differentiated T cells for a period of time to yield TREG cells.

25. The method of embodiment 24, wherein said culture medium further comprises pemetrexed.

26. The method of any one of embodiments 24-25, wherein said IL-2 is present in said culture medium at a concentration of about 100 IU/mL.

27. The method of any one of embodiments 24-26, wherein said TGF-β is present in said culture medium at a concentration of about 10 ng/mL.

28. The method of embodiment 25, wherein said pemetrexed is present in said culture medium at a concentration of up to 100 nM.

29. The method of embodiment 25, wherein said pemetrexed is present in said culture medium at a concentration of about 10 nM.

30. The method of any one of embodiments 28-29, wherein said IL-2 is present in said culture medium at a concentration of about 100 IU/mL.

31. The method of any one of embodiments 28-30, wherein said TGF-β is present in said culture medium at a concentration of about 10 ng/mL.

32. A method for differentiating de-differentiated T cells to TREG cells, comprising:

culturing de-differentiated T cells, wherein said de-differentiated T cells express RAPTOR and RICTOR at a level that is at least 10% reduced relative to control T cells in a culture medium comprising IL-2 and TGF-β;

adding anti-CD3/anti-CD28 coated magnetic beads at a ratio of 3:1 (bead:T cell ratio);

incubating said de-differentiated T cells for a period of time to yield TREG cells.

33. The method of embodiment 32, wherein said culture medium further comprises pemetrexed.

34. The method of any one of embodiments 32-33, wherein said IL-2 is present in said culture medium at a concentration of about 100 IU/mL.

35. The method of any one of embodiments 32-34, wherein said TGF-β is present in said culture medium at a concentration of about 10 ng/mL.

36. The method of embodiment 33, wherein said pemetrexed is present in said culture medium at a concentration of up to 100 nM.

37. The method of embodiment 33, wherein said pemetrexed is present in said culture medium at a concentration of about 10 nM.

38. The method of any one of embodiments 36-37, wherein said IL-2 is present in said culture medium at a concentration of about 100 IU/mL.

39. The method of any one of embodiments 36-38, wherein said TGF-β is present in said culture medium at a concentration of about 10 ng/ml.

40. The method of any one of embodiments 24-39, wherein said culture medium is X-Vivo 20 media supplemented with 5% AB serum.

41. The method of any one of embodiments 24-40, wherein said period of time is between 3 days and 40 days.

42. The method of any one of embodiments 1-41, wherein said de-differentiated T cells have a reduced expression of RAPTOR and RICTOR relative to a control population of T cells 43. A TREG cell produced by the method of any one of embodiments 1-22 and 24-42.

44. A TREG cell or hybrid TREG/Th2 cell produced by the method of any one of embodiments 1-22 and 24-42, wherein lymphocytes collected by apheresis for subsequent T cell culture are obtained in the steady-state or after subject treatment with an anti-TNF-□ therapeutic that is relatively selective in terms of neutralizing the serum, cell-free form of TNF-α, most notably the recombinant receptor molecule etanercept or the monoclonal antibody adalimumab.

45. A TREG cell or hybrid TREG/Th2 cell produced by the method of any one of embodiments 1-22 and 24-42, wherein the TREG cell or hybrid TREG/Th2 cell or a population thereof has increased expression by flow cytometry of at least one the following molecules relative to control Th1/Tc1 cells: CD25, CD27, 2B4, BTLA, CTLA4, TIGIT, TIM3, ICOS, LAIR1, OX40, and combinations thereof.

46. A TREG cell or hybrid TREG/Th2 cell produced by the method of any one of embodiments 1-22 and 24-42, wherein the TREG cell or hybrid TREG/Th2 cell or a population thereof has reduced secretion of inflammatory cytokines relative to control Th1/Tc1 cells, including IFN-γ and TNF-α.

47. A TREG cell or hybrid TREG/Th2 cell produced by the method of any one of embodiments 1-22 and 24-42, wherein said TREG cell or hybrid TREG/Th2 cell or a population thereof has altered expression of T cell fate transcription factors relative to control Th1/Tc1 cells, most notably a decrease in TBET and an increase in FOXP3.

48. A TREG cell or hybrid TREG/Th2 cell produced by the method of any one of embodiments 1-22 and 24-42, wherein said TREG cell or hybrid TREG/Th2 cell or a population thereof has additional phenotypic traits relative to control Th1/Tc1 cells, including: increased secretion of the Th2 cytokine IL-4; and increased expression of the Th2 transcription factor GATA3.

49. A population of TREG or TREG/Th2 cells having at least 5% of CD4+ or CD8+ T cells that express GATA3.

50. A population of TREG or TREG/Th2 cells having at least 5% of CD4+ or CD8+ T cells that express FoxP3

51. A population of TREG or TREG/Th2 cells having at least 10% of CD4+ or CD8+ T cells that express CD73.

52. A population of TREG or $T_{REG}$/Th2 cells having at least 10% of CD4+ or CD8+ T cells that express CD103.

53. A population of TREG or TREG/Th2 cells having at least 20% of CD4+ or CD8+ T cells that express CD150.

54. A population of TREG or TREG/Th2 cells that expresses at least 5 pg/mL/1×106 cells/day of IL-4 after co-stimulation with anti-CD3/anti-CD28 beads at a bead:T cell ratio of 3:1.

55. A population of TREG or TREG/Th2 cells that expresses at least 100 pg/mL/1×106 cells/day of IL-2 after co-stimulation with anti-CD3/anti-CD28 beads at a bead:T cell ratio of 3:1.

56. A population of TREG or TREG/Th2 cells that expresses less than 100 pg/mL/1×106 cells/day of IFN-γ or GM-CSF after co-stimulation with anti-CD3/anti-CD28 beads at a bead:T cell ratio of 3:1.

57. A population of TREG or TREG/Th2 cells that expresses less than 100 pg/mL/1×106 cells/day of TNF-α or IL-17F after co-stimulation with anti-CD3/anti-CD28 beads at a bead:T cell ratio of 3:1.

58. A population of TREG or TREG/Th2 cells having one or more of the following properties:

at least 10% increased expression of one or more of: CD25, CD27, 2B4, BTLA, CTLA4, TIGIT, TIM3, ICOS, LAIR1, OXO40, and combinations thereof, as measured by flow cytometry relative to control Th1/Tc1 cells;

at least 10% decreased secretion of IFN-γ relative to control Th1/Tc1 cells;

at least 10% decreased secretion of TNF-α relative to control Th1/Tc1 cells;

at least 10% decreased expression of TBET relative to control Th1/Tc1 cells;

at least 10% increased expression of FOXP3 relative to control Th1/Tc1 cells;

at least 5% of $CD4^+$ or $CD8^+$ T cells that express GATA3 as measured by flow cytometry;

at least 5% of $CD4^+$ or $CD8^+$ T cells that express FOXP3 as measured by flow cytometry;

at least 5% of $CD4^+$ or $CD8^+$ T cells that express CD73 as measured by flow cytometry;

at least 5% of $CD4^+$ or $CD8^+$ T cells that express CD103 as measured by flow cytometry;

at least 5% of $CD4^+$ or $CD8^+$ cells that express both FOXP3 and GATA3 as measured by flow cytometry;

at least 20% of $CD4^+$ or $CD8^+$ T cells that express CD150 as measured by flow cytometry;

at least a 50% increase in expression of one or more of: GATA3, FoxP3, CD73, CD103, and CD150 relative to a population of T cells characteristic of the T cells from which the population of $T_{REG}$ Or $T_{REG}$/Th2 cells was produced;

secretion of at least 5 pg/mL/$1\times10^6$ cells/day of IL-4 after co-stimulation with anti-CD3/anti-CD28 beads at a bead:T cell ratio of 3:1;

secretion of at least 100 pg/mL/$1\times10^6$ cells/day of IL-2 after co-stimulation with anti-CD3/anti-CD28 beads at a bead:T cell ratio of 3:1;

secretion of less than 100 pg/mL/$1\times10^6$ cells/day of IFN-γ after co-stimulation with anti-CD3/anti-CD28 beads at a bead:T cell ratio of 3:1;

secretion of less than 100 pg/mL/$1\times10^6$ cells/day of GM-CSF after co-stimulation with anti-CD3/anti-CD28 beads at a bead:T cell ratio of 3:1;

secretion of less than 10 pg/mL/$1\times10^6$ cells/day of TNF-α after co-stimulation with anti-CD3/anti-CD28 beads at a bead:T cell ratio of 3:1;

secretion of less than 10 pg/mL/$1\times10^6$ cells/day of IL-17 after co-stimulation with anti-CD3/anti-CD28 beads at a bead:T cell ratio of 3:1; and combinations thereof.

59. A TREG or TREG/Th2 cell having one or more of the following properties:

at least 10% increased expression of one or more of: CD25, CD27, 2B4, BTLA, CTLA4, TIGIT, TIM3, ICOS, LAIR1, OXO40, and combinations thereof, as measured by flow cytometry relative to control Th1/Tc1 cells;

at least 10% decreased secretion of IFN-γ relative to control Th1/Tc1 cells;

at least 10% decreased secretion of TNF-α relative to control Th1/Tc1 cells;

at least 10% decreased expression of TBET relative to control Th1/Tc1 cells;

at least 10% increased expression of FOXP3 relative to control Th1/Tc1 cells;

secretion of at least 5 pg/mL/$1\times10^6$ cells/day of IL-4 after co-stimulation with anti-CD3/anti-CD28 beads at a bead:T cell ratio of 3:1;

secretion of at least 100 pg/mL/$1\times10^6$ cells/day of IL-2 after co-stimulation with anti-CD3/anti-CD28 beads at a bead:T cell ratio of 3:1;

secretion of less than 100 pg/mL/$1\times10^6$ cells/day of IFN-γ after co-stimulation with anti-CD3/anti-CD28 beads at a bead:T cell ratio of 3:1;

secretion of less than 100 pg/mL/$1\times10^6$ cells/day of GM-CSF after co-stimulation with anti-CD3/anti-CD28 beads at a bead:T cell ratio of 3:1;

secretion of less than 10 pg/mL/$1\times10^6$ cells/day of TNF-α after co-stimulation with anti-CD3/anti-CD28 beads at a bead:T cell ratio of 3:1;

secretion of less than 10 pg/mL/$1\times10^6$ cells/day of IL-17 after co-stimulation with anti-CD3/anti-CD28 beads at a bead:T cell ratio of 3:1;

expression of GATA3, FOXP3, CD73 and CD103; and combinations thereof.

60. The method of any one of claims 1-41, wherein the de-differentiated T cells have one or more of the following properties:

at least a 10% decrease, and more preferably, a 50% decrease in mRNA expression of one or more of granzyme B, IL-10, and IFN-γ relative to a control T cell population incubated under the same conditions without temsirolimus, vitamin D and the IL-2 signaling inhibitor;

at least a 10% increase, and more preferably, a 50% increase in mRNA expression of one or more of Nanog, KLF4, KLF10 and CD127 relative to a control T cell population incubated under the same conditions without temsirolimus, vitamin D and the IL-2 signaling inhibitor;

at least a 10% decrease, and more preferably a 50% decrease in mRNA expression of one or more of T-Bet and STAT1 relative to a control T cell population incubated under the same conditions without temsirolimus, vitamin D and the IL-2 signaling inhibitor;

HIF-1-α expression within about 20% of a control T cell population incubated under the same conditions without temsirolimus, vitamin D and the IL-2 signaling inhibitor;

at least a 10% increase, and more preferably a 50% increase, in p62 expression relative to a control T cell population incubated under the same conditions without temsirolimus, vitamin D and the IL-2 signaling inhibitor;

an expression level of RAPTOR or RICTOR reduced by at least 50% and more preferably by 90% relative to a control population of T cells manufactured under the same conditions as the culture input population of cells without temsirolimus, IL-2 signaling inhibitor and Vitamin D;

an expression level of RAPTOR or RICTOR normalized by a housekeeping protein is reduced by at least 50% and more preferably by 90% relative to a control population of T cells manufactured under the same conditions as the culture input population of cells without temsirolimus, IL-2 signaling inhibitor and Vitamin D; and combinations thereof.

61. The method of any one of claims 1-41, wherein the de-differentiated T cells have one or more of the following properties:

at least a 10% decrease, and more preferably, a 50% decrease in mRNA expression of one or more of granzyme B, IL-10, and IFN-γ relative to a control T cell incubated under the same conditions without temsirolimus, vitamin D and the IL-2 signaling inhibitor;

at least a 10% increase, and more preferably, a 50% increase in mRNA expression of one or more of Nanog, KLF4, KLF10 and CD127 relative to relative to a control T cell incubated under the same conditions without temsirolimus, vitamin D and the IL-2 signaling inhibitor;

at least a 10% decrease, and more preferably a 50% decrease in mRNA expression of one or more of T-Bet and STAT1 relative to a control T cell incubated under the same conditions without temsirolimus, vitamin D and the IL-2 signaling inhibitor;

HIF-1-α expression within about 20% of a control T cell incubated under the same conditions without temsirolimus, vitamin D and the IL-2 signaling inhibitor;

at least a 10% increase, and more preferably a 50% increase, in p62 expression relative to a control T cell population incubated under the same conditions without temsirolimus, vitamin D and the IL-2 signaling inhibitor;

an expression level of RAPTOR or RICTOR reduced by at least 50% and more preferably by 90% relative to a control T cell manufactured under the same conditions as the culture input population of cells without temsirolimus, IL-2 signaling inhibitor and Vitamin D;

an expression level of RAPTOR or RICTOR normalized by a housekeeping protein is reduced by at least 50% and more preferably by 90% relative to a control T cell manufactured under the same conditions as the culture input population of cells without temsirolimus, IL-2 signaling inhibitor and Vitamin D; and combinations thereof.

What is claimed is:

1. A method for manufacturing induced hybrid $T_{REG}$/Th2 cells, comprising:

culturing T cells in a first culture medium comprising vitamin D, temsirolimus, and an IL-2 signaling inhibitor for a first period of time sufficient to yield de-differentiated T cells;

separating said de-differentiated T cells from the first culture medium;

culturing de-differentiated T cells in a second culture medium comprising IL-2, IL-4, and TGF-β;

adding anti-CD3/anti-CD28 coated magnetic beads at a ratio of 3:1 (bead:T cell ratio) to the second culture medium;

incubating said de-differentiated T cells in the second culture medium for a second period of time to yield induced hybrid $T_{REG}$/Th2 cells.

2. The method of claim 1, wherein said second culture medium further comprises pemetrexed.

3. The method of claim 1, wherein said IL-2 is present in said second culture medium at a concentration of about 10,000 IU/mL.

4. The method of claim 1, wherein said TGF-β is present in said second culture medium at a concentration of about 10 ng/mL.

5. The method of claim 2, wherein said pemetrexed is present in said second culture medium at a concentration of up to 100 nM.

6. The method of claim 1, wherein said second period of time is between 3 days and 40 days.

7. The method of claim 1, wherein said IL-4 is present in said second culture medium at a concentration of about 1000 IU/mL.

8. The method of claim 1, wherein the temsirolimus is present in said first culture medium at a concentration of at least 1 μM.

9. The method of claim 1, wherein said IL-2 signaling inhibitor is an anti-IL-2 receptor antibody or fragment thereof.

10. The method of claim 1, wherein said IL-2 signaling inhibitor is basiliximab or daclizumab.

11. The method of claim 1, wherein said IL-2 signaling inhibitor is present in said first culture medium at a concentration of 5 to 50 μg/mL.

12. The method of claim 1, wherein said first period of time is about 3 days.

13. The method of claim 1, further comprising adding anti-CD3/anti-CD28 coated magnetic beads to said first culture medium at a bead:T cell ratio of 1:1 to 1:12.

14. The method of claim 13, wherein said bead:T cell ratio is 1:3.

15. The method of claim 1, wherein said first culture medium further comprises 5% human serum.

16. The method of claim 1, wherein said vitamin D is present in said first culture medium at about 0.03 nM to about 1 nM.

17. The method of claim 1, further comprising:

measuring an expression level of RAPTOR or RICTOR in said T cells, wherein said first period of time lasts until the expression level of RAPTOR or RICTOR in the T cells is at least 50% reduced relative to a control population of T cells cultured under the same conditions as the T cells in the absence of temsirolimus, IL-2 signaling inhibitor and vitamin D.

* * * * *